(12) United States Patent
Liverton et al.

(10) Patent No.: US 9,738,661 B2
(45) Date of Patent: Aug. 22, 2017

(54) HCV NS3 PROTEASE INHIBITORS

(71) Applicants: Merck Sharp & Dohme Corp., Rahway, NJ (US); MSD Italia S.R.L., Rome (IT)

(72) Inventors: Nigel J. Liverton, Harleysville, PA (US); Vincenzo Summa, Pomezia (IT); Steven Harper, Ariccia (IT); John A. McCauley, Maple Glen, PA (US); Joseph J. Romano, Frederick, PA (US); Michael T. Rudd, Collegeville, PA (US)

(73) Assignees: MERCK SHARP & DOHME CORP., Rahway, NJ (US); MSD ITALIA S.R.L., Rome (IT)

( * ) Notice: Subject to any disclaimer, the term of this patent is extended or adjusted under 35 U.S.C. 154(b) by 0 days.

(21) Appl. No.: 14/638,733

(22) Filed: Apr. 3, 2015

(65) Prior Publication Data
US 2015/0266897 A1 Sep. 24, 2015

Related U.S. Application Data

(62) Division of application No. 12/447,342, filed as application No. PCT/US2007/022460 on Oct. 23, 2007, now abandoned.

(60) Provisional application No. 60/997,434, filed on Oct. 3, 2007, provisional application No. 60/854,912, filed on Oct. 27, 2006.

(51) Int. Cl.
| | |
|---|---|
| A61K 31/519 | (2006.01) |
| C07D 498/22 | (2006.01) |
| C07D 498/08 | (2006.01) |
| C07D 498/18 | (2006.01) |
| C07K 5/083 | (2006.01) |
| C07K 5/087 | (2006.01) |
| A61K 31/407 | (2006.01) |
| A61K 31/4192 | (2006.01) |
| A61K 31/437 | (2006.01) |
| A61K 31/439 | (2006.01) |
| A61K 45/06 | (2006.01) |
| A61K 38/00 | (2006.01) |

(52) U.S. Cl.
CPC .......... *C07D 498/22* (2013.01); *A61K 31/407* (2013.01); *A61K 31/4192* (2013.01); *A61K 31/437* (2013.01); *A61K 31/439* (2013.01); *A61K 45/06* (2013.01); *C07D 498/08* (2013.01); *C07D 498/18* (2013.01); *C07K 5/0804* (2013.01); *C07K 5/0806* (2013.01); *C07K 5/0808* (2013.01); *C07K 5/0812* (2013.01); *A61K 38/00* (2013.01)

(58) Field of Classification Search
None
See application file for complete search history.

(56) References Cited

U.S. PATENT DOCUMENTS

| | | |
|---|---|---|
| 3,480,613 A | 11/1969 | Walton |
| 6,323,180 B1 | 11/2001 | Llinas-Brunet et al. |
| 6,608,027 B1 | 8/2003 | Tsantrizos et al. |
| 6,777,395 B2 | 8/2004 | Bhat et al. |
| 6,955,174 B2 | 10/2005 | Friedrichs et al. |
| 7,470,664 B2 | 12/2008 | Holloway et al. |
| 7,973,040 B2 | 7/2011 | Harper et al. |
| 2002/0019363 A1 | 2/2002 | Ismaili et al. |
| 2002/0107138 A1 | 8/2002 | Hoveyda et al. |
| 2003/0236216 A1 | 12/2003 | Devos et al. |
| 2004/0006007 A1 | 1/2004 | Gosselin et al. |
| 2004/0063658 A1 | 4/2004 | Roberts et al. |
| 2004/0067901 A1 | 4/2004 | Bhat et al. |
| 2004/0229776 A1 | 11/2004 | Chen et al. |
| 2004/0229818 A1 | 11/2004 | Llinas-Brunet |
| 2004/0254159 A1 | 12/2004 | Hasvold et al. |

(Continued)

FOREIGN PATENT DOCUMENTS

| | | |
|---|---|---|
| EP | 1719773 A1 | 11/2006 |
| GB | 2337262 A | 11/1999 |

(Continued)

OTHER PUBLICATIONS

U.S. Appl. No. 12/477,342, filed Apr. 27, 2009.

(Continued)

*Primary Examiner* — Craig Ricci
(74) *Attorney, Agent, or Firm* — Julie M. Lake; John C. Todaro

(57) ABSTRACT

The present invention relates to macrocyclic compounds of formula (I) that are useful as inhibitors of the hepatitis C virus (HCV) NS3 protease, their synthesis, and their use for treating or preventing HCV infections.

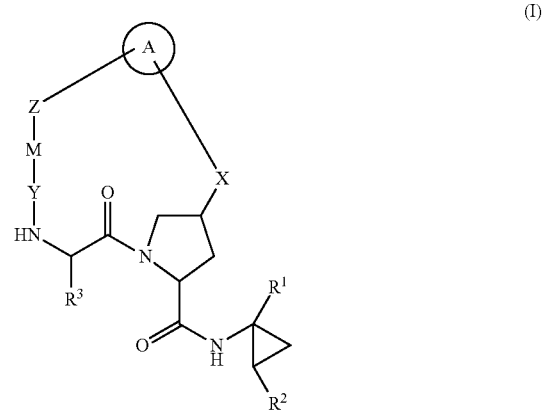

7 Claims, No Drawings

(56) References Cited

U.S. PATENT DOCUMENTS

| | | |
|---|---|---|
| 2004/0266668 A1 | 12/2004 | Nakajima et al. |
| 2005/0020503 A1 | 1/2005 | Llinas-Brunet et al. |
| 2005/0038240 A1 | 2/2005 | Connolly et al. |
| 2006/0257980 A1 | 11/2006 | Li |
| 2007/0027071 A1 | 2/2007 | Holloway et al. |
| 2010/0298210 A1 | 11/2010 | Liverton et al. |

FOREIGN PATENT DOCUMENTS

| | | |
|---|---|---|
| GB | 2430621 A | 4/2007 |
| WO | 97/41211 A1 | 11/1997 |
| WO | 98/22496 A2 | 5/1998 |
| WO | 98/46630 A1 | 10/1998 |
| WO | 99/07733 A2 | 2/1999 |
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |
| WO | 00/09543 A2 | 2/2000 |
| WO | 00/25780 A1 | 5/2000 |
| WO | 00/59929 A1 | 10/2000 |
| WO | 01/00622 A1 | 1/2001 |
| WO | 01/47883 A1 | 7/2001 |
| WO | 01/60379 A1 | 8/2001 |
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 2004/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | 2005/080399 A1 | 9/2005 |
| WO | 2006/008556 A1 | 1/2006 |
| WO | 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | 2006/046030 A1 | 5/2006 |
| WO | 2006/046039 A2 | 5/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/002924 A2 | 1/2008 |
| WO | 2008/051475 A2 | 5/2008 |
| WO | 2008/051477 A2 | 5/2008 |
| WO | 2008/051514 A2 | 5/2008 |
| WO | 2008/057028 A1 | 5/2008 |
| WO | 2008/057208 A2 | 5/2008 |
| WO | 2008/057209 A1 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

Youla S. Tsantrizos, The Design of a Potent Inhibitor of the Hepatitis C Virus NS3 Protease: BILN 2061—From the NMR Tube to the Clinic, 76 Biopolymers (Peptide Science) 309-323 (2004).

Han (Advances in Characterization of Pharmaceutical Hydrates. Trends in Bio/Pharmaceutical Industry, pp. 25-29. Mar. 2006).

Vippagunta et al (Adv Drug Deliv Rev 48:3-26, 2001).

Stella et al (Prodrugs: Challenges and Rewards, Part 1, 2007).

Youwei Yan et al., Complex of NS3 protease and NS4A peptide of BK strain hepatitis C virus: A 2.2 Angstrom resolution structure in a hexagonal crystal form, 7 Protein Science 837 (1998).

Brian W. Dymock et al., "Novel Approaches to the Treatment of Hepatitis C Virus Infection," 11 Antiviral Chemistry & Chemotherapy 79-96 (2000).

Hugo R. Rosen & David R. Gretch, "Hepatitis C virus: current understanding and prospects for future therapies," 5 Molec. Med. Today 393-99 (1999).

Darius Moradpour & Hubert E. Blum, "Current and evolving therapies for hepatitis C," 11 Euro. J. Gastroenterol. Hepatol. 1189-1202 (1999).

Ralf Bartenschlager, "Candidate Targets for Hepatitis C Virus-Specific Antiviral Therapy," 40(5-6) Intervirology 378-93 (1997).

Georg M. Lauer & Bruce D. Walker, "Hepatitis C Virus Infection," 345(1) N. Engl. J. Med. 41-52 (2001); correction: 345(19) N. Engl. J. Med. 1425-26 (2001).

Brain W. Dymock, "Emerging therapies for hepatitis C virus infection," 6 Emerging Drugs 13-42 (2001).

Charlene Crabb, Infectious Diseases. "Hard-Won Advances Spark Excitement about Hepatitis C," Science 506-507 (2001).

Rogers E. Harry-O'Kuru et al., "A Short, Flexible Route toward 2'-C-Branched Ribonucleosides," 62 J. Org. Chem. 1754-59 (1997).

Michael S. Wolfe & Rogers E. Harry-O'Kuru, "A Concise Synthesis of 2'-C-Methylribonucleosides," 36(42) Tetrahedron Letters 7611-14 (1995).

Scott J. Miller et al., "Application of Ring-Closing Metathesis to the Synthesis of Rigidified Amino Acids and Peptides," 118 J. Am. Chem. Soc. 9606-14 (1996).

Jason S. Kingsbury et al., "A Recyclable Ru-Based Metathesis Catalyst," 121 J. Am. Chem. Soc. 791-99 (1999).

Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).

(56) References Cited

OTHER PUBLICATIONS

Alois Furstner et al., "Total Synthesis and Structural Refinement of the Cyclic Tripyrrole Pigment Nonylprodigiosin," 64 J. Org. Chem. 8275-80 (1999).
Tina M. Trnka & Robert H. Grubbs, "The Development of L2X2R-CHR Olefin Metathesis Catalysts: An Organometallic Success Story," 34 Acc. Chem. Res. 18-29 (2001).
A. Srikrishna et al., "Enantiospecific Construction of the BC-ring System of Taxanes," 45 Tetrahedron Letters 2939-42 (2004).
Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-46 (2004).
Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).
Paola Conti et al., "Chemoenzymatic Synthesis of the Enantiomers of Desoxymuscarine," 9 Tetrahedron: Asymmetry 657-65 (1998).
Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).
D. Becker & N. Haddad, "Steric Effects in Intramolecular [2+2] Photocycloaddition of C=C Double Bonds to Cyclohexenones," 49(4) Tetrahedron 947-64 (1993).
Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).
Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).
Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).
Herbert O. House et al., "Cyclization of Unsaturated Hydroxylamine Derivatives," 41(5) J. Org. Chem. 855-63 (1976).
Theophil Eicher et al., "Bryophyte Constituents; 7: New Synthesis of (+)—Rosmarinic Acid and Related Compounds," Synthesis 755-62 (Jun. 1996).
Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).
Marc-Andre Poupart et al., "Solid-Phase Synthesis of Peptidomimetic Inhibitors for the Hepatitis C Virus NS3 Protease," 66(14) J. Org. Chem. 4743-51 (2001).
Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).
Anthony C. Allison & Elsie M. Eugui, "Immunosuppressive and other anti-rheumatic activities of mycophenolate mofetil," 44 Agents and Actions Supplements 165-88 (1993).
Joel Kirschbaum, "Amantadine," 12 Profiles of Drug Substances, Excipients and Related Methodology 1-36 (1983).

T. K. Chakaborty et al., "Alpha-Phenylglycinol as chiral auxilliary in diastereoselective Strecker synthesis of alpha-amino acids," 51(33) Tetrahedron 9179-90 (1995).
W. Clark Still et al., "Rapid Chromatographic Technique for Preparative Separations with Moderate Resolution," 43(14) J. Org. Chem. 2923-25 (1978).
Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).
Paul Aeberli et al., "Neuropharmacological investigation of N-benzylsulfamides," 10(4) J. Med. Chem. 636-42 (1967).
Nathalie Goudreau & Montse Llinas-Brunet, "The Therapeutic Potential of NS3 Protease Inhibitors in HCV Infection," 14(9) Expert Opinion 1129-44 (2005).
Volker Lohmann et al., "Selective Stimulation of Hepatitis C Virus and Pestivirus NS5B RNA Polymerase Activity by GTP," 274(16) J. Bio. Chem. 10807-15 (1999).
V. Lohmann et al., "Replication of Subgenomic Hepatitis C Virus RNAs in a Hepatoma Cell Line," 285 Science 110-13 (1999).
Kevin X. Chen et al. "Novel Potent Hepatitis C Virus NS3 Serine Protease Inhibitors Derived from Proline-Based Macrocycles," 49 J. Med. Chem. 995-1005 (2006).
Yuri Goldberg et al., "Highly regioselective bromination of 2,3-dimethylanisole with N-bromosuccinimide," 57 J. Org. Chem. 6374-76 (1992).
Manfred Schlosser et al., "8-Methoxyisoquinoline derivatives through ortho-selective metallation of 2-(3-methoxyphenyl)ethylamines," 32(17) Tetrahedron Letters 1965-66 (1991).
Angela Casini et al., "Carbonic Anhydrase inhibitors inhibition of cytosolic isozymes I and II with sulfamide derivatives," 13(5) Bioorg. Med. Chem. Lett. 837-40 (2003).
Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).
Duane E. Rudisill & J. K. Stille, "Palladium-catalyzed synthesis of 2-substituted indoles," 54(25) J. Org. Chem. 5856-66 (2002).
Makoto Satoh et al., "Palladium-Catalyzed Cross-Coupling Reaction of (1-Ethoxy-1-alken-2-yl)boranes with ortho-Functionalized Iodoarenes. A Novel and Convenient Synthesis of Benzo-Fused Heteroaromatic Compounds," Synthesis Communications 373-377 (Apr. 1987).
Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).
Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).
John A. McCauley et al., "Bismacrocyclic Inhibitors of Hepatitis C NS3/4A Protease," 47 Angew. Chem. Int. Ed. 9104-07 (2008).
Ashok Arasappan et al., "P2-P4 Macrocyclic inhibitors of hepatitis C virus NS3-4A serine protease," 16 Bioorganic & Medicinal Chemistry Letters 3960-65 (2006).

HCV NS3 PROTEASE INHIBITORS

FIELD OF THE INVENTION

The present invention relates to macrocyclic compounds that are useful as inhibitors of the hepatitis C virus (HCV) NS3 protease, the synthesis of such compounds, and the use of such compounds for treating HCV infection and/or reducing the likelihood or severity of symptoms of HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 3.9 million infected people in the United States alone, according to the U.S. Center for Disease Control, roughly five times the number of people infected with the human immunodeficiency virus (HIV). According to the World Health Organization, there are more than 170 million infected individuals worldwide, with at least 3 to 4 million people being infected each year. Once infected, about 20% of people clear the virus, but about 80% of those infected harbor HCV the rest of their lives. Ten to 20% of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The current state of the art in the treatment of HCV infection has been discussed in the following references: B. Dymock et al., "Novel approaches to the treatment of hepatitis C virus infection," 11 *Antiviral Chem. & Chemotherapy* 79-96 (2000); H. Rosen et al., "Hepatitis C virus: current understanding and prospects for future therapies," 5 *Molec. Med. Today* 393-399 (1999); D. Moradpour et al., "Current and evolving therapies for hepatitis C," 11 *Euro. J. Gastroenterol. Hepatol.* 1189-1202 (1999); R. Bartenschlager, "Candidate Targets for Hepatitis C Virus-Specific Antiviral Therapy," 40(5-6) *Intervirology* 378-393 (1997); G. M. Lauer & B. D. Walker, "Hepatitis C Virus Infection," 345 *N. Engl. J. Med.* 41-52 (2001); B. W. Dymock, "Emerging therapies for hepatitis C virus infection," 6 *Emerging Drugs* 13-42 (2001); and C. Crabb, "Hard-Won Advances Spark Excitement about Hepatitis C," *Science:* 506-507 (2001).

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein. Because it is responsible for an intramolecular cleavage at the NS3/4A site and for downstream intermolecular processing at the NS4A/4B, NS4B/5A and NS5A/5B junctions, the NS3 protease is considered a prime drug target. Previous research has identified classes of peptides, such as hexapeptides as well as tripeptides discussed in U.S. Patent Application Publications US2005/0020503, US2004/0229818, and US2004/00229776, showing degrees of activity in inhibiting the NS3 protease. The aim of the present invention is to provide further compounds which exhibit activity against the HCV NS3 protease.

SUMMARY OF THE INVENTION

The present invention relates to novel macrocyclic compounds of formula (I) and/or pharmaceutically acceptable salts or hydrates thereof. These compounds are useful in the inhibition of HCV (hepatitis C virus) NS3 (non-structural 3) protease, the prevention or treatment of one or more of the symptoms of HCV infection, either as compounds or their pharmaceutically acceptable salts or hydrates (when appropriate), or as pharmaceutical composition ingredients. As pharmaceutical composition ingredients, these compounds, salts and hydrates may be the primary active therapeutic agent, and, when appropriate, may be combined with other therapeutic agents including but not limited to other HCV antivirals, anti-infectives, immunomodulators, antibiotics or vaccines. More particularly, the present invention relates to a compound of formula (I) and/or a pharmaceutically acceptable salt or hydrate thereof:

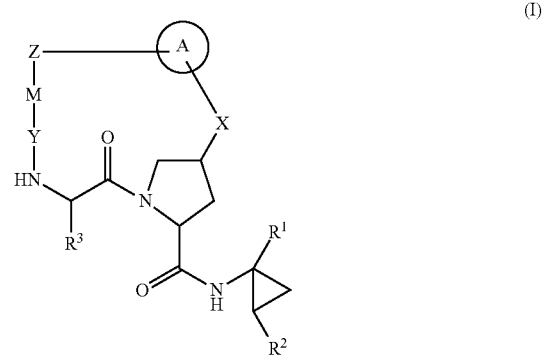

(I)

wherein:

Ⓐ is one or more rings selected from the group consisting of:
1) aryl rings,
2) $C_3$-$C_8$ cycloalkyl rings, and
3) heterocyclic rings in which the heterocyclic ring system attaches to Z and X at points that are two independently selected ring atoms that are either two a carbon ring atoms or one carbon ring atom and one nitrogen ring atom, and the heterocyclic ring system is selected from the group consisting of:
  a) 5- or 6-membered saturated or unsaturated monocyclic rings with 1, 2, or 3 heteroatom ring atoms independently selected from the group consisting of N, O or S,
  b) 8-, 9- or 10-membered saturated or unsaturated bicyclic rings with 1, 2, or 3 heteroatom ring atoms independently selected from the group consisting of N, O or S, and
  c) 11- to 15-membered saturated or unsaturated tricyclic rings with 1, 2, 3, or 4 heteroatom ring atoms independently selected from the group consisting of N, O or S, wherein Ⓐ is substituted with 0 to 4 independently selected substituents W, $R^5$ or oxo; wherein for stable heterocyclic rings containing S or N, the heterocyclic ring is unsubstituted at the S or N atom or is substituted at the S or N atom by oxo; wherein said W and $R^5$ substitutions are located on one or more ring atoms selected from C and N; and provided that the 10-membered unsaturated bicyclic ring is not quinoline, quinazoline or isoquinoline with the following modes of attachment

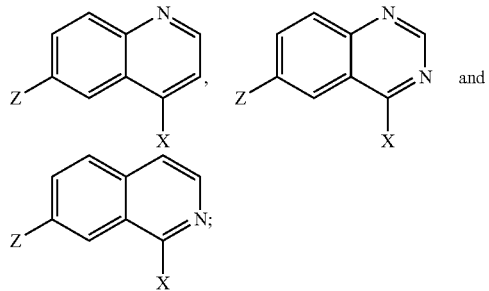

$R^1$ is selected from the group consisting of —$CO_2R^{10}$, —$CONR^{10}SO_2R^6$, —$CONR^{10}SO_2NR^8R^9$, tetrazolyl, —$CONHP(O)R^{11}R^{12}$, and —$P(O)R^{11}R^{12}$;

$R^2$ is selected from the group consisting of $C_1$-$C_6$ alkyl, $C_2$-$C_6$ alkenyl, and $C_3$-$C_8$ cycloalkyl, wherein said $R^2$ are substituted with 0 to 3 independently selected halogen atoms;

$R^3$ is selected from the group consisting of H, $C_1$-$C_8$ alkyl, $C_3$-$C_8$ cycloalkyl, $C_3$-$C_8$ cycloalkyl($C_1$-$C_8$)alkyl, phenyl($C_1$-$C_8$)alkyl, naphthyl($C_1$-$C_8$)alkyl, and Het groups, wherein when $R^3$ is not H, said $R^3$ is substituted with 0 to 3 substituents independently selected from the group consisting of halogen atoms, —$OR^{10}$, —$SR^{10}$, —$N(R^{10})_2$, —$N(C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —S(O)($C_1$-$C_6$ alkyl), —$NR^{10}SO_2R^6$, $SO_2N(R^6)_2$, —$NHCOOR^6$, —$NHCOR^6$, —$NHCONHR^6$, —$CO_2R^{10}$, —$C(O)R^{10}$, and —$CON(R^{10})_2$;

Het is selected from the group consisting of substituted and unsubstituted 5- and 6-membered saturated heterocyclic rings having 1 or 2 heteroatoms independently selected from N, O and S, wherein said substituted rings are substituted with 1 to 3 substituents independently selected from halogen atoms, —$OR^{10}$, —$SR^{10}$, —$N(R^{10})_2$, —$N(C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —S(O)($C_1$-$C_6$ alkyl), —$NR^{10}SO_2R^6$, $SO_2N(R^6)_2$, —$NHCOOR^6$, —$NHCOR^6$, —$NHCONHR^6$, —$CO_2R^{10}$, —$C(O)R^{10}$, and —$CON(R^{10})_2$;

$R^5$ is selected from the group consisting of H, halogen atoms, —OH, $C_1$-$C_6$ alkoxy, $C_1$-$C_6$ alkyl, —CN, —$CF_3$, —$OCF_3$, —C(O)OH, —C(O)$CH_3$, $SR^{10}$, —$SO_2(C_1$-$C_6$ alkyl), $C_3$-$C_8$ cycloalkyl, $C_3$-$C_8$ cycloalkoxy, $C_1$-$C_6$ haloalkyl, —$N(R^7)_2$, phenyl, naphthyl, —O-phenyl, —O-naphthyl, heteroaryl and heterocyclyl groups; wherein:

said $R^5$ heteroaryl is selected from the group consisting of 5- and 6-membered aromatic rings having 1, 2 or 3 heteroatoms independently selected from N, O and S, and said $R^5$ heteroaryl is attached through a ring atom selected from C or N, said $R^5$ heterocyclyl is selected from the group consisting of 5- to 7-membered saturated or unsaturated non-aromatic rings having 1, 2, 3 or 4 heteroatoms independently selected from N, O and S, and said $R^5$ heterocyclyl is attached through a ring atom selected from C or N, said $R^5$ heteroaryl, heterocyclyl, cycloalkyl, cycloalkoxy, alkyl and alkoxy groups are substituted with 0 to 4 substituents independently selected from the group consisting of halogen atoms, —$OR^{10}$, —$SR^{10}$, —$N(R^{10})_2$, —$N(C_1$-$C_6$ alkyl)O($C_1$-$C_6$ alkyl), $C_1$-$C_6$ alkyl, $C_1$-$C_6$ haloalkyl, halo($C_1$-$C_6$ alkoxy), —$NO_2$, —CN, —$CF_3$, —$SO_2(C_1$-$C_6$ alkyl), —S(O)($C_1$-$C_6$ alkyl), —$NR^{10}SO_2R^6$, $SO_2N(R^6)_2$, —$NHCOOR^6$, —$NHCOR^6$, —$NHCONHR^6$, —$CO_2R^{10}$, —$C(O)R^{10}$, and —$CON(R^{10})_2$, and 2 adjacent substituents of said $R^5$ heteroaryl, heterocyclyl, cycloalkyl, cycloalkoxy, alkyl and alkoxy groups may be taken together to form a 3-6-membered cyclic ring containing 0 to 3 heteroatoms independently selected from N, O and S;

$R^6$ is selected from the group consisting of $C_1$-$C_6$ alkyl, $C_3$-$C_6$ cycloalkyl, $C_3$-$C_6$ cycloalkyl($C_1$-$C_5$)alkyl, phenyl, naphthyl, phenyl($C_1$-$C_4$)alkyl, naphthyl($C_1$-$C_4$)alkyl, heteroaryl, heteroaryl($C_1$-$C_4$ alkyl), heterocyclyl, and heterocyclyl($C_1$-$C_8$ alkyl) groups, wherein said $R^6$ are substituted with 0 to 2 independently selected W substituents, each $R^6$ heteroaryl is independently selected from the group consisting of 5- and 6-membered aromatic rings having 1, 2 or 3 heteroatoms independently selected from N, O and S, and said $R^6$ heteroaryl is attached through a ring atom selected from C or N, and each $R^6$ heterocyclyl is independently selected from the group consisting of 5- to 7-membered saturated or unsaturated non-aromatic rings having 1, 2, 3 or 4 heteroatoms independently selected from N, O and S, and said $R^6$ heterocyclyl is attached through a ring atom selected from C or N;

Y is selected from the group consisting of —C(O)—, —$SO_2$—, —OC(O)—, —C(O)N(D)L- and -LN(D)C(O)—. and -LN(D)C(O)—, where D is selected from the group consisting of H, $C_1$-$C_6$ alkyl and $C_1$-$C_6$ alkenyl groups, L is selected from the group consisting of a direct bond, -G-($C_1$-$C_6$ alkylene)-, —($C_1$-$C_6$ alkylene)-G-, -G-($C_1$-$C_6$ alkenylene)-, and —($C_1$-$C_6$ alkenylene)-G-, groups, where said G is selected from the group consisting of a direct bond, —O—, —N— and —S—, said alkylene and alkenylene groups are substituted with 0 to 4 substituents E independently selected from the group consisting of $C_1$-$C_6$ alkyl and $C_1$-$C_6$ alkenyl groups, and said D and E may be taken together to form a 3- to 6-membered ring containing 0 to 3 heteroatoms selected from N, O and S;

Z is selected from the group consisting of —C(O)— and a direct bond;

M is selected from the group consisting of $C_1$-$C_{12}$ alkylenes and $C_2$-$C_{12}$ alkenylenes, wherein said M is substituted with 0 to 2 substituents F independently selected from the group consisting of $C_1$-$C_8$ alkyl, =$CH_2$, $C_3$-$C_8$ cycloalkyl ($C_1$-$C_8$ alkyl), and aryl($C_1$-$C_8$ alkyl), and 2 adjacent substituents F may be taken together to form a 3- to 6-membered ring containing 0 to 3 heteroatoms selected from the group consisting of N, O and S, and one or more adjacent substituents F may be taken together and/or with an adjacent D or E to form a 3- to 6-membered ring containing 0 to 3 heteroatoms independently selected from the group consisting of N, O and S;

X is selected from the group consisting of —O—, —$CH_2O$—, —NHC(O)O—, —$CH_2NHC(O)O$—, —C≡$CCH_2O$—, —C(O)O—, —$(CH_2)_3O$—, —OC(O)NH—, —$(CH_2)_2C(O)NH$—, —C(O)NH— and a direct bond;

each $R^7$ is independently selected from the group consisting of H, $C_1$-$C_6$ alkyl, $C_3$-$C_6$ cycloalkyl, $C_3$-$C_6$ cycloalkyl($C_1$-$C_5$)alkyl, phenyl, naphthyl, phenyl($C_1$-$C_4$)alkyl, naphthyl($C_1$-$C_4$)alkyl, heteroaryl, heteroaryl($C_1$-$C_4$ alkyl), heterocyclyl, and heterocyclyl($C_1$-$C_8$ alkyl) groups, wherein
  when $R^7$ is not H, said $R^7$ are substituted with 0 to 2 W substituents,
  each $R^7$ heteroaryl is independently selected from the group consisting of 5- and 6-membered aromatic rings having 1, 2 or 3 heteroatoms independently selected from N, O and S, and said $R^7$ heteroaryl is attached through a ring atom selected from C or N, and
  each $R^7$ heterocyclyl is independently selected from the group consisting of 5- to 7-membered saturated or unsaturated non-aromatic rings having 1, 2, 3 or 4 heteroatoms independently selected from N, O and S, and said $R^7$ heterocyclyl is attached through a ring atom selected from C or N, and
  said $R^7$ may be taken together with the atom to which it is attached and a second $R^7$ substituent to form a 4- to 7-membered heterocyclic ring;
  each W is independently selected from the group consisting of halogen atoms, —$OR^{10}$, $C_1$-$C_6$ alkyl, —CN, —$CF_3$, —$NO_2$, —$SR^{10}$, —$CO_2R^{10}$, —$CON(R^{10})_2$, —$C(O)R^{10}$, —$N(R^{10})C(O)R^{10}$, —$SO_2(C_1$-$C_6$ alkyl), —$S(O)(C_1$-$C_6$ alkyl), $C_3$-$C_8$ cycloalkyl, $C_3$-$C_8$ cycloalkoxy, $C_1$-$C_6$ haloalkyl, —$N(R^{10})_2$, —$N(C_1$-$C_6$ alkyl)$O(C_1$-$C_6$ alkyl), halo($C_1$-$C_6$ alkoxy), —$NR^{10}SO_2R^{10}$, —$SO_2N(R^{10})_2$, —$NHCOOR^{10}$, —$NHCONHR^{10}$, phenyl, naphthyl, heteroaryl and heterocyclyl groups; wherein
    said W heteroaryl is selected from the group consisting of 5- and 6-membered aromatic rings having 1, 2 or 3 heteroatoms independently selected from N, O and S, and said W heteroaryl is attached through a ring atom selected from C or N,
    said W heterocyclyl is selected from the group consisting of 5- to 7-membered saturated or unsaturated non-aromatic rings having 1, 2, 3 or 4 heteroatoms independently selected from N, O and S, and said W heterocyclyl is attached through a ring atom selected from C or N;
  $R^8$ is selected from the group consisting of $C_1$-$C_8$ alkyl, $C_3$-$C_8$ cycloalkyl, $C_3$-$C_8$ cycloalkyl($C_1$-$C_8$ alkyl), phenyl, naphthyl, phenyl($C_1$-$C_4$)alkyl, naphthyl($C_1$-$C_4$)alkyl, heteroaryl, heterocyclic, heteroaryl($C_1$-$C_4$ alkyl), and heterocyclyl($C_1$-$C_8$ alkyl) groups, wherein
    said $R^8$ are substituted with 0 to 4 substituents selected from the group consisting of phenyl, naphthyl, $C_3$-$C_8$ cycloalkyl, heteroaryl, heterocyclyl, $C_1$-$C_6$ alkyl, halo($C_1$-$C_6$ alkoxy), halogen atoms, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, —$C(O)R^{10}$, $C_1$-$C_6$ haloalkyl, —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, and —$C(O)N(R^{10})_2$,
    each $R^8$ heteroaryl is independently selected from the group consisting of 5- and 6-membered aromatic rings having 1, 2 or 3 heteroatoms independently selected from N, O and S, and said $R^8$ heteroaryl is attached through a ring atom selected from C or N,
    each $R^8$ heterocyclyl is independently selected from the group consisting of 5- to 7-membered saturated or unsaturated non-aromatic rings having 1, 2, 3 or 4 heteroatoms independently selected from N, O and S, and said $R^8$ heterocyclyl is attached through a ring atom selected from C or N, and
    2 adjacent substituents of said $R^8$ may be taken together to form a 3- to 6-membered ring containing 0 to 3 heteroatoms independently selected from the group consisting of N, O and S;
  $R^9$ is selected from the group consisting of $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, $C_3$-$C_8$ cycloalkoxy, phenyl, naphthyl, phenyl($C_1$-$C_4$) alkyl, naphthyl($C_1$-$C_4$)alkyl, heteroaryl, heterocyclyl, heteroaryl($C_1$-$C_4$ alkyl), or heterocyclyl($C_1$-$C_8$ alkyl) groups, wherein
    said $R^9$ are substituted with 0 to 4 substituents selected from the group consisting of phenyl, naphthyl, $C_3$-$C_8$ cycloalkyl, heteroaryl, heterocyclyl, $C_1$-$C_6$ alkyl, halo($C_1$-$C_6$ alkoxy), halogen atoms, —$OR^{10}$, —$SR^{10}$, —$N(R^{10})_2$, —$N(C_1$-$C_6$ alkyl)$O(C_1$-$C_6$ alkyl), $C_1$-$C_6$ alkyl, —$C(O)R^1$, $C_1$-$C_6$ haloalkyl, —$NO_2$, —CN, —$CF_3$, —$SO_2(C_1$-$C_6$ alkyl), —$S(O)(C_1$-$C_6$ alkyl), —$NR^{10}SO_2R^6$, —$SO_2N(R^6)_2$, —$NHCOOR^6$, —$NHCOR^6$, —$NHCONHR^6$, —$CO_2R^{10}$, and —$C(O)N(R^{10})_2$,
    each $R^9$ heteroaryl is independently selected from the group consisting of 5- and 6-membered aromatic rings having 1, 2 or 3 heteroatoms independently selected from N, O and S, and said $R^9$ heteroaryl is attached through a ring atom selected from C or N,
    each $R^9$ heterocyclyl is independently selected from the group consisting of 5- to 7-membered saturated or unsaturated non-aromatic rings having 1, 2, 3 or 4 heteroatoms independently selected from N, O and S, and said $R^9$ heterocyclyl is attached through a ring atom selected from C or N, and
    2 adjacent substituents of said $R^9$ may be taken together to form a 3- to 6-membered ring containing 0 to 3 heteroatoms independently selected from the group consisting of N, O and S, and
  $R^8$ and $R^9$ may be taken together, with the N to which they are attached, to form a 4- to 8-membered monocyclic ring containing 0 to 2 additional heteroatoms independently selected from N, O and S;
  each $R^{10}$ is independently selected from the group consisting of H and $C_1$-$C_6$ alkyl;
  each $R^{11}$ is independently selected from the group consisting of $C_1$-$C_6$ alkyl, $C_1$-$C_4$ alkenyl, —$OR^{13}$, —$N(R^{10})$—V—$CO_2R^{10}$, —O—V—$CO_2R^{10}$, —S—V—$CO_2R^{10}$, —$N(R^{10})(R^{13})$, —$R^{14}$, and —$N(R^{10})SO_2R^6$;
  each $R^{12}$ is independently selected from the group consisting of —$OR^{13}$, —$N(R^{10})$—V—$CO_2R^{10}$, —O—V—$CO_2R^{10}$, —S—V—$CO_2R^{10}$, and —$N(R^{10})(R^{13})$;
  $R^{11}$ and $R^{12}$ may be taken together, with the phosphorus atom to which they are attached, to form a 5- to 7-membered monocyclic ring;
  each V is independently selected from the group consisting of —CH($R^{15}$)— and —($C_1$-$C_4$ alkylene)-CH($R^{15}$)—;
  each $R^{13}$ is independently selected from the group consisting of H, $C_1$-$C_6$ alkyl, $C_2$-$C_6$ alkenyl, $C_3$-$C_8$ cycloalkyl, aryl, heteroaryl, and heterocyclyl groups, wherein
    when $R^{13}$ is not H, said $R^{13}$ is substituted with 0 to 2 substituents independently selected from the group consisting of phenyl, naphthyl, phenyl($C_1$-$C_4$ alkyl), naphthyl($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halogen atoms, —$OC(O)OR^6$, —$OC(O)R^6$, —$OR^{10}$, —$SR^{10}$, —$N(R^{10})_2$, —$C(O)R^{10}$, —$NO_2$, —CN, —$CF_3$, —$SO_2(C_1$-$C_6$ alkyl), —$S(O)(C_1$-$C_6$ alkyl), —NR¹⁰SO₂R⁶, —SO₂N(R⁶)₂, —NHCOOR⁶, —NHCOR⁶, —NHCONHR⁶, —CO₂R¹⁰, and —C(O)N(R¹⁰)₂, each R¹³ heteroaryl is independently selected from the group consisting of 5- and 6-membered aromatic rings having 1, 2 or 3 heteroatoms independently selected from N, O and S, and said R¹³ heteroaryl is attached through a ring atom selected from C or N, each R¹³ heterocyclyl is independently selected from the group consisting of 5- to 7-membered saturated or unsaturated non-aromatic rings having 1, 2, 3 or 4 heteroatoms independently selected from N, O and S, and said R¹³ heterocyclyl is attached through a ring atom selected from C or N, and 2 adjacent substituents of said R¹³ may be taken together to form a 3- to 6-membered ring containing 0 to 3 heteroatoms independently selected from the group consisting of N, O and S;

R¹⁴ is selected from the group consisting of $C_1$-$C_6$ alkyl, $C_2$-$C_6$ alkenyl, phenyl, naphthyl and heteroaryl, wherein each R¹⁴ heteroaryl is independently selected from the group consisting of 5- and 6-membered aromatic rings having 1, 2 or 3 heteroatoms independently selected from N, O and S, and said R¹⁴ heteroaryl is attached through a ring atom selected from C or N, and said R¹⁴ phenyl, naphthyl or heteroaryl may be substituted with 0 to 2 substituents independently selected from the group consisting of $C_1$-$C_6$ alkyl, halogen atoms, —OC(O)OR⁶, —OC(O)R⁶, —OR¹⁰, —SR¹⁰, —N(R¹⁰)₂, —C(O)R¹⁰, —NO₂, —CN, —CF₃, —SO₂($C_1$-$C_6$ alkyl), —S(O)($C_1$-$C_6$ alkyl), —NR¹⁰SO₂R⁶, —SO₂N(R⁶)₂, —NHCOOR⁶, —NHCOR⁶, —NHCONHR⁶, —CO₂R¹⁰, and —C(O)N(R¹⁰)₂; and each R¹⁵ is independently selected from the group consisting of $C_1$-$C_6$ alkyl, $C_2$-$C_6$ alkenyl, $C_3$-$C_8$ cycloalkyl, phenyl, naphthyl, heteroaryl, and heterocyclyl groups, wherein said R¹⁵ are substituted with 0 to 2 substituents independently selected from the group consisting of $C_1$-$C_6$ alkyl, halogen atoms, —OC(O)OR⁶, —OC(O)R⁶, —OR¹⁰, —SR¹⁰, —N(R¹⁰)₂, —C(O)R¹⁰, —NO₂, —CN, —CF₃, —SO₂($C_1$-$C_6$ alkyl), —S(O)($C_1$-$C_6$ alkyl), —NR¹⁰SO₂R⁶, —SO₂N(R⁶)₂, —NHCOOR⁶, —NHCOR⁶, —NHCONHR⁶, —CO₂R¹⁰, and —C(O)N(R¹⁰)₂, each R¹⁵ heteroaryl is independently selected from the group consisting of 5- and 6-membered aromatic rings having 1, 2 or 3 heteroatoms independently selected from N, O and S, and said R¹⁵ heteroaryl is attached through a ring atom selected from C or N, each R¹⁵ heterocyclyl is independently selected from the group consisting of 5- to 7-membered saturated or unsaturated non-aromatic rings having 1, 2, 3 or 4 heteroatoms independently selected from N, O and S, and said R¹⁵ heterocyclyl is attached through a ring atom selected from C or N, and 2 adjacent substituents of said R¹⁵ are optionally taken together to form a 3- to 6-membered ring containing 0 to 3 heteroatoms independently selected from the group consisting of N, O and S.

The present invention also includes pharmaceutical compositions containing a compound of the present invention and methods of preparing such pharmaceutical compositions.

The present invention further includes methods of treating or reducing the likelihood or severity of one or more symptoms of HCV infection.

Other embodiments, aspects and features of the present invention are either further described in or will be apparent from the ensuing description, examples and appended claims.

DETAILED DESCRIPTION OF THE INVENTION

The present invention includes compounds of formula (I) above, and pharmaceutically acceptable salts and/or hydrates thereof. These compounds and their pharmaceutically acceptable salts and/or hydrates are HCV protease inhibitors (e.g., HCV NS3 protease inhibitors).

In one embodiment of the invention, Ⓐ is selected from the group consisting of
1) aryl rings,
2) cyclohexyl rings, and
3) heterocyclic rings in which the heterocyclic ring system attaches to Z and X at points that are two independently selected ring atoms that are either two a carbon ring atoms or one carbon ring atom and one nitrogen ring atom, and the heterocyclic ring system is selected from the group consisting of:
   a) 5- or 6-membered saturated or unsaturated monocyclic rings containing 1, 2, or 3 nitrogen atoms, and
   b) 8-, 9- or 10-membered saturated or unsaturated bicyclic rings containing 1 or 2 nitrogen atoms, wherein said Ⓐ is substituted with 0 to 4 independently selected substituents W, R⁵ or oxo; wherein for stable heterocyclic rings containing S or N, the heterocyclic ring is unsubstituted at the S or N atom or is substituted at the S or N atom by oxo; wherein said W and R⁵ substitutions are located on one or more ring atoms selected from C and N; and provided that the 10-membered unsaturated bicyclic ring is not quinoline, quinazoline or isoquinoline.

In a preferred group of this embodiment, Ⓐ is unsubstituted or mono-substituted with a moiety selected from the group consisting of —Br, —Cl, —CN, phenyl, —O-phenyl, —OCF₃, —OCH₃, —C(O)OH, —CH₃ and —C(O)CH₃.

In another embodiment of the invention, Ⓐ is selected from the group of rings consisting of:

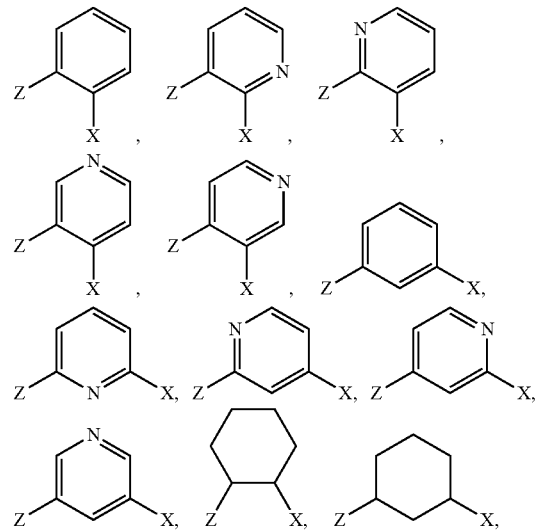

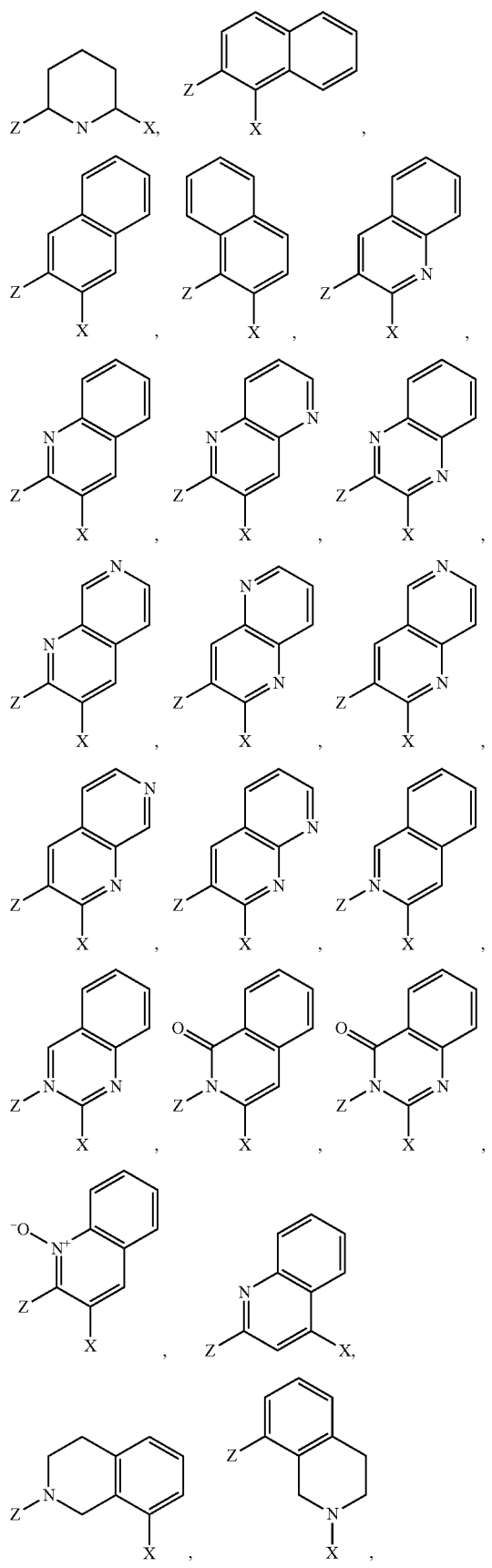
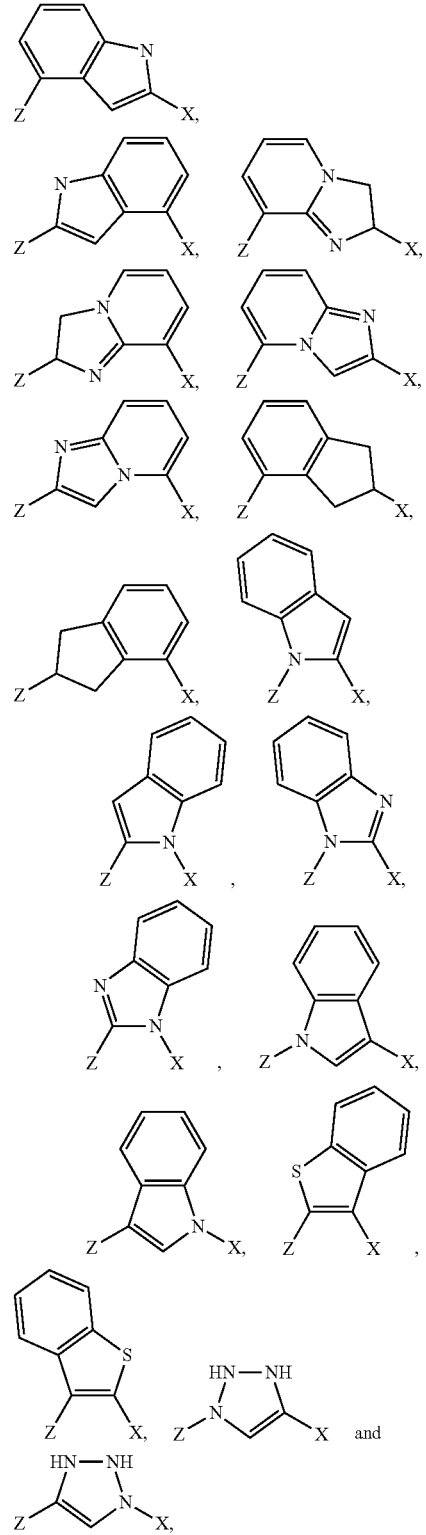
which may be substituted as indicated above. In a preferred group of this embodiment of the invention, $R^5$ is independently selected from the group consisting of H, —Br, —Cl, —CN, phenyl, —O-phenyl, —OCF$_3$, —OCH$_3$, —OH, $C_1$-$C_6$ alkoxy, $C_1$-$C_6$ alkyl, —CF$_3$, —C(O)OH, and —C(O)CH$_3$.

In another embodiment of the invention, $R^1$ is $-CO_2R^{10}$ or $-CONR^{10}SO_2R^6$. In a preferred group of this embodiment, $R^1$ is $-C(O)OH$ or $-C(O)NHSO_2$cyclopropyl.

In another embodiment of the invention, $R^2$ is $C_1$-$C_6$ alkyl or $C_2$-$C_6$ alkenyl. In a preferred group of this embodiment, $R^2$ is $-CH=CH_2$, $-CH_2CH_3$, or $-CH_2CH=CH_2$.

In another embodiment of the invention, $R^3$ is H, $C_1$-$C_8$ alkyl or $C_3$-$C_8$ cycloalkyl. In a preferred group of this embodiment, $R^3$ is H, $-C(CH_3)_3$, $-(CH_2)_3CH_3$, cyclohexyl, or $-CH(CH_3)_2$.

In another embodiment of the invention, M is $C_1$-$C_{12}$ alkylene or $C_2$-$C_{12}$ alkenylene, wherein said M is substituted with 0 to 2 substituents F selected from the group consisting of $C_1$-$C_8$ alkyl, and $=CH_2$. In a preferred group of this embodiment, M is selected from the group consisting of $-CH=CH(CH_2)_5$, $-(CH_2)_7-$, $-CH_2CH=CH(CH_2)_4-$, $-(CH_2)_6-$, $-CH=CH(CH_2)_4-$, $-CH=CH(CH_2)_3C(CH_3)_2CH_2-$, $-CH=CH(CH_2)_3-$, $-(CH_2)_5-$, $-CH=CH(CH_2)_3-$, $-(CH_2)_4-$, $-(CH_2)_3-$, $-CH=CH(CH_2)_2C(CH_3)_2CH_2-$, $-(CH_2)_4C(CH_3)_2CH_2-$, $-C(=CH_2)(CH_2)_5-$, $-C(=CH_2)(CH_2)_3-$, $-CH_2CH=CH(CH_2)_3-$. In some embodiments, M is selected from the group consisting of

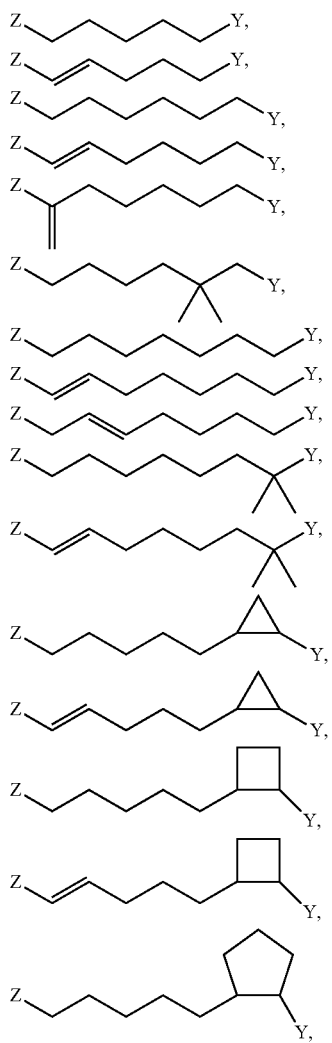

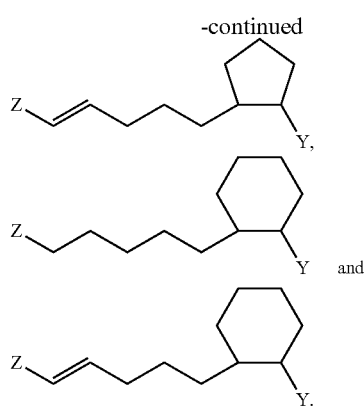

In another embodiment of the invention, Y is selected from $-C(O)N(D)L-$ and $-LN(D)C(O)-$.

In still another embodiment, one or more substituents F are taken together and/or with one or more substituents chosen from substituents D and E to form a 3- to 6-membered ring containing 0 to 3 heteroatoms selected from the group consisting of N, O and S. That is, two adjacent substituents F may be taken together to form a 3- to 6-membered ring containing 0 to 3 heteroatoms independently selected from the group consisting of N, O and S, or one substituent F may be taken together with an adjacent D or E to form a 3- to 6-membered ring containing 0 to 3 heteroatoms independently selected from the group consisting of N, O and S.

In another embodiment of the invention, the compound of the invention is selected from the exemplary species depicted in Examples 1 through 109 shown below.

Other embodiments of the present invention include the following:

(a) A pharmaceutical composition comprising an effective amount of a compound of formula (I) and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination which is (i) a compound of formula (I) and (ii) a second therapeutic agent selected from the group consisting of HCV antiviral agents, immunomodulators, and anti-infective agents; wherein the compound of formula (I) and the second therapeutic agent are each employed in an amount that renders the combination effective for inhibiting HCV NS3 protease, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV NS3 protease in a subject in need thereof which comprises administering to the subject an effective amount of a compound of formula (I).

(g) A method of treating HCV infection and/or reducing the likelihood or severity of symptoms of HCV infection in a subject in need thereof which comprises administering to the subject an effective amount of a compound of formula (I).

(h) The method of (g), wherein the compound of formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV NS3 protease in a subject in need thereof which comprises administering to the subject the pharmaceutical composition of (a), (b), or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b), or (c) or the combination of (d) or (e).

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (k) above are understood to include all embodiments of the compounds, including such embodiments as result from combinations of embodiments.

The present invention also includes a compound of the present invention for use (i) in, (ii) as a medicament for, or (iii) in the preparation of a medicament for: (a) inhibiting HCV NS3 protease, or (b) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

As used herein, all ranges are inclusive, and all sub-ranges are included within such ranges, although not necessarily explicitly set forth. In addition, the term "or," as used herein, denotes alternatives that may, where appropriate, be combined; that is, the term "or" includes each listed alternative separately as well as their combination.

As used herein, the term "alkyl" refers to any linear or branched chain alkyl group having a number of carbon atoms in the specified range. Thus, for example, "$C_1$-6 alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl. Alkyl groups may be substituted as indicated.

The term "halogenated" refers to a group or molecule in which a hydrogen atom has been replaced by a halogen. Similarly, the term "haloalkyl" refers to a halogenated alkyl group. The term "halogen" (or "halo") refers to atoms of fluorine, chlorine, bromine and iodine (alternatively referred to as fluoro, chloro, bromo, and iodo).

The term "alkoxy" refers to an "alkyl-O—" group. Alkoxy groups may be substituted as indicated.

The term "alkylene" refers to any linear or branched chain alkylene group (or alternatively "alkanediyl") having a number of carbon atoms in the specified range. Thus, for example, "—$C_1$-6 alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—. Alkylene groups may be substituted as indicated.

The term "cycloalkyl" refers to any cyclic ring of an alkane or alkene having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl. The term "cycloalkoxy" refers to a "cycloalkyl-O—" group. Cycloalkyl groups may be substituted as indicated.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. Carbocycle groups may be substituted as indicated, for example with $C_{1-6}$ alkyl, $C_{1-6}$ alkenyl, $C_{1-6}$ alkynyl, aryl, halogen, —$NH_2$ or —OH. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which both rings are saturated is a saturated bicyclic ring system. Saturated carbocyclic rings are also referred to as cycloalkyl rings, e.g., cyclopropyl, cyclobutyl, etc. A fused bicyclic carbocycle in which one or both rings are unsaturated is an unsaturated bicyclic ring system. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include

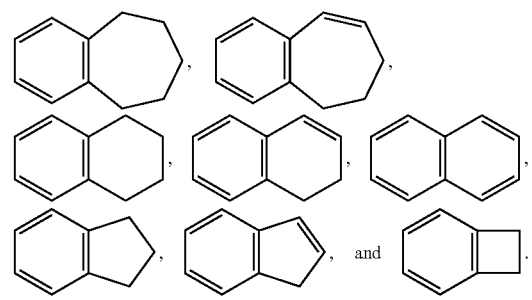

Depicted ring systems include, where appropriate, an indication of the variable to which a particular ring atom is attached. For example, the indole structure

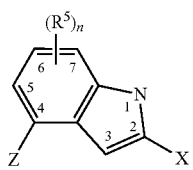

shows ring atom 2 is directly attached to variable X and ring atom 4 is directly attached to variable Z. Variable $R^5$ is shown as a floating variable which can be attached to any ring atom, provided that such attachment results in formation of a stable ring.

The term "aryl" refers to aromatic mono- and polycarbocyclic ring systems, also referred to as "arenes," wherein the individual carbocyclic rings in the polyring systems are fused or attached to each other via a single bond. Suitable aryl groups include phenyl, naphthyl, and biphenylenyl. Aryl groups may be substituted as indicated.

Unless indicated otherwise, the term "heterocycle" (and variations thereof such as "heterocyclic" or "heterocyclyl") broadly refers to (i) a stable 4- to 8-membered, saturated or unsaturated monocyclic ring, (ii) a stable 7- to 12-membered bicyclic ring system, or (iii) a stable 11- to 15-membered tricyclic ring system, wherein each ring in (ii) and (iii) is independent of, or fused to, the other ring or rings and each ring is saturated or unsaturated, and the monocyclic ring, bicyclic ring system or tricyclic ring system contains one or more heteroatoms (e.g., from 1 to 6 heteroatoms, or from 1 to 4 heteroatoms) independently selected from N, O and S and a balance of carbon atoms (the monocyclic ring typically contains at least one carbon atom and the bicyclic and tricyclic ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Heterocycle groups may be substituted as indicated, and unless otherwise specified, the substituents may be attached to any atom in the ring, whether a heteroatom or a carbon atom, provided that a stable chemical structure results.

Saturated heterocyclics form a subset of the heterocycles. Unless expressly stated to the contrary, the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring, a stable 7- to 12-membered bicyclic ring system, or a stable 11- to 15-membered tricyclic ring system, which consists of carbon atoms and one or more heteroatoms independently selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Unsaturated heterocyclics form another subset of the heterocycles. Unless expressly stated to the contrary, the term "unsaturated heterocyclic" generally refers to a heterocycle as defined above in which the entire ring system (whether mono- or poly-cyclic) is not saturated, i.e., such rings are either unsaturated or partially unsaturated. Unless expressly stated to the contrary, the term "heteroaromatic ring" refers a stable 5- or 6-membered monocyclic aromatic ring, a stable 7- to 12-membered bicyclic ring system, or a stable 11- to 15-membered tricyclic ring system, which consists of carbon atoms and one or more heteroatoms selected from N, O and S. In the case of substituted heteraromatic rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

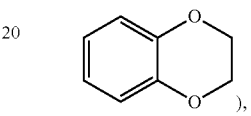), imidazo(2,1-b)(1,3)thiazole, (i.e.,

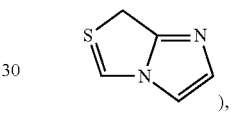), and benzo-1,3-dioxolyl (i.e.,

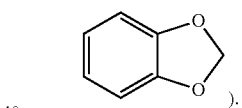).

In certain contexts herein,

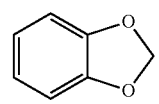

is alternatively referred to as phenyl having as a substituent methylenedioxy attached to two adjacent carbon atoms.

Unless otherwise specifically noted as only "unsubstituted" or only "substituted", alkyl, cycloalkyl, aryl and heterocycle groups are unsubstituted or substituted. Preferably, the substituents are selected from the group which includes, but is not limited to, halo, $C_1$-$C_{20}$ alkyl, —$CF_3$, —$NH_2$, —$N(C_1$-$C_6$ alkyl$)_2$, —$NO_2$, oxo, —CN, —$N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

When any variable (e.g., $R^7$ and $R^{10}$) occurs more than one time in any constituent or in formula (I) or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers. For the purposes of the present invention a reference to a compound of formula (I) is a reference to the compound per se, or to any one of its tautomers per se, or to mixtures of two or more tautomers.

The compounds of the present inventions are useful in the inhibition of HCV protease (e.g., HCV NS3 protease) and the treatment of HCV infection and/or reduction of the likelihood or severity of symptoms of HCV infection. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus, the compounds of this invention may be commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt (or hydrate) and other agents.

As used herein, the term "prodrug" is intended to encompass an inactive drug form or compound that is converted into an active drug form or compound by the action of enzymes, chemicals or metabolic processes in the body of an individual to whom it is administered.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HCV NS3 protease and treating HCV infection and/or reducing the likelihood or severity of symptoms of HCV infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, $18^{th}$ edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention also relates to a method of inhibiting HCV NS3 protease, inhibiting HCV replication, treating HCV infection and/or reducing the likelihood or severity of symptoms of HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, R7025 (an enhanced interferon (Roche)), interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), pegylated interferon-α2a (Pegasys™), interferon-α2b (such as Intron-A interferon available from Schering Corp., Kenilworth, N.J.), pegylated interferon-α2b (PegIntron™), a recombinant consensus interferon (such as interferon alphacon-1), albuferon (interferon-α bound to human serum albumin (Human Genome Sciences)), and a purified interferon-α product. Amgen's recombinant consensus interferon has the brand name Infergen®. Levovirin is the L-enantiomer of ribavirin which has shown immunomodulatory activity similar to ribavirin. Viramidine represents an analog of ribavirin disclosed in International Patent Application Publication WO 01/60379. In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in International Patent Application Publications WO 98/22496, WO 98/46630, WO 99/07733, WO 99/07734, WO 99/38888, WO 99/50230, WO 99/64442, WO 00/09543, WO 00/59929, WO 02/48116 and WO 02/48172, British Patent No. GB 2 337 262, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in International Patent Application Publications WO 97/41211 and WO 01/00622; another IMPDH inhibitor, such as that disclosed in WO 00/25780; or mycophenolate mofetil. See A. C. Allison and E. M. Eugui, 44 (Suppl.) *Agents Action* 165 (1993).

For the treatment of HCV infection, the compounds of the present invention may also be administered in combination with the antiviral agent amantadine (1-aminoadamantane). For a comprehensive description of this agent, see J. Kirschbaum, 12 *Anal. Profiles Drug Subs*. 1-36 (1983).

For the treatment of HCV infection, the compounds of the present invention may also be administered in combination with the antiviral agent polymerase inhibitor R7128 (Roche).

The compounds of the present invention may also be combined for the treatment of HCV infection with antiviral 2'-C-branched ribonucleosides disclosed in R. E. Harry-O'Kuru et al., 62 *J. Org. Chem*. 1754-59 (1997); M. S. Wolfe et al., 36 *Tet. Lett*. 7611-14 (1995); U.S. Pat. No. 3,480,613; and International Patent Application Publications WO 01/90121, WO 01/92282, WO 02/32920, WO 04/002999, WO 04/003000 and WO 04/002422; the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in International Patent Application Publications WO 02/51425, assigned to Mitsubishi Pharma Corp.; WO 01/79246, WO 02/32920, WO 02/48165 and WO2005/003147 (including R1656, (2'R)-2'-deoxy-2'-fluoro-2'-C-methylcytidine, shown as compounds 3-6 on page 77); WO 01/68663; WO 99/43691; WO 02/18404 and WO2006/021341, and U.S. Patent Application Publication US2005/0038240, including 4'-azido nucleosides such as R1626, 4'-azidocytidine; U.S. Patent Application Publications US2002/0019363, US2003/0236216, US2004/0006007 and US2004/0063658; and International Patent Application Publications WO 02/100415, WO 03/026589, WO 03/026675, WO 03/093290, WO 04/011478, WO 04/013300 and WO 04/028481; the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in International Patent Application Publications WO 02/057287, WO 02/057425, WO 03/068244, WO 2004/000858, WO 04/003138 and WO 2004/007512; U.S. Pat. No. 6,777,392 and U.S. Patent Application Publication US2004/0067901; the content of each is incorporated herein by reference in its entirety. Other such HCV polymerase inhibitors include, but are not limited to, valopicitabine (NM-283; Idenix) and 2'-F-2'-beta-methylcytidine (see also WO 2005/003147).

In one embodiment, nucleoside HCV NS5B polymerase inhibitors that are used in combination with the present HCV NS3 protease inhibitors are selected from the following compounds: 4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C, 2-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C, 2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as those disclosed in International Patent Application Publications WO 01/77091; WO 01/47883; WO 02/04425; WO 02/06246; WO 02/20497; WO 2005/016927 (in particular JTK003); the content of each is incorporated herein by reference in its entirety; and HCV-796 (Viropharma Inc.).

In one embodiment, non-nucleoside HCV NS5B polymerase inhibitors that are used in combination with the present HCV NS3 protease inhibitors are selected from the following compounds: 14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis (trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-a]

[2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

The HCV NS3 protease inhibitory activity of the present compounds may be tested using assays known in the art. One such assay is HCV NS3 protease time-resolved fluorescence (TRF) assay as described below and in International Patent Application Publication WO2006/102087. Other examples of such assays are described in e.g., International Patent Application Publication WO2005/046712. HCV NS3 protease inhibitors, such as those described herein have a Ki less than 50 μM, such as less than 10 μM, and less than 100 nM. Ki is determined by an NS3 protease assay. The assay is performed in a final volume of 100 μl in assay buffer containing 50 mM HEPES, pH 7.5, 150 mM NaCl, 15% glycerol, 0.15% Triton X-100, 10 mM DTT, and 0.1% PEG 8000. NS3 protease is pre-incubated with various concentrations of inhibitors in DMSO for 30 minutes. The reaction is initiated by adding the TRF peptide substrate (final concentration 100 nM). NS3 mediated hydrolysis of the substrate is quenched after 1 hour at room temperature with 100 μl of 500 mM MES, pH 5.5. Product fluorescence is detected using either a VICTOR V2 or Fusion fluorophotometer (Perkin Elmer Life and Analytical Sciences) with excitation at 340 nm and emission at 615 nm with a 400 μs delay. Testing concentrations of different enzyme forms are selected to result in a signal to background ratio (S/B) of 10-30. $IC_{50}$ values are derived using a standard four-parameter fit to the data. Ki values are derived from $IC_{50}$ values using the following formula, $$IC_{50}=K_i(1+[S]/K_M), \quad \text{Eqn (1),}$$

where [S] is the concentration of substrate peptide in the reaction and $K_M$ is the Michaelis constant. See P. Gallinari et al., 38 Biochem. 5620-32(1999); P. Gallinari et al., 72 J. Virol. 6758-69 (1998); M. Taliani et al., 240 Anal. Biochem. 60-67 (1996).

The present invention also includes processes for making compounds of formula (I). The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice.

Olefin metathesis catalysts include the following Ruthenium based species: F. Miller et al., 118 J. Am. Chem. Soc. 9606 (1996); G. Kingsbury et al., 121 J. Am. Chem. Soc. 791 (1999); H. Scholl et al., 1 Org. Lett. 953 (1999); U.S. Patent Application Publication US2002/0107138; K. Furstner et al., 64 J. Org. Chem. 8275 (1999). The utility of these catalysts in ring closing metathesis is well known in the literature (e.g. Trnka and Grubbs, 34 Acc. Chem. Res. 18 (2001).

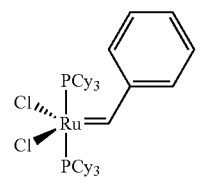

F

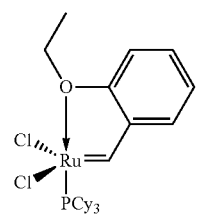

G

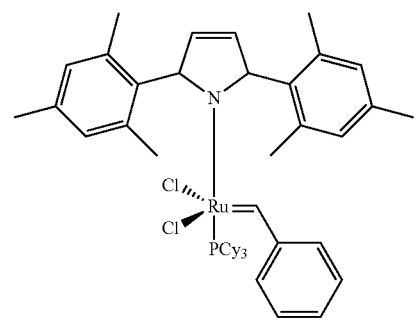

H

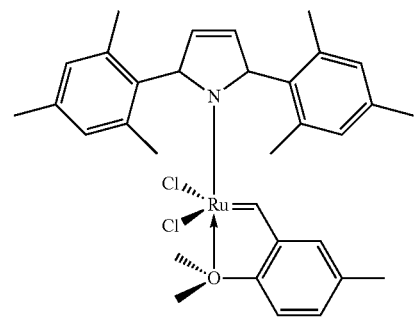

J (Zhan catalyst 1A, Zannan Pharma Ltd.)

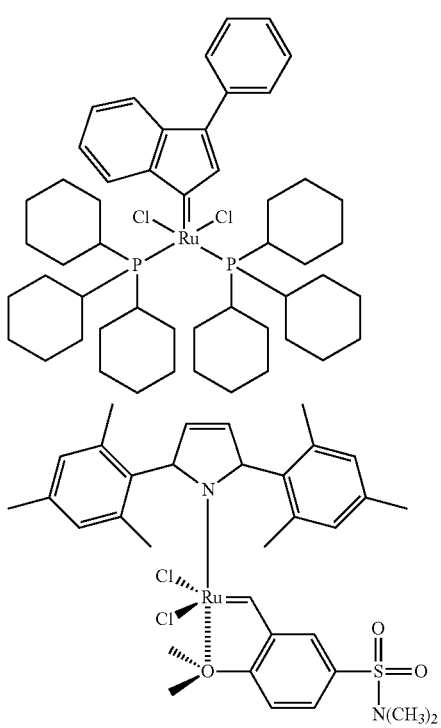

Zhan ruthenium metathesis catalyst RC-303
(Zhan catalyst 1B, RC-303,
Zannan Pharma Ltd.)

The following examples serve only to illustrate the invention and its practice. The examples are not to be construed as limitations on the scope or spirit of the invention.

LIST OF ABBREVIATIONS

BOC (also Boc) t-Butyloxycarbonyl
B(OMe)$_3$ Trimethyl borate
BOP Benzotriazole-1-yl-oxy-tris-(dimethylamino)-phosphonium hexafluorophosphate
Brosyl chloride 4-Bromophenyl sulfonylchloride
tBuOH t-Butanol
BuLi Butyllithium
CAN Ceric ammonium nitrate
CDCl$_3$ Deuterio-trichloromethane
CDI N,N'-Carbonyl diimidazole
CH$_3$CN Acetonitrile
mCPBA m-Chloroperbenzoic acid
Cs$_2$CO$_3$ Cesium carbonate
CuI Copper iodide
Cu(I)Br.SMe$_2$ Copper (I) bromide dimethyl sulfide complex
DABCO 1,4-diazabicyclo[2.2.2]octane
DBA (also dba) Dibenzylidene acetone
DBU 1,8-Diazabicyclo[5.4.0]undec-7-ene
DCC Dicyclohexylcarbodiimide
DCE Dichloroethane
DCM Dichloromethane
DEAD Diethyl azodicarboxylate
DIAD Diisopropyl azodicarboxylate
DIEA Diethylamine
DIPA Diethylpropylamine
DIPEA Diisopropylethylamine
DMAP 4-Dimethylamino pyridine
DMF Dimethylformamide
DMSO Dimethyl Sulfoxide
DPPF (also dppf) 1,1'-bid(Diphenylphosphino)ferrocene
EDC N-(3-Dimethylaminopropyl)-N'-ethylcarbodiimide
ESI Electrospray ionization
Et$_2$O Diethyl ether
EtOAc Ethyl Acetate
EtOH Ethanol
H$_2$ Hydrogen or hydrogen atmosphere
HATU O-(7-Azabenzotriazol-1-yl)-N,N,N',N'-tetramethyluronium hexafluorophosphate
HBr Hydrobromic acid
HCl Hydrochloric acid
HMPA Hexamethylphosphoramide
HOAc Acetic acid
HOAt 1-Hydroxy-7-azabenzotriazole
HOBT 1-Hydroxy benzotriazole
H$_2$O Water
H$_2$O$_2$ Hydrogen peroxide
HPLC High performance liquid chromatography
I$_2$ Iodine
KHSO$_4$ Potassium bisulfate
K$_2$SO$_4$ Potassium sulfate
K$_2$CO$_3$ Potassium carbonate
KOH Potassium hydroxide
LAH Lithium aluminium hydride
LCMS High performance liquid chromatography-mass spectrometry
LiOH Lithium hydroxide
LiOH.H$_2$O Lithium hydroxide monohydrate
LRMS Low resolution mass spectrometry
Me$_3$Al Trimethylaluminium
MeLi Methyllithium
MeOH Methanol
MgSO$_4$ Magnesium Sulfate
MsCl Mesyl chloride
N$_2$ Nitrogen or nitrogen atmosphere
NH$_4$Cl Ammonium chloride
NH$_4$OH Ammonium hydroxide
Nle Norleucine
NMP N-Methyl pyrrolidinone
NaH Sodium hydride
NaHCO$_3$ Sodium hydrogen carbonate (sodium bicarbonate)
NaHSO$_3$ Sodium bisulfite
NaOH Sodium hydroxide
NaOMe Sodium methoxide
Na$_2$SO$_3$ Sodium sulfite
Na$_2$S$_2$O$_3$ Sodium thiosulfate
Na$_2$SO$_4$ Sodium sulfate (anhydrous)
PCy$_3$ Tricyclohexyl phosphine
POBr Phosphoryl bromide
POBr$_3$ Phosphoryl tribromide
P$_2$O$_5$ phosphorus pentoxide (P$_4$O$_{10}$)
Pd/C Palladium on carbon
PhMe Toluene
PPh$_3$ Triphenylphosphine
RT Room temperature, approximately 25 C
Ru/C Ruthenium on carbon
SiO$_2$ Silica or silica gel
TBAF Tetrabutylammonium fluoride
TBTU O-Benzotriazol-1-yl-N,N,N',N'-tetramethyluronium tetrafluoroborate
TEA Triethylamine
TFA Trifluoroacetic acid
THF Tetrahydofuran
TIPSOTf Triisopropylsilyl triflate
TMSCl Chlorotrimethyl silane
TsCl p-Toluenesulfonyl chloride
Zn(CN)$_2$ Zinc cyanide

Synthesis of Intermediates

Intermediates A

| Intermediate # | Structure | Name | Literature Reference |
|---|---|---|---|
| A1 | 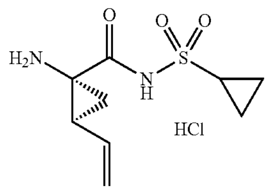 | (1R,2S)-1-Amino-N-(cyclopropylsulfonyl)-2-vinylcyclopropanecarboxamide hydrochloride | U.S. Pat. No. 6,995,174 |
| A2 | 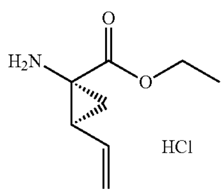 | Ethyl(1R,2S)-1-amino-2-vinylcyclopropanecarboxylate hydrochloride | U.S. Pat. No. 6,323,180 |

Intermediate A3: (1R,2R)-1-Amino-N-(cyclopropylsulfonyl)-2-ethylcyclopropanecarboxamide hydrochloride

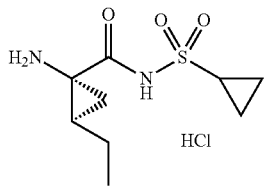

Step 1: t-Butyl ((1R,2R)-1-{[(cyclopropylsulfonyl)amino]carbonyl}-2-ethylcyclopropyl)carbamate

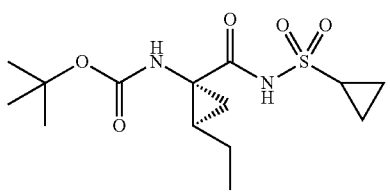 [SMILES: CC[C@@H]1C[C@]1(NC(=O)OC(C)(C)C)C(=O)NS(=O)(=O)C1CC1]

A hydrogenation vessel was charged with a MeOH (1000 mL) slurry of t-butyl ((1R,2S)-1-{[(cyclopropylsulfonyl)amino]carbonyl}-2-vinylcyclopropyl)carbamate (164 g, 0.50 mol) (U.S. Pat. No. 6,995,174) and 5% Ru/C (dry, 7.5 wt %, 12.4 g) and stirred. The vessel was placed under $N_2$ (20 psi) and vented to atmospheric pressure (3×) to remove residual oxygen. The vessel was then placed under $H_2$ (50 psi). After 20 hours, the vessel was vented to atmospheric pressure. The reaction slurry was then transferred out of the reaction vessel and filtered through SOLKA FLOK (34 g, wetted with 100 mL MeOH) to yield a clear, light brown solution. The SOLKA FLOK was rinsed with MeOH (200 mL×2). The combined MeOH solutions were concentrated under reduced pressure to yield crude product as a white solid (153 g). The crude product was slurried in EtOAc (800 mL), warmed to 40° C. and aged 30 minutes. The solution was then seeded, aged 30 minutes, and heptane (500 mL) was added via addition funnel over 30 minutes. The partially crystallized solid was cooled to RT and aged overnight, after which additional heptane (500 mL) was added. After 1 hour, additional heptane (250 mL) was added via addition funnel, and the white slurry aged for 1 hour. The solution was filtered, and the solid was rinsed with heptane/EtOAc (500 mL, 4:1) and dried under reduced pressure to give t-butyl ((1R,2R)-1-{[(cyclopropylsulfonyl)amino]carbonyl}-2-ethylcyclopropyl)carbamate (125.9 g).

Step 2: (1R,2R)-1-Amino-N-(cyclopropylsulfonyl)-2-ethylcyclopropanecarboxamide hydrochloride (Intermediate A3)

A solution of the product from Step 1 (92 g, 0.28 mol) in DCM (1200 mL) was cooled to 0° C., and HCl was bubbled through the solution for 10 minutes. The cooling bath was then removed, and the reaction mixture stirred for 2 hours. $N_2$ was bubbled through the reaction mixture for 5 minutes, and the volatiles evaporated. The residue was azeotroped with DCM (3×) to give an off-white powder (75 g). LRMS $(M+H)^+$ Calcd.=233; found 233.

Intermediate A4:
Trans-4-pent-4-en-1-yltetrahydrofuran-3-ol

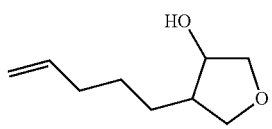

To a mixture of CuI (1.66 g, 8.71 mmol) in THF (100 mL) at −5° C., a 0.5M solution of bromo(pent-4-en-1-yl)magnesium (116 mL, 5.81 mmol) was added. The solution was stirred for 1 hour and cooled to −20° C. 3,6-Dioxabicyclo[3.1.0]hexane (5.0 g, 58.1 mmol) was added dropwise, and the reaction mixture was slowly warmed to RT and stirred for 15 hours. The reaction mixture was quenched with NH₄Cl$_{(aq.)}$ and extracted with Et₂O (3×). The combined organics were washed with H₂O and brine, dried over Na₂SO₄, filtered and concentrated. The crude product was purified on SO₂ (gradient elution, 10-100% EtOAc/hexanes). ¹H NMR (500 MHz, CDCl₃) δ 5.83-5.75 (m, 1H); 5.04-4.95 (m, 2H); 4.14-4.07 (m, 3H); 3.85 (m, 1H); 3.70 (m, 1H); 3.44 (m, 1H); 2.07 (m, 3H); 1.45 (m, 3H) ppm.

Intermediate A5:
Trans-2-pent-4-en-1ylcyclopentanol

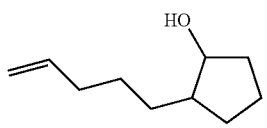

A solution of 5-bromopent-1-ene (11.81 mL, 100 mmol) in Et₂O (100 mL) was added to magnesium (2.43 g, 100 mmol) over 20 minutes. The resulting suspension was heated under reflux for 40 minutes, then cooled to 20° C., taken up in a syringe, and added dropwise at −5° C. to a stirred suspension of CuI (3.17 g, 16.6 mmol) in THF (160 mL). The resulting solution was stirred for 30 minutes at −5° C., then cooled to −20° C. Cyclopentene oxide (7.21 mL, 83 mmol) was added dropwise, and the resulting mixture was warmed to 20° C. over 2 hours, then stirred for 48 hours. The reaction was quenched by addition of NH₄Cl$_{(aq.)}$; then the layers were separated, and the aqueous layer was extracted with Et₂O. The combined organic phases were washed with H₂O and brine, then dried over Na₂SO₄. Filtration and removal of the volatiles gave a residue that was purified by column chromatography on SiO₂ (gradient elution, 1-100% EtOAc/petroleum ether) to afford the title compound (7.92 g, 62%) as a liquid. ¹H NMR (400 MHz, CDCl₃) δ 5.88-5.76 (m, 1H), 5.01 (d, J=17.2 Hz, 1H), 4.95 (d, J=10.6 Hz, 1H), 3.83 (br s, 1H), 2.12-2.00 (m, 2H), 1.99-1.84 (m, 2H), 1.76-1.30 (m, 7H), 1.24-1.11 (m, 2H).

Intermediate A6:
(1R,2R)-2-pent-4-en-1-ylcyclopentyl acetate

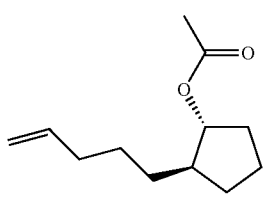

AMANO LIPASE PS (7.0 g, 64.7 mmol) was added to a solution of trans-2-pent-4-en-1-ylcyclopentanol (10.0 g, 64.7 mmol) and vinyl acetate (19.5 g, 129.4 mmol) in Et₂O (275 mL). The mixture was stirred for 16 hours, then filtered through CELITE. The filtrate was concentrated to afford a residue that was purified by column chromatography on SiO₂ (gradient elution, 0-100% Et₂O/petroleum ether) to afford in the first fractions the title compound (5.43 g, 43%). ¹H NMR (300 MHz, CDCl₃) δ 5.89-5.72 (m, 1H), 5.00 (d, J=18.1 Hz, 1H), 4.95 (d, J=11.0 Hz, 1H), 4.82-4.73 (m, 1H), 2.11-1.98 (m, 2H), 2.03 (s, 3H), 1.98-1.85 (m, 3H), 1.71- 1.60 (m, 3H), 1.50-1.35 (m, 3H), 1.29-1.14 (m, 2H); [α]$_D$=−36.1 (c=0.73 in CHCl₃). The later fractions contained enantio-enriched (1S,2S)-2-pent-4-en-1-ylcyclopentanol.

Intermediate A7:
(1R,2R)-2-pent-4-en-1-ylcyclopentanol

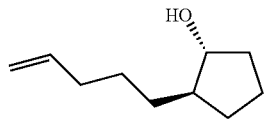

A stirred solution of (1R,2R)-2-pent-4-en-1-ylcyclopentyl acetate (3.79 g, 19.3 mmol) in MeOH (320 ml) was treated with methanolic NaOMe (25%, 8.1 ml, 35.4 mmol) and stirred for 15 hours at 20° C. DOWEX 50WX8-100 ion-exchange resin (washed with MeOH) was added portionwise until the pH was neutral, then the mixture was filtered through CELITE. The filtrate was concentrated in vacuo, and the residue was partitioned between EtOAc and H₂O. The organic layer was separated, washed with brine, and dried over Na₂SO₄. Filtration and removal of the volatiles afforded the title compound (2.61 g, 88%) as a liquid that was used directly in the subsequent reactions. [α]D −37.3 (c=0.65, CHCl₃).

Intermediates B

Intermediate B1:
N-[(Pent-4-en-1-yloxy)carbonyl]-L-norleucine

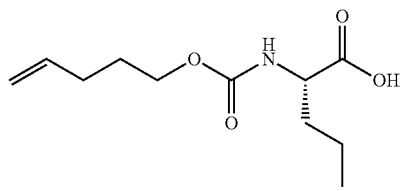 [SMILES: C=CCCCOC(=O)N[C@@H](CCC)C(=O)O]

To a solution of 1-penten-4-ol (0.95 g, 11.0 mmol) in DMF (15 mL) at 0° C., carbonyldiimidazole (1.79 g, 11.0 mmol) was added. The reaction mixture was warmed to RT and stirred for 30 minutes. L-norleucine methyl ester hydrochloride (2.0 g, 11.0 mmol) was then added, and the reaction mixture was heated to 50° C. and stirred for 15 minutes. Upon cooling, the reaction mixture was diluted with Et₂O and washed (2×) with H₂O. The organic layer was dried over Na₂SO₄, filtered and concentrated. The crude product was purified by SiO₂ chromatography (gradient elution, 10-90% EtOAc/hexanes) to afford 2.1 g (74%) methyl N-[(pent-4-en-1-yloxy)carbonyl]-L-norleucinate as a clear oil.

To a stirred solution of methyl N-[(pent-4-enyloxy)carbonyl]-L-norleucinate (8.50 g, 33.03 mmol) in THF (20 mL) was added 1N NaOH (20 mL). This reaction solution was stirred at RT for 3 hours, then acidified to pH 3 with 1N HCl and extracted with (3×250 mL) EtOAc. The combined EtOAc layer was washed with 50 mL H₂O, 50 mL brine, dried over Na₂SO₄, filtered and concentrated to give 7.09 g (88%) of the title product as clear oil. LRMS (ESI) m/z 244 [(M+H)⁺; calcd for C₁₂H₂₂NO₄: 244].

Intermediate B2: (2S)-3,3-Dimethyl-2-{[(pent-4-en-1-yloxy)carbonyl]amino}butanoic acid

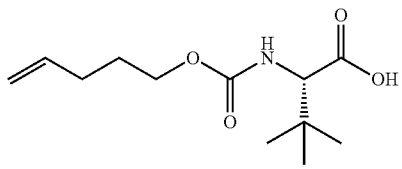 [SMILES: C=CCCCOC(=O)N[C@H](C(=O)O)C(C)(C)C]

DIPEA (9.85 g, 76.2 mmol) was added dropwise to a 0° C. solution of 4-penten-1-ol (7.22 g, 83.9 mmol) and triphosgene (11.3 g, 38.1 mmol) in 160 mL dioxane. The resulting white suspension was stirred for 5 minutes at 0° C., then allowed to warm to 25° C. over 1 hour. The suspension was cooled to 0° C. with an ice bath, and 1N NaOH (76.2 mL) and L-t-butylglycine (10.0 g, 76.2 mmol) were added. The reaction mixture was warmed to 25° C. and stirred for 18 hours. The dioxane was removed in vacuo, and the reaction mixture was basified to pH 12 with 1N NaOH. The aqueous layer was extracted with DCM (3×150 mL), then acidified to pH~1 with 6N HCl. The aqueous layer was extracted again with DCM (3×150 mL). The combined organic layers were dried over $MgSO_4$, and concentrated to give the compound as a tan oil (13.7 g, 73.9% yield). LRMS (ESI) m/z 244 [(M+H)$^+$; calcd for $C_{12}H_{22}NO_4$ 244].

The following carbamate intermediates (B3-B19) were prepared using the chemistry described for the preparation of Intermediate B2, by utilizing the appropriate amino acid and alcohol.

| Int. | Amino Acid | Alcohol | Structure | Name | LRMS (M + H)$^+$ |
|---|---|---|---|---|---|
| B1 | L-Norleucine | 4-Penten-1-ol | 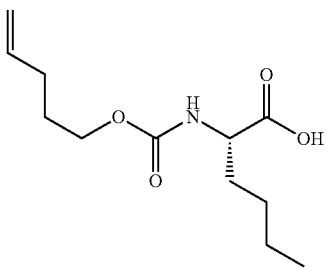 [SMILES: C=CCCCOC(=O)N[C@@H](CCCC)C(=O)O] | N-[(Pent-4-en-1-yloxy)carbonyl]-L-norleucine | 244.3 |
| B2 | L-t-Butyl-glycine | 4-Penten-1-ol | 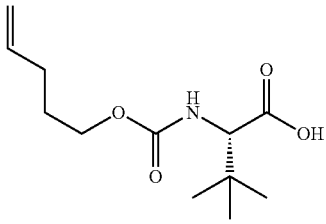 [SMILES: C=CCCCOC(=O)N[C@H](C(=O)O)C(C)(C)C] | (2S)-3,3-Dimethyl-2-{[(pent-4-en-1-yloxy)carbonyl]amino}butanoic acid | 244.2 |
| B3 | L-Norleucine | 3-Buten-1-ol | 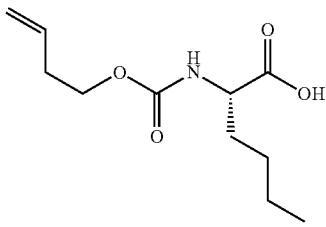 [SMILES: C=CCCOC(=O)N[C@@H](CCCC)C(=O)O] | N-[(but-3-en-1-yloxy)carbonyl]-L-norleucine | 230.3 |
| B4 | L-Norleucine | 5-Hexen-1-ol | 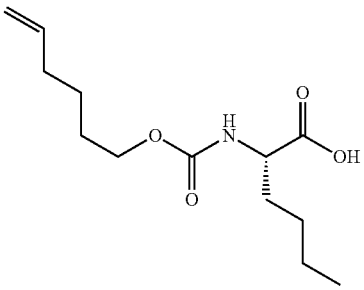 [SMILES: C=CCCCCOC(=O)N[C@@H](CCCC)C(=O)O] | N-[(hex-5-en-1-yloxy)carbonyl]-L-norleucine | 258.3 |

-continued

| Int. | Amino Acid | Alcohol | Structure | Name | LRMS (M + H)+ |
|---|---|---|---|---|---|
| B5 | L-Norleucine | 6-Hepten-1-ol | 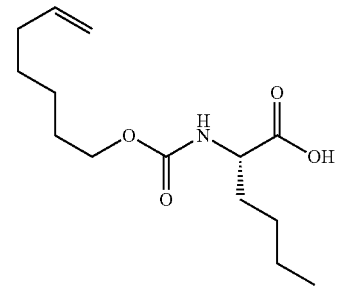 [SMILES: C=CCCCCCOC(=O)N[C@@H](CCCC)C(=O)O] | N-[(hept-6-en-1-yloxy)carbonyl]-L-norleucine | 272.3 |
| B6 | L-Norleucine | 7-Octen-1-ol | 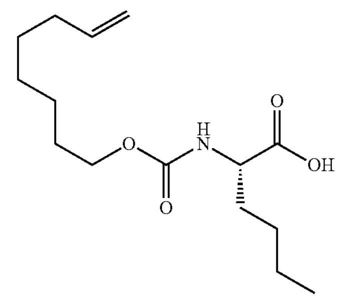 [SMILES: C=CCCCCCCOC(=O)N[C@@H](CCCC)C(=O)O] | N-[(oct-7-en-1-yloxy)carbonyl]-L-norleucine | 286.4 |
| B7 | L-Valine | 4-Penten-1-ol | 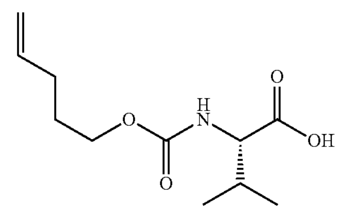 [SMILES: C=CCCCOC(=O)N[C@H](C(=O)O)C(C)C] | N-[(Pent-4-en-1-yloxy)carbonyl]-L-valine | 230.3 |
| B8 | L-Valine | 4-Propen-1-ol | 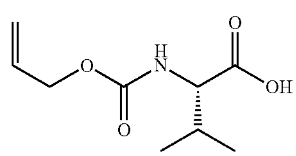 | N-[(allyloxy)carbonyl]-L-valine | 202.2 |
| B9 | L-Valine | 4-Buten-1-ol | 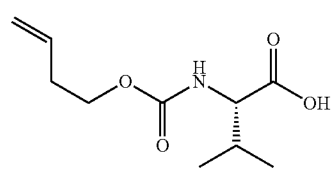 | N-[(but-3-en-1-yloxy)carbonyl]-L-valine | 216.3 |
| B10 | L-t-Butyl-glycine | 5-Hexen-1-ol | 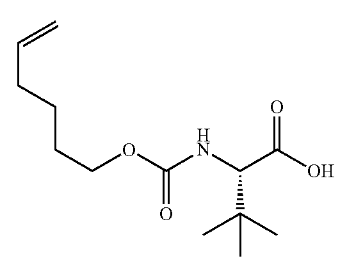 [SMILES: C=CCCCCOC(=O)N[C@H](C(=O)O)C(C)(C)C] | N-[(Hex-5-en-1-yloxy)carbonyl]-3-methyl-L-valine | 258.3 |

| Int. | Amino Acid | Alcohol | Structure | Name | LRMS (M + H)+ |
|---|---|---|---|---|---|
| B11 | L-t-Butyl-glycine | 6-Hepten-1-ol | 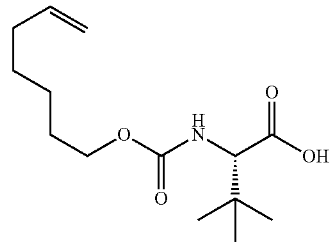 [SMILES: C=CCCCCCOC(=O)N[C@H](C(=O)O)C(C)(C)C] | N-[(Hept-6-en-1-yloxy)carbonyl]-3-methyl-L-valine | 272.3 |
| B12 | L-t-Butyl-glycine | 3-Buten-1-ol | 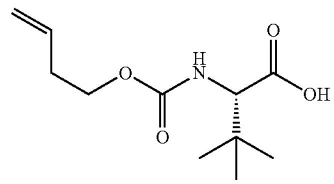 [SMILES: C=CCCOC(=O)N[C@H](C(=O)O)C(C)(C)C] | N-[(But-3-en-1-yloxy)carbonyl]-3-methyl-L-valine | 230.3 |
| B13 | L-t-Butyl-glycine | 2,2-Dimethylhex-5-en-1-ol Ref: 56 *J. Org. Chem.* 1623 (1991). | 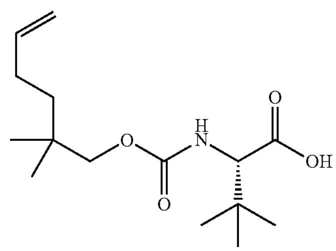 [SMILES: C=CCCC(C)(C)COC(=O)N[C@H](C(=O)O)C(C)(C)C] | N-{(2,2-Dimethylhex-5-en-1-yl)oxy]carbonyl}-3-methyl-L-valine | 286.3 |
| B14 | L-t-Butyl-glycine | Allyl alcohol | 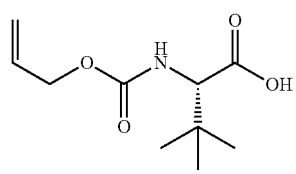 | N-[(allyloxy)carbonyl]-3-methyl-L-valine | 215.2 |
| B15 | L-t-Butyl-glycine | 7-Octen-1-ol | 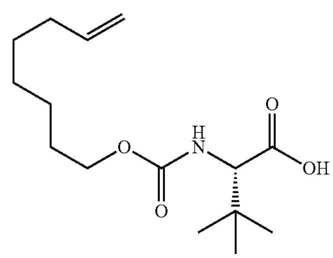 [SMILES: C=CCCCCCCOC(=O)N[C@H](C(=O)O)C(C)(C)C] | 3-Methyl-N-[(oct-7-en-1-yloxy)carbonyl]-L-valine | 286.3 |
| B16 | L-Cyclohexyl-glycine | 6-Hepten-1-ol | 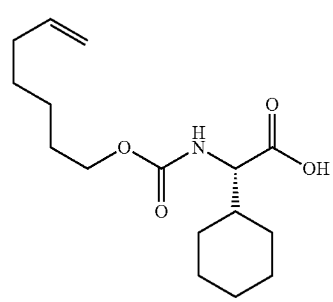 [SMILES: C=CCCCCCOC(=O)N[C@H](C(=O)O)C1CCCCC1] | (2S)-Cyclohexyl{[(hept-6-en-1-yloxy)carbonyl]amino}acetic acid | 298.3 |

| Int. | Amino Acid | Alcohol | Structure | Name | LRMS (M + H)+ |
|---|---|---|---|---|---|
| B17 | L-Cyclohexyl-glycine | 5-Hexen-1-ol | 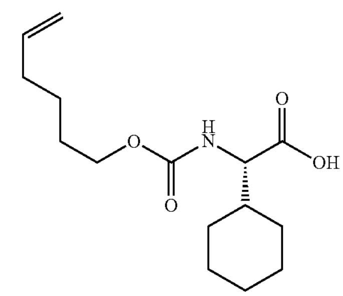 [SMILES: C=CCCCCOC(=O)N[C@H](C(=O)O)C1CCCCC1] | (2S)-Cyclohexyl{[(hex-5-en-1-yloxy)carbonyl]amino} acetic acid | 284.4 |
| B18 | L-t-Butyl-glycine | 6-Heptyn-1-ol | 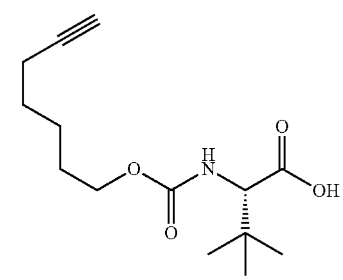 [SMILES: C#CCCCCCOC(=O)N[C@H](C(=O)O)C(C)(C)C] | N-[(hept-6-yn-1-yloxy)carbonyl]-3-methyl-L-valine | 270.2 |
| B19 | L-Cyclohexyl-glycine | 2,2-dimethylhept-6-en-1-ol Ref: WO 2005/030796 | 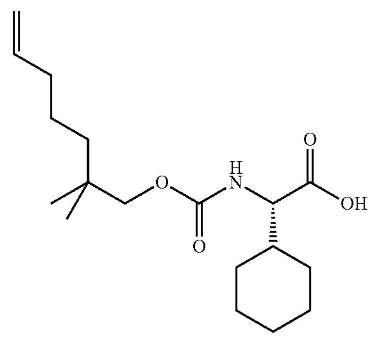 [SMILES: C=CCCCC(C)(C)COC(=O)N[C@H](C(=O)O)C1CCCCC1] | (2S)-cyclohexyl({[(2,2-dimethylhept-6-en-1-yl)oxy]carbonyl}amino) acetic acid | 326.5 |

Intermediate B20: 3-Methyl-N-{[methyl(pent-4-en-1-yl)amino]carbonyl}-L-valine

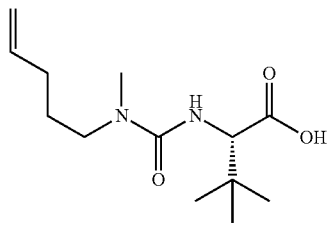 [SMILES: C=CCCCN(C)C(=O)N[C@H](C(=O)O)C(C)(C)C]

Step 1: Methyl 3-methyl-N-{[methyl(pent-4-en-1-yl)amino]carbonyl}-L-valinate

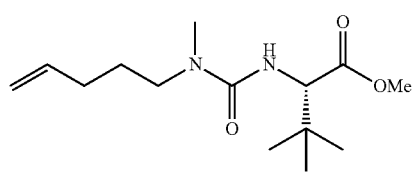 [SMILES: C=CCCCN(C)C(=O)N[C@H](C(=O)OC)C(C)(C)C]

To a solution of N-methylpent-4-en-1-amine (ref: 2(20) Org. Biomol. Chem. 3006-17 (2004)) (2.0 g, 21.2 mmol) in THF (20 mL), methyl 3-methyl-N-(oxomethylene)-L-valinate (ref: EP 0 486 948 A2) (3.5 g, 20.2 mmol) was added. After 2 hours, the solvent was removed in vacuo, and the crude material was purified on $SO_2$ (40% EtOAc/hexanes) to yield the title compound. LRMS (M+H)+ 271.3.

Step 2: N-{[(1,1-Dimethylpent-4-en-1-yl)amino]carbonyl}-L-valine (Intermediate B20)

To a solution of the product from step 1, methyl 3-methyl-N-{[methyl(pent-4-en-1-yl)amino]carbonyl}-L-valinate, (3.0 g, 11.2 mmol) in THF (40 mL), 1M LiOH (56.0 mL, 1M solution 56.0 mmol) was added. The reaction mixture was stirred at 50° C. under $N_2$ for 1 hour, cooled to RT, and THF was removed in vacuo. $KHSO_{4(aq.)}$ was then added, and the mixture extracted with DCM (3×). The combined organic extracts were dried over anhydrous $Na_2SO_4$, and the solvent was removed in vacuo to give the title compound as a colorless oil (2.95 g). LRMS (M+H)+=257.3.

Intermediate B21: (2S)-Cyclopentyl[({[(1R,2R)-2-pent-4-en-1-ylcyclopentyl]oxy}carbonyl)amino]acetic acid

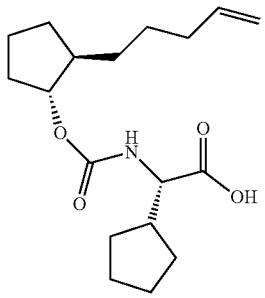 [SMILES: C=CCCC[C@@H]1CCC[C@H]1OC(=O)N[C@H](C(=O)O)C1CCCC1]

Step 1: Methyl (2S)-cyclopentyl(isocyanato)acetate

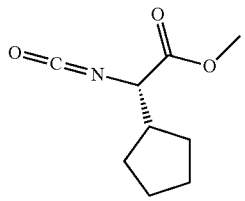

A suspension of methyl (2S)-amino(cyclopentyl)acetate hydrochloride (3.21 g, 16.57 mmol) in DCM (69 mL) and saturated NaHCO$_{3(aq.)}$ (132 mL) was cooled to 0° C. and treated with triphosgene (2.21 g, 7.46 mmol). The mixture was stirred at 0° C. for 3 hours, then warmed to 20° C. and diluted with DCM. The layers were separated, and the aqueous phase was re-extracted with DCM. The combined organic phases were washed with brine and dried over Na$_2$SO$_4$. Filtration and removal of the volatiles afforded the title compound (2.95 g, 97%) as an oily solid that was used directly in subsequent steps. $^1$H NMR (400 MHz, DMSO-d$_6$) δ 4.36 (d, J=4.8 Hz, 1H), 3.73 (s, 1H), 2.35-2.24 (m, 1H), 1.76-1.24 (m, 8H).

Step 2: Methyl (2S)-cyclopentyl[({[(1R,2R)-2-pent-4-en-1-ylcyclopentyl]oxy}carbonyl)amino]acetate

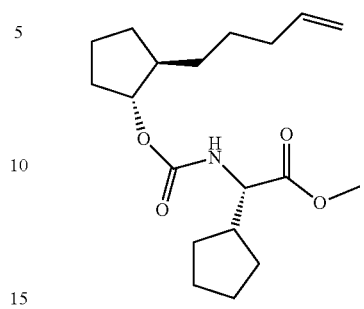

A solution of methyl (2S)-cyclopentyl(isocyanato)acetate (1.57 g, 8.56 mmol) and (1R,2R)-2-pent-4-en-1-ylcyclopentanol (1.20 g, 7.78 mmol) in PhMe (56 mL) was treated portionwise with DMAP (0.95 g, 7.78 mmol). The resulting mixture was stirred for 5 hours at 85° C., then cooled to 20° C., and diluted with EtOAc and HCl$_{(aq.)}$ (1N). The organic layer was separated, washed with brine, and dried over Na$_2$SO$_4$. Filtration and removal of the volatiles gave a residue that was purified by column chromatography (gradient elution, 4-40% Et$_2$O/petroleum ether) to afford the title compound (1.97 g, 76%) as an oil. LCMS (ES+) m/z 338 (M+H)$^+$.

Step 3: (2S)-Cyclopentl[({[(1R,2R)-2-pent-4-en-1-ylcyclopentyl]oxy}carbonyl)amino]acetic acid A mixture of methyl (2S)-cyclopentyl[({[(1R,2R)-2-pent-4-en-1-ylcyclopentyl]oxy}carbonyl)amino]acetate (1.97 g, 5.84 mmol) and LiOH.H$_2$O (0.74 g, 17.51 mmol) in a 1:1 mixture of THF:H$_2$O (60 mL) was heated to 40° C. The solution was stirred for 4 hours, then cooled to 20° C. The THF was removed under reduced pressure, and the residual aqueous solution was extracted with EtOAc. The organic phase was washed with H$_2$O and brine, then dried over Na$_2$SO$_4$. Filtration and removal of the volatiles afforded the title compound (1.85 g, 98%) as an oil that was used directly in subsequent steps. $^1$H NMR (400 MHz, DMSO-d$_6$) δ 12.25 (br s, 1H), 7.28 (d, J=8.1 Hz, 1H), 5.84-5.71 (m, 1H), 4.98 (d, J=17.4 Hz, 1H), 4.92 (d, J=10.1 Hz, 1H), 4.60-4.52 (m, 1H), 3.78 (t, J=8.0 Hz, 1H), 2.18-2.05 (m, 1H), 2.04-1.94 (m, 3H), 1.91-1.74 (m, 3H), 1.70-1.06 (m, 15H).

Intermediates B21a-B24a

Intermediates B21a-B24a were prepared in a manner similar to that utilized to prepare Intermediate B21.

| Int. | Amino Acid | Alcohol | Structure | Name | LRMS (M + H)$^+$ |
|---|---|---|---|---|---|
| B21a | L-cyclopentylglycine | trans-4-pent-4-en-1-yltetrahydrofuran-3-ol | 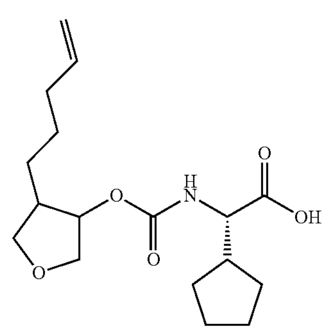 [SMILES: C=CCCCC1COCC1OC(=O)N[C@H](C(=O)O)C1CCCC1] | (2S)-cyclopentyl({[(trans-4-pent-4-en-1-yltetrahydrofuran-3-yl)oxy]carbonyl}amino)acetic acid | |

-continued

| Int. | Amino Acid | Alcohol | Structure | Name | LRMS (M + H)+ |
|---|---|---|---|---|---|
| B22 | L-tBu-glycine | trans-2-pent-4-en-1-ylcyclopentanol | 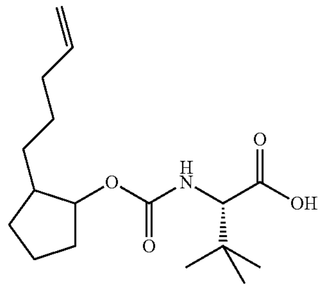 [SMILES: C=CCCCC1CCCC1OC(=O)N[C@H](C(=O)O)C(C)(C)C] | 3-methyl-N-{[(trans-2-pent-4-en-1-ylcyclopentyl)oxy]carbonyl}-L-valine | 312.4 |
| B22a | L-tBu-glycine | (1R,2R)-2-pent-4-en-1-ylcyclopentanol | 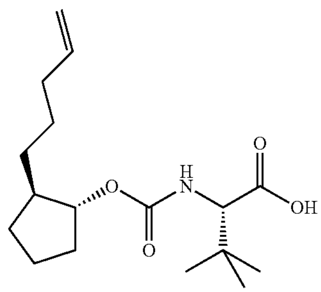 [SMILES: C=CCCC[C@@H]1CCC[C@H]1OC(=O)N[C@H](C(=O)O)C(C)(C)C] | 3-methyl-N-({[(1R,2R)-2-pent-4-en-1-ylcyclopentyl]oxy}carbonyl)-L-valine | 312.4 |
| B23 | L-cyclopentyl-glycine | trans-2-pent-4-en-1-ylcyclopentanol | 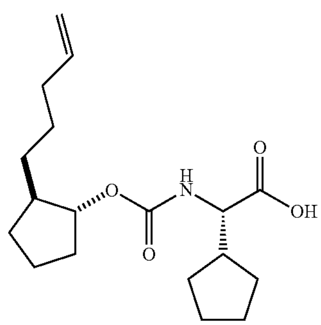 [SMILES: C=CCCC[C@@H]1CCC[C@H]1OC(=O)N[C@H](C(=O)O)C1CCCC1] | (2S)-cyclopentyl({[trans-(2-pent-4-en-1-ylcyclopentyl)oxy]carbonyl}amino)acetic acid | 324.2 |
| B23a | L-cyclopentyl-glycine | (1R,2R)-2-pent-4-en-1-ylcyclopentanol | 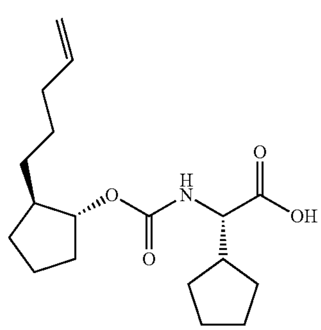 [SMILES: C=CCCC[C@@H]1CCC[C@H]1OC(=O)N[C@H](C(=O)O)C1CCCC1] | (2S)-cyclopentyl[({[(1R,2R)-2-pent-4-en-1-ylcyclopentyl]oxy}carbonyl)amino]acetic acid | 324.2 |

| Int. | Amino Acid | Alcohol | Structure | Name | LRMS (M + H)+ |
|---|---|---|---|---|---|
| B23b | L-cyclopentyl-glycine | (1S,2S)-2-pent-4-en-1-ylcyclopentanol | 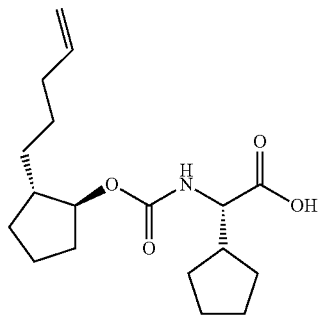 [SMILES: C=CCCC[C@H]1CCC[C@@H]1OC(=O)N[C@H](C(=O)O)C1CCCC1] | (2S)-cyclopentyl[({[(1S,2S)-2-pent-4-en-1-ylcyclopentyl]oxy}carbonyl)amino]acetic acid | 324.2 |
| B24 | L-cyclohexyl-glycine | Trans-2-pent-4-en-1-ylcyclopentanol | 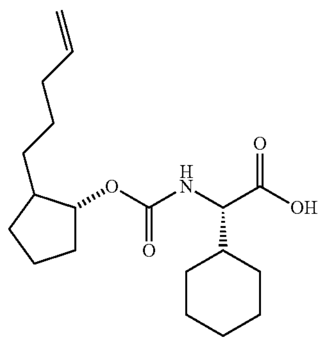 [SMILES: C=CCCCC1CCC[C@H]1OC(=O)N[C@H](C(=O)O)C1CCCCC1] | (2S)-cyclohexyl({[(2-pent-4-en-1-ylcyclopentyl)oxy]carbonyl}amino)acetic acid | 338.3 |
| B24a | L-cyclohexyl-glycine | (1R,2R)-2-pent-4-en-1-ylcyclopentanol | 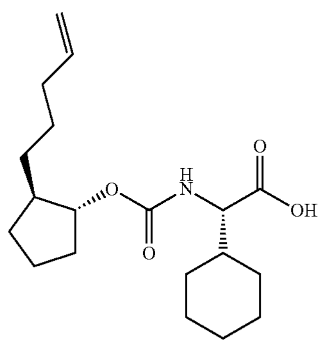 [SMILES: C=CCCC[C@@H]1CCC[C@H]1OC(=O)N[C@H](C(=O)O)C1CCCCC1] | (2S)-cyclohexyl[({[(1R,2R)-2-pent-4-en-1-ylcyclopentyl]oxy}carbonyl)amino]acetic acid | 360.3 (M + Na)+ |

Intermediates B25a and B25b: 3-Methyl-N-({[(1R,2R)-2-pent-4-en-1-ylcyclopropyl]oxy}carbonyl)-L-valine and 3-methyl-N-({[(1S,2S)-2-pent-4-en-1-ylcyclopropyl]oxy}carbonyl)-L-valine

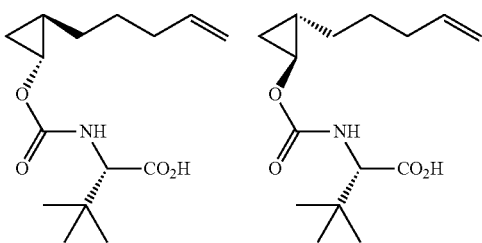

Step 1: [(1E)-Hepta-1,6-dien-1-yloxy](trimethyl)silane

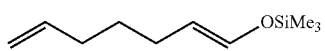

A solution (0.5M) of butenyl magnesium bromide in THF (200 ml, 100 mmol) was added at −70° C. to Cu(I)Br.SMe₂ complex (734 mg, 3.57 mmol) and HMPA (29.8 ml, 171 mmol). After stirring for 10 minutes, a solution of acrolein (4.00 g, 71.4 mmol) and TMSCl (18.25 mL, 143 mmol) in THF (59.8 mL) was added over 30 minutes. After 2 hours, TEA (20 mL) was added, and the mixture was diluted with anhydrous hexane. H₂O (5 mL) was added, and the mixture was filtered through CELITE. The filtrate was washed (7×) with 16 mL portions of H₂O, and then extracted with hexane. The organic layer was washed with brine and dried over Na₂SO₄, then concentrated to give a residue that was distilled (bp c. 80° C., 20 mbar) to furnish the title compound (7.68 g, 58%) as a liquid that was used directly in the subsequent reaction.

Step 2: Trimethyl {[(1S,2S)-2-pent-4-en-1-ylcyclopropyl]oxy}silane

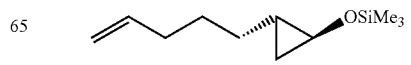

A solution of diethyl zinc in toluene (15%, 3.29 mL, 3.62 mmol) was added to a solution of the product of Step 1 (303 mg, 1.64 mmol) in hexane (3.62 mL), and the resultant solution was cooled with an ice bath before careful addition of diiodomethane (292 L, 3.62 mmol). The reaction was stirred at 0° C. for 1 hour, and then warmed to 20° C. The reaction was then quenched with pyridine (0.80 mL) and stirred for 15 minutes before pouring onto petrol. The reaction mixture was filtered through CELITE and concentrated to afford the title compound as an oil that was used directly in the subsequent step.

Step 3: 2-Pent-4-en-1-ylcyclopropanol

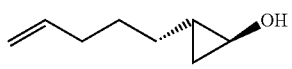

A solution of trimethyl {[(1S,2S)-2-pent-4-en-1-ylcyclopropyl]oxy}silane (5.81 g, 29.3 mmol) in THF (42 mL) was cooled to 0° C. and treated with a solution of TBAF in THF (1M, 35.2 mL, 35.2 mmol). The mixture was stirred at 0° C. for 10 minutes, and then warmed to 15° C. over 1 hour. The mixture was poured into H$_2$O (900 mL) and extracted (2×) with EtOAc. The combined organic extracts were washed with brine, dried over Na$_2$SO$_4$ and evaporated to afford a residue, which was purified by column chromatography on SiO$_2$, eluting with Et$_2$O in petroleum ether (0-66%) to give the title compound (2.63 g, 71%) as an oil that was used directly in the subsequent reaction.

Step 4: Methyl 3-methyl-N-({[(1R,2R)-2-pent-4-en-1-ylcyclopropyl]oxy}carbonyl)-L-valinate and methyl 3-methyl-N-({[(1S,2S)-2-pent-4-en-1-ylcyclopropyl]oxy}carbonyl)-L-valinate

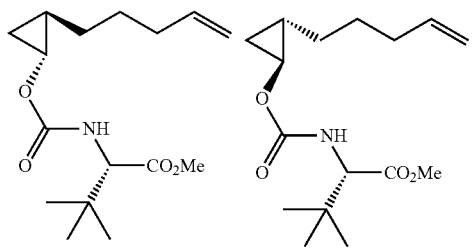

The alcohol of Step 3 was treated, according to the procedure above described for Intermediate B21 Step 2, with methyl 3-methyl-N-(oxomethylene)-L-valinate (1.221 g, 7.13 mmol) and DMAP (0.871 g, 7.13 mmol) to afford a residue that was purified by flash chromatography on SiO$_2$ (gradient elution, 0-30% Et$_2$O/petroleum ether) to afford two fractions of the title compound (815 mg and 598 mg, 38.4% and 28.2%) as oils. LCMS (ES+) m/z 320.1 (M+Na)$^+$.

Step 5: 3-Methyl-N-({[(1R,2R)-2-pent-4-en-1-ylcyclopropyl]oxy}carbonyl)-L-valine or 3-methyl-N-({[(1S,2S)-2-pent-4-en-1-ylcyclopropyl]oxy}carbonyl)-L-valine The esters of Step 4 were treated, according to the procedure described for Intermediate B21 Step 3, with LiOH.H$_2$O afforded the title compounds as oils (95%). LCMS (ES+) m/z 282.2 (M–H)$^-$.

Intermediate B26: (2S)-Cyclopentyl[({[(1R,2R)-1-methyl-2-pent-4-en-1-ylcyclopentyl]oxy}carbonyl)amino]acetic acid

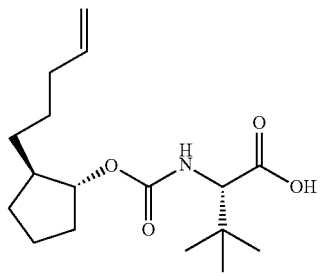 [SMILES: C=CCCC[C@@H]1CCC[C@H]1OC(=O)N[C@H](C(=O)O)C(C)(C)C]

Step 1: (2R)-2-Pent-4-en-1-ylcyclopentanone

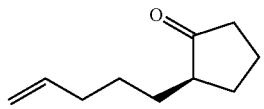

Dess-Martin periodinane (6.27 g, 14.78 mmol) was added to a stirred solution of Intermediate A7 (2.00 g, 12.97 mmol) in DCM (120 ml). The mixture was stirred RT for 1 hour, and then diluted with DCM and washed several times with a 1:1 mixture of saturated NaHCO$_{3(aq.)}$ and Na$_2$S$_2$O$_{3(aq.)}$ (1M). The mixture was then with H$_2$O and brine. The organics were dried over Na$_2$SO$_4$ and concentrated to give a residue that was dissolved in pentane, filtered, and concentrated. The resulting oil was used directly in the subsequent reaction.

Step 2: (1R,2R)-1-methyl-2-pent-4-en-1-ylcyclopentanol

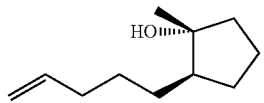

A solution (2M) of Me$_3$Al in toluene (9.85 ml, 19.71 mmol) was added dropwise to a stirred solution of 2,6-di-t-butyl-4-methylphenol (8.68 g, 39.4 mmol) in PhMe (66 mL). After the evolution of gas had finished, the mixture was stirred at RT for 1 hour and then cooled to −78° C. (2R)-2-pent-4-en-1-ylcyclopentanone (1.0 g, 6.57 mmol) was added followed by a solution of MeLi (1.6 M) in Et$_2$O (12.32 ml, 19.71 mmol). The resulting mixture was stirred at −78° C. for 2 hours and then treated with a further portion of MeLi solution (12.32 mL, 19.71 mmol). The mixture was stirred for 1 hour and then poured into HCl$_{(aq.)}$ (1N). The organic layer was washed with brine dried over Na$_2$SO$_4$ and concentrated to give a residue that was purified by column chromatography on SiO$_2$ (gradient elution, 0-20% EtOAc/petroleum ether) to give the title compound (0.77 g, 70%) as a clear oil.

Step 3: (2S)-cyclopentyl[({[(1R,2R)-1-methyl-2-pent-4-en-1-ylcyclopentyl]oxy}carbonyl)amino]acetic acid The alcohol of Step 2 (0.77 g, 4.58 mmol) was treated, according to the procedure described for Intermediate B21 Step 2, with methyl (2S)-cyclopentyl(isocyanato)acetate (3 eq) and DMAP (1.3 eq) afforded a residue that was purified by flash chromatography (gradient elution, 5-40% Et$_2$O/petroleum ether). The resulting oil was hydrolysed as described for Intermediate B21, Step 3 to furnish the title compound (0.53 g, 34%) as an oil. LCMS (ES+) m/z 338.8 (M+H)$^+$.

Intermediate B27: N-({[(1R,2S)-2-allylcyclopentyl]oxy}carbonyl)-3-methyl-L-valine

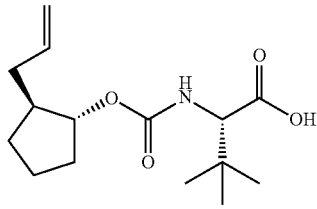 [SMILES: C=CC[C@@H]1CCC[C@H]1OC(=O)N[C@H](C(=O)O)C(C)(C)C]

Intermediate B27 was prepared in a manner similar to that utilized to prepare (2S)-cyclopentyl[({[(1R,2R)-1-methyl-2-pent-4-en-1-ylcyclopentyl]oxy}carbonyl)amino]acetic acid. LCMS (ES+) m/z 283.1.

Intermediate B28: (2S)-[({[(1R,2S)-2-allylcyclopentyl]oxy}carbonyl)amino](cyclopenyl)acetic acid

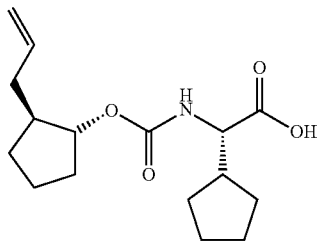

Intermediate B28 was prepared in a manner similar to that utilized to prepare (2S)-cyclopentyl[({[(1R,2R)-1-methyl-2-pent-4-en-1-ylcyclopentyl]oxy}carbonyl)amino]acetic acid. LCMS (ES+) m/z 283.1.

Intermediate B29: (2S)-({[(3R)(3S)-3-(Allyloxy)piperidin-1-yl]carbonyl}amino) (cyclohexyl)acetic acid

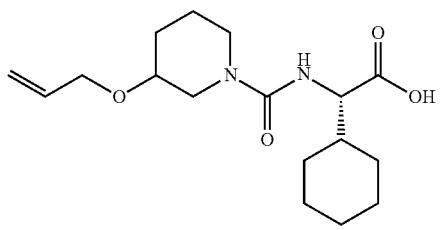 [SMILES: C=CCOC1CCCN(C(=O)N[C@H](C(=O)O)C2CCCCC2)C1]

Step 1: t-Butyl (3R)(3S)-3-(allyloxy)piperidine-1-carboxylate

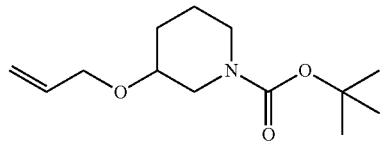 [SMILES: C=CCOC1CCCN(C(=O)OC(C)(C)C)C1]

An oven-dried, 3-neck, 1-L round-bottom flask under N$_2$ was charged with N-Boc-(3R)(3S)-3-hydroxypiperidine (10.0 g, 49.7 mmol) and DMSO (100 mL). KOtBu (5.58 g, 49.7 mmol) was added in a single portion. The reaction mixture was stirred at RT for 30 minutes, after which allyl bromide (4.30 mL, 49.7 mmol) in DMSO (50 mL) was added dropwise via an addition funnel. After 20 hours, the contents of the reaction flask were poured into 5% KHSO$_4$ and extracted (3×) with Et$_2$O. The combined organic portions were washed with brine, dried with anhydrous MgSO$_4$, filtered and evaporated. The crude product was subjected to flash column chromatography (90/10 hexanes/EtOAc). Evaporation of fractions containing product gave the title compound as a colorless oil. LRMS (M+H)$^+$=242.3.

Step 2: (3R)(3S)-3-(Allyloxy)piperidine

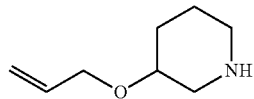

A 500-mL round-bottom flask was charged with the product of Step 1 (9.60 g, 39.8 mmol) and EtOAc (150 mL), and then cooled in an ice bath under N$_2$. The reaction solution was saturated with HCl$_{(g)}$ and stirred for 1 hour with cooling then for 2 hours at RT. Evaporation under reduced pressure gave a white solid, which was triturated with Et$_2$O and isolated. The solid was poured into 10M NaOH$_{(aq)}$ and extracted (3×) with DCM, dried with anhydrous MgSO$_4$, filtered and rotary evaporated to give the title compound as a colorless oil.

Step 3: Methyl (2S)-cyclohexyl(isocyanato)acetate

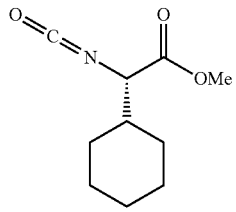 [SMILES: COC(=O)[C@@H](N=C=O)C1CCCCC1]

A 50-0 mL round-bottom flask was charged with saturated NaHCO$_3$ (80 mL) and DCM (80 mL) and cooled in an ice bath with vigorous stirring. Methyl (2S)-amino(cyclohexyl)acetate hydrochloride (4.0 g, 19.26 mmol) was added followed by triphosgene (1.886 g, 6.36 mmol). The contents of the reaction flask were stirred for 1 hour with cooling, and then the contents were poured into a separatory funnel. The layers were separated, and the aqueous layers were extracted with DCM (20 mL). The combined organic portions were dried with anhydrous MgSO₄, filtered and evaporated to give the title compound as a colorless oil. ¹H NMR (CDCl₃): δ 3.90 (d, J4, 1H), 3.81 (s, 3H), 1.88-1.83 (m, 1H), 1.79-1.76 (m, 2H), 1.69-1.62 (m, 2H), 1.54-1.48 (m, 1H), 1.29-1.11 (m, 5H) ppm.

Step 4: Methyl(2S)-({[(3R)(3S)-3-(allyloxy)piperidin-1-yl]carbonyl}amino (cyclohexyl) acetate

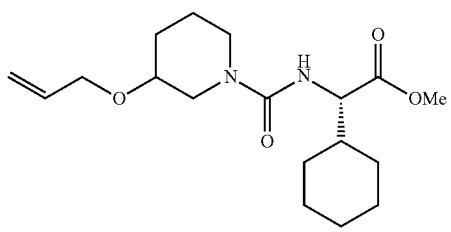 [SMILES: C=CCOC1CCCN(C(=O)N[C@H](C(=O)OC)C2CCCCC2)C1]

A 500-mL round-bottom flask was charged with the product of Step 3 (3.80 g, 19.27 mmol) and THF (50 mL). The product of Step 2 (3.80 g, 19.27 mmol) was added, and the resulting solution stirred for 24 hours at RT. The solvent was removed by evaporation, and the crude product was purified by flash column chromatography (60/40 hexanes/EtOAc), to yield the title compound as a colorless oil. LRMS (M+H)=339.3.

Step 5: (2S)-({[(3R)(3S)-3-(Allyloxy)piperidin-1-yl]carbonyl}amino)(cyclohexyl)acetic acid (Intermediate B29)

A 500-mL round-bottom flask was charged with the product of Step 4 (7.00 g, 20.68 mmol), MeOH (20 mL), and THF (20 mL). LiOH (M, 62.0 mL, 62.0 mmol) was added, and the resulting solution was stirred at RT for 18 hours. The organic solvents were removed under reduced pressure, and the remaining aqueous was poured into 5% K₂SO₄. The mixture was extracted (3×) with EtOAc, the combined organic portions dried with anhydrous MgSO₄, filtered and rotary-evaporated to give the title compound as a white foam/oil. LRMS (M+H)=325.3.

Step 6: (2S)-({[(3S) or (3R)-3-(Allyloxy)piperidin-1-yl]carbonyl}amino)(cyclohexyl) acetic acid (Intermediate B29a) (2S)-({[(3R) and (3S)-3-(allyloxy)piperidin-1-yl]carbonyl}amino) (cyclohexyl) acetic acid (Intermediate B29b)

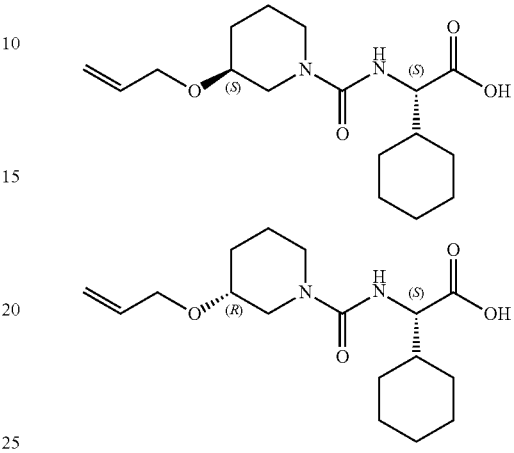

The mixture of diastereomers, (2S)-({[(3R)(3S)-3-(Allyloxy)piperidin-1-yl]carbonyl}amino)(cyclohexyl)acetic acid (4.00 g, 12.33 mmol), was resolved by preparative chiral SFC using a CHIRALPAK AD (2×25 cm, 10μ) with a mobile phase of 80/20 CO₂/MeOH, having a flow rate of 70 mL/minute, and a detector of λ=214 nm. Evaporation of like fractions gave the title compounds as colorless oils. The first eluting diastereomer was (2S)-({[(3S) or (3R)-3-(Allyloxy)piperidin-1-yl]carbonyl}amino)(cyclohexyl) acetic acid (LRMS (M+H)=325.3), and the second eluting diastereomer was (2S)-({[(3R) or (3S)-3-(allyloxy)piperidin-1-yl]carbonyl}amino)(cyclohexyl) acetic acid (LRMS (M+1)=325.3).

Intermediates B30-B34

Intermediates B30-B34 were prepared in a manner similar to that utilized to prepare Intermediate B29.

| Int. | Amino Acid | Alcohol | Structure | Name | LRMS (M + H)⁺ |
|------|------------|---------|-----------|------|---------------|
| B30 | L-cyclopentyl-glycine | N-Boc-(3S)-pyrrolidin-3-ol | 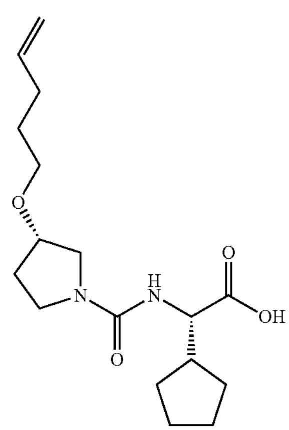 [SMILES: C=CCCCO[C@H]1CCN(C(=O)N[C@H](C(=O)O)C2CCCC2)C1] | (2S)-cyclopentyl({[(3S)-3-(pent-4-en-1-yloxy)pyrrolidin-1-yl]carbonyl}amino)acetic acid | 325.4 |

-continued

| Int. | Amino Acid | Alcohol | Structure | Name | LRMS (M + H)+ |
|---|---|---|---|---|---|
| B31 | L-cyclopentyl-glycine | N-Boc-(3R)-pyrrolidin-3-ol | 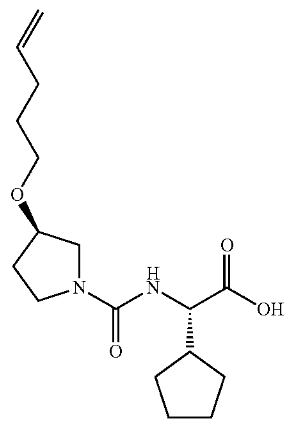 [SMILES: C=CCCCO[C@@H]1CCN(C(=O)N[C@H](C(=O)O)C2CCCC2)C1] | (2S)-cyclopentyl({[(3R)-3-(pent-4-en-1-yloxy)pyrrolidin-1-yl]carbonyl}amino)acetic acid | 325.4 |
| B32 | L-cyclohexyl-glycine | N-Boc-piperidin-4-ol | 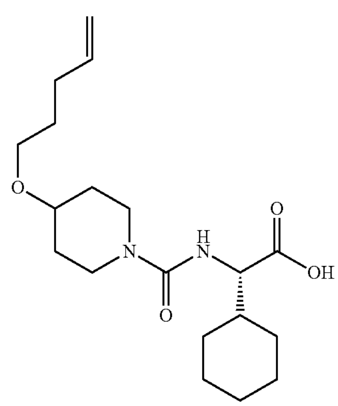 [SMILES: C=CCCCOC1CCN(C(=O)N[C@H](C(=O)O)C2CCCCC2)CC1] | (2S)-cyclohexyl({[4-(pent-4-en-1-yloxy)piperidin-1-yl]carbonyl}amino)acetic acid | 353.3 |
| B33 | L-cyclohexyl-glycine | N-Boc-azetidin-3-ol | 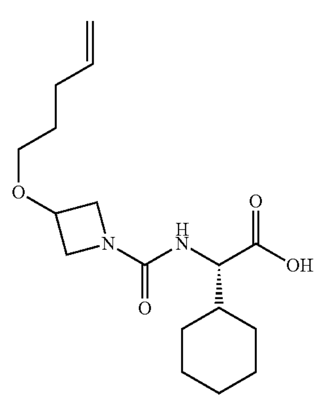 [SMILES: C=CCCCOC1CN(C(=O)N[C@H](C(=O)O)C2CCCCC2)C1] | (2S)-cyclohexyl({[3-(pent-4-en-1-yloxy)azetidin-1-yl]carbonyl}amino)acetic acid | 325.3 |

| Int. | Amino Acid | Alcohol | Structure | Name | LRMS (M + H)+ |
|---|---|---|---|---|---|
| B34 | L-cyclohexyl-glycine | N-Boc-(3S)-pyrrolidin-3-ol | 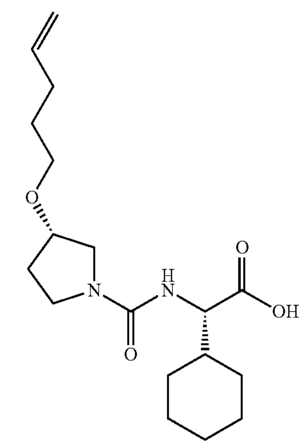 [SMILES: C=CCCCO[C@H]1CCN(C(=O)N[C@H](C(=O)O)C2CCCCC2)C1] | (2S)-cyclohexyl({[(3S)-3-(pent-4-en-1-yloxy)pyrrolidin-1-yl]carbonyl}amino)acetic acid | 339.4 |

Intermediates C

Intermediate C1: 4-Bromo-1-methyl-1H-indole-2-carboxylic acid

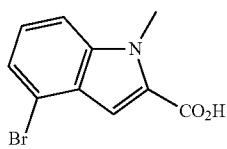

To a solution of 4-bromo-1H-indole-2-carboxylic acid (514 mg, 2.14 mmol) in DMF (16 mL), dimethyl carbonate (4.5 mL, 53.4 mmol) and DABCO (25 mg, 0.214 mmol) was added, and the solution was heated to 120° C. for 7 hours. The reaction was diluted with EtOAc, and the organics were washed with $H_2O$ (2×), 1N HCl (1×), and brine (1×). The organics were dried over $Na_2SO_4$, filtered, concentrated, and the resulting residue was purified on $SiO_2$ (gradient elution, 15-40% EtOAc/hexanes) to yield the intermediate ester as a white solid. MeOH (3 mL), $H_2O$ (1.5 mL) and LiOH monohydrate (3 eq.) were added to a solution of the ester in THF (3 mL), and left to stir for 16 hours. The reaction mixture was concentrated, and the residue was partitioned between EtOAc and 1N HCl, and extracted with EtOAc (2×). The organics were combined, washed with brine (1×), dried over $Na_2SO_4$, filtered, and concentrated to yield the title compound as a white solid. LRMS (M+H)+ Calcd.=254; found 254.

Intermediate C2: 4-Bromo-1H-indole-2-carboxylic acid

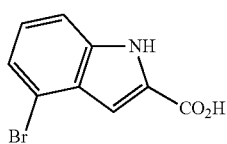 [SMILES: O=C(O)c1cc2c(Br)cccc2[nH]1]

The title compound is commercially available.

Intermediate C3: 8-Bromoimidazo[1,2-a]pyridine-2-carboxylic acid

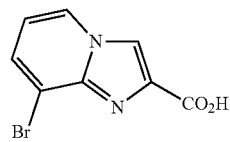 [SMILES: O=C(O)c1cn2cccc(Br)c2n1]

To a solution of 2-amino-3-bromopyridine (7.4 g, 0.0428 mol) in dimethoxyethane (70 mL) under $N_2$, ethylbromopyruvate (9.28 g, 0.0428 mol) was added, and the mixture stirred at RT for 18 hours. The resulting solids were filtered and washed with $Et_2O$, then re-suspended in absolute EtOH (40 mL) and refluxed for 2 hours. The reaction was concentrated to remove EtOH, diluted with $K_2CO_{3(aq.)}$ and extracted with DCM (2×100 mL). The DCM extracts were dried over $Na_2SO_4$, filtered and concentrated to give a foam (9.2 g). The foam was dissolved in THF (230 mL) and treated with 1N NaOH (170 mL, 0.170 mol) at 40° C. for 2 hours. The reaction was cooled to RT, diluted with 1N HCl (170 mL, 0.170 mol) and concentrated to remove the THF (pH of mixture=3.0). The mixture was cooled to 0° C., aged for 30 minutes and filtered. The cake was washed with $H_2O$ (40 mL) and dried under vacuum to give 7.94 g. LRMS (M+H)+241.

Intermediate C4: 5-Bromoimidazo[1,2-a]pyridine-2-carboxylic acid

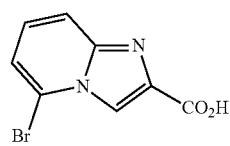 [SMILES: O=C(O)c1cn2c(Br)cccc2n1]

The title compound was prepared in a manner similar to that utilized to prepare 8-bromoimidazo[1,2-a]pyridine-2-carboxylic acid from ethyl 5-bromoimidazo[1,2-a]pyridine-2-carboxylate (ref: WO 91/08211). LRMS (M+H)+241.

Intermediate C5: 4-Bromoindane-2(R,S)-carboxylic acid

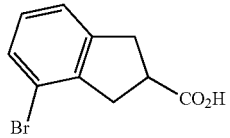 [SMILES: O=C(O)C1Cc2cccc(Br)c2C1]

Diethylmalonate (3.8 mL, 25 mmol) in THF (25 mL) was slowly added to a solution of NaH (60% in mineral oil, 2.1 g, 87 mmol) in THF (20 mL) at 0° C. while under $N_2$. The solution was stirred for 30 minutes at 0° C. and then for 30 minutes at 25° C. The solution was cooled to 0° C. and slowly added to a solution of 1-bromo-2,3-bis(bromomethyl)benzene (8.5 g, 25 mmol) in THF (25 mL), and then warmed and stirred at 25° C. for 2 hours. The reaction mixture was quenched by pouring into 300 mL of 1N HCl and 200 mL of EtOAc/$Et_2O$ while stirring. The mixture was extracted with EtOAc (2×), and the organics were combined washed with brine, dried over $Na_2SO_4$, filtered, and concentrated. The residue was purified on $SiO_2$ (gradient elution, 0-25% EtOAc/hexanes) to yield the di-ester as a clear oil. To a solution of the di-ester (3.4 g, 9.97 mmol) in MeOH (25 mL), 3N NaOH (16.6 mL, 49.8 mmol) was added, and the mixture was warmed to 50° C. for 4 hours. The mixture was then cooled to 25° C. and filtered to yield a white solid (1.54 g). This solid was dissolved in 6M HCl, and the reaction mixture was heated to reflux for 12 hours. The reaction mixture was extracted with EtOAc (2×), combined organics, washed with brine, dried over $MgSO_4$, filtered and concentrated. The title compound was as a tan solid after crystallizing from hot hexanes (548 mg, 9% yield). $^1$H NMR (500 Mhz) ($CDCl_3$) δ 7.32 (d, 1H, J=7.8 Hz), 7.14 (d, 1H, J=7.6 Hz), 7.04 (t, 1H, J=7.6 Hz), 3.43-3.3 (m, 4H).

Intermediate C6: 4-Bromo-1-phenyl-1H-indole-2-carboxylic acid

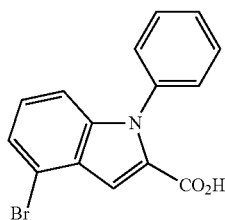 [SMILES: O=C(O)c1cc2c(Br)cccc2n1-c1ccccc1]

To a solution of 4-bromo-1H-indole-2-carboxylic acid (500 mg, 2.08 mmol) in DCM (75 mL), phenylboronic acid (508 mg, 4.17 mmol), copper (II) acetate (757 mg, 4.17 mmol), pyridine (0.337 mL, 4.17 mmol), 4A molecular sieves (3 g), and TEA (0.581 mL, 4.17 mmol) were added. After 15 hours, the mixture was diluted with DCM, filtered through CELITE, and the filtrate was washed with 1N HCl (2×) and brine (1×). The organic layers were dried over $Na_2SO_4$, and the solvent was removed in vacuo. The crude material was purified on $SO_2$ (98/2/0.2/0.2 of DCM/MeOH/HOAc/$H_2O$) to yield the title compound. LRMS ESI$^+$ (M+H)$^+$ 272.2.

Intermediate C7: 3-Bromo-5-(trifluoromethoxy)benzyl methanesulfonate

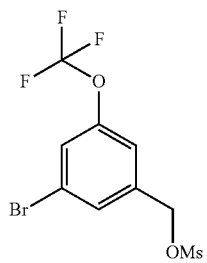 [SMILES: CS(=O)(=O)OCc1cc(Br)cc(OC(F)(F)F)c1]

Step 1: [3-Bromo-5-(trifluoromethoxy)phenyl]methanol

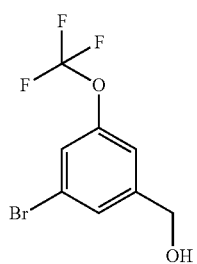 [SMILES: OCc1cc(Br)cc(OC(F)(F)F)c1]

To a solution of LAH (100 mL, 1M in $Et_2O$, 100 mmol) that had been cooled to −70° C., a solution of 3-bromo-5-(trifluoromethoxy)benzoic acid (12.0 g, 42.1 mmol) was added slowly. The mixture was then slowly warmed to RT and stirred overnight. After recooling to −70° C., the reaction was quenched with $H_2O$ (4 mL), 2N NaOH (4 mL), more $H_2O$ (8 mL), and then warmed to RT. The mixture was then filtered through CELITE, $MgSO_4$ was added, and the mixture was filtered again. The solvent was removed in vacuo to yield the title compound as a colorless oil. LRMS ESI$^+$ (M+H)$^+$ 272.2.

Step 2: 3-Bromo-5-(trifluoromethoxy)benzyl methanesulfonate

To a solution of the product from Step 1 (11.4 g, 42.1 mmol) in DCM (100 mL), DIEA (16.0 mL, 92.6 mmol) and MsCl (3.6 mL, 46.3 mmol) were added slowly at 0° C. After 1 hour, the reaction was poured into $KHSO_{4(aq.)}$ and extracted with DCM (3×). The combined organic layers were extracted with brine, dried over $MgSO_4$, and the solvent was removed in vacuo. The crude material was purified on $SiO_2$ (gradient elution, 0-100% EtOAc/hexanes) to yield the title compound as a colorless oil. $^1$H NMR (500 MHz) ($CDCl_3$) δ 7.51 (s, 1H), 7.42 (s, 1H), 7.22 (s, 1H), 5.20 (s, 2H), 3.04 (s, 3H).

Intermediate C8: 3-Chloro-4-phenylpyridin-2-ol

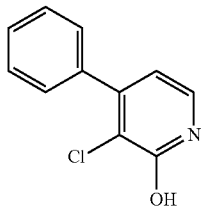 [SMILES: Oc1nccc(-c2ccccc2)c1Cl]

Step 1: 3-Chloro-4-iodopyridine

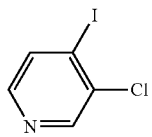

The title compound was prepared according to the following reference: 35 Heterocycles 151-69 (1993). To a solution of DIPA (3.77 mL, 26.4 mmol) in THF (20 mL) under $N_2$ in a dry ice bath, n-BuLi (10.6 mL, 26.4 mmol) was added. The mixture was stirred in an ice bath for 20 minutes, then treated dropwise over 10 minutes with a solution of 3-chloropyridine (2.51 mL, 26.4 mmol) in 5 mL THF, keeping the temperature less than −70° C. The lithiopyridine partially precipitated as a colorless solid in a light orange solution. The mixture was stirred for 30 minutes in a dry ice bath, and then $I_2$ (6.71 g, 26.4 mmol) in 15 mL THF was added, keeping the temperature less then −65° C. The solution was then allowed to warm to 0° C. and was placed in an ice bath for 2 hours, and then poured into 10% $NaHSO_3$ and extracted with ether (150 mL; 3×). The organics were washed with 50 mL each of $NaHSO_3$, $NaHCO_3$, $H_2O$, and brine. The residue was purified on $SiO_2$ (gradient elution, 2-20% EtOAc/hexanes) to give the title compound (3.35 g, 85% pure). This was then recrystallized from hot hexanes plus a few mL of EtOAc to dissolve initially to give the title compound as a white powder (1.95 g). LRMS ESI$^+$ (M+H)$^+$ 240.0.

Step 2: 3-Chloro-4-phenylpyridine

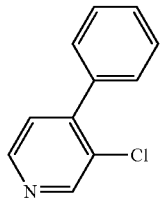 [SMILES: Clc1cnccc1-c1ccccc1]

To a solution of the product from Step 1 (1.3 g, 5.43 mmol), phenylboronic acid (827 mg, 6.79 mmol), $PCy_3$ (228 mg, 0.814 mmol), and $Cs_2CO_3$ (4.25 g, 13.03 mmol) in dioxane (10 mL), $Pd_2(dba)_3$ (497 mg, 0.543 mmol) was added under $N_2$. The mixture was then heated to 95° C. for 18 hours, filtered and extracted with $H_2O$ and EtOAc. The organic layer was dried over $MgSO_4$, and the solvent was removed in vacuo. The residue was purified on $SiO_2$ (gradient elution, 5-30% EtOAc/hexanes) to give the title compound as a colorless oil (1.03 g). LRMS ESI$^+$ (M+H)$^+$ 190.2.

Step 3: 3-Chloro-4-phenylpyridin-2-ol

To a solution of the product from Step 2 (348 mg, 1.83 mmol) in DCM (10 mL), mCPBA (950 mg, 5.51 mmol) was added. After 2 hours, the mixture was extracted with 10% $NaHSO_{3(aq.)}$ and then $NaHCO_3$ and brine. The organic layer was dried over $MgSO_4$, and the solvent was removed in vacuo to give crude 3-chloro-4-phenylpyridine 1-oxide as a white solid (230 mg). This solid was then dissolved in acetic anhydride (1.05 mL, 11.18 mmol) and heated to 150° C. for 18 hours. The residue was purified on $SiO_2$ (gradient elution, 5-30% EtOAc/hexanes) to give 150 mg of 3-chloro-4-phenylpyridin-2-yl acetate, which was dissolved in MeOH (20 mL), combined with $K_2CO_3$ (419 mg, 3.03 mmol) and heated to 65° C. for 10 minutes. The mixture was then filtered, and the solvent was removed in vacuo to yield the title compound (125 mg). LRMS ESI$^+$ (M+H)$^+$ 206.1.

Intermediate C9: 5-Bromo-2-chlorobenzyl methanesulfonate

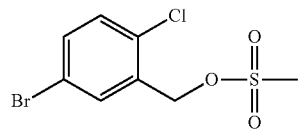

To a solution of (5-bromo-2-chlorophenyl)methanol (1.0 g, 4.52 mmol) in DCM (23 mL), TEA (0.88 mL, 6.32 mmol) and MsCl (0.49 mL, 6.32 mmol) in DCM (10 mL) were added at 0° C. After 4 hours, the mixture was then extracted with $H_2O$, the organic layer was dried over $MgSO_4$, and the solvent was removed in vacuo. The crude material was purified on $SiO_2$ (gradient elution, 0-30% EtOAc/hexanes) to yield the title compound as a white solid (1.03 g). $^1$H NMR (500 MHz) (CDCl$_3$) δ 7.62 (m, 1H), 7.43 (m, 1H), 7.28 (s, 1H), 5.27 (s, 2H), 3.08 (s, 3H) ppm.

Intermediate C10: 3-Bromo-5-methoxybenzyl methanesulfonate

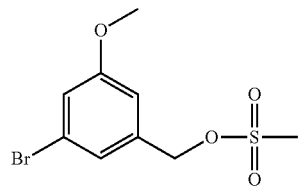

The title compound was prepared according to the procedure given for Intermediate C9 using (3-bromo-5-methoxyphenyl)methanol (ref: 43 J. Med. Chem. 599 (2000)). $^1$H NMR (500 MHz) (CDCl$_3$) δ 7.13 (s, 1H), 7.05 (s, 1H), 6.87 (s, 1H), 5.14 (s, 2H), 3.80 (s, 3H), 2.98 (s, 3H) ppm.

Intermediate C11: Methyl(4R)-4-[(7-methoxy-3-vinylquinolin-2-yl)oxy]-L-prolinate hydrochloride

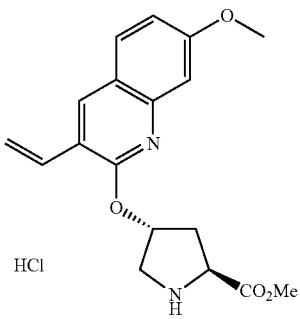 [SMILES: C=Cc1cc2ccc(OC)cc2nc1O[C@H]1CN[C@H](C(=O)OC)C1 ; Cl]

Step 1: 3-Bromo-7-methoxyquinoline 1-oxide

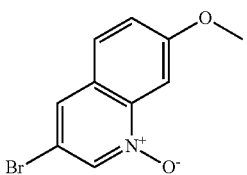

To a solution of 3-bromo-7-methoxyquinoline (2.0 g, 8.40 mmol) in DCM (42 mL) at RT, mCPBA (2.9 g, 16.8 mmol) was added, and the reaction mixture was stirred at RT for 1 hour. A second portion of mCPBA (2.9 g, 16.8 mmol) was then added, and the reaction mixture was stirred at RT for 18 hours. The reaction mixture was poured onto 10% $Na_2SO_{3(aq.)}$ and DCM, and the layers were separated. The organic layer was washed with $NaHCO_3$, dried over $MgSO_4$, filtered and concentrated. The resulting product was used with no further purification. LRMS $(M+H)^+=254.2$.

Step 2: 3-Bromo-7-methoxyquinolin-2(1H)-one

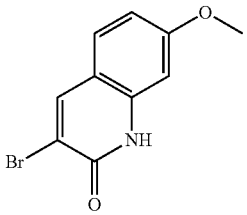

To a solution of 3-bromo-7-methoxyquinoline 1-oxide (2.04 g, 8.03 mmol) in EtOAc (50 mL) and 15% $K_2CO_{3(aq.)}$ (15 mL) at RT, TsCl (1.68 g, 8.83 mmol) was added. The reaction mixture was stirred vigorously at RT for 18 hours, at which time the product was collected by filtration and washed with EtOAc. The solid was dried in vacuo and used with no further purification. LRMS $(M+H)^+=254.1$.

Step 3: 1-t-Butyl 2-methyl (2S,4R)-4-[(3-bromo-7-methoxyquinolin-2-yl)oxy]pyrrolidine-1,2-dicarboxylate

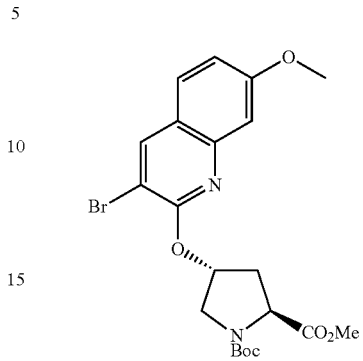

To a solution of 3-bromo-7-methoxyquinolin-2(1H)-one (1.31 g, 5.17 mmol) and 1-t-butyl 2-methyl (2S,4S)-4-{[(4-bromophenyl)sulfonyl]oxy}pyrrolidine-1,2-dicarboxylate (2.0 g, 4.31 mmol) in NMP (21.5 mL), $Cs_2CO_3$ (2.11 g, 6.46 mmol) was added, and the reaction mixture was stirred for 40 hours at 40° C. An additional portion of 1-t-butyl 2-methyl (2S,4S)-4-{[(4-bromophenyl)sulfonyl]oxy}pyrrolidine-1,2-dicarboxylate (1.0 g, 2.16 mmol) was added, and the reaction mixture was stirred at 40° C. for 16 hours. The reaction mixture was cooled and poured onto a mixture of EtOAc and $H_2O$, and the layers were separated. The organic layer was washed with $H_2O$ (2×), $NaHCO_3$ (2×) and brine, dried over $Mg_2SO_4$, filtered and concentrated. The product was used with no further purification. LRMS $(M+H-Boc)^+=381.2$.

Step 4: 1-t-Butyl 2-methyl (2S,4R)-4-[(7-methoxy-3-vinylquinolin-2-yl)oxy]pyrrolidine-1,2-dicarboxylate

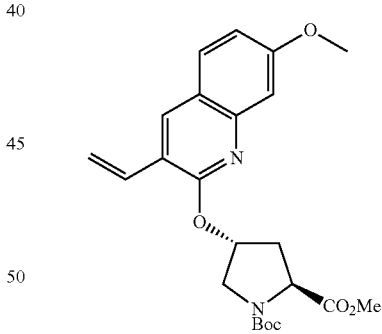

To a solution of 1-t-butyl 2-methyl (2S,4R)-4-[(3-bromo-7-methoxyquinolin-2-yl)oxy]pyrrolidine-1,2-dicarboxylate (2.0 g, 4.2 mmol) in EtOH (30 mL), TEA (0.87 mL, 6.23 mmol) was added. Potassium vinyltrifluoroborate (0.84 g, 6.23 mmol) and dichloro[1,1'-bis(diphenylphosphino)ferrocene]palladium(II) dichloromethane adduct (0.17 g, 0.21 mmol) were then added, and the reaction mixture was stirred at 100° C. for 2 hours. The reaction mixture was worked up with EtOAc and $H_2O$, and the layers were separated. The organic layer was washed with brine, dried over $MgSO_4$, filtered and concentrated. The crude material was purified on $SiO_2$ (gradient elution, 0-40% EtOAc/hexanes) to yield the title compound as an oil.

LRMS $(M+H-tBu)^+=373.3$.

Step 5: Methyl (4R)-4-[(7-methoxy-3-vinylquinolin-2-yl)oxy]-L-prolinate hydrochloride (Intermediate C11)

A solution of 1-t-butyl 2-methyl (2S,4R)-4-[(7-methoxy-3-vinylquinolin-2-yl)oxy]pyrrolidine-1,2-dicarboxylate (0.85 g, 1.98 mmol) in 4M HCl in dioxane (10 mL) was stirred at RT for 2 hours. The reaction mixture was concentrated, and the product was used with no further purification. LRMS (M+H-tBu)$^+$=329.3.

Intermediate C12: Methyl (4R)-4-[(3-vinylquinolin-2-yl)oxy]-L-prolinate hydrochloride

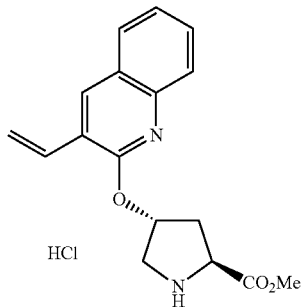 [SMILES: C=Cc1cc2ccccc2nc1O[C@H]1CN[C@H](C(=O)OC)C1 ; Cl]

Intermediate C12 can be prepared according to the procedure described for Intermediate C11 using 3-bromoquinoline instead of 3-bromo-7-methoxyquinoline in Step 1.

Intermediate C13: Methyl (4R)-4-[(2-chloroquinolin-3-yl)oxy]-L-prolinate hydrochloride

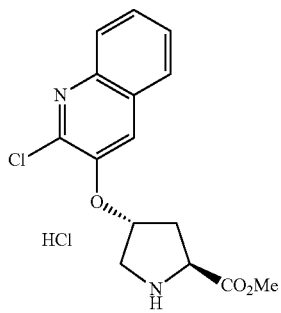 [SMILES: COC(=O)[C@@H]1C[C@@H](Oc2cc3ccccc3nc2Cl)CN1 ; Cl]

Step 1: 2-chloroquinolin-3-ol

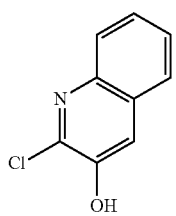

A suspension of 2-chloroquinoline-3-boronic acid (15 g, 72.3 mmol) and NH$_4$Cl (7.16 g, 134 mmol) in Et$_2$O:H$_2$O (600 mL) was treated dropwise with H$_2$O$_{2(aq.)}$ (30%, 62 mL, 709 mmol). The mixture was stirred for 16 hours, then the precipitate was filtered, washed with H$_2$O and Et$_2$O, then dried at 60° C. over P$_2$O$_5$ to afford the title compound (11.5 g, 89%). LCMS (ES+) m/z 180 (M+H)$^+$.

Step 2: 1-t-Butyl 2-methyl (2S,4R)-4-[(2-chloroquinolin-3-yl)oxy]pyrrolidine-1,2-dicarboxylate

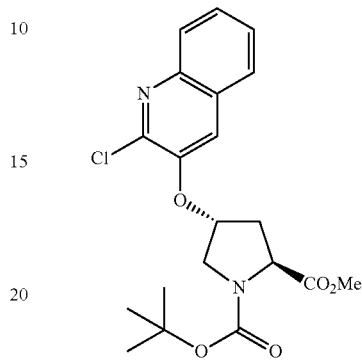

A solution of the 2-chloroquinolin-3-ol (4.00 g, 22.27 mmol), 1-t-butyl 2-methyl (2S,4S)-4-hydroxypyrrolidine-1,2-dicarboxylate (5.74 g, 23.38 mmol) and PPh$_3$ (7.01 g, 26.7 mmol) in anhydrous THF (250 mL) was cooled to 0° C. and treated dropwise with DEAD (4.65 g, 26.7 mmol). The mixture was stirred for 3 hours at 20° C., then treated at 0° C. with further PPh$_3$ (1.75 g, 6.67 mmol) and DEAD (1.16 g, 6.67 mmol). After stirring for 3 hours at 20° C., the mixture was concentrated, and the residue was purified on SiO$_2$ (15% EtOAc/petroleum ether) to furnish the title compound (5.08 g, 56%) as a white solid. LCMS (ES+) m/z 307 (M+H-Boc)$^+$.

Step 3: Methyl (4R)-4-[(2-chloroquinolin-3-yl)oxy]-L-prolinate hydrochloride A solution of 1-t-butyl 2-methyl (2S,4R)-4-[(2-chloroquinolin-3-yl)oxy]pyrrolidine-1,2-dicarboxylate (8.9 g, 21.9 mmol) in HCl/dioxane (4 N, 80 mL) was prepared at 0° C. The mixture was stirred for 1 hour at 0° C., then at 20° C. for 2 hours. Further HCl/dioxane (4N, 10 mL) was added, and the mixture was stirred for 1 hour. Removal of the volatiles and trituration of the residue with Et$_2$O afforded the title compound (7.19 g, 96%) as a solid that was used directly in subsequent steps. LCMS (ES+) m/z 307 (M+H)$^+$.

Intermediate C14: (2S,4R)-4-[(2-bromo-6-methoxyquinolin-3-yl)oxy]-2-(methoxycarbonyl) pyrrolidinium chloride

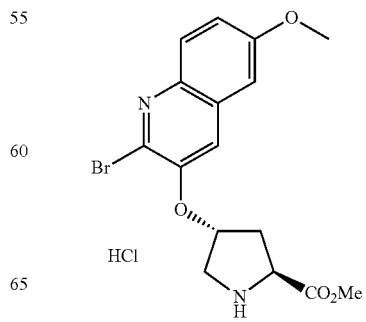

Step 1: 2-Bromo-6-methoxyquinoline

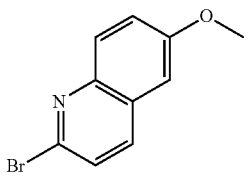

6-Methoxyquinolin-2(1H)-one (6.81 g, 38.9 mmol) was carefully added to POBr$_3$ (18.9 g, 66.1 mmol) at 60° C. and the resulting solution was stirred at 140° C. for 2.5 hours. The reaction mixture was cooled and poured onto crushed ice, and the solid was collected by filtration. Purification of this material on SiO$_2$ (gradient elution, 5-12% EtOAc/petroleum ether) afforded the title compound (4.57 g, 49.3%) as a solid. LCMS (ES+) m/z 238, 240 (M+H)$^+$.

Step 2: (2-Bromo-6-methoxyquinolin-3-yl)boronic acid

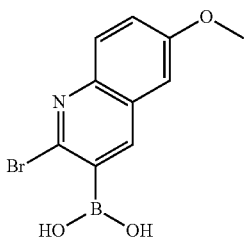 [SMILES: COc1ccc2nc(Br)c(B(O)O)cc2c1]

n-BuLi (1.6 N in hexanes, 14.4 mL, 23.0 mmol) was added at −78° C. to a solution of 2,2,6,6-tetramethylpiperidine (3.11 g, 22.05 mmol) in anhydrous THF (59 mL), and the mixture was then warmed to 0° C. for 30 minutes. The mixture was cooled back to −78° C. and treated with a solution of 2-bromo-6-methoxyquinoline (4.57 g, 19.17 mmol) in THF (14 mL). After stirring for 1 hour, a solution of B(OMe)$_3$ (2.46 mL, 22.05 mmol) in THF (14 mL) was added, and the mixture was maintained at −78° C. for a further 2 hours. A mixture of THF (14 mL) and H$_2$O (3.5 mL) was added, then the solution was warmed to −10° C. and treated with H$_2$O (70 mL) and Et$_2$O (70 mL). NaOH$_{(aq.)}$ (1N, 75 mL) was added, and the aqueous layer was separated and acidified to pH 4 with HCl$_{(aq.)}$ (3N). The aqueous phase was extracted with Et$_2$O, and the combined extracts were washed with brine and dried over Na$_2$SO$_4$. Filtration and removal of the volatiles afforded the title compound (4.64 g, 86% yield) as an oily solid that was used directly in the subsequent step. LCMS (ES+) m/z 282, 284 (M+H)$^+$.

Step 3: 2-Bromo-6-methoxyquinolin-3-ol

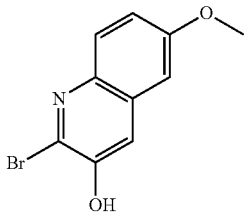

H$_2$O$_{2(aq.)}$ (30%, 32.8 mL, 321 mmol) was added dropwise to a stirred solution of (2-bromo-6-methoxyquinolin-3-yl)boronic acid (4.64 g, 16.45 mmol) and NH$_4$Cl (3.29 g, 61.5 mmol) in Et$_2$O (82 mL) and H$_2$O (82 mL). After 13 hours, NH$_4$Cl (3.29 g, 61.5 mmol) and H$_2$O$_{2(aq.)}$ (30%, 32.8 mL, 321 mmol) were added, and the mixture was stirred for 48 hours. The precipitate was collected and washed with H$_2$O, then dried at 50° C. to afford the title compound (4.18 g, 100%) as a solid that was used directly in the subsequent step. LCMS (ES+) m/z 254, 256 (M+H)$^+$.

Step 4: 1-t-Butyl 2-methyl (2S,4R)-4-[(2-bromo-6-methoxyquinolin-3-yl)oxy]pyrrolidine-1,2-dicarboxylate

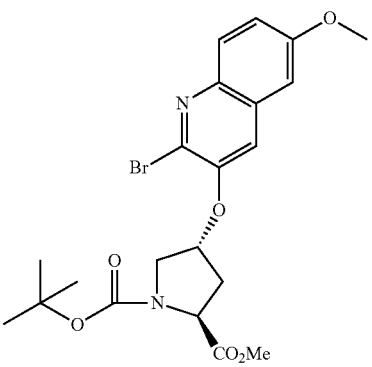 [SMILES: COC(=O)[C@@H]1C[C@@H](Oc2cc3cc(OC)ccc3nc2Br)CN1C(=O)OC(C)(C)C]

Cs$_2$CO$_3$ (10.7 g, 32.9 mmol) was added to a stirred mixture of 1-t-butyl 2-methyl (2S,4S)-4-{[(4-bromophenyl)sulfonyl]oxy}pyrrolidine-1,2-dicarboxylate (8.78 g, 18.9 mmol) and 2-bromo-6-methoxyquinolin-3-ol (4.18 g, 16.45 mmol) in NMP (46 mL). The resulting mixture was stirred at 50° C. for 3 hours, then cooled and diluted with EtOAc. The organics were washed with saturated NaHCO$_{3(aq.)}$, H$_2$O and brine, then dried over Na$_2$SO$_4$. Filtration and removal of the volatiles gave a residue that was purified by column chromatography on SiO$_2$ (gradient elution, 1-100% EtOAc/petroleum ether) to give the title compound (5.56 g, 70.2%). LCMS (ES+) m/z 481, 483 (M+H)$^+$.

Step 5: (2S,4R)-4-[(2-bromo-6-methoxyquinolin-3-yl)oxy]-2-(methoxycarbonyl)pyrrolidinium chloride A solution of 1-t-butyl 2-methyl (2S,4R)-4-[(2-bromo-6-methoxyquinolin-3-yl)oxy]pyrrolidine-1,2-dicarboxylate (5.01 g, 10.40 mmol) in HCl/dioxane (4 N, 31 ml) was prepared at 0° C., and the mixture was stirred at 20° C. for 40 minutes. The volatiles were evaporated, and the residue was triturated with Et$_2$O to afford an approximately 1:1 mixture of the title compound and (2S,4R)-4-[(2-chloro-6-methoxyquinolin-3-yl)oxy]-2-(methoxycarbonyl) pyrrolidinium chloride (4.34 g) as a solid that was used directly in subsequent steps. LCMS (ES+) m/z 381, 383 (M+H)$^+$.

Intermediate C15: (2S,4R)-4-[(3-chloroquinoxalin-2-yl)oxy]-2-(methoxycarbonyl)pyrrolidinium chloride

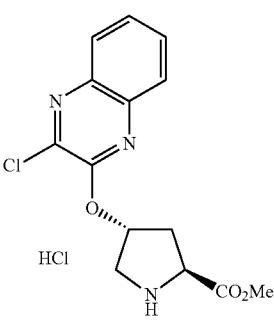 [SMILES: COC(=O)[C@@H]1C[C@@H](Oc2nc3ccccc3nc2Cl)CN1 ; Cl]

Step 1: 1-t-Butyl 2-methyl (2S,4R)-4-[(3-chloroquinoxalin-2-yl)oxy]pyrrolidine-1,2-dicarboxylate

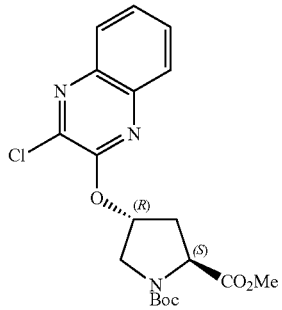

A solution of 3-chloroquinoxalin-2-ol (1.44 g, 7.97 mmol) and 1-t-butyl 2-methyl (2S,4S)-4-hydroxypyrrolidine-1,2-dicarboxylate (2.05 g, 8.37 mmol) in THF (190 ml) was cooled to 0° C., then treated with PPh$_3$ (2.51 g, 9.57 mmol). DIAD (1.86 ml, 9.57 mmol) was added dropwise, and the mixture was stirred at 20° C. for 1 hour. After evaporation of the volatiles, the residue was purified on SiO$_2$ (gradient elution, 0-70% EtOAc/petroleum ether) to afford the title compound (2.5 g, 77%). LCMS (ES+) m/z 408 (M+H)$^+$.

Step 2: (2S,4R)-4-[(3-chloroquinoxalin-2-yl)oxy]-2-(methoxycarbonyl)pyrrolidinium chloride A solution of 1-t-butyl 2-methyl (2S,4R)-4-[(3-chloroquinoxalin-2-yl)oxy]pyrrolidine-1,2-dicarboxylate (1.05 g, 2.57 mmol) in HCl/dioxane (4 N, 5 mL) was prepared at 0° C., then stirred for 2 hours at 20° C. The reaction mixture was concentrated to afford a residue that was triturated with Et$_2$O to afford the title compound (0.88 g, 98%) as a white solid that was used directly in subsequent reactions. LCMS (ES+) m/z 308 (M+H)$^+$.

Intermediate C16: Methyl (4R)-4-[(2-bromo-6-chloroquinolin-3-yl)oxy]-L-prolinate hydrochloride

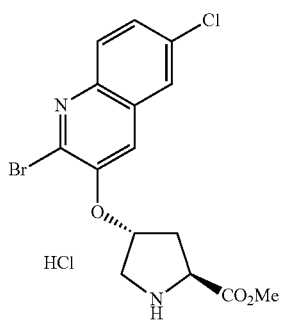 [SMILES: COC(=O)[C@@H]1C[C@@H](Oc2cc3cc(Cl)ccc3nc2Br)CN1 ; Cl]

Step 1: 2-Bromo-6-chloroquinolin-3-yl)boronic acid

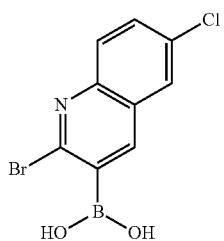 [SMILES: OB(O)c1cc2cc(Cl)ccc2nc1Br]

A solution of 2,2,6,6-tetramethylpiperidine (1.34 g, 9.52 mmol) in THF (25 mL) was cooled to −78° C. and treated with BuLi (6.21 mL, 1.6N in hexanes, 9.93 mmol). The mixture was warmed to 0° C. for 30 minutes, then cooled back to −78° C. A solution of 2-bromo-6-chloroquinoline (2.01 g, 8.28 mmol) in THF (6 mL) was added dropwise, and the mixture was stirred for 1 hour. A solution of B(OMe)$_3$ (0.99 g, 9.52 mmol) in THF (6 ml) was added dropwise, and the resulting mixture was maintained at −78° C. for 2 hours. The reaction was quenched by addition of a 4:1 mixture of THF:H$_2$O (7.5 mL), then the mixture was warmed to −10° C. and diluted with H$_2$O and Et$_2$O. NaOH$_{(aq.)}$ (1N, 75 mL) was added, and then the aqueous layer was separated and acidified to pH 4 by addition of HCl$_{(aq.)}$ (3N). The mixture was extracted with Et$_2$O, and the organic phase was washed with brine and dried over Na$_2$SO$_4$. Removal of volatiles afforded the title compound as an oil that was used directly in the subsequent step (2.04 g, 86%). LCMS (ES+) m/z 258.1, 260.1 (M+H)$^+$.

Step 2: 2-Bromo-6-chloroquinolin-3-ol

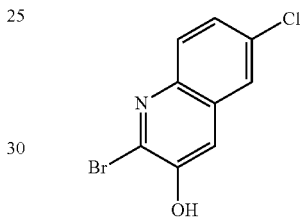

A mixture of 2-bromo-6-chloroquinolin-3-yl)boronic acid (2.04 g, 7.11 mmol) and NH$_4$Cl (0.71 g, 13.30 mmol) in a 1:1 mixture of H$_2$O:Et$_2$O (55 mL) was treated dropwise with H$_2$O$_{2(aq.)}$ (30%, 7.10 mL). The mixture was stirred at 20° C., and further portions of H$_2$O$_{2(aq.)}$ (30%, 7.10 mL) were added after 3 hours and after 24 hours. The reaction was judged complete after 48 hours, and the mixture was extracted with EtOAc. The organic layer was washed with brine and dried over Na$_2$SO$_4$. Filtration and removal of the volatiles afforded the title compound (1.52 g, 83%) as a solid. $^1$H NMR (300 MHz, DMSO-d$_6$) δ 11.41 (s, 1H), 8.04 (s, 1H), 7.88 (d, J=8.9 Hz, 1H), 7.62 (s, 1H), 7.56 (d, J=8.9 Hz, 1H).

Step 3: Methyl (4R)-4-[(2-bromo-6-chloroquinolin-3-yl)oxy]-L-prolinate

Cs$_2$CO$_3$ (2.27 g, 6.96 mmol) was added to a stirred solution of 1-t-butyl 2-methyl (2S,4S)-4-{[(4-bromophenyl)sulfonyl]oxy}pyrrolidine-1,2-dicarboxylate (1.62 g, 3.48 mmol) and 2-bromo-6-methoxyquinolin-3-ol (0.90 g, 3.48 mmol) in NMP (46 mL). The resulting mixture was stirred at 50° C. for 3 hours, then cooled and diluted with EtOAc and saturated NaHCO$_{3(aq.)}$. The organic phase was separated, washed with H$_2$O and brine, then dried over Na$_2$SO$_4$. Filtration and removal of the volatiles gave a residue that was taken up in DCM (22 mL) then treated with TFA (4.5 mL). The resulting solution was stirred for 1 hour, then diluted with saturated NaHCO$_{3(aq.)}$. The organic layer was separated, washed with brine and dried over Na$_2$SO$_4$. Filtration and removal of the volatiles afforded the title compound (0.67 g, 81%) as a solid that was used directly in subsequent reactions. LCMS (ES+) m/z 385.0, 387.0 (M+H)$^+$.

Intermediate C17: Methyl(4R)-4-[(3-but-3-en-1-yl-7-methoxyquinoxalin-2-yl)oxy]-L-prolinate hydrochloride

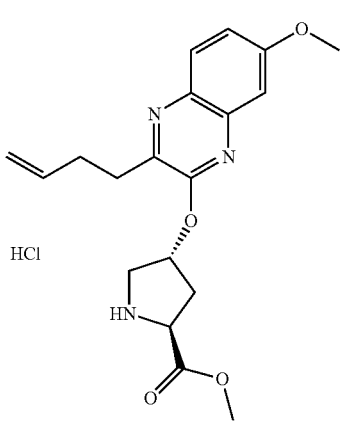 [SMILES: C=CCCc1nc2ccc(OC)cc2nc1O[C@H]1CN[C@H](C(=O)OC)C1 ; Cl]

Step 1: 1-t-Butyl 2-methyl (2S,4R)-4-[(3-but-3-en-1-yl-7-methoxyquinoxalin-2-yl)oxy]pyrrolidine-1,2-dicarboxylate

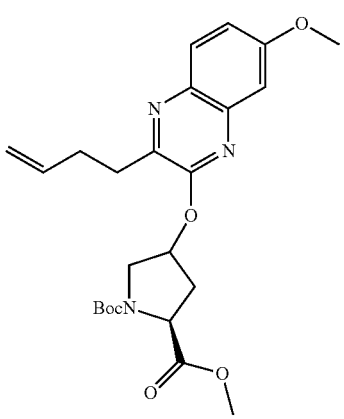 [SMILES: C=CCCc1nc2ccc(OC)cc2nc1OC1C[C@@H](C(=O)OC)N(C(=O)OC(C)(C)C)C1]

Ethyl 2-oxohex-5-enoate (1.130 g, 7.24 mmol) and 4-methoxybenzene-1,2-diamine (1 g, 7.24 mmol) were dissolved in EtOH (24.1 mL), and the resulting mixture was heated to 50° C. for 1 hour. The mixture was cooled and concentrated under reduced pressure to give a solid that was taken up in NMP (18 ml). This solution was treated with 1-t-butyl 2-methyl (2S,4S)-4-{[(4-bromophenyl)sulfonyl]oxy}pyrrolidine-1,2-dicarboxylate (3.23 g, 6.95 mmol) and $Cs_2CO_3$ (3.40 g, 10.42 mmol). The resulting mixture was stirred at 60° C. for 12 hours and then cooled and diluted with EtOAc and $HCl_{(aq.)}$ (1 N). The organic phase was separated and washed with $HCl_{(aq.)}$ (1N), saturated $NaHCO_3$ $_{(aq.)}$ and brine. The dried organics ($Na_2SO_4$) were concentrated to give a residue containing a mixture of isomers that was purified on $SO_2$ (15% EtOAc/petroleum ether) to give the title compound (0.57 g, 17%) as a solid. LCMS (ES+) m/z 458.3 (M+H)$^+$.

Step 2: Methyl(4R)-4-[(3-but-3-en-1-yl-7-methoxyquinoxalin-2-yl)oxy]-L-prolinate hydrochloride The product of Step 1 was treated as described for Intermediate C15, Step 2, to afford the title compound (98%) as a solid. LCMS (ES+) m/z 358.3 (M+H)$^+$.

Intermediate C18: Methyl (4R)-4-[(2-bromo-6-methoxy-1,5-naphthyridin-3-yl)oxy]-L-prolinate

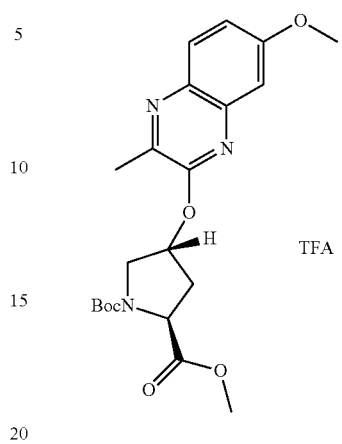

2-Bromo-6-methoxy-1,5-naphthyridine was treated according to the procedures described for Intermediate C15, Steps 1-3, to afford the title compound (11%) as a solid. LCMS (ES+) m/z 480.2 (M+H)$^+$.

Intermediate C19: (2S,4R)-4-[(3-Bromo-2-naphthyl)oxy]-2-(methoxycarbonyl)pyrrolidinium chloride

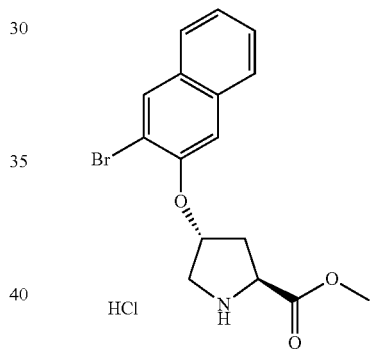

Intermediate C19 can be prepared according to the procedure described for Intermediate C14, Steps 4-5, using 3-bromo-2-naphthol instead of 2-bromo-6-methoxyquinolin-3-ol. LCMS (ES) m/z 350.4 (M+H)$^+$.

Intermediate C20: (2S,4R)-4-[(3-Bromo-1,8-naphthyridin-2-yl)oxy]-2-(methoxycarbonyl)pyrrolidinium chloride

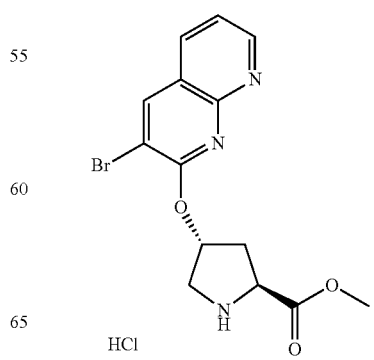

Step 1: Methyl 2-hydroxy-1,8-naphthyridine-3-carboxylate

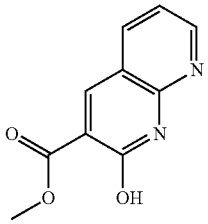

A solution of 30 wt % NaOMe in MeOH (27.9 g, 155 mmol) was added to a solution of 2-aminonicotinaldehyde (5 g, 40.9 mmol) and dimethyl malonate (8.11 g, 61.4 mmol) in MeOH (200 mL). The yellow suspension was stirred for 3 days, and the yellow solids were filtered, suspended in $H_2O$, filtered and washed with MeOH. The crude product (5.30 g) was taken crude onto the next step. M+H=204.9.

Step 2: 2-Hydroxy-1,8-naphthyridine-3-carboxylic acid

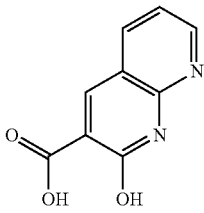 [SMILES: O=C(O)c1cc2cccnc2nc1O]

A mixture of the product of Step 1 (5.30 g, 26.0 mmol) and LiOH (3.11 g, 130 mmol) were heated at 65° C. and stirred in THF/$H_2O$ (20 mL each) for 2 hours. The reaction was cooled, and the white precipitate filtered and washed with $H_2O$ and THF. The solids were dried in vacuo, giving the desired product (4.94 g). M+H=190.9.

Step 3: 3-Bromo-1,8-naphthyridin-2-ol

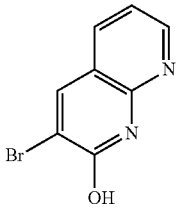 [SMILES: Oc1nc2ncccc2cc1Br]

A solution of bromine (3.78 g, 23.7 mmol) in pyridine (4 mL) and DMF (8 mL) was added to the product of Step 2 (450 mg, 2.37 mmol) and heated at 105° C. for 1 hour. The reaction was cooled; $H_2O$ was added, and the mixture filtered. The filtrate was extracted with EtOAc (2×). The organic layers washed with brine and saturated $NH_4Cl_{(aq.)}$ and dried over $Na_2SO_4$. The solvent was concentrated in vacuo, and the resulting gum was triturated with DCM, and filtered to give a brown solid (156 mg) as desired product. M+H=224.9.

Step 4: (2S,4R)-4-[(3-Bromo-1,8-naphthyridin-2-yl)oxy]-2-(methoxycarbonyl)pyrrolidinium chloride Intermediate C20 can be prepared according to the procedure described for Intermediate C14, Steps 4-5, using 3-bromo-1,8-naphthyridin-2-ol instead of 2-bromo-6-methoxyquinolin-3-ol. LCMS (ES) m/z 350.4 $(M+H)^+$.

Intermediate C21: (2S,4R)-4-[(3-Bromo-1,6-naphthyridin-2-yl)oxy]-2-(methoxycarbonyl) pyrrolidinium chloride

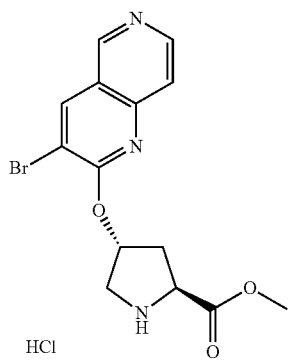 [SMILES: COC(=O)[C@@H]1C[C@@H](Oc2nc3ccncc3cc2Br)CN1 ; Cl]

Intermediate C21 can be prepared according to the procedure described for Intermediate C20, using 4-aminonicotinaldehyde instead of 2-aminonicotinaldehyde. LCMS (ES) m/z 353.5 $(M+H)^+$.

Intermediate C22: (2S,4R)-4-[(3-Bromo-1,5-naphthyridin-2-yl)oxy]-2-(methoxycarbonyl) pyrrolidinium chloride

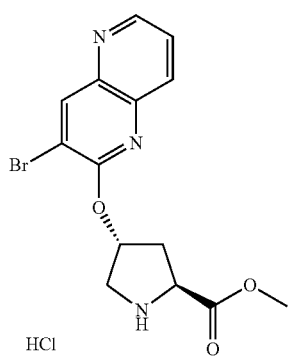 [SMILES: COC(=O)[C@@H]1C[C@@H](Oc2nc3cccnc3cc2Br)CN1 ; Cl]

Intermediate C22 can be prepared according to the procedure described for Intermediate C20, using 5-aminonicotinaldehyde instead of 2-aminonicotinaldehyde. LCMS (ES) m/z 353.5 $(M+H)^+$.

Intermediate C23: (2S,4R)-4-[(3-bromo-1,7-naph-thyridin-2-yl)oxy]-2-(methoxycarbonyl) pyrrolidinium chloride

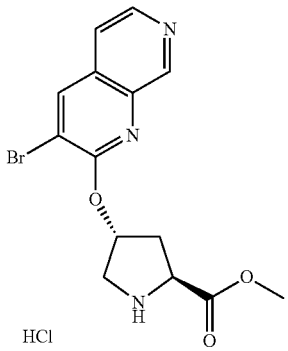 [SMILES: COC(=O)[C@@H]1C[C@@H](Oc2nc3cnccc3cc2Br)CN1 ; Cl]

Intermediate C22 can be prepared according to the procedure described for Intermediate C20, using 3-aminonicotinaldehyde instead of 2-aminonicotinaldehyde. LCMS (ES) m/z 353.5 (M+H)+.

Example 1

(2R,4S,7S,16E)-7-t-Butyl-N-((1R,2S)-1-{[(cyclopropylsulfonyl)amino]carbonyl}-2-vinylcyclopropyl)-6,9-dioxo-3,4,6,7,8,9,12,13,14,15-decahydro-2H,11H-2,5-methanopyrido[2,3-k][1,10,3,6]dioxadiazacyclononadecine-4-carboxamide

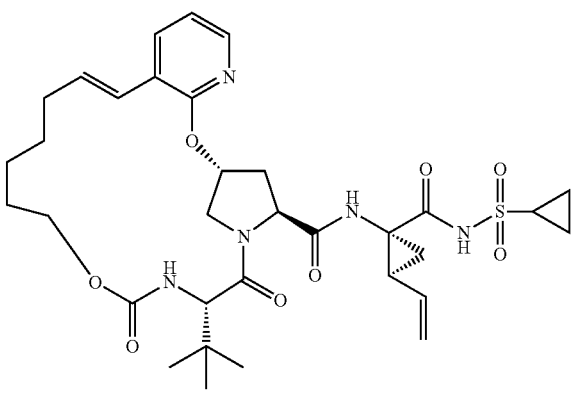 [SMILES: C=C[C@@H]1C[C@]1(NC(=O)[C@@H]1C[C@@H]2CN1C(=O)[C@H](C(C)(C)C)NC(=O)OCCCCC/C=C/c1cccnc1O2)C(=O)NS(=O)(=O)C1CC1]

Step 1: 1-t-Butyl 2-methyl (2S,4R)-4-[(3-bromopyridin-2-yl)oxy]pyrrolidine-1,2-dicarboxylate

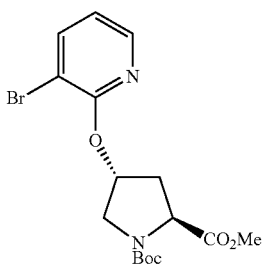 [SMILES: COC(=O)[C@@H]1C[C@@H](Oc2ncccc2Br)CN1C(=O)OC(C)(C)C]

To a solution of 1-t-butyl 2-methyl (2S,4S)-4-{[(4-bromophenyl)sulfonyl]oxy}pyrrolidine-1,2-dicarboxylate (1.718 g, 3.70 mmol) and 3-bromopyridin-2-ol (0.773 g, 4.44 mmol) in NMP (18.50 mL) under N₂, Cs₂CO₃ (1.808 g, 5.55 mmol) was added. The mixture was then heated to 40° C. After 17 hours, the reaction was complete, and H₂O and EtOAc were added. The organic layer was then extracted with H₂O (3×), NaHCO₃ (2×) and brine (2×). The organic layer was dried over MgSO₄, and the solvent was removed in vacuo. The crude product was purified on SiO₂ (gradient elution, 0-40% EtOAc/hexanes) to yield 1.04 g of the title compound. LRMS ESI+ ((M-Boc)+H)+ 301.2.

Step 2: 1-t-Butyl 2-methyl (2S,4R)-4-[(3-vinylpyridin-2-yl)oxy]pyrrolidine-1,2-dicarboxylate

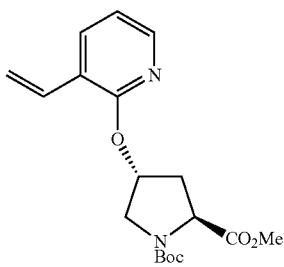 [SMILES: C=Cc1cccnc1O[C@@H]1C[C@@H](C(=O)OC)N(C(=O)OC(C)(C)C)C1]

To a solution of a portion of the product from Step 1 (1.0 g, 2.49 mmol) in EtOH (25 mL), TEA (0.52 mL, 3.74 mmol), potassium vinyltrifluoroborate (0.50 g, 3.74 mmol) and PdCl₂(dppf)-DCM complex (0.102 g, 0.125 mmol) were added. The mixture was then heated to reflux for 17 hours. The EtOH was removed in vacuo, taken up in EtOAc, and washed with H₂O. The organic layer was then dried over MgSO₄, and the solvent was removed in vacuo. The crude product was purified on SiO₂ (gradient elution, 0-40% EtOAc/hexanes) to yield 565 mg of the title compound. LRMS ESI+ ((M-Boc)+H)+ 249.2.

Step 3: Methyl (4R)-4-[(3-vinylpyridin-2-yl)oxy]-L-prolinate hydrochloride

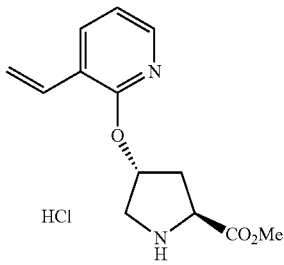 [SMILES: C=Cc1cccnc1O[C@H]1CN[C@H](C(=O)OC)C1 ; Cl]

A portion of the product from Step 2 (360 mg, 1.0 mmol) was dissolved in 4M HCl in dioxane (12.9 mL, 51.6 mmol). After 1 hour, the solvent was removed in vacuo, Et₂O (50 mL) was added, and the solvent was removed in vacuo again to yield 294 mg of the title compound. LRMS ESI+ (M+H)+ 249.3.

Step 4: Methyl N-[(hept-6-en-1-yloxy)carbonyl]-3-methyl-L-valyl-(4R)-4-[(3-vinylpyridin-2-yl)oxy]-L-prolinate

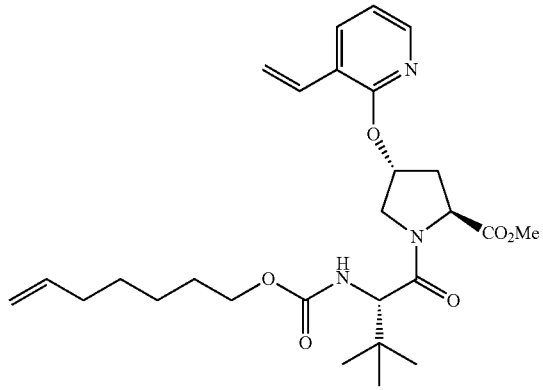 [SMILES: C=CCCCCCOC(=O)N[C@H](C(=O)N1C[C@H](Oc2ncccc2C=C)C[C@H]1C(=O)OC)C(C)(C)C]

To a solution of the product from Step 3 (294 mg, 1.0 mmol) in DMF (10 mL) was added Intermediate B7 (336 mg, 1.24 mmol), DIEA (0.72 mL, 4.13 mmol), and HATU (550 mg, 1.48 mmol). After 1 hour, the mixture was extracted with H$_2$O and EtOAc. The organic layer was washed with H$_2$O and brine, and then dried over MgSO$_4$. The solvent was removed in vacuo, and the crude product was purified on SiO$_2$ (gradient elution, 0-40% EtOAc/hexanes) to yield 453 mg of the title compound. LRMS ESI$^+$ (M+H)$^+$ 502.4.

Step 5: Methyl (2R,4S,7S,16E)-7-t-butyl-6,9-dioxo-3,4,6,7,8,9,12,13,14,15-decahydro-2H,11H-2,5-methanopyrido[2,3-k][1,10,3,6]dioxadiazacyclononadecine-4-carboxylate

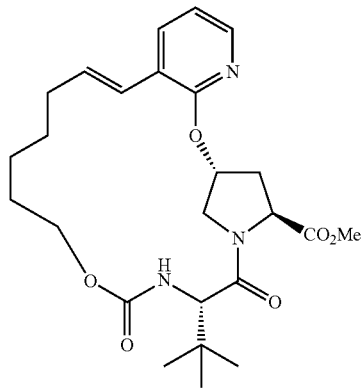 [SMILES: COC(=O)[C@@H]1C[C@@H]2CN1C(=O)[C@H](C(C)(C)C)NC(=O)OCCCCC/C=C/c1cccnc1O2]

To a solution of a portion of the product from Step 4 (450 mg, 0.90 mmol) in DCM (179 mL), the Zhan 1b catalyst (79 mg, 0.11 mmol) was added. After 16 hours, the reaction was concentrated in vacuo, and the crude product was purified on SiO$_2$ (gradient elution, 0-45% EtOAc/hexanes) to yield 396 mg of the title compound. LRMS ESI$^+$ (M+H)$^+$ 474.3.

Step 6: (2R,4S,7S,16E)-7-t-Butyl-6,9-dioxo-3,4,6,7,8,9,12,13,14,15-decahydro-2H,11H-2,5-methanopyrido[2,3-k][1,10,3,6]dioxadiazacyclononadecine-4-carboxylic acid

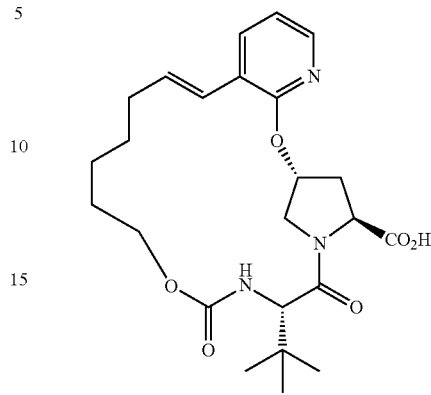

To a solution of a portion of the product from Step 5 (200 mg, 0.42 mmol) in THF (1.5 mL), MeOH (1.5 mL) and H$_2$O (0.75 mL), LiOH.H$_2$O (177 mg, 4.22 mmol) was added. After 1 hour, 1N HCl and Et$_2$O were added. The organic layer was separated, and the aqueous layer was washed with EtOAc. The combined organic layers were then dried over MgSO$_4$, and the solvent was removed in vacuo to yield 194 mg of the title compound. LRMS ESI$^+$ (M+H)$^+$460.3.

Step 7: (2R,4S,7S,16E)-7-t-Butyl-N-((1R,2S)-1-{[(cyclopropylsulfonyl)amino]carbonyl}-2-vinylcyclopropyl)-6,9-dioxo-3,4,6,7,8,9,12,13,14,15-decahydro-2H,11H-2,5-methanopyrido[2,3-k][1,10,3,6]dioxadiazacyclononadecine-4-carboxamide To a solution of a portion of the product from Step 6 (100 mg, 0.218 mmol) in DMF (2.2 mL), Intermediate A1 (70 mg, 0.26 mmol), DIEA (0.114 mL, 0.65 mmol), and HATU (108 mg, 0.283 mmol) were added. After 15 minutes, the mixture was partitioned between EtOAc and 1N HCl. The organic layer was separated, dried over MgSO$_4$, and the solvent was removed in vacuo. The crude product was purified on SiO$_2$ (gradient elution, 0-70% EtOAc/hexanes) to yield 129 mg of the title compound. LRMS ESI$^+$ (M+H)$^+$ 672.4.

Example 2

(2R,4S,7S,16E)-7-t-Butyl-N-((1R,2R)-1-{[(cyclopropylsulfonyl)amino]carbonyl}-2-ethylcyclopropyl)-6,9-dioxo-3,4,6,7,8,9,12,13,14,15-decahydro-2H,11H-2,5-methanopyrido[2,3-k][1,10,3,6]dioxadiazacyclononadecine-4-carboxamide

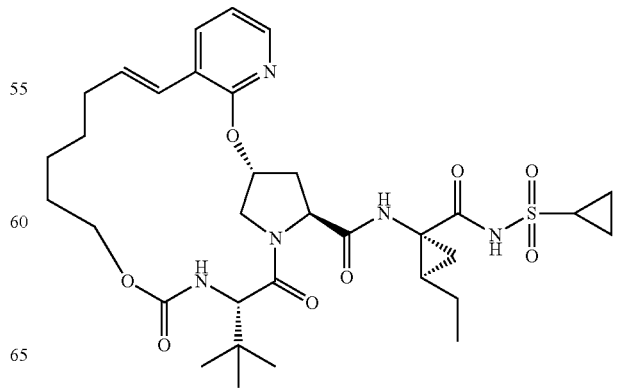

To a solution of a portion of the product from Example 1, Step 6 (90 mg, 0.196 mmol) in DMF (2.2 mL), Intermediate A3 (63 mg, 0.235 mmol), DIEA (0.137 mL, 0.78 mmol), and HATU (97 mg, 0.255 mmol) was added. After 1 hour, the mixture was partitioned between EtOAc and 1N HCl. The organic layer was separated, dried over MgSO₄, and the solvent was removed in vacuo. The crude product was purified on SiO₂ (gradient elution, 0-70% EtOAc/hexanes) to yield 110 mg of the title compound. LRMS ESI⁺ (M+H)⁺ 674.4.

Example 3

(2R,4S,7S)-7-t-Butyl-N-((1R,2S)-1-{[(cyclopropyl-sulfonyl)amino]carbonyl}-2-vinylcyclopropyl)-6,9-dioxo-3,4,6,7,8,9,12,13,14,15,16,17-dodecahydro-2H,11H-2,5-methanopyrido[2,3-k][1,10,3,6]dioxadiazacyclononadecine-4-carboxamide

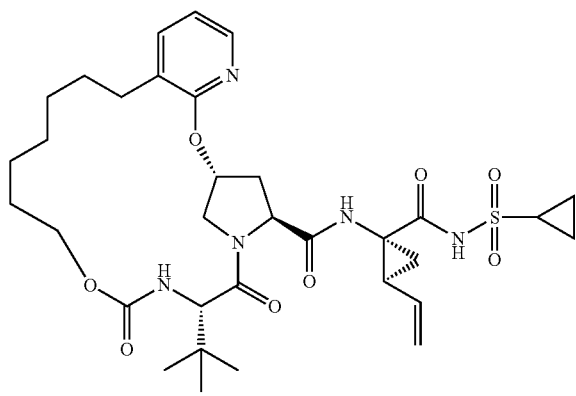 [SMILES: C=C[C@@H]1C[C@]1(NC(=O)[C@@H]1C[C@@H]2CN1C(=O)[C@H](C(C)(C)C)NC(=O)OCCCCCCCc1cccnc1O2)C(=O)NS(=O)(=O)C1CC1]

Step 1: Methyl (2R,4S,7S)-7-t-butyl-6,9-dioxo-3,4,6,7,8,9,12,13,14,15,16,17-dodecahydro-2H, 11H-2,5-methanopyrido[2,3-k][1,10,3,6]dioxadiazacyclononadecine-4-carboxylate

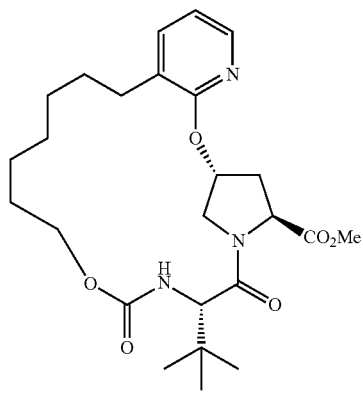 [SMILES: COC(=O)[C@@H]1C[C@@H]2CN1C(=O)[C@H](C(C)(C)C)NC(=O)OCCCCCCCc1cccnc1O2]

To a solution of a portion of the product from Example 1, Step 5 (200 mg, 0.422 mmol) in EtOAc (4.5 mL), 10% Pd/C (22.5 mg, 0.021 mmol) was added. The mixture was then place under H₂, stirred for 17 hours, and filtered through a pad of glass wool. The solvent was then removed in vacuo to yield 195 mg of the title compound. LRMS ESI⁺ (M+H)⁺ 476.4.

Step 2: (2R,4S,7S)-7-t-Butyl-6,9-dioxo-3,4,6,7,8,9,12,13,14,15,16,17-dodecahydro-2H,11H-2,5-methanopyrido[2,3-k][1,10,3,6]dioxadiazacyclononadecine-4-carboxylic acid

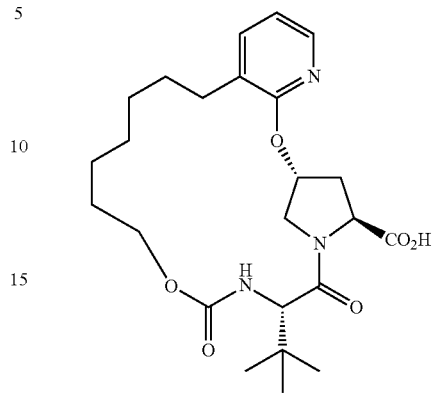

To a solution of a portion of the product from Step 1 (190 mg, 0.40 mmol) in THF (1.5 mL), MeOH (1.5 mL) and H₂O (0.75 mL) LiOH.H₂O (168 mg, 4.0 mmol) was added. After 1 hour, 1N HCl and Et₂O were added. The organic layer was separated, and the aqueous layer was washed with EtOAc. The combined organic layers were then dried over MgSO₄, and the solvent was removed in vacuo to yield 184 mg of the title compound. LRMS ESI⁺ (M+H)⁺462.3.

Step 3: (2R,4S,7S)-7-t-Butyl-N-((1R,2S)-1-{[(cyclopropylsulfonyl)amino]carbonyl}-2-vinylcyclopropyl)-6,9-dioxo-3,4,6,7,8,9,12,13,14,15,16,17-dodecahydro-2H,11H-2,5-methanopyrido[2,3-k][1,10,3,6]dioxadiazacyclononadecine-4-carboxamide To a solution of a portion of the product from Step 2 (93 mg, 0.201 mmol) in DMF (2.0 mL), Intermediate A1 (64.5 mg, 0.242 mmol), DIEA (0.141 mL, 0.81 mmol), and HATU (100 mg, 0.262 mmol) were added. After 1 hour, the mixture was partitioned between EtOAc and 1N HCl. The organic layer was separated, dried over MgSO₄, and the solvent was removed in vacuo. The crude product was purified on SiO₂ (gradient elution, 0-70% EtOAc/hexanes) to yield 107 mg of the title compound. LRMS ESI⁺ (M+H)⁺ 674.4.

Example 4

(2R,4S,7S)-7-t-Butyl-N-((1R,2R)-1-{[(cyclopropyl-sulfonyl)amino]carbonyl}-2-ethylcyclopropyl)-6,9-dioxo-3,4,6,7,8,9,12,13,14,15,16,17-dodecahydro-2H,11H-2,5-methanopyrido[2,3-k][1,10,3,6]dioxadiazacyclononadecine-4-carboxamide

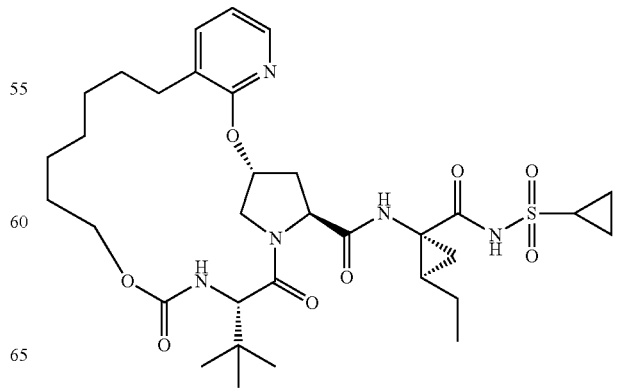

To a solution of a portion of the product from Example 3, Step 2 (95 mg, 0.206 mmol) in DMF (2.2 mL), Intermediate A3 (66 mg, 0.247 mmol), DIEA (0.144 mL, 0.82 mmol), and HATU (102 mg, 0.268 mmol) were added. After 1 hour, the mixture was partitioned between EtOAc and 1N HCl. The organic layer was separated, dried over MgSO$_4$, and the solvent was removed in vacuo. The crude product was purified on SiO$_2$ (gradient elution, 0-70% EtOAc/hexanes) to yield 106 mg of the title compound. LRMS ESI$^+$ (M+H)$^+$ 676.4.

Example 5

(1R,2S)-1-({[(2R,4S,7S)-7-Butyl-6,9-dioxo-3,4,6,7,8,9,12,13,14,15,16,17-dodecahydro-2H,11H-2,5-methano-1,10,5,8-benzodioxadiazacyclononadecin-4-yl]carbonyl}amino)-2-vinylcyclopropanecarboxylic acid

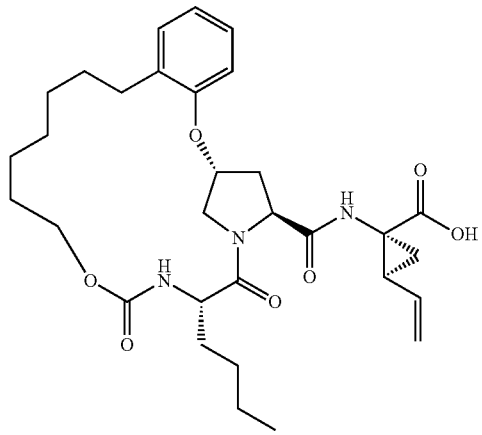 [SMILES: C=C[C@@H]1C[C@]1(NC(=O)[C@@H]1C[C@@H]2CN1C(=O)[C@H](CCCC)NC(=O)OCCCCCCCc1ccccc1O2)C(=O)O]

Step 1: 1-t-Butyl 2-methyl (2S,4R)-4-(2-allylphenoxyl)pyrrolidine-1,2-dicarboxylate

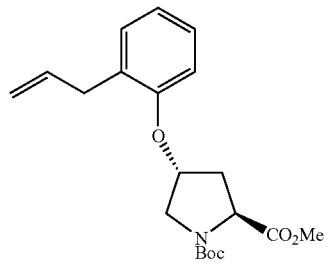 [SMILES: C=CCc1ccccc1O[C@@H]1C[C@@H](C(=O)OC)N(C(=O)OC(C)(C)C)C1]

To a solution of 1-t-butyl 2-methyl (2S,4S)-4-hydroxy-pyrrolidine-1,2-dicarboxylate (0.2 g, 0.815 mmol), 2-allyl-phenol (0.117 mL, 0.897 mmol), and PPh$_3$ (0.233 g, 0.889 mmol), DEAD (0.139 mL, 0.881 mmol) was added at 0° C.

The mixture was then warmed to RT. After 23 hours, the reaction was complete, and the solvent was removed in vacuo. The crude product was purified on SiO$_2$ (gradient elution, 0-30% EtOAc/hexanes) to yield 0.21 g of the title compound. LRMS ESI$^+$ ((M-Boc)+H)$^+$ 262.3.

Step 2: Methyl (4R)-4-(2-allylphenoxy)-L-prolinate hydrochloride

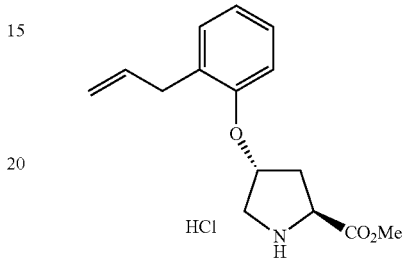

To a portion of the product from Step 1 (0.2 g, 0.553 mmol) was added HCl in dioxane (4M, 9.6 mL, 38.7 mmol). After 1 hour, the solvent was removed in vacuo to yield the title product. LRMS ESI$^+$ (M+H)$^+$ 262.3.

Step 3: Methyl N-[(hex-5-en-1-yloxy)carbonyl]-L-norleucyl-(4R)-4-(2-allylphenoxy)-L-prolinate

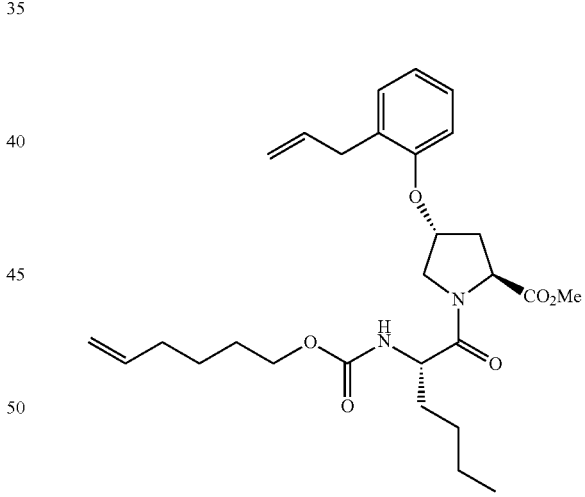

To a solution of the product from Step 2 (165 mg, 0.55 mmol) in DMF (10 mL), Intermediate B4 (214 mg, 0.83 mmol), DIEA (0.49 mL, 2.76 mmol), and TBTU (0.267 mg, 0.83 mmol) were added. After 1 hour, the mixture was extracted with 1N HCl and EtOAc. The organic layer was washed with H$_2$O and brine, and then dried over MgSO$_4$. The solvent was removed in vacuo, and the crude product was purified on SiO$_2$ (gradient elution, 5-40% EtOAc/hexanes) to yield 270 mg of the title compound. LRMS ESI$^+$ (M+H)$^+$ 501.4.

Step 4: Methyl (2R,4S,7S,15E/Z)-7-butyl-6,9-dioxo-3,4,6,7,8,9,12,13,14,17-decahydro-2H,11H-2,5-methano-1,10,5,8-benzodioxadiazacyclononadecine-4-carboxylate

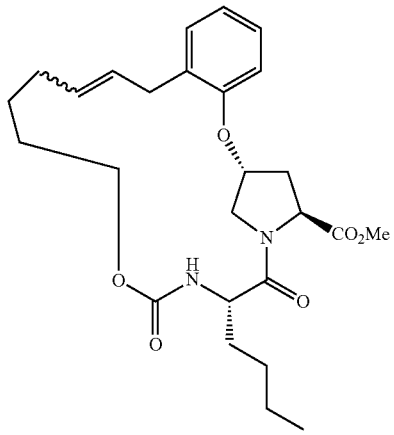 [SMILES: CCCC[C@@H]1NC(=O)OCCCCC=CCc2ccccc2O[C@@H]2C[C@@H](C(=O)OC)N(C2)C1=O]

To a solution of a portion of the product from Step 3 (196 mg, 0.39 mmol) in DCE (80 mL), the Zhan 1a catalyst (26 mg, 0.039 mmol) was added, and the mixture was heated to reflux under $N_2$. After 2 hours, the reaction was concentrated in vacuo, and the crude product was purified on $SiO_2$ (gradient elution, 10-60% EtOAc/hexanes) to yield 185 mg of the title compound as a mixture of olefin isomers. LRMS $ESI^+$ $(M+H)^+$ 473.3.

Step 5: Methyl (2R,4S,7S)-7-butyl-6,9-dioxo-3,4,6,7,8,9,12,13,14,15,16,17-dodecahydro-2H, 11H-2,5-methano-1,10,5,8-benzodioxadiazacyclononadecine-4-carboxylate

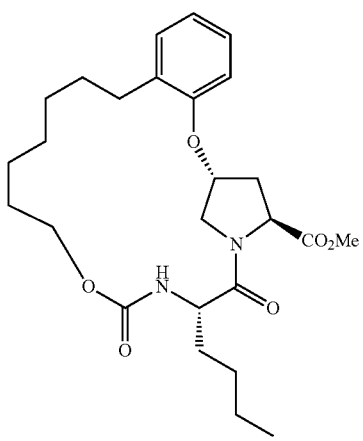 [SMILES: CCCC[C@@H]1NC(=O)OCCCCCCCc2ccccc2O[C@@H]2C[C@@H](C(=O)OC)N(C2)C1=O]

To a solution of a portion of the product from Step 4 (185 mg, 0.39 mmol) in EtOAc (10 mL), 10% Pd/C (15 mg, 0.014 mmol) was added. The mixture was then placed under $H_2$, stirred for 5 hours, and filtered through a pad of glass wool. The solvent was then removed in vacuo to yield 158 mg of the title compound. LRMS $ESI^+$ $(M+H)^+$ 475.4.

Step 6: (2R,4S,7S)-7-Butyl-6,9-dioxo-3,4,6,7,8,9,12,13,14,15,16,17-dodecahydro-2H,11H-2,5-methano-1,10,5,8-benzodioxadiazacyclononadecine-4-carboxylic acid

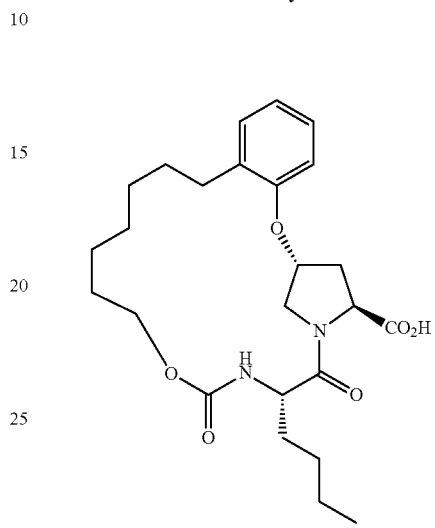

To a solution of a portion of the product from Step 5 (158 mg, 0.33 mmol) in THF (10 mL), MeOH (5 mL) and $H_2O$ (2 mL), $LiOH \cdot H_2O$ (80 mg, 3.3 mmol) was added. After 1 hour, 1N HCl and $Et_2O$ were added. The organic layer was separated, and the aqueous layer was washed with EtOAc. The combined organic layers were then dried over $MgSO_4$, and the solvent was removed in vacuo to yield 150 mg of the title compound. LRMS $ESI^+$ $(M+H)^+$461.4.

Step 7: (1R,2S)-1-({[(2R,4S,7S)-7-Butyl-6,9-dioxo-3,4,6,7,8,9,12,13,14,15,16,17-dodecahydro-2H, 11H-2,5-methano-1,10,5,8-benzodioxadiazacyclononadecin-4-yl]carbonyl}amino)-2-vinylcyclopropanecarboxylic acid To a solution of a portion of the product from Step 6 (150 mg, 0.218 mmol) in DMF (15 mL), Intermediate A2 (128 mg, 0.66 mmol), DIEA (0.595 mL, 3.3 mmol), and TBTU (214 mg, 0.66 mmol) were added. After 30 minutes, the mixture was partitioned between EtOAc and 1N HCl. The organic layer was separated, dried over $MgSO_4$, and the solvent was removed in vacuo. The crude ester was taken up in THF (10 mL), MeOH (5 mL) and $H_2O$ (2 mL) and $LiOH \cdot H_2O$ (80 mg, 3.3 mmol) was added. After 1 hour, 1N HCl and $Et_2O$ were added. The organic layer was separated, and the aqueous layer was washed with EtOAc. The combined organic layers were then dried over $MgSO_4$ and the solvent was removed in vacuo. The crude product was purified by reverse-phase chromotography (95/5 $H_2O$/ACN with 0.15% TFA to 5/95) to yield 100 mg of the title compound. LRMS $ESI^+$ $(M+H)^+$ 570.3.

Example 6

(2R,4S,7S)-7-Butyl-N-((1R,2S)-1-{[(cyclopropylsulfonyl)amino]carbonyl}-2-vinylcyclopropyl)-6,9-dioxo-3,4,6,7,8,9,12,13,14,15,16,17-dodecahydro-2H,11H-2,5-methano-1,10,5,8-benzodioxadiazacyclononadecine-4-carboxamide

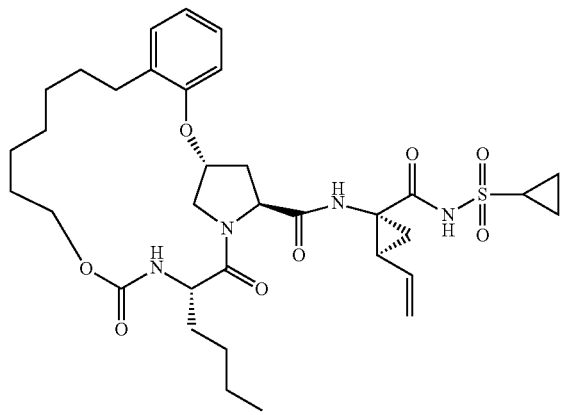 [SMILES: C=C[C@@H]1C[C@]1(NC(=O)[C@@H]1C[C@@H]2CN1C(=O)[C@H](CCCC)NC(=O)OCCCCCCCc1ccccc1O2)C(=O)NS(=O)(=O)C1CC1]

To a solution of the acid from Example 5, Step 7 (30 mg, 0.053 mmol) in DMF (0.34 mL), under $N_2$, carbonyldiimidazole (13 mg, 0.079 mmol) was added, and the mixture stirred at 40° C. for 1 hour. Cyclopropylsulfonamide (10 mg, 0.079 mmol) and DBU (8 mg, 0.053 mmol) were added, and the reaction stirred overnight (15 hours) at 40° C. The reaction was directly purified by reverse-phase chromatography, and the resulting product was concentrated in vacuo to give the title compound as a white solid (24 mg). LRMS ESI$^+$ (M+H)$^+$673.3.

Example 7

(2R,4S,7S,15E)-20-Bromo-7-t-butyl-N-((1R,2S)-1-{[(cyclopropylsulfonyl)amino]carbonyl}-2-vinylcyclopropyl)-6,9-dioxo-3,4,6,7,8,9,12,13,14,17-decahydro-2H,11H-2,5-methano-1,10,5,8-benzodioxadiazacyclononadecine-4-carboxamide

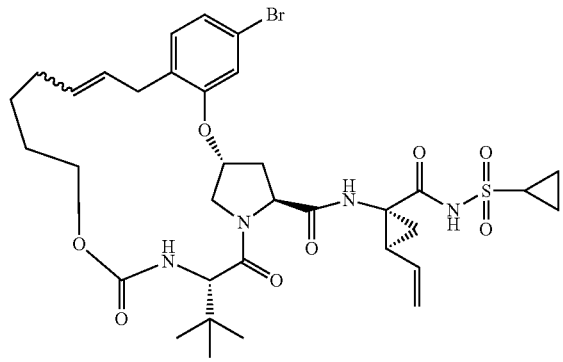 [SMILES: C=C[C@@H]1C[C@]1(NC(=O)[C@@H]1C[C@@H]2CN1C(=O)[C@H](C(C)(C)C)NC(=O)OCCCCC=CCc1ccc(Br)cc1O2)C(=O)NS(=O)(=O)C1CC1]

Prepared according to Example 5, Steps 1-4 and 6-7 and Example 6 starting from 2-allyl-5-bromophenol in place of 2-allylphenol in Example 5, Step 1. LRMS ESI$^+$ (M+H)$^+$ 751.3.

Example 8

(2R,4S,7S)-20-Bromo-7-t-butyl-N-((1R,2R)-1-{[(cyclopropylsulfonyl)amino]carbonyl}-2-ethylcyclopropyl)-6,9-dioxo-3,4,6,7,8,9,12,13,14,15,16,17-dodecahydro-2H,11H-2,5-methano-1,10,5,8-benzodioxadiazacyclononadecine-4-carboxamide

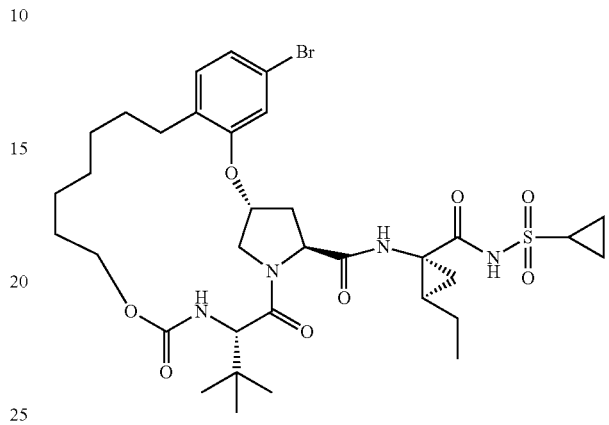

To a solution of the product from Example 7 (280 mg, 0.373 mmol) in EtOAc (15 mL) was added Pd/C (30 mg). The mixture was then placed under $H_2$ and stirred for 4 hours. After filtering through glass wool, the solvent was removed in vacuo to yield 280 mg of the title compound. LRMS ESI$^+$ (M+H)$^+$ 755.3.

Example 9

(2R,4S,7S)-7-t-Butyl-20-cyano-N-((1R,2R)-1-{[(cyclopropylsulfonyl)amino]carbonyl}-2-ethylcyclopropyl)-6,9-dioxo-3,4,6,7,8,9,12,13,14,15,16,17-dodecahydro-2H,11H-2,5-methano-1,10,5,8-benzodioxadiazacyclononadecine-4-carboxamide

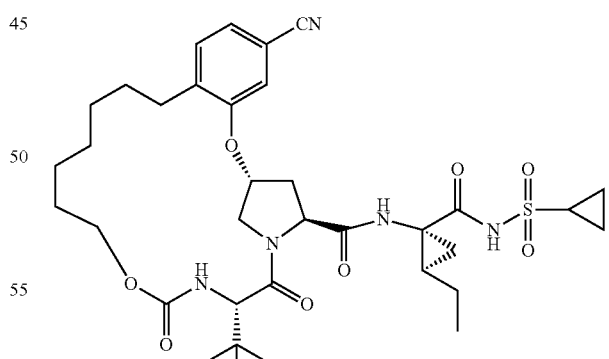

To a solution of the product from Example 8 (25 mg, 0.033 mmol) in DMF (3 mL) and $H_2O$ (0.5 mL), $Zn(CN)_2$ (3.9 mg, 0.033 mmol), $Pd_2(dba)_3$ (3 mg, 3.3 mol), and DPPF (1.8 mg, 3.3 mol) were added under $N_2$. The mixture was then heated to 120° C. for 20 hours. The mixture was then filtered and then purified by reverse-phase chromatography to yield the title compound. LRMS ESI$^+$ (M+H)$^+$ 700.3.

Example 10

(2R,4S,7S)-7-t-Butyl-N-((1R,2R)-1-{[(cyclopropyl-sulfonyl)amino]carbonyl}-2-ethylcyclopropyl)-6,9-dioxo-20-phenyl-3,4,6,7,8,9,12,13,14,15,16,17-do-decahydro-2H,11H-2,5-methano-1,10,5,8-benzodioxadiazacyclononadecine-4-carboxamide

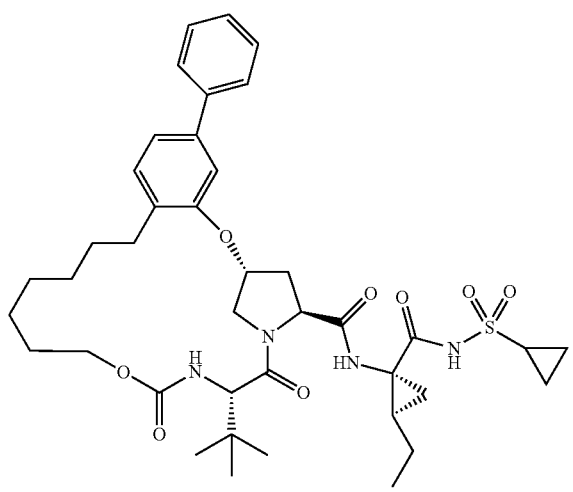 [SMILES: CC[C@@H]1C[C@]1(NC(=O)[C@@H]1C[C@@H]2CN1C(=O)[C@H](C(C)(C)C)NC(=O)OCCCCCCCc1ccc(-c3ccccc3)cc1O2)C(=O)NS(=O)(=O)C1CC1]

To a solution of the product from Example 8 (20 mg, 0.027 mmol) in dioxane (1.75 mL), phenylboronic acid (9.7 mg, 0.08 mmol), $Cs_2CO_3$ (21 mg, 0.064 mmol) $Pd_2(dba)_3$ (2.4 mg, 2.6 mol), and $PCy_3$ (1.1 mg, 3.9 mol) were added under $N_2$. The mixture was then heated to 95° C. for 9 hours. The mixture was then filtered and then purified by reverse-phase chromatography to yield the title compound. LRMS ESI$^+$ (M+H)$^+$ 751.4.

Example 11

(2R,4S,7S)-7-t-Butyl-N-((1R,2R)-1-{[(cyclopropyl-sulfonyl)amino]carbonyl}-2-ethylcyclopropyl)-6,9-dioxo-3,4,6,7,8,9,12,13,14,15,16,17-dodecahydro-2H,11H-2,5-methano-1,10,5,8-benzodioxadiazacyclononadecine-4-carboxamide To a solution of the product from Example 8 (21 mg, 0.028 mmol) in THF (5 mL) and 2N HOAc (5 mL), sodium acetate (34 mg, 0.42 mmol) and 10% Pd/C (2 mg) were added. The mixture was then hydrogenated on a PARR apparatus for 18 hours. The mixture was then filtered, basified with $NaHCO_3$, and extracted with EtOAc. After drying over $MgSO_4$, the solvent was removed in vacuo. The residue was purified by reverse-phase chromatography to yield the title compound. LRMS ESI$^+$ (M+H)$^+$ 675.3.

By using the appropriate procedures, the appropriate B intermediates in place of Intermediate B4 or Intermediate B5, and appropriate phenol or hydroxyl-heterocycle in place of 3-bromopyridin-2-ol or 2-allylphenol, the following compounds were prepared, using the appropriate Intermediates according to the procedures indicated. For each Example, Step 1 of the procedure uses either phenol or hydroxyl heterocycle as indicated.

| Ex. | Structure | Name | LRMS (M + H)$^+$ | Procedure | Step 1 | Int. |
|---|---|---|---|---|---|---|
| 13 | 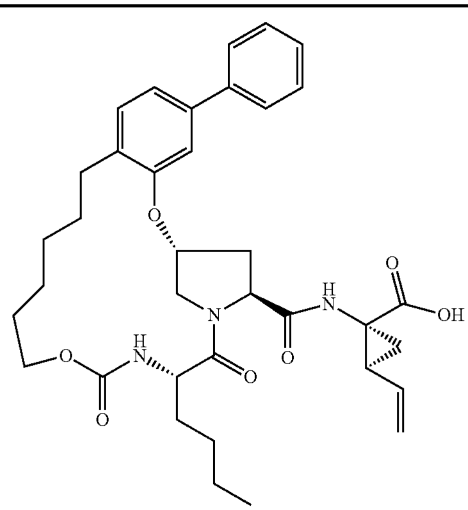 | (1R,2S)-1-(({[(2R,4S,7S)-7-butyl-6,9-dioxo-19-phenyl-3,4,6,7,8,9,11,12,13,14,15,16-dodecahydro-2H-2,5-methano-1,10,5,8-benzodioxadiaza cyclooctadecin-4-yl]carbonyl}amino)-2-vinylcyclopropane carboxylic acid | 632.4 | See Example 5 | 2-allyl-5-phenol-phenol. Ref: U.S. Pat. No. 2,548,704 | B1 |

-continued

| Ex. | Structure | Name | LRMS (M + H)+ | Procedure | Step 1 | Int. |
|---|---|---|---|---|---|---|
| 14 | 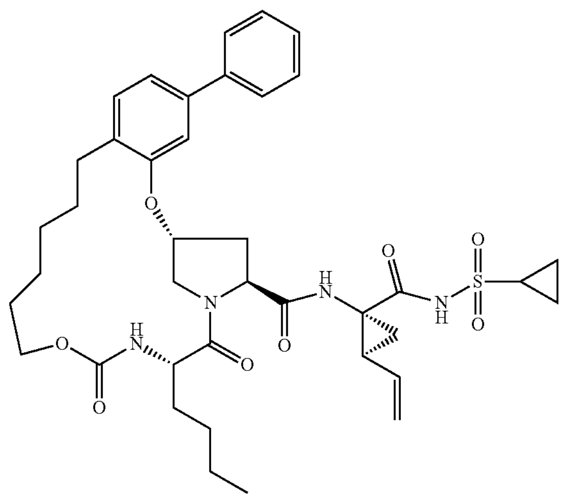 [SMILES: C=C[C@@H]1C[C@]1(NC(=O)[C@@H]1C[C@@H]2CN1C(=O)[C@H](CCCC)NC(=O)OCCCCCCc1ccc(-c3ccccc3)cc1O2)C(=O)NS(=O)(=O)C1CC1] | (2R,4S,7S)-7-butyl-N-((1R,2S)-1-{[(cyclopropylsulfonyl)amino]carbonyl}-2-vinylcyclopropyl)-6,9-dioxo-19-phenyl-3,4,6,7,8,9,11,12,13,14,15,16-dodecahydro-2H-2,5-methano-1,10,5,8-benzodioxadiaza cyclooctadecine-4-carboxamide | 735.5 | See Example 6 | 2-allyl-5-phenyl-phenol. Ref: U.S. Pat. No. 2,548,704 | B1 |
| 16 | 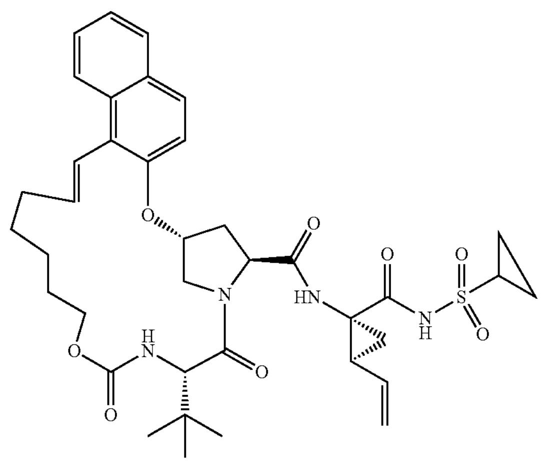 [SMILES: C=C[C@@H]1C[C@]1(NC(=O)[C@@H]1C[C@@H]2CN1C(=O)[C@H](C(C)(C)C)NC(=O)OCCCCC/C=C/c1c(ccc3ccccc13)O2)C(=O)NS(=O)(=O)C1CC1] | (8R,10S,13S,22E)-13-t-butyl-N-((1R,2S)-1-{[(cyclopropylsulfonyl)amino]carbonyl}-2-vinylcyclopropyl)-12,15-dioxo-9,10,12,13,14,15,18,19,20,21-decahydro-8H,17H-8,11-methanonaphtho[2,1-k][1,10,3,6]dioxadiaza cyclononadecine-10-carboxamide | 721.4 | See Example 1 | 1-bromo-2-naphthol | B11 |
| 17 | 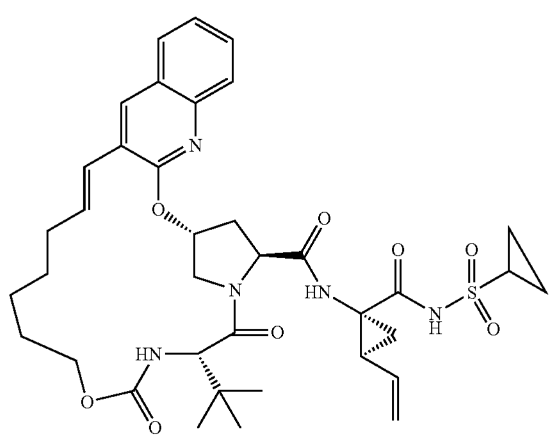 [SMILES: C=C[C@@H]1C[C@]1(NC(=O)[C@@H]1C[C@@H]2CN1C(=O)[C@H](C(C)(C)C)NC(=O)OCCCCC/C=C/c1cc3ccccc3nc1O2)C(=O)NS(=O)(=O)C1CC1] | (2R,4S,7S,16E)-7-t-butyl-N-((1R,2S)-1-{[(cyclopropylsulfonyl)amino]carbonyl}-2-vinylcyclopropyl)-6,9-dioxo-3,4,6,7,8,9,12,13,14,15-decahydro-2H,11H-2,5-methano[1,10,3,6]dioxadiazacyclo nonadecino[11,12-b]quinoline-4-carboxamide | 722.5 | See Example 1 | 3-bromo quinolin-2-ol. Ref: 70 J. Org. Chem. 175 (2005). | B11 |

| Ex. | Structure | Name | LRMS (M + H)+ | Procedure | Step 1 | Int. |
|---|---|---|---|---|---|---|
| 18 | 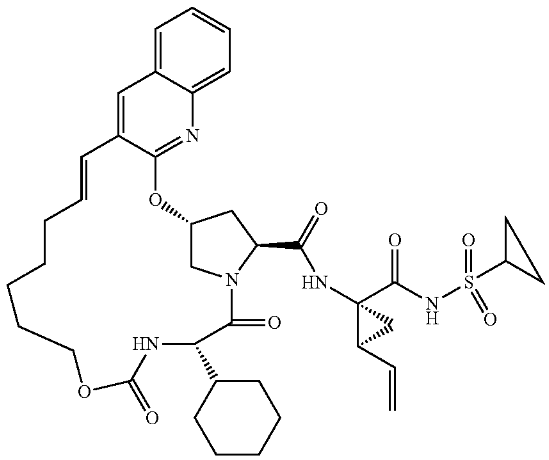 [SMILES: C=C[C@@H]1C[C@]1(NC(=O)[C@@H]1C[C@@H]2CN1C(=O)[C@H](C1CCCCC1)NC(=O)OCCCCC/C=C/c1cc3ccccc3nc1O2)C(=O)NS(=O)(=O)C1CC1] | (2R,4S,7S,16E)-7-cyclohexyl-N-((1R,2S)-1-{[(cyclopropylsulfonyl)amino]carbonyl}-2-vinylcyclopropyl)-6,9-dioxo-3,4,6,7,8,9,12,13,14,15-decahydro-2H,11H-2,5-methano[1,10,3,6]dioxadiazacyclononadecino[11,12-b]quinoline-4-carboxamide | 748.7 | See Example 1 | 3-bromo quinolin-2-ol. Ref: 70 J. Org. Chem. 175 (2005). | B16 |
| 19 | 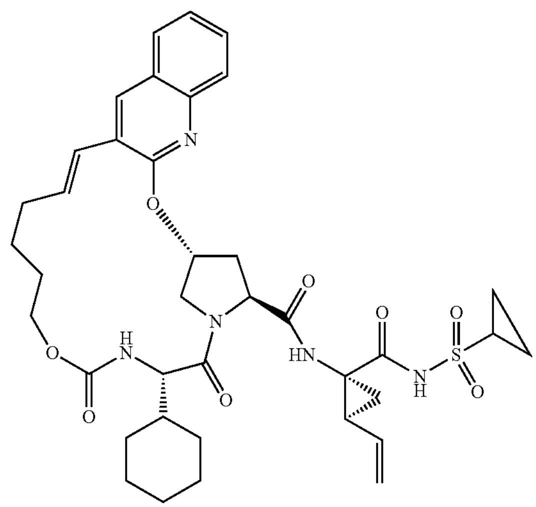 [SMILES: C=C[C@@H]1C[C@]1(NC(=O)[C@@H]1C[C@@H]2CN1C(=O)[C@H](C1CCCCC1)NC(=O)OCCCC/C=C/c1cc3ccccc3nc1O2)C(=O)NS(=O)(=O)C1CC1] | (2R,4S,7S,15E)-7-cyclohexyl-N-((1R,2S)-1-{[(cyclopropylsulfonyl)amino]carbonyl}-2-vinylcyclopropyl)-6,9-dioxo-3,4,6,7,8,9,11,12,13,14-decahydro-2H-2,5-methano[1,10,3,6]dioxadiazacyclooctadecino[11,12-b]quinoline-4-carboxamide | 734.6 | See Example 1 | 3-bromo quinolin-2-ol. Ref: 70 J. Org. Chem. 175 (2005). | B17 |
| 20 | 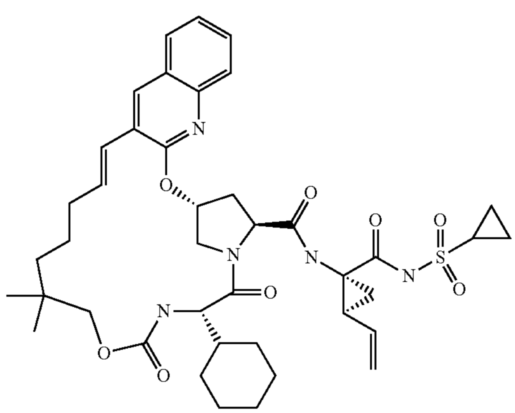 [SMILES: C=C[C@@H]1C[C@]1(NC(=O)[C@@H]1C[C@@H]2CN1C(=O)[C@H](C1CCCCC1)NC(=O)OCC(C)(C)CCC/C=C/c1cc3ccccc3nc1O2)C(=O)NS(=O)(=O)C1CC1] | (2R,4S,7S,16E)-7-cyclohexyl-N-((1R,2S)-1-{[(cyclopropylsulfonyl)amino]carbonyl}-2-vinylcyclopropyl)-12,12-dimethyl-6,9-dioxo-3,4,6,7,8,9,12,13,14,15-decahydro-2H,11H-2,5-methano[1,10,3,6]dioxadiazacyclononadecino[11,12-b]quinoline-4-carboxamide | 776.8 | See Example 1 | 3-bromo quinolin-2-ol. Ref: 70 J. Org. Chem. 175 (2005). | B19 |

-continued

| Ex. | Structure | Name | LRMS (M + H)+ | Procedure | Step 1 | Int. |
|---|---|---|---|---|---|---|
| 21 | 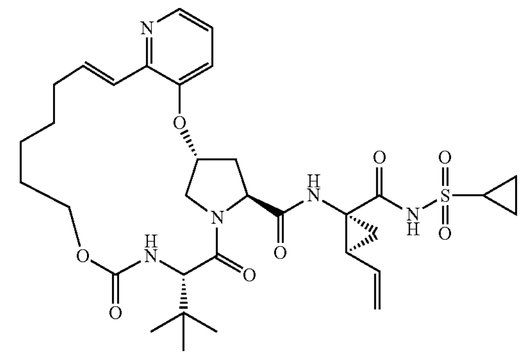 [SMILES: C=C[C@@H]1C[C@]1(NC(=O)[C@@H]1C[C@@H]2CN1C(=O)[C@H](C(C)(C)C)NC(=O)OCCCCC/C=C/c1ncccc1O2)C(=O)NS(=O)(=O)C1CC1] | (2R,4S,7S,16E)-7-t-butyl-N-((1R,2S)-1-{[(cyclopropylsulfonyl)amino]carbonyl}-2-vinylcyclopropyl)-6,9-dioxo-3,4,6,7,8,9,12,13,14,15-decahydro-2H,11H-2,5-methanopyrido[3,2-k][1,10,3,6]dioxadiazacyclononadecine-4-carboxamide | 672.4 | See Example 1 | 2-bromopyridin-3-ol | B11 |
| 22 | 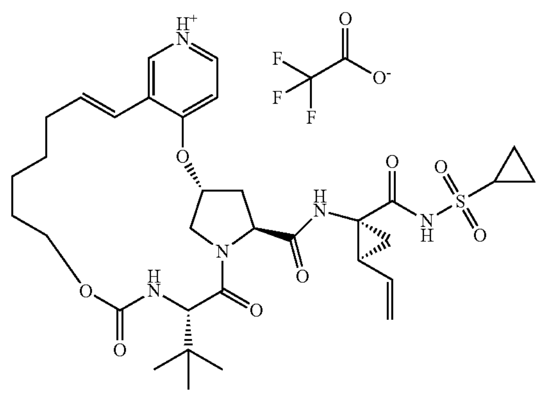 | (2R,4S,7S,16E)-7-t-butyl-4-{[((1R,2S)-1-{[(cyclopropylsulfonyl)amino]carbonyl}-2-vinylcyclopropyl)amino]carbonyl}-6,9-dioxo-3,4,6,7,8,9,12,13,14,15-decahydro-2H,11H-2,5-methanopyrido[4,3-k][1,10,3,6]dioxadiazacyclononadecin-19-ium trifluoroacetate | 672.4 | See Example 1 | 3-bromopyridin-4(1H)-one | B11 |
| 23 | 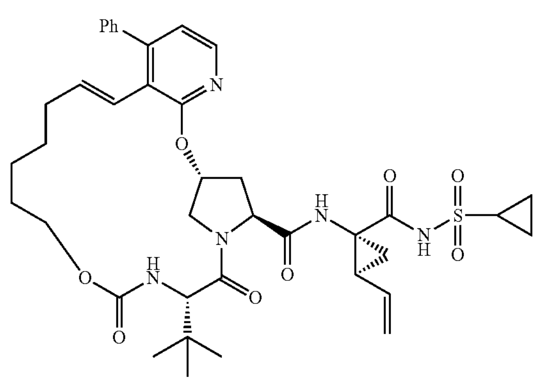 [SMILES: C=C[C@@H]1C[C@]1(NC(=O)[C@@H]1C[C@@H]2CN1C(=O)[C@H](C(C)(C)C)NC(=O)OCCCCC/C=C/c1c(-c3ccccc3)ccnc1O2)C(=O)NS(=O)(=O)C1CC1] | (2R,4S,7S,16E)-7-t-butyl-N-((1R,2S)-1-{[(cyclopropylsulfonyl)amino]carbonyl}-2-vinylcyclopropyl)-6,9-dioxo-18-phenyl-3,4,6,7,8,9,12,13,14,15-decahydro-2H,11H-2,5-methanopyrido[2,3-k][1,10,3,6]dioxadiazacyclononadecine-4-carboxamide | | See Example 1 | 3-chloro-4-phenylpyridin-2-ol | B11 |

Example 24

(1R,2S)-1-({[(4R,6S,9S,16E)-9-Butyl-8,11-dioxo-3,12-dioxa-7,10-diazatricyclo[16.3.1.1^{4,7}]tricosa-1(22),16,18,20-tetraen-6-yl]carbonyl}amino)-2-vinylcyclopropanecarboxylic acid

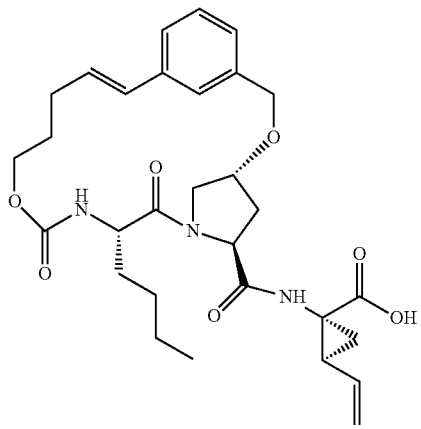 [SMILES: C=C[C@@H]1C[C@]1(NC(=O)[C@@H]1C[C@@H]2CN1C(=O)[C@H](CCCC)NC(=O)OCCC/C=C/c1cccc(c1)CO2)C(=O)O]

Step 1: 1-t-Butyl 2-methyl (2S,4R)-4-[(3-iodobenzyl)oxy]pyrrolidine-1,2-dicarboxylate

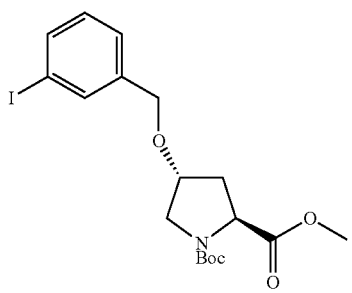 [SMILES: COC(=O)[C@@H]1C[C@@H](OCc2cccc(I)c2)CN1C(=O)OC(C)(C)C]

To a solution of 1-t-butyl 2-methyl (2S,4R)-4-hydroxypyrrolidine-1,2-dicarboxylate (1.5 g, 6.12 mmol) and 1-(bromomethyl)-3-iodobenzene (2.18 g, 7.34 mmol) in DMF (20 mL), Cs$_2$CO$_3$ (5.98 g, 18.4 mmol) was added at RT. After 3 days, EtOAc was added, and the mixture was extracted with 1N HCl and then H$_2$O. The organic layer was dried over Na$_2$SO$_4$, and the solvent was removed in vacuo. The crude product was purified on SiO$_2$ (gradient elution, 5-70% EtOAc/hexanes) to yield 1.5 g of the title compound. LRMS ESI$^+$ ((M-Boc)+H)$^+$ 362.2.

Step 2: 1-t-Butyl 2-methyl (2S,4R)-4-[(3-vinylbenzyl)oxy]pyrrolidine-1,2-dicarboxylate

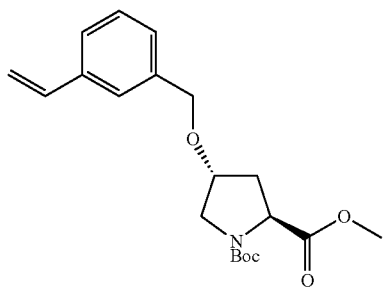 [SMILES: C=Cc1cccc(CO[C@@H]2C[C@@H](C(=O)OC)N(C(=O)OC(C)(C)C)C2)c1]

To a degassed solution of the product from Step 1 (1.4 g, 3.03 mmol) in PhMe (20 mL), vinyltributyltin (1.06 mL, 3.64 mmol) and Pd(PPh$_3$)$_4$ (70 mg, 0.06 mmol) were added. The mixture was then heated to reflux for 1 hour. The solvent was removed in vacuo, and the crude material was purified on SiO$_2$ (gradient elution, 5-50% EtOAc/hexanes) to yield 700 mg of the title compound. LRMS ESI$^+$ ((M-Boc)+H)$^+$ 262.3.

Step 3: Methyl (4R)-4-[(3-vinylbenzyl)oxy]-L-prolinate hydrochloride

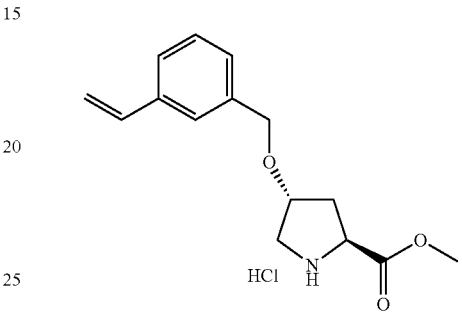

To the product from Step 2 (700 mg, 1.94 mmol) was added HCl/dioxane (20 mL, 4M, 60 mmol). After 1 hour, the solvent was removed in vacuo to yield 575 mg of the title compound. LRMS ESI$^+$ (M+H)$^+$ 262.3

Step 4: Methyl N-[(pent-4-en-1-yloxy)carbonyl]-L-norleucyl-(4R)-4-[(3-vinylbenzyl)oxy]-L-prolinate

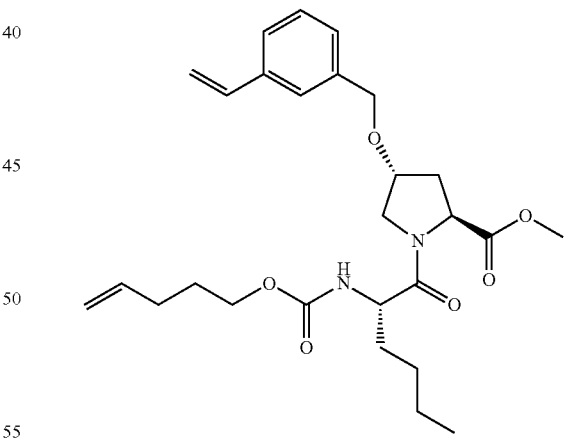

To a solution of the product from Step 3 (300 mg, 1.0 mmol) in DMF (5 mL), Intermediate B1 (368 mg, 1.51 mmol), DIEA (0.702 mL, 4.03 mmol), EDC (386 mg, 2.01 mmol), and HOAt (274 mg, 2.01 mmol) were added at RT. After 2 hours, the reaction diluted with NaHCO$_{3(aq.)}$ and extracted with EtOAc (3×). The combined organic layers were extracted with H$_2$O and then brine, dried over Na$_2$SO$_4$, and the solvent was removed in vacuo. The residue was purified on SiO$_2$ (gradient elution, 5-75% EtOAc/hexanes) to yield the title compound. LRMS ESI$^+$ (M+H)$^+$ 487.4.

Step 5: Methyl (4R,6S,9S,16E)-9-butyl-8,11-dioxo-3,12-dioxa-7,10-diazatricyclo[16.3.1.1$^{4,7}$]tricosa-1(22),16,18,20-tetraene-6-carboxylate

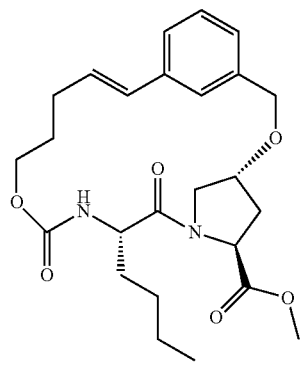 [SMILES: CCCC[C@@H]1NC(=O)OCCC/C=C/c2cccc(c2)CO[C@@H]2C[C@@H](C(=O)OC)N(C2)C1=O]

The title compound was prepared according to Example 1, Step 5 using the product from Step 4. LRMS ESI$^+$ (M+H)$^+$ 459.4.

Step 6: (4R,6S,9S,16E)-9-Butyl-8,11-dioxo-3,12-dioxa-7,10-diazatricyclo[16.3.1.1$^{4,7}$]tricosa-1(22),16,18,20-tetraene-6-carboxylic acid

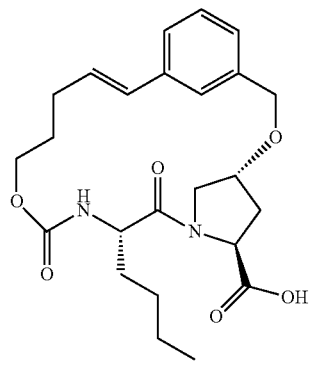 [SMILES: CCCC[C@@H]1NC(=O)OCCC/C=C/c2cccc(c2)CO[C@@H]2C[C@@H](C(=O)O)N(C2)C1=O]

To a solution of the product from Step 5 (160 mg, 0.35 mmol) in THF (3 mL) and MeOH (0.5 mL), LiOH (3.49 mL, 1M solution, 3.49 mmol) was added. After 1 hour, the solution was acidified to pH 6 with 1N HCl and extracted with EtOAc (3×). The combined organic layers were washed with H$_2$O and then brine, dried over Na$_2$SO$_4$, and the solvent was removed in vacuo to yield the title compound. LRMS ESI$^+$ (M+H)$^+$ 445.4.

Step 7: (1R,2S)-1-({[(4R,6S,9S,16E)-9-Butyl-8,11-dioxo-3,12-dioxa-7,10-diazatricyclo[16.3.1.1$^{4,7}$]tricosa-1 (22), 16,18,20-tetraen-6-yl]carbonyl}amino)-2-vinylcyclopropanecarboxylic acid Using the product from Step 6, the title compound was prepared according to Example 5, Step 7. LRMS ESI$^+$ (M+H)$^+$ 554.4.

Example 25

(1R,2S)-1-({[(4R,6S,9S)-9-Butyl-8,11-dioxo-3,12-dioxa-7,10-diazatricyclo[16.3.1.1$^{4,7}$]tricosa-1(22),18,20-trien-6-yl]carbonyl}amino)-2-vinylcyclopropanecarboxylic acid

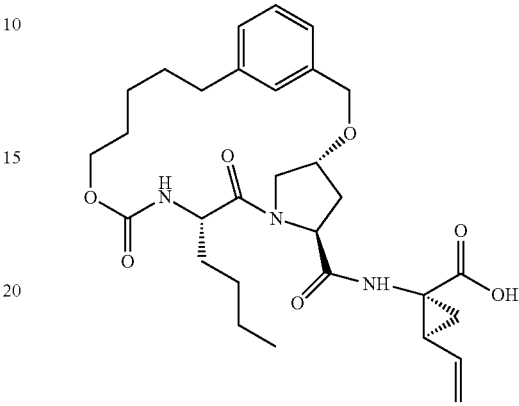

Step 1: 2-(Trimethylsilyl)ethyl (4R)-4-[(3-vinylbenzyl)oxy]-L-prolinate hydrochloride

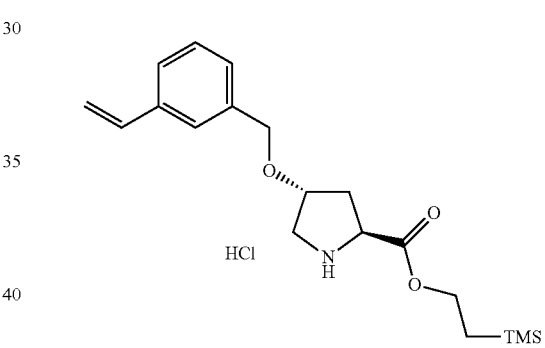

Using 1-t-butyl 2-[2-(trimethylsilyl)ethyl](2S,4R)-4-hydroxypyrrolidine-1,2-dicarboxylate, the title compound was prepared according to Example 24, Steps 1-3. LRMS ESI$^+$ (M+H)$^+$ 348.3.

Step 2: 2-(Trimethylsilyl)ethyl N-[(pent-4-en-1-yloxy)carbonyl]-L-norleucyl-(4R)-4-[(3-vinylbenzyl)oxy]-L-prolinate

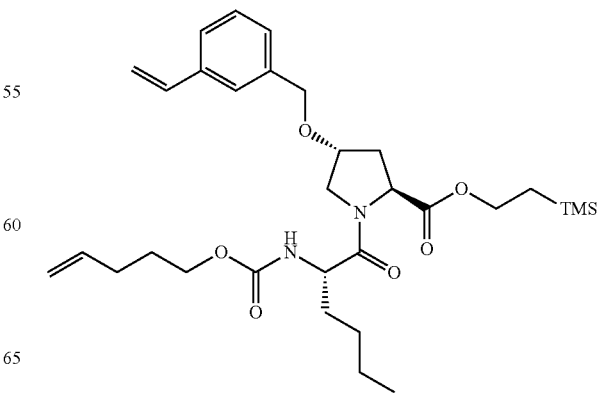

Using the product from Step 1, the title compound was prepared according to Example 24, step 4. LRMS ESI+ (M+H)+ 573.4.

Step 3: 2-(Trimethylsilyl)ethyl (4R,6S,9S,16E)-9-butyl-8,11-dioxo-3,12-dioxa-7,10-diazatricyclo[16.3.1.1^{4,7}]tricosa-1(22), 16,18,20-tetraene-6-carboxylate

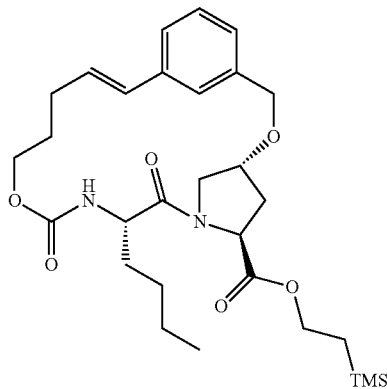 [SMILES: CCCC[C@@H]1NC(=O)OCCC/C=C/c2cccc(c2)CO[C@@H]2C[C@@H](C(=O)OCC[Si](C)(C)C)N(C2)C1=O]

Using the product from Step 2, the title compound was prepared according to Example 24, Step 5. LRMS ESI+ (M+H)+ 545.4.

Step 4: 2-(Trimethylsilyl)ethyl (4R,6S,9S)-9-butyl-8,11-dioxo-3,12-dioxa-7,10-diazatricyclo[16.3.1.1^{4,7}]tricosa-1(22),18,20-triene-6-carboxylate

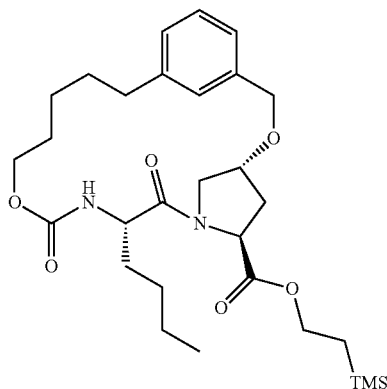 [SMILES: CCCC[C@@H]1NC(=O)OCCCCCc2cccc(c2)CO[C@@H]2C[C@@H](C(=O)OCC[Si](C)(C)C)N(C2)C1=O]

Using the product from Step 3, the title compound was prepared according to Example 3, Step 1. LRMS ESI+ (M+H)+ 547.4.

Step 5: (4R,6S,9S)-9-Butyl-8,11-dioxo-3,12-dioxa-7,10-diazatricyclo[16.3.1.1^{4,7}]tricosa-1(22), 18,20-triene-6-carboxylic acid

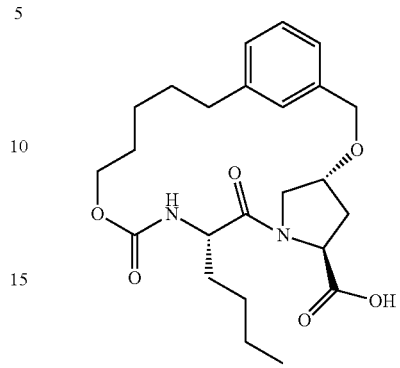

2-(Trimethylsilyl)ethyl (4R,6S,9S)-9-butyl-8,11-dioxo-3,12-dioxa-7,10-diazatricyclo[16.3.1.1^{4,7}]tricosa-1(22),18,20-triene-6-carboxylate (60 mg, 0.11 mmol) in THF (3 mL), TBAF (0.137 mL, 1M solution in THF, 0.137 mmol) were added to a solution of the product from Step 4. After 2 hours, the solvent was removed in vacuo to yield the title compound as an oil. LRMS ESI+ (M+H)+ 447.3.

Step 6: (1R,2S)-1-({[(4R,6S,9S)-9-Butyl-8,11-dioxo-3.12-dioxa-7,10-diazatricyclo[16.3.1.1^{4,7}]tricosa-1 (22),18,20-trien-6-yl]carbonyl}amino)-2-vinylcyclopropanecarboxylic acid Using the product from Step 5, the title compound was prepared according to Example 5, Step 7. LRMS ESI+ (M+H)+ 556.4.

Example 26

(4R,6S,9S,16E)-9-Butyl-N-((1R,2S)-1-{[(cyclopropylsulfonyl)amino]carbonyl}-2-vinylcyclopropyl)-8,11-dioxo-3,12-dioxa-7,10-diazatricyclo[16.3.1.1^{4,7}]tricosa-1 (22),16,18,20-tetraene-6-carboxamide

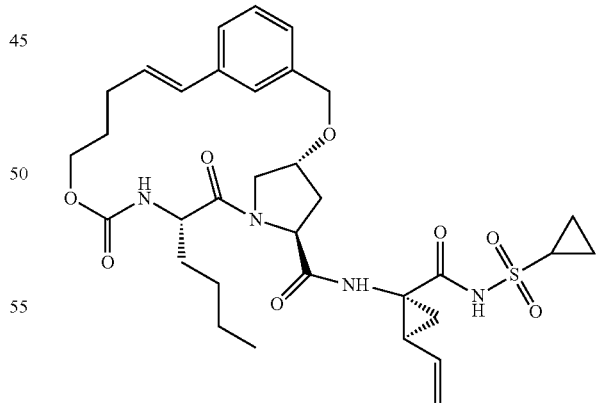

To a solution of the product from Example 24, Step 6 (150 mg, 0.337 mmol) in DMF (5 mL), Intermediate A1 (108 mg, 0.41 mmol), DIEA (0.147 mL, 0.844 mmol), and TBTU (163 mg, 0.51 mmol) were added. After 2 hours, the mixture was diluted with NaHCO$_{3(aq.)}$ and extracted with EtOAc. The organic layer was washed with brine, dried over Na$_2$SO$_4$, and the solvent was removed in vacuo. The crude material was purified by reverse-phase chromatography (gradient elution, 5-95% acetonitrile/H$_2$O (with 0.15% TFA)) to yield the title compound. LRMS ESI$^+$ (M+H)$^+$ 657.5.

Example 27

(4R,6S,9S)—N-((1R,2S)-1-{[(Cyclopropylsulfonyl)amino]carbonyl}-2-vinylcyclopropyl)-9-isopropyl-8,11-dioxo-3,12-dioxa-7,10-diazatricyclo[16.3.1.1$^{4,7}$]tricosa-1 (22), 18,20-triene-6-carboxamide

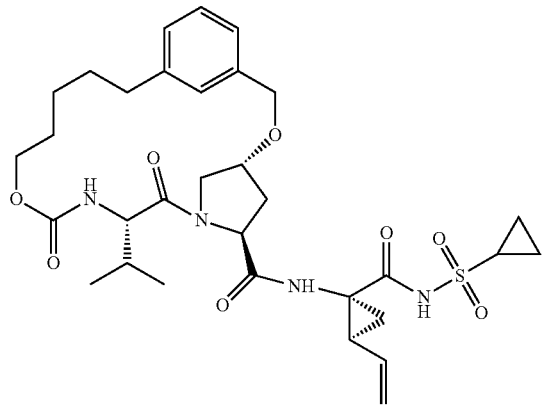 [SMILES: C=C[C@@H]1C[C@]1(NC(=O)[C@@H]1C[C@@H]2CN1C(=O)[C@H](C(C)C)NC(=O)OCCCCCc1cccc(c1)CO2)C(=O)NS(=O)(=O)C1CC1]

Step 1: Methyl (4R,6S,9S,16E)-9-isopropyl-8,11-dioxo-3,12-dioxa-7,10-diazatricyclo[16.3.1.1$^{4,7}$]tricosa-1(22), 16,18,20-tetraene-6-carboxylate

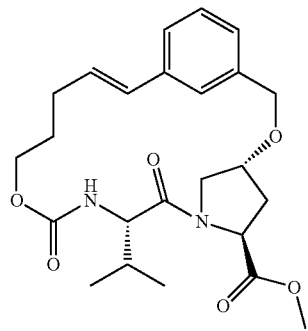 [SMILES: COC(=O)[C@@H]1C[C@@H]2CN1C(=O)[C@H](C(C)C)NC(=O)OCCC/C=C/c1cccc(c1)CO2]

Following the general procedure outlined in Example 24, the title compound was prepared using Intermediate B7 in place of Intermediate B1. LRMS ESI$^+$ (M+H)$^+$ 445.3.

Step 2: Methyl (4R,6S,9S)-9-isopropyl-8,11-dioxo-3,12-dioxa-7,10-diazatricyclo[16.3.1.1$^{4,7}$]tricosa-1 (22), 18,20-triene-6-carboxylate

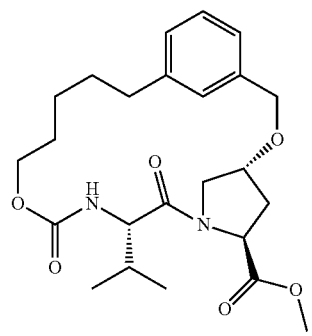 [SMILES: COC(=O)[C@@H]1C[C@@H]2CN1C(=O)[C@H](C(C)C)NC(=O)OCCCCCc1cccc(c1)CO2]

Using the product from Step 1, the title compound was prepared according to Example 3, Step 1. LRMS ESI$^+$ (M+H)$^+$ 447.4.

Step 3: (4R,6S,9S)—N-((1R,2S)-1-{[(Cyclopropylsulfonyl)amino]carbonyl}-2-vinylcyclopropyl)-9-isopropyl-8,11-dioxo-3,12-dioxa-7,10-diazatricyclo[16.3.1.1$^{4,7}$]tricosa-1(22), 18,20-triene-6-carboxamide Using the product from Step 2, the title compound was prepared according to Example 26. LRMS ESI$^+$ (M+H)$^+$ 645.4.

By using the appropriate procedures, the appropriate B intermediates in place of Intermediate B1 or Intermediate B7, and appropriate benzylating reagent in Step 1 in place of 1-bromo-3-(bromomethyl)benzene, the following compounds were prepared.

| Ex. | Structure | Name | LRMS (M + H)$^+$ | Procedure | Step 1 | Int. |
|---|---|---|---|---|---|---|
| 29 | 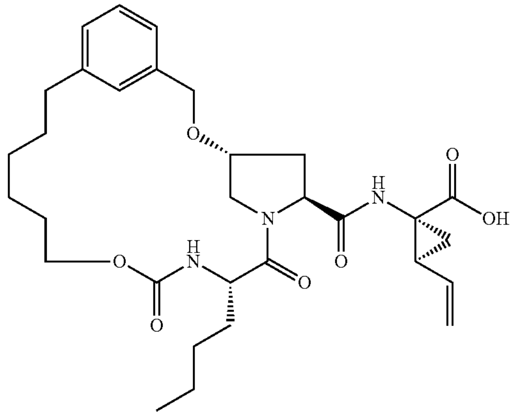 [SMILES: C=C[C@@H]1C[C@]1(NC(=O)[C@@H]1C[C@@H]2CN1C(=O)[C@H](CCCC)NC(=O)OCCCCCCc1cccc(c1)CO2)C(=O)O] | (1R,2S)-1-({[(4R,6S,9S)-9-butyl-8,11-dioxo-3,12-dioxa-7,10-diazatricyclo[17.3.1.1$^{4,7}$]tetracosa-1(23),19,21-trien-6-yl]carbonyl}amino)-2-vinylcyclopropanecarboxylic acid | 570.4 | See Example 25 | 1-iodo-3-(bromomethyl)benzene | B4 |

-continued

| Ex. | Structure | Name | LRMS (M + H)+ | Procedure | Step 1 | Int. |
|---|---|---|---|---|---|---|
| 30 | 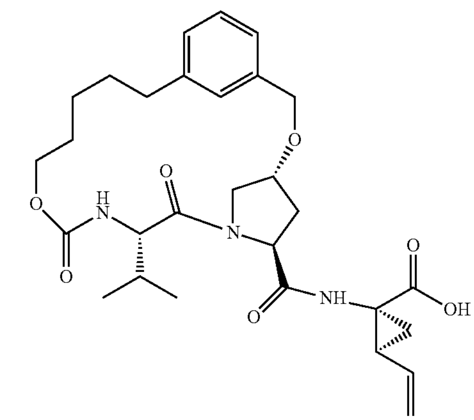 [SMILES: C=C[C@@H]1C[C@]1(NC(=O)[C@@H]1C[C@@H]2CN1C(=O)[C@H](C(C)C)NC(=O)OCCCCCc1cccc(c1)CO2)C(=O)O] | (1R,2S)-1-({[(4R,6S,9S)-9-isopropyl-8,11-dioxo-3,12-dioxa-7,10-diazatricyclo[16.3.1.1$^{4,7}$]tricosa-1(22),18,20-trien-6-yl]carbonyl}amino)-2-vinylcyclopropane carboxylic acid | 542.4 | See Example 25 | 1-iodo-3-(bromomethyl)benzene | B7 |
| 31 | 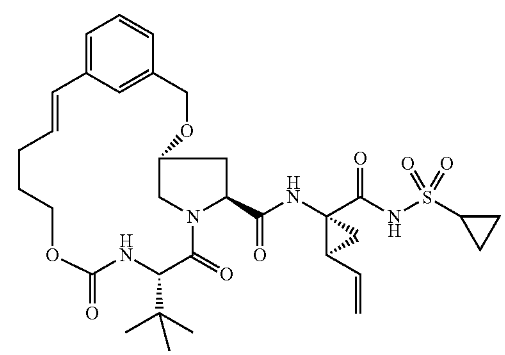 [SMILES: C=C[C@@H]1C[C@]1(NC(=O)[C@@H]1C[C@@H]2CN1C(=O)[C@H](C(C)(C)C)NC(=O)OCCC/C=C/c1cccc(c1)CO2)C(=O)NS(=O)(=O)C1CC1] | (4R,6S,9S,16E)-9-t-butyl-N-((1R,2S)-1-{[(cyclopropylsulfonyl)amino]carbonyl}-2-vinylcyclopropyl)-8,11-dioxo-3,12-dioxa-7,10-diazatricyclo[16.3.1.1$^{4,7}$]tricosa-1(22),16,18,20-tetraene-6-carboxamide | 657.3 | See Example 26 | 1-iodo-3-(bromomethyl)benzene | B2 |
| 32 | 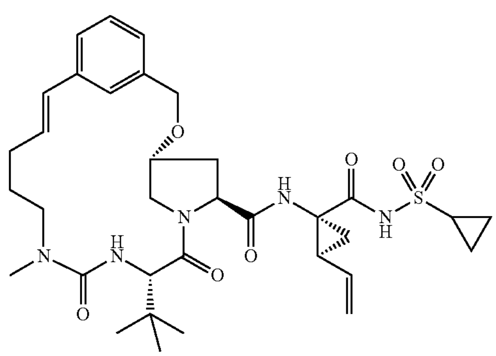 [SMILES: C=C[C@@H]1C[C@]1(NC(=O)[C@@H]1C[C@@H]2CN1C(=O)[C@H](C(C)(C)C)NC(=O)N(C)CCC/C=C/c1cccc(c1)CO2)C(=O)NS(=O)(=O)C1CC1] | (4R,6S,9S,16E)-9-t-butyl-N-((1R,2S)-1-{[(cyclopropylsulfonyl)amino]carbonyl}-2-vinylcyclopropyl)-12-methyl-8,11-dioxo-3-oxa-7,10,12-triazatricyclo[16.3.1.1$^{4,7}$]tricosa-1(22),16,18,20-tetraene-6-carboxamide | 670.4 | See Example 26 | 1-iodo-3-(bromomethyl)benzene | B20 |
| 33 | 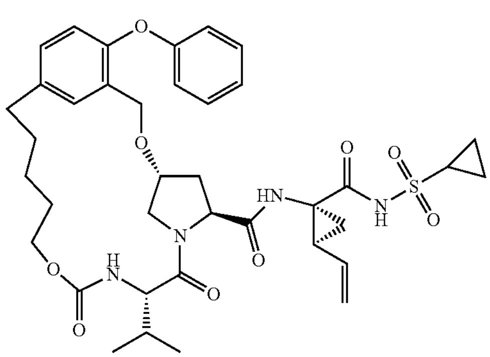 [SMILES: C=C[C@@H]1C[C@]1(NC(=O)[C@@H]1C[C@@H]2CN1C(=O)[C@H](C(C)C)NC(=O)OCCCCCc1ccc(Oc3ccccc3)c(c1)CO2)C(=O)NS(=O)(=O)C1CC1] | (4R,6S,9S)-N-((1R,2S)-1-{[(cyclopropylsulfonyl)amino]carbonyl}-2-vinylcyclopropyl)-9-isopropyl-8,11-dioxo-21-phenoxy-3,12-dioxa-7,10-diazatricyclo[16.3.1.1$^{4,7}$]tricosa-1(22),18,20-triene-6-carboxamide | | See Example 26 | | B7 |

-continued

| Ex. | Structure | Name | LRMS (M + H)+ | Procedure | Step 1 | Int. |
|---|---|---|---|---|---|---|
| 34 | 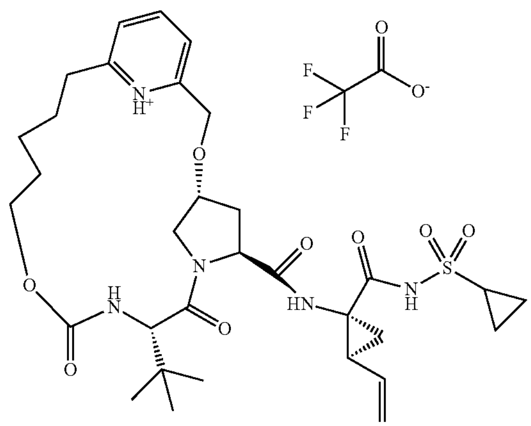 [SMILES: C=C[C@@H]1C[C@]1(NC(=O)[C@@H]1C[C@@H]2CN1C(=O)[C@H](C(C)(C)C)NC(=O)OCCCCCc1cccc([nH+]1)CO2)C(=O)NS(=O)(=O)C1CC1 ; O=C([O-])C(F)(F)F] | (4R,6S,9S)-9-t-butyl-6-{[((1R,2S)-1-{[(cyclopropyl sulfonyl)amino] carbonyl}-2-vinylcyclo propyl)amino] carbonyl}-8,11-dioxo-3,12-dioxa-7,10-diaza-22-azoniatricyclo [16.3.1.1$^{4,7}$]tricosa-1(22),18,20-triene trifluoroacetate | 661.3 | See Example 26 | (6-bromo pyridin-2-yl)methyl methane sulfonate. Ref: 61 Tetrahedron 12100 (2005). | B2 |
| 35 | 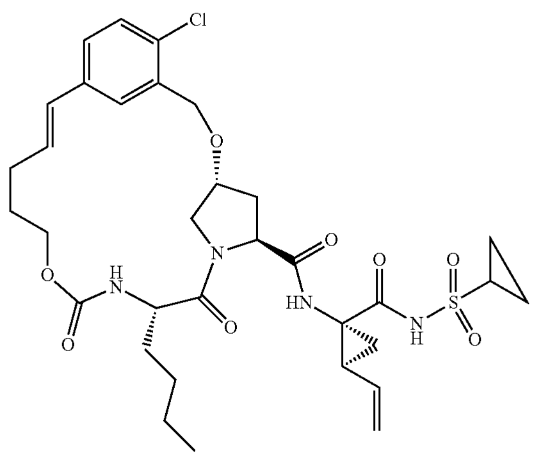 [SMILES: C=C[C@@H]1C[C@]1(NC(=O)[C@@H]1C[C@@H]2CN1C(=O)[C@H](CCCC)NC(=O)OCCC/C=C/c1ccc(Cl)c(c1)CO2)C(=O)NS(=O)(=O)C1CC1] | (4R,6S,9S,16E)-9-butyl-21-chloro-N-((1R,2S)-1-{[(cyclopropyl sulfonyl)amino] carbonyl}-2-vinylcyclo propyl)-8,11-dioxo-3,12-dioxa-7,10-diazatricyclo [16.3.1.1$^{4,7}$]tricosa-1(22),16,18,20-tetraene-6-carboxamide | 691.3 | See Example 26 | 5-bromo-2-chloro benzyl methane sulfonate (C9) | B1 |
| 36 | 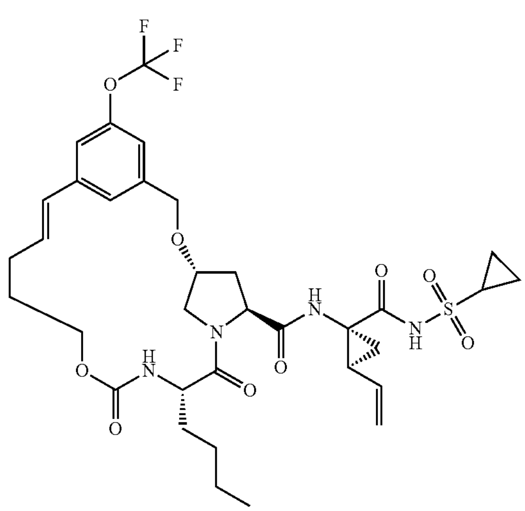 [SMILES: C=C[C@@H]1C[C@]1(NC(=O)[C@@H]1C[C@@H]2CN1C(=O)[C@H](CCCC)NC(=O)OCCC/C=C/c1cc(cc(OC(F)(F)F)c1)CO2)C(=O)NS(=O)(=O)C1CC1] | (4R,6S,9S,16E)-9-butyl-N-((1R,2S)-1-{[(cyclopropyl sulfonyl)amino] carbonyl}-2-vinylcyclo propyl)-8,11-dioxo-20-(trifluoromethoxy)-3,12-dioxa-7,10-diazatricyclo [16.3.1.1$^{4,7}$]tricosa-1(22),16,18,20-tetraene-6-carboxamide | 741.3 | See Example 26 | 3-bromo-5-(trifluoro methoxy) benzyl methane sulfonate (C7) | B1 |

| Ex. | Structure | Name | LRMS (M + H)+ | Procedure | Step 1 | Int. |
|---|---|---|---|---|---|---|
| 37 | 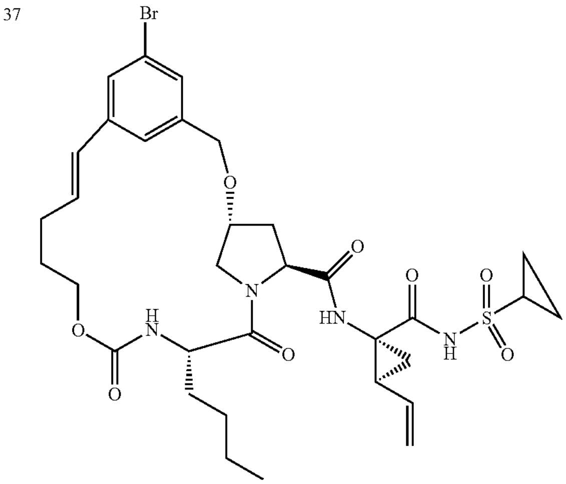 | (4R,6S,9S,16E)-20-bromo-9-butyl-N-((1R,2S)-1-{[(cyclopropyl sulfonyl)amino] carbonyl}-2-vinylcyclo propyl)-8,11-dioxo-3,12-dioxa-7,10-diazatricyclo [16.3.1.1[4,7]]tricosa-1(22),16,18,20-tetraene-6-carboxamide | 736.3 | See Example 26 | 1,3-dibromo-5-(bromo methyl) benzene | B1 |
| 38 | 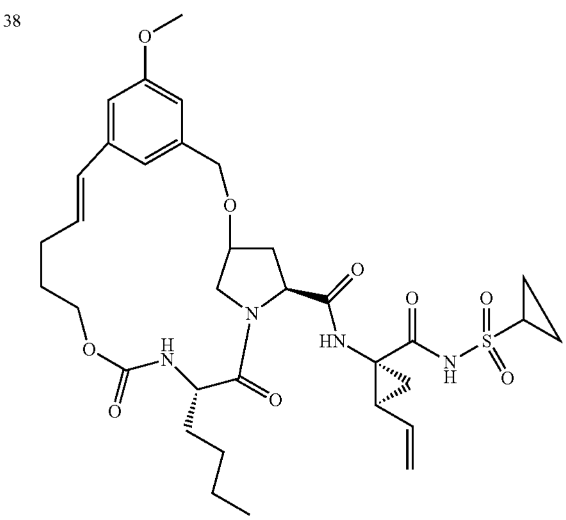 | (4R,6S,9S,16E)-9-butyl-N-((1R,2S)-1-{[(cyclopropyl sulfonyl)amino] carbonyl}-2-vinylcyclo propyl)-20-methoxy-8,11-dioxo-3,12-dioxa-7,10-diazatricyclo [16.3.1.1[4,7]]tricosa-1(22),16,18,20-tetraene-6-carboxamide | 687.6 | See Example 26 | 3-bromo-5-methoxy benzyl methane sulfonate (C10) | B1 |

Example 40

(5R,7S,10S)-10-Butyl-N-((1R,2S)-1-{[(cyclopropyl-sulfonyl)amino]carbonyl}-2-vinylcyclopropyl)-3,9,12-trioxo-4,13-dioxa-2,8,11-triazatricyclo [17.3.1.1[5,8]]tetracosa-1(23), 19,21-triene-7-carboxamide

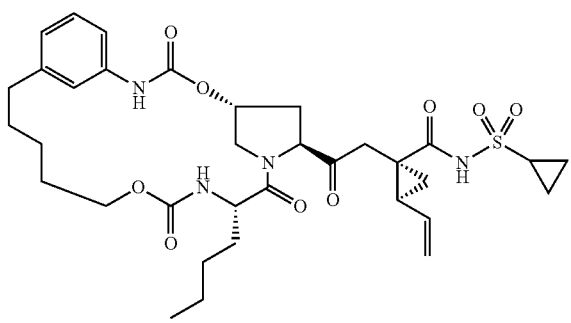 [SMILES: C=C[C@@H]1C[C@]1(CC(=O)[C@@H]1C[C@@H]2CN1C(=O)[C@H](CCCC)NC(=O)OCCCCCc1cccc(c1)NC(=O)O2)C(=O)NS(=O)(=O)C1CC1]

Step 1: 1-t-Butyl 2-methyl (2S,4R)-4-({[(3-bro-mophenyl)amino]carbonyl}oxy)pyrrolidine-12-di-carboxylate

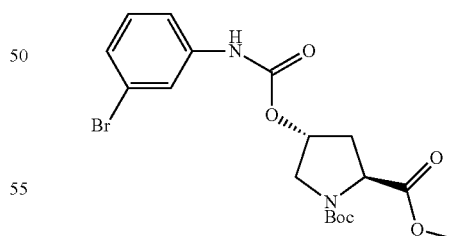

To a solution of 1-t-butyl 2-methyl (2S,4R)-4-hydroxy-pyrrolidine-1,2-dicarboxylate (1.0 g, 4.08 mmol) in DCM (15 mL), 1-bromo-3-isocyanatobenzene (807 mg, 4.08 mmol), TEA (0.97 mL, 6.93 mmol), and DMAP (100 mg, 0.815 mmol) were added. After 15 hours, the mixture was diluted with NaHCO$_3$ and extracted with EtOAc. The organic layer was washed with H$_2$O and then brine, dried over Na$_2$SO$_4$, and the solvent was removed in vacuo. The crude material was purified on SiO$_2$ (gradient elution, 5-75% EtOAc/hexanes) to yield the title compound. LRMS ESI+ ((M-Boc)+H)+ 343.1.

Step 2: (5R,7S,10S)-10-Butyl-N-((1R,2S)-1-{[(cyclopropylsulfonyl)amino]carbonyl}-2-vinylcyclopropyl)-3,9,12-trioxo-4,13-dioxa-2,8,11-triazatricyclo[17.3.1.1⁵,⁸]tetracosa-1(23), 19,21-triene-7-carboxamide Using the product from Step 1, the title compound was prepared according to Example 3. LRMS ESI⁺ (M+H)⁺ 688.4.

Example 41

(5R,7S,10S)-10-t-Butyl-N-((1R,2S)-1-{[(cyclopropylsulfonyl)amino]carbonyl}-2-vinyl cyclopropyl)-22-methoxy-3,9,12-trioxo-4,13-dioxa-2,8,11-triazatricyclo[19.3.1.1⁵,⁸]hexacosa-1(25),21,23-triene-7-carboxamide

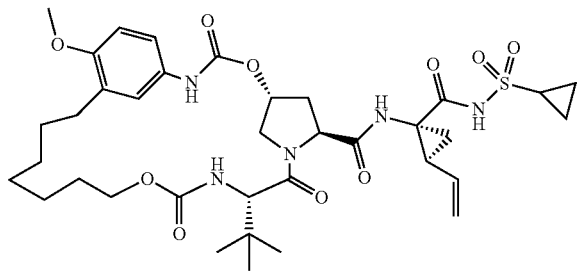 [SMILES: C=C[C@@H]1C[C@]1(NC(=O)[C@@H]1C[C@@H]2CN1C(=O)[C@H](C(C)(C)C)NC(=O)OCCCCCCCc1cc(ccc1OC)NC(=O)O2)C(=O)NS(=O)(=O)C1CC1]

The title compound was prepared using the procedures of Example 40, and replacing 3-bromoaniline with 3-bromo-4-methoxyaniline.

Example 42

(6R,8S,11S,18E)-N-((1R,2S)-1-{[(Cyclopropylsulfonyl)amino]carbonyl}-2-vinylcyclopropyl)-11-isopropyl-4,10,13-trioxo-5,14-dioxa-3,9,12-triazatricyclo[18.3.1.1⁶,⁹]pentacosa-1(24), 18,20,22-tetraene-8-carboxamide

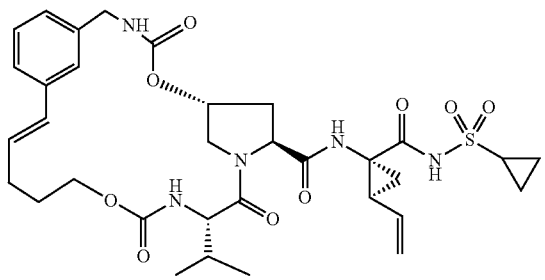 [SMILES: C=C[C@@H]1C[C@]1(NC(=O)[C@@H]1C[C@@H]2CN1C(=O)[C@H](C(C)C)NC(=O)OCCC/C=C/c1cccc(c1)CNC(=O)O2)C(=O)NS(=O)(=O)C1CC1]

Step 1: 1-t-Butyl 2-methyl (2S,4R)-4-({[(3-bromobenzyl)amino]carbonyl}oxy)pyrrolidine-1,2-dicarboxylate

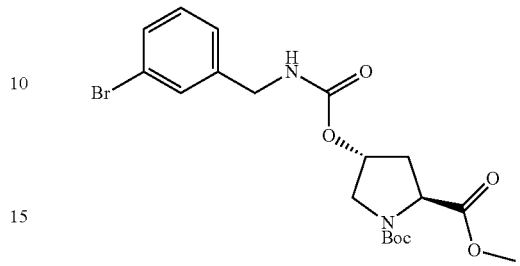

To a solution of 1-t-butyl 2-methyl (2S,4R)-4-hydroxy-pyrrolidine-1,2-dicarboxylate (4.41 g, 17.97 mmol) in DMF (70 mL) cooled to 0° C., CDI (2.91 g, 17.97 mmol) was added. After stirring at RT for 30 minutes, 1-(3-bromophenyl) methanamine hydrochloride (4.0 g, 17.97 mmol) was added, and the mixture was heated to 50° C. for 15 hours. The reaction was then diluted with EtOAc, washed with $H_2O$ and then brine, dried over $Na_2SO_4$, and the solvent was removed in vacuo. The crude material was purified on $SiO_2$ (gradient elution, 5-75% EtOAc/hexanes) to yield the title compound. LRMS ESI⁺ ((M-Boc)+H)⁺ 359.2.

Step 2: (6R,8S,11S,18E)-N-((1R,2S)-1-{[(Cyclopropylsulfonyl)amino]carbonyl}-2-vinylcyclo propyl)-11-isopropyl-4,10,13-trioxo-5,14-dioxa-3,9,12-triazatricyclo[18.3.1.1⁶,⁹]pentacosa-1(24), 18,20,22-tetraene-8-carboxamide Using the product from Step 1 and Intermediate B7, the title compound was prepared according to Example 1. LRMS ESI⁺ (M+H)⁺ 686.4.

By using the appropriate procedures, the appropriate B intermediates in place of Intermediate B1 or Intermediate B7 or N-[(Hept-6-en-1-yloxy)carbonyl]-3-methyl-L-valine, and appropriate amino compound in Step 1, the following compounds were prepared.

| Ex. | Structure | Name | LRMS (M + H)⁺ | Procedure | Step 1 | Int. |
|---|---|---|---|---|---|---|
| 43 | 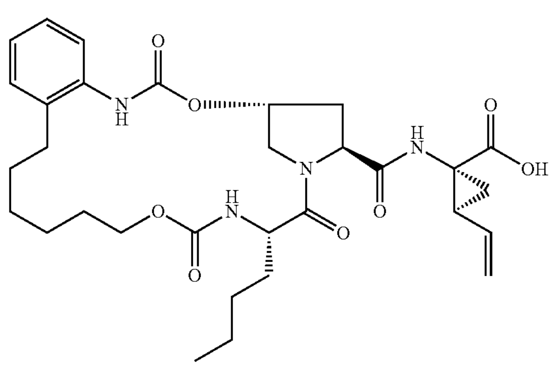 [SMILES: C=C[C@@H]1C[C@]1(NC(=O)[C@@H]1C[C@@H]2CN1C(=O)[C@H](CCCC)NC(=O)OCCCCCCc1ccccc1NC(=O)O2)C(=O)O] | (1R,2S)-1-({[(4R,6S,9S)-9-butyl-2,8,11-trioxo-1,2,5,6,8,9,10,11,13,14,15,16,17,18-tetradecahydro-4H-4,7-methano-3,12,1,7,10-benzodioxatriaza cycloicosin-6-yl]carbonyl}amino)-2-vinylcyclopropane carboxylic acid | 599.3 | See Example 39 | 2-bromophenyl isocyanate | B4 |

-continued

| Ex. | Structure | Name | LRMS (M + H)+ | Procedure | Step 1 | Int. |
|---|---|---|---|---|---|---|
| 44 | 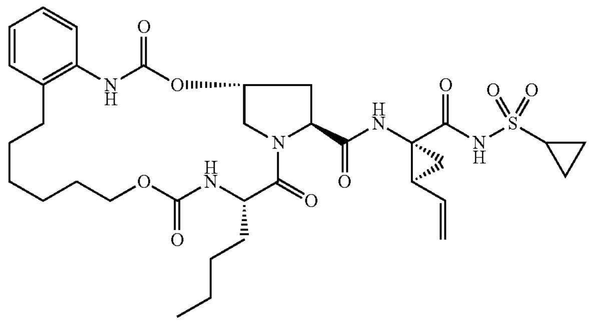 [SMILES: C=C[C@@H]1C[C@]1(NC(=O)[C@@H]1C[C@@H]2CN1C(=O)[C@H](CCCC)NC(=O)OCCCCCCc1ccccc1NC(=O)O2)C(=O)NS(=O)(=O)C1CC1] | (4R,6S,9S)-9-butyl-N-((1R,2S)-1-{[(cyclopropylsulfonyl)amino]carbonyl}-2-vinylcyclopropyl)-2,8,11-trioxo-1,2,5,6,8,9,10,11,13,14,15,16,17,18-tetradecahydro-4H-4,7-methano-3,12,1,7,10-benzodioxatriazacycloicosine-6-carboxamide | 702.4 | See Example 40 | 2-bromophenyl isocyanate | B4 |
| 46 | 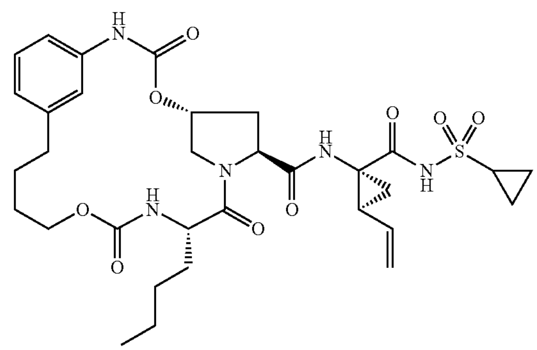 [SMILES: C=C[C@@H]1C[C@]1(NC(=O)[C@@H]1C[C@@H]2CN1C(=O)[C@H](CCCC)NC(=O)OCCCCc1cccc(c1)NC(=O)O2)C(=O)NS(=O)(=O)C1CC1] | (5R,7S,10S)-10-butyl-N-((1R,2S)-1-{[(cyclopropylsulfonyl)amino]carbonyl}-2-vinylcyclopropyl)-3,9,12-trioxo-4,13-dioxa-2,8,11-triazatricyclo[16.3.1.1$^{5,8}$]tricosa-1(22),18,20-triene-7-carboxamide | 674.4 | See Example 40 | 3-bromophenyl isocyanate | B3 |
| 47 | 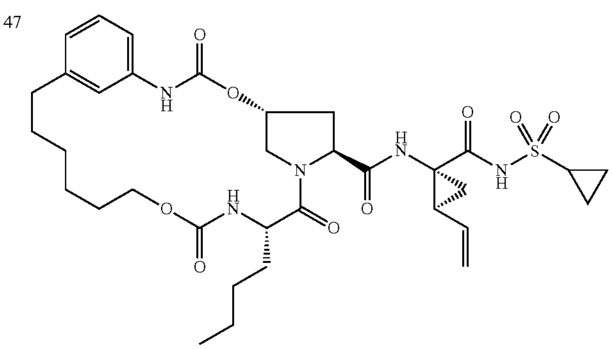 | (5R,7S,10S)-10-butyl-N-((1R,2S)-1-{[(cyclopropylsulfonyl)amino]carbonyl}-2-vinylcyclopropyl)-3,9,12-trioxo-4,13-dioxa-2,8,11-triazatricyclo[18.3.1.1$^{5,8}$]pentacosa-1(24),20,22-triene-7-carboxamide | 702.4 | See Example 40 | 3-bromophenyl isocyanate | B4 |
| 48 | 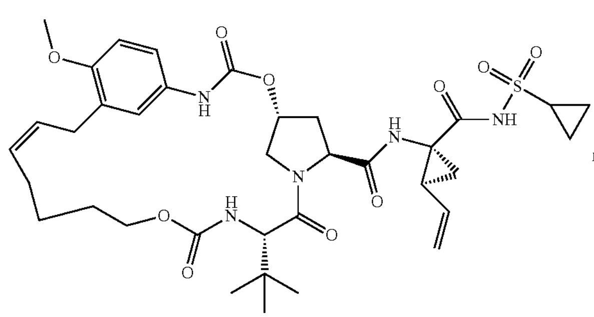 [SMILES: C=C[C@@H]1C[C@]1(NC(=O)[C@@H]1C[C@@H]2CN1C(=O)[C@H](C(C)(C)C)NC(=O)OCCCC/C=C\Cc1cc(ccc1OC)NC(=O)O2)C(=O)NS(=O)(=O)C1CC1] | (5R,7S,10S,19E)-10-t-butyl-N-((1R,2S)-1-{[(cyclopropylsulfonyl)amino]carbonyl}-2-vinylcyclopropyl)-22-methoxy-3,9,12-trioxo-4,13-dioxa-2,8,11-triazatricyclo[19.3.1.1$^{5,8}$]hexacosa-1(25),18,21,23-tetraene-7-carboxamide | | See Example 40 | 2-bromo-4-isocyanato-1-methoxybenzene. Ref: 16 Biorg. Med. Chem. Lett. 404 (2006) | B11 |

| Ex. | Structure | Name | LRMS (M + H)+ | Procedure | Step 1 | Int. |
|---|---|---|---|---|---|---|
| 49 | 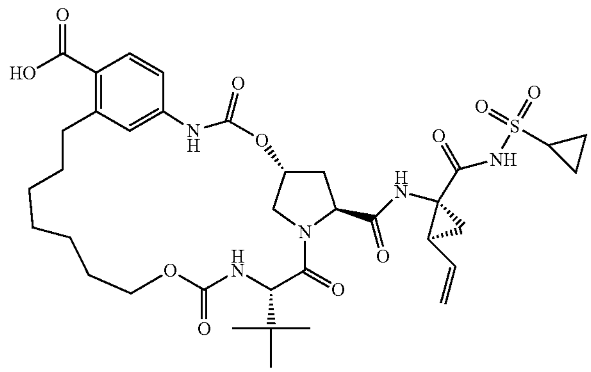 [SMILES: C=C[C@@H]1C[C@]1(NC(=O)[C@@H]1C[C@@H]2CN1C(=O)[C@H](C(C)(C)C)NC(=O)OCCCCCCCc1cc(ccc1C(=O)O)NC(=O)O2)C(=O)NS(=O)(=O)C1CC1] | (5R,7S,10S)-10-t-butyl-7-{[((1R,2S)-1-{[(cyclopropyl sulfonyl)amino] carbonyl}-2-vinylcyclopropyl) amino]carbonyl}-3,9,12-trioxo-4,13-dioxa-2,8,11-triazatricyclo [19.3.1.1^{5,8}]hexacosa-1(25),21,23-triene-22-carboxylic acid | | See Example 40 | 4-amino-2-bromo benzoic acid | B11 |
| 50 | 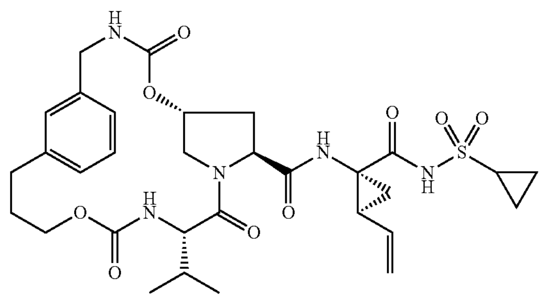 [SMILES: C=C[C@@H]1C[C@]1(NC(=O)[C@@H]1C[C@@H]2CN1C(=O)[C@H](C(C)C)NC(=O)OCCCc1cccc(c1)CNC(=O)O2)C(=O)NS(=O)(=O)C1CC1] | (6R,8S,11S)-N-((1R,2S)-1-{[(cyclopropyl sulfonyl)amino] carbonyl}-2-vinylcyclopropyl)-11-isopropyl-4,10,13-trioxo-5,14-dioxa-3,9,12-triazatricyclo [16.3.1.1^{6,9}]tricosa-1(22),18,20-triene-8-carboxamide | 660.4 | See Example 41 | 1-(3-bromo phenyl) methanamine | B8 |
| 51 | 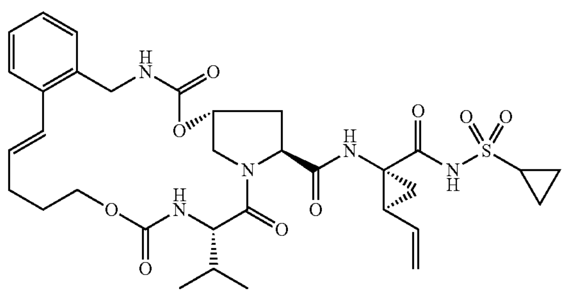 [SMILES: C=C[C@@H]1C[C@]1(NC(=O)[C@@H]1C[C@@H]2CN1C(=O)[C@H](C(C)C)NC(=O)OCCC/C=C/c1ccccc1CNC(=O)O2)C(=O)NS(=O)(=O)C1CC1] | (5R,7S,10S,17E)-N-((1R,2S)-1-{[(cyclopropyl sulfonyl)amino] carbonyl}-2-vinylcyclopropyl)-10-isopropyl-3,9,12-trioxo-1,2,3,6,7,9,10,11,12,14,15,16-dodecahydro-5H-5,8-methano-4,13,2,8,11-benzodioxatriazacyclo icosine-7-carboxamide | 686.4 | See Example 42 | 1-(3-bromo phenyl) methanamine | B7 |

Example 52

(5R,7S)—N-((1R,2S)-1-{[(Cyclopropylsulfonyl) amino]carbonyl}-2-vinylcyclopropyl)-15,15,24-trimethyl-3,9,12-trioxo-6,7,9,10,11,12,14,15,16,17-decahydro-3H,5H-2,23-epimino-5,8-methano-4,13,8,11-benzodioxadiazacyclohenicosine-7-carboxamide

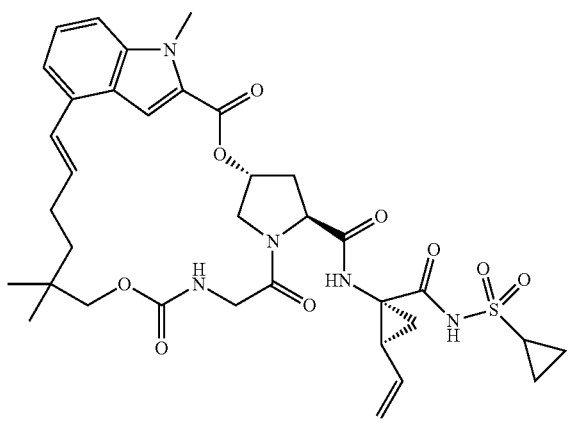 [SMILES: C=C[C@@H]1C[C@]1(NC(=O)[C@@H]1C[C@@H]2CN1C(=O)CNC(=O)OCC(C)(C)CC/C=C/c1cccc3c1cc(n3C)C(=O)O2)C(=O)NS(=O)(=O)C1CC1]

Step 1: 1-t-Butyl 2-[2-(trimethylsilyl)ethyl](2S,4R)-4-hydroxypyrrolidine-1,2-dicarboxylate

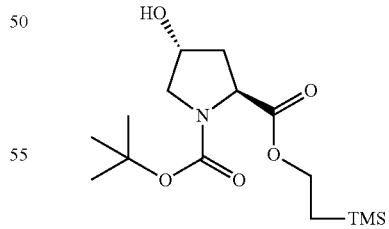

To a solution of N-Boc-L-4-hydroxyproline (14.5 g, 0.0591 mol) in toluene (175 mL), O-2-trimethylsilyl-N,N'-diisopropylisourea (29.0 g, 0.118 mol) (T. Eicher, SYNTHESIS 755-762 (1996)) was added, and the mixture heated to reflux for 3 hours. The reaction mixture was cooled, concentrated to an oil and redissolved in DCM (150 mL) and H$_2$O (1 mL). The mixture was stirred for 1 hour, filtered and the filtrate concentrated to an oil. The oil was dissolved in 20%

EtOAc/hexanes (200 mL) and stirred, the solids were filtered, and the filtrate was concentrated to an oil and purified on SiO₂ (20-60% EtOAc/hexanes) to yield 9.4 g (48% yield) of the title compound. LRMS (M+H)⁺ Calcd.=332; found 332.

Step 2: 1-t-Butyl 2-[2-(trimethylsilyl)ethyl](2S,4R)-4-{[(4-bromo-1-methyl-1H-indol-2-yl)carbonyl]oxy}pyrrolidine-1,2-dicarboxylate

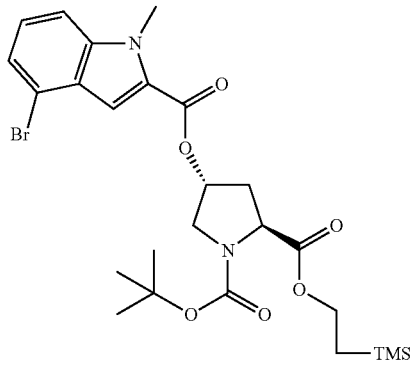 [SMILES: Cn1c(C(=O)O[C@@H]2C[C@@H](C(=O)OCC[Si](C)(C)C)N(C(=O)OC(C)(C)C)C2)cc2c(Br)cccc21]

To a solution of Intermediate C1 (360 mg, 1.4 mmol) in DMF (10 mL), carbonyl diimidazole (230 mg, 1.4 mmol) was added, and heated to 40° C. for 2 hours while under N₂. To the reaction solution, the title compound from Step 1 (564 mg, 1.7 mmol) and DBU (0.318 mL, 2.12 mmol) were added. The reaction mixture was heated to 40 C for an additional 2 hours. The reaction mixture was diluted with EtOAc, and the organics were washed with 1N HCl (2×), brine, saturated NaHCO₃ (2×), and brine. The organics were then dried over Na₂SO₄, filtered, and concentrated. The resulting residue was purified on SiO₂ (gradient elution, 10-40% EtOAc/hexanes) to yield the product as a white foam (556 mg, 69% yield). LRMS (M+H)⁺ Calcd.=567, 569; found 567, 569.

Step 3: 2-[2-(Trimethylsilyl)ethyl](2S,4R)-4-{[(4-bromo-1-methyl-1H-indol-2-yl)carbonyl]oxy}pyrrolidine-2-carboxylate

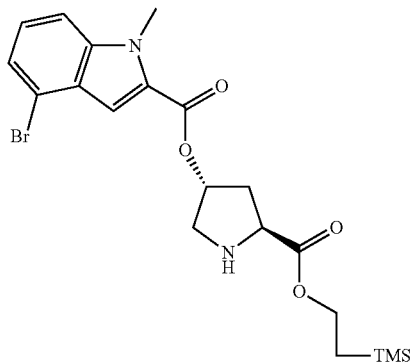 [SMILES: Cn1c(C(=O)O[C@H]2CN[C@H](C(=O)OCC[Si](C)(C)C)C2)cc2c(Br)cccc21]

To a solution of the compound from Step 2 (554 mg, 0.98 mmol) in DCM (4 mL), TFA (1 mL) was added, and the mixture was stirred for 1 hour. The reaction mixture was concentrated. The resulting residue was partitioned between EtOAc and saturated NaHCO₃, and extracted with EtOAc (2×); the organics were combined, washed with brine, dried over Na₂SO₄, filtered, and concentrated to yield the title compound as a pale yellow oil (340 mg). LRMS (M+H)⁺ Calcd.=467, 469; found 467, 469.

Step 4: 2-(Trimethylsilyl)ethyl N-{[(2,2-dimethylhex-5-en-1-yl)oxy]carbonyl}-3-methyl-L-valyl-(4R)-4-{[(4-bromo-1-methyl-1H-indol-2-yl)carbonyl]oxy}-L-prolinate

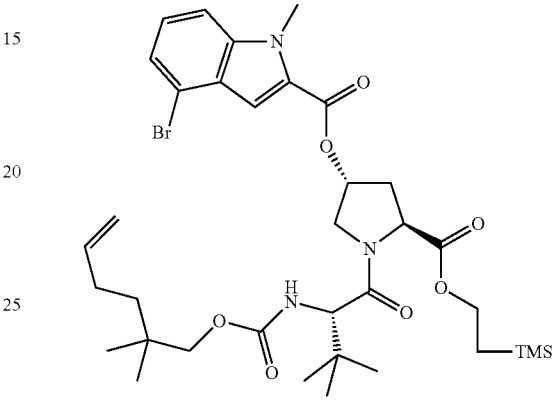

To a solution of the compound from Step 3 (340 mg, 0.727 mmol) and Intermediate B13 (249 mg, 0.873 mmol) in DMF (5 mL), HATU (332 mg, 0.873 mmol) and DIEA (0.36 mL, 2.2 mmol) were added, and the mixture was stirred for 15 hours. The reaction mixture is diluted with EtOAc; the organics were washed with 1N HCl (2×), brine, saturated NaHCO₃ (2×), brine. The organics were then dried over Na₂SO₄, filtered, and concentrated. The resulting residue was purified on SiO₂ (gradient elution, 1.5% acetone/DCM) to yield the title compound as a white foam (402 mg). LRMS (M+H)⁺ Calcd.=734, 736; found 734, 736.

Step 5: 2-(Trimethylsilyl)ethyl N-[(2,2-dimethylhex-5-en-1-yl)oxy]carbonyl-3-methyl-L-valyl-(4R)-4-{[(1-methyl-4-vinyl-1H-indol-2-yl)carbonyl]oxy}-L-prolinate

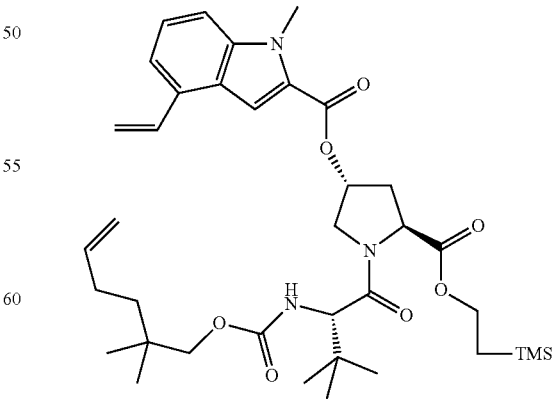

N₂ was bubbled through a solution of the compound from Step 4 (400 mg, 0.54 mmol) in PhMe (8 mL) for 30 minutes, and then tributyl(vinyl)tin (0.19 mL, 0.65 mmol) and tetrakistriphenylphosphine palladium (63 mg, 0.05 mmol) were added. The reaction solution was heated to reflux for 2 hours, concentrated, and purified the resulting residue on $SiO_2$ (gradient elution, 0-1.5% acetone/DCM) to yield the title compound as a yellow oil (320 mg). LRMS $(M+H)^+$ Calcd.=682; found 682.

Step 6: 2-(Trimethylsilyl)ethyl (5R,7S)-15,15,24-trimethyl-3,9,12-trioxo-6,7,9,10,11,12,14,15,16,17-decahydro-3H,5H-2,23-epimino-5,8-methano-4,13,8,11-benzodioxadiazacyclohenicosine-7-carboxylate

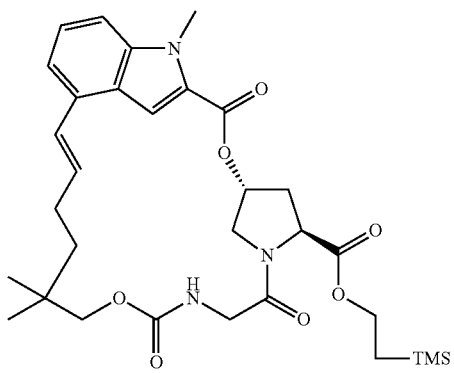 [SMILES: Cn1c2cc3c(cccc31)/C=C/CCC(C)(C)COC(=O)NCC(=O)N1C[C@@H](C[C@H]1C(=O)OCC[Si](C)(C)C)OC2=O]

$N_2$ was bubbled through a solution of the compound from Step 5 (320 mg, 0.47 mmol) in DCM (80 mL) for 30 minutes, and then Neolyst M1 catalyst (75 mg, 23 wt %) was added. The dark solution was stirred for 6 hours, and $N_2$ was bubbled through the solution for 30 minutes, after which additional NEOLYST M1 catalyst (75 mg, 23 wt %) was added, and the solution was stirred for 15 hours. Concentrated and purified the resulting residue on $SiO_2$ (gradient elution, 10-40% EtOAc/hexanes) to yield the title compound as a yellow oil (259 mg). LRMS $(M+H)^+$ Calcd.=654; found 654.

Step 7: (5R,7S)—N-((1R,2S)-1-{[(Cyclopropylsulfonyl)amino]carbonyl}-2-vinylcyclopropyl)-15,15,24-trimethyl-3,9,12-trioxo-6,7,9,10,11,12,14,15,16,17-decahydro-3H,5H-2,23-epimino-5,8-methano-4,13,8,11-benzodioxadiazacyclohenicosine-7-carboxamide To a solution of the compound from Step 6 (86 mg, 0.13 mmol) in THF (3 mL), TBAF (1M in THF, 0.66 mL, 0.66 mmol) was added, and the mixture was stirred for 30 minutes. The reaction solution was concentrated to dryness, and the resulting residue was dissolved in DMF (4 mL). To this solution, Intermediate A1 (84 mg, 0.32 mmol), HATU (120 mg, 0.32 mmol), and DIEA (0.22 mL, 0.66 mmol) were added, and the mixture was stirred for 18 hours. The crude reaction mixture was purified by reverse-phase HPLC to yield the title compound as a white solid (40 mg). LRMS $(M+H)^+$ Calcd.=766; found 766.

Example 53

(5R,7S)—N-((1R,2S)-1-{[(Cyclopropylsulfonyl)amino]carbonyl}-2-vinylcyclopropyl)-15,15,24-trimethyl-3,9,12-trioxo-6,7,9,10,11,12,14,15,16,17,18,19-dodecahydro-3H,5H-2,23-epimino-5,8-methano-4,13,8,11-benzodioxadiazacyclohenicosine-7-carboxamide

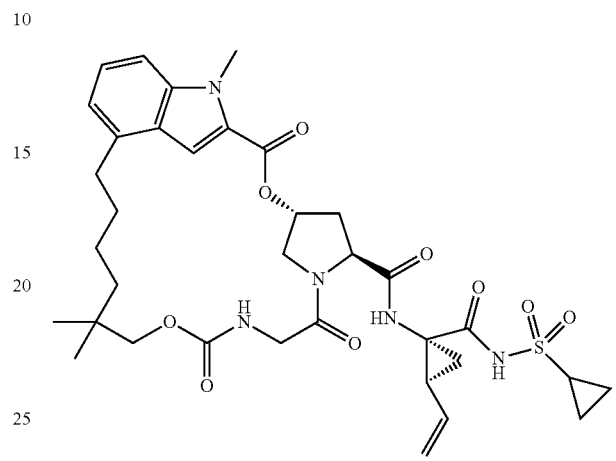

Step 1: 2-(Trimethylsilyl)ethyl (5R,7S)-15,15,24-trimethyl-3,9,12-trioxo-6,7,9,10,11,12,14,15,16,17,18,19-dodecahydro-3H,5H-2,23-epimino-5,8-methano-4,13,8,11-benzodioxadiazacyclohenicosine-7-carboxylate

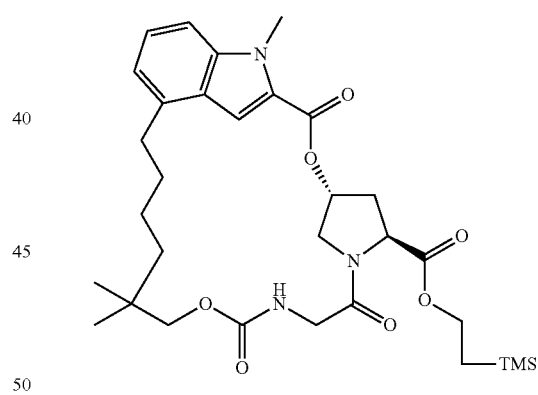

To a solution of the compound from Example 1 Step 6 (173 mg, 0.27 mmol) in EtOAc (6 mL), 10% Pd/C (42 mg) was added, and the reaction mixture was placed under $H_2$ for 15 hours. The reaction mixture was filtered, and the filtrate is concentrated to yield the title compound as a clear oil (170 mg). LRMS $(M+H)^+$ Calcd.=656; found 656.

Step 2: (5R,7S)—N-((1R,2S)-1-{[(Cyclopropylsulfonyl)amino]carbonyl}-2-vinylcyclopropyl)-15,15,24-trimethyl-3,9,12-trioxo-6,7,9,10,11,12,14,15,16,17,18,19-dodecahydro-3H,5H-2,23-epimino-5,8-methano-4,13,8,11-benzodioxadiazacyclohenicosine-7-carboxamide Hydrolysis of the trimethylsilylethyl ester and coupling with Intermediate A1 was carried out as described in Example 52 Step 7 to afford the title compound. LRMS $(M+H)^+$ Calcd.=768; found 768.

Example 54

(5R,7S)—N-((1R,2R)-1-{[(Cyclopropylsulfonyl)amino]carbonyl}-2-ethylcyclopropyl)-5,15,24-trimethyl-3,9,12-trioxo-6,7,9,10,11,12,14,15,16,17,18,19-dodecahydro-3H,5H-2,23-epimino-5,8-methano-4,13,8,11-benzodioxadiazacyclohenicosine-7-carboxamide

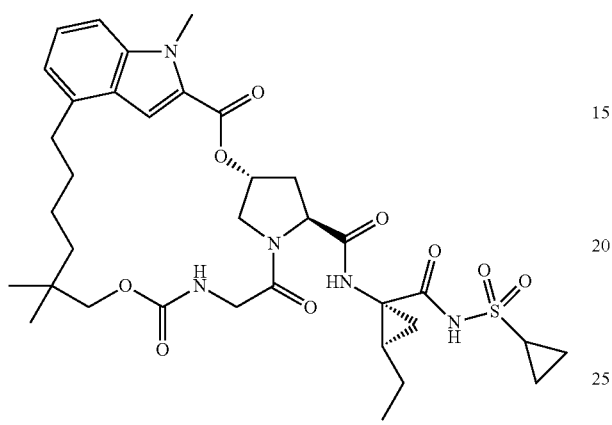

Hydrolysis of the trimethylsilylethyl ester (Example 52 Step 1) and coupling to Intermediate A3 as described in Example 52 Step 7 afforded the title compound. LRMS (M+H)$^+$ Calcd.=770; found 770.

By using the appropriate A, B, and C intermediates in place of Intermediates A1, B13, and C1 respectively, the following compounds were prepared.

| Ex. | Structure | Name | LRMS (M + H)$^+$ | Procedure | Int. |
|---|---|---|---|---|---|
| 55 | 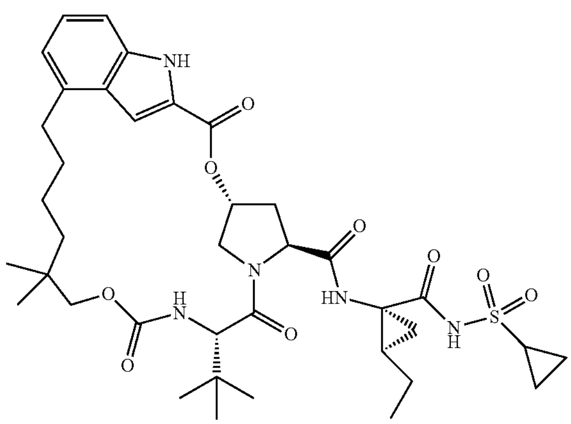 [SMILES: CC[C@@H]1C[C@]1(NC(=O)[C@@H]1C[C@@H]2CN1C(=O)[C@H](C(C)(C)C)NC(=O)OCC(C)(C)CCCCc1cccc3[nH]c(cc13)C(=O)O2)C(=O)NS(=O)(=O)C1CC1] | (5R,7S,10S)-10-t-butyl-N-((1R,2R)-1-{[(cyclopropylsulfonyl)amino]carbonyl}-2-ethylcyclopropyl)-15,15-dimethyl-3,9,12-trioxo-6,7,9,10,11,12,14,15,16,17,18,19-dode cahydro-3H,5H-2,23-epimino-5,8-methano-4,13,8,11-benzodioxadiaza-cyclohenicosine-7-carboxamide | 756 | See Example 54 | A3, B13, C2 |
| 56 | 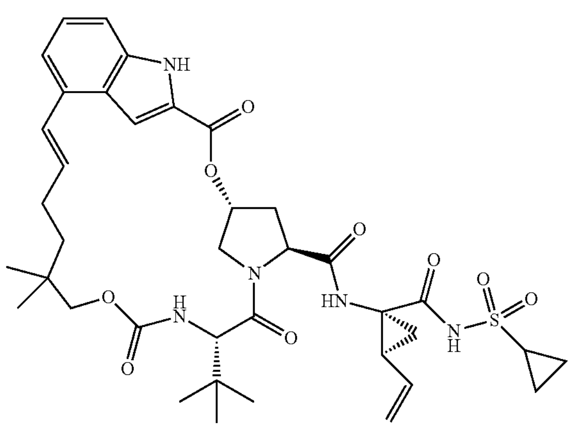 [SMILES: C=C[C@@H]1C[C@]1(NC(=O)[C@@H]1C[C@@H]2CN1C(=O)[C@H](C(C)(C)C)NC(=O)OCC(C)(C)CC/C=C/c1cccc3[nH]c(cc13)C(=O)O2)C(=O)NS(=O)(=O)C1CC1] | (5R,7S,10S)-10-t-butyl-N-((1R,2S)-1-{[(cyclopropylsulfonyl)amino]carbonyl}-2-vinylcyclopropyl)-15,15-dimethyl-3,9,12-trioxo-6,7,9,10,11,12,14,15,16,17-decahydro-3H,5H-2,23-epimino-5,8-methano-4,13,8,11-benzodioxadiazacyclohenicosine-7-carboxamide | 752 | See Example 52 | A1, B13, C2 |

| Ex. | Structure | Name | LRMS (M + H)+ | Procedure | Int. |
|---|---|---|---|---|---|
| 57 | 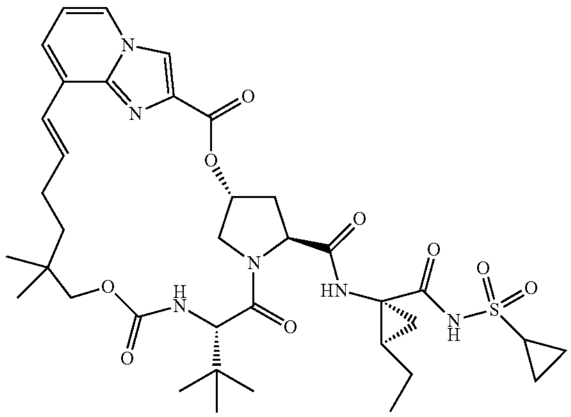 [SMILES: CC[C@@H]1C[C@]1(NC(=O)[C@@H]1C[C@@H]2CN1C(=O)[C@H](C(C)(C)C)NC(=O)OCC(C)(C)CC/C=C/c1cccn3cc(nc13)C(=O)O2)C(=O)NS(=O)(=O)C1CC1] | (5R,7S,10S)-10-t-butyl-N-((1R,2R)-1-{[(cyclopropylsulfonyl)amino]carbonyl}-2-ethylcyclopropyl)-15,15-dimethyl-3,9,12-trioxo-6,7,9,10,11,12,14,15,16,17-decahydro-5H-5,8-methano-23,2-methenopyrido[2,3-n][1,10,3,6,13]dioxatriazacyclohenicosine-7-carboxamide | 755 | See Example 52 | A3, B13, C3 |
| 58 | 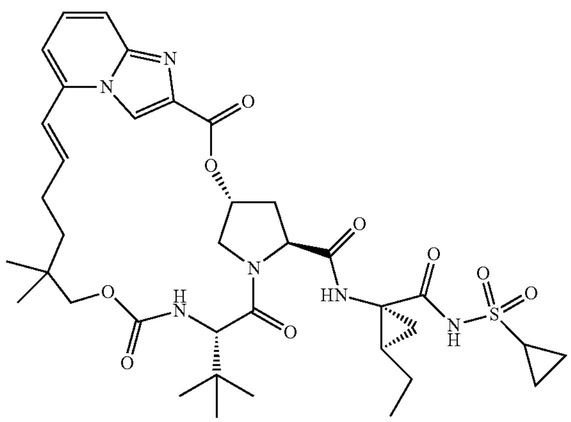 [SMILES: CC[C@@H]1C[C@]1(NC(=O)[C@@H]1C[C@@H]2CN1C(=O)[C@H](C(C)(C)C)NC(=O)OCC(C)(C)CC/C=C/c1cccc3nc(cn13)C(=O)O2)C(=O)NS(=O)(=O)C1CC1] | (5R,7S,10S)-10-t-butyl-N-((1R,2R)-1-{[(cyclopropylsulfonyl)amino]carbonyl}-2-ethylcyclopropyl)-15,15-dimethyl-3,9,12-trioxo-6,7,9,10,11,12,14,15,16,17-decahydro-3H,5H-2,23-epiazeno-5,8-methanopyrido[1,2-n][1,10,3,6,14]dioxatri-azacyclohenicosine-7-carboxamide | 755 | See Example 52 | A3, B13, C4 |
| 59 | 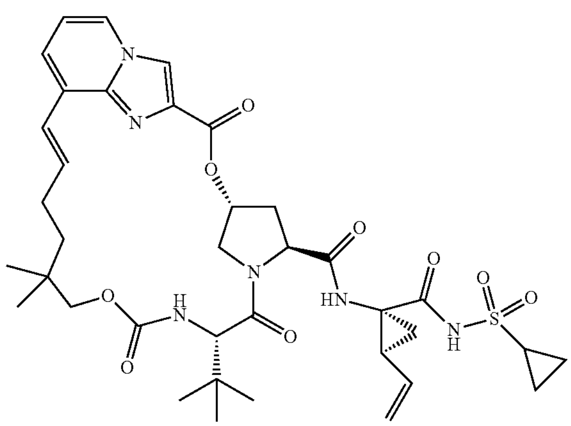 [SMILES: C=C[C@@H]1C[C@]1(NC(=O)[C@@H]1C[C@@H]2CN1C(=O)[C@H](C(C)(C)C)NC(=O)OCC(C)(C)CC/C=C/c1cccn3cc(nc13)C(=O)O2)C(=O)NS(=O)(=O)C1CC1] | (5R,7S,10S)-10-t-butyl-N-((1R,2S)-1-{[(cyclopropylsulfonyl)amino]carbonyl}-2-vinylcyclopropyl)-3,9,12-trioxo-6,7,9,10,11,12,14,15,16,17-decahydro-5H-5,8-methano-23,2-methenopyrido[2,3-n][1,10,3,6,13]dioxatriazacyclohenicosine-7-carboxamide | 725 | See Example 52 | A1, B10, C3 |

| Ex. | Structure | Name | LRMS (M + H)+ | Procedure | Int. |
|---|---|---|---|---|---|
| 60 | 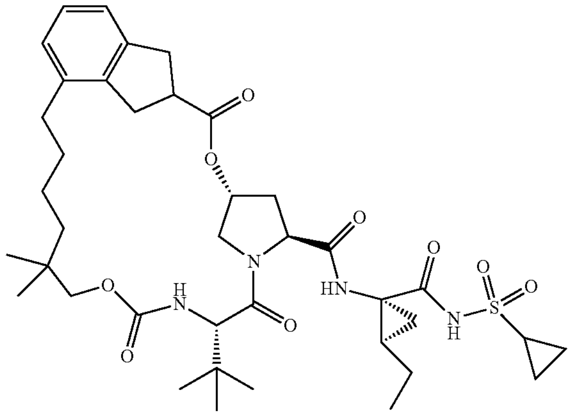 [SMILES: CC[C@@H]1C[C@]1(NC(=O)[C@@H]1C[C@@H]2CN1C(=O)[C@H](C(C)(C)C)NC(=O)OCC(C)(C)CCCCc1cccc3c1CC(C3)C(=O)O2)C(=O)NS(=O)(=O)C1CC1] | (2R or S,5R,7S,10S)-10-t-butyl-N-((1R,2R)-1-{[(cyclopropylsulfonyl)amino]carbonyl}-2-ethylcyclopropyl)-15,15-dimethyl-3,9,12-trioxo-2,3,6,7,9,10,11,12,14,15,16,17,18,19-tetradecahydro-1H,5H-2,23:5,8-dimethano-4,13,8,11-benzodioxadiaza cyclohenicosine-7-carboxamide Earlier eluting diastereomer by reverse phase chromatography | 757 | See Example 54 | A3, B13, C5 |
| 61 | 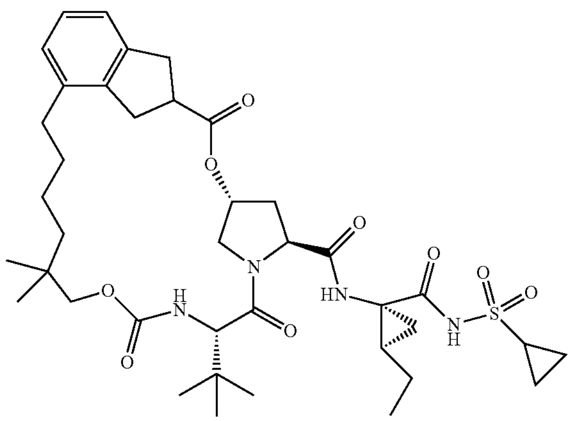 [SMILES: CC[C@@H]1C[C@]1(NC(=O)[C@@H]1C[C@@H]2CN1C(=O)[C@H](C(C)(C)C)NC(=O)OCC(C)(C)CCCCc1cccc3c1CC(C3)C(=O)O2)C(=O)NS(=O)(=O)C1CC1] | (2S or R,5R,7S,10S)-10-t-butyl-N-((1R,2R)-1-{[(cyclopropylsulfonyl)amino]carbonyl}-2-ethylcyclopropyl)-15,15-dimethyl-3,9,12-trioxo-2,3,6,7,9,10,11,12,14,15,16,17,18,19-tetradecahydro-1H,5H-2,23:5,8-dimethano-4,13,8,11-benzodioxadiaza cyclohenicosine-7-carboxamide Later eluting diastereomer by reverse phase chromatography | 757 | See Example 54 | A3, B13, C5 |
| 62 | 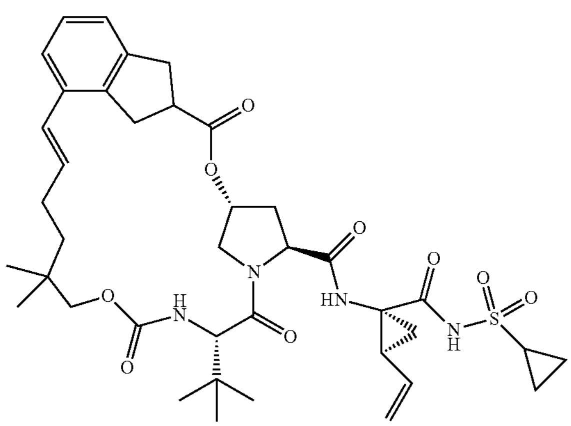 [SMILES: C=C[C@@H]1C[C@]1(NC(=O)[C@@H]1C[C@@H]2CN1C(=O)[C@H](C(C)(C)C)NC(=O)OCC(C)(C)CC/C=C/c1cccc3c1CC(C3)C(=O)O2)C(=O)NS(=O)(=O)C1CC1] | (2R or S,5R,7S,10S)-10-t-butyl-N-((1R,2S)-1-{[(cyclopropylsulfonyl)amino]carbonyl}-2-vinylcyclopropyl)-15,15-dimethyl-3,9,12-trioxo-2,3,6,7,9,10,11,12,14,15,16,17-dodecahydro-1H,5H-2,23:5,8-dimethano-4,13,8,11-benzodioxadiaza cyclohenicosine-7-carboxamide Earlier eluting diastereomer by reverse phase chromatography | 753 | See Example 52 | A1, B13, C5 |

| Ex. | Structure | Name | LRMS (M + H)+ | Procedure | Int. |
|---|---|---|---|---|---|
| 63 | 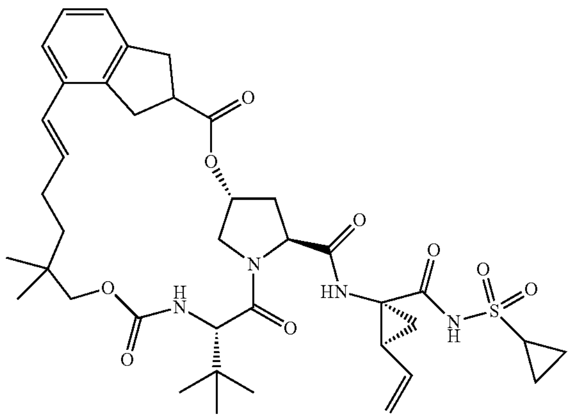 [SMILES: C=C[C@@H]1C[C@]1(NC(=O)[C@@H]1C[C@@H]2CN1C(=O)[C@H](C(C)(C)C)NC(=O)OCC(C)(C)CC/C=C/c1cccc3c1CC(C3)C(=O)O2)C(=O)NS(=O)(=O)C1CC1] | (2S or R,5R,7S,10S)-10-t-butyl-N-((1R,2S)-1-{[(cyclopropylsulfonyl)amino]carbonyl}-2-vinylcyclopropyl)-15,15-dimethyl-3,9,12-trioxo-2,3,6,7,9,10,11,12,14,15,16,17-dodecahydro-1H,5H-2,23:5,8-dimethano-4,13,8,11-benzodioxadiazacyclohenicosine-7-carboxamide Later eluting diastereomer by reverse phase chromatography | 753 | See Example 52 | A1, B13, C5 |
| 64 | 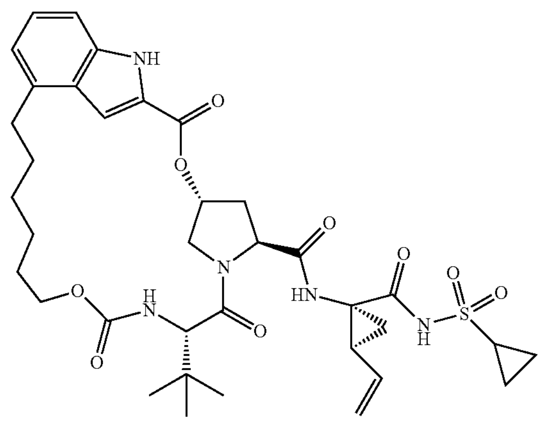 [SMILES: C=C[C@@H]1C[C@]1(NC(=O)[C@@H]1C[C@@H]2CN1C(=O)[C@H](C(C)(C)C)NC(=O)OCCCCCCc1cccc3[nH]c(cc13)C(=O)O2)C(=O)NS(=O)(=O)C1CC1] | (5R,7S,10S)-10-t-butyl-N-((1R,2S)-1-{[(cyclopropylsulfonyl)amino]carbonyl}-2-vinylcyclopropyl)-3,9,12-trioxo-6,7,9,10,11,12,14,15,16,17,18,19-dodecahydro-3H,5H-2,23-epimino-5,8-methano-4,13,8,11-benzodioxadiazacyclohenicosine-7-carboxamide | 726 | See Example 53 | A1, B10, C2 |
| 65 | 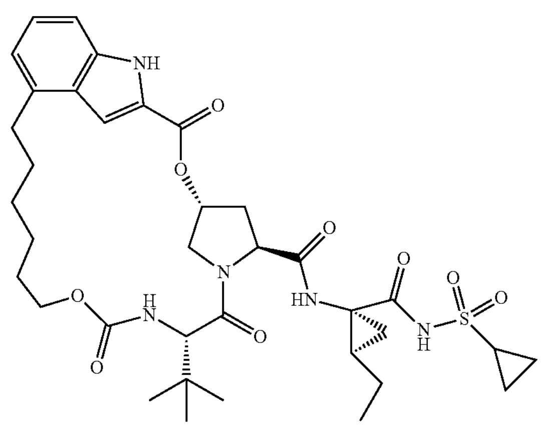 [SMILES: CC[C@@H]1C[C@]1(NC(=O)[C@@H]1C[C@@H]2CN1C(=O)[C@H](C(C)(C)C)NC(=O)OCCCCCCc1cccc3[nH]c(cc13)C(=O)O2)C(=O)NS(=O)(=O)C1CC1] | (5R,7S,10S)-10-t-butyl-N-((1R,2R)-1-{[(cyclopropylsulfonyl)amino]carbonyl}-2-ethylcyclopropyl)-3,9,12-trioxo-6,7,9,10,11,12,14,15,16,17,18,19-dodecahydro-3H,5H-2,23-epimino-5,8-methano-4,13,8,11-benzodioxadiazacyclohenicosine-7-carboxamide | 728 | See Example 54 | A3, B10, C2 |

-continued

| Ex. | Structure | Name | LRMS (M + H)+ | Procedure | Int. |
|---|---|---|---|---|---|
| 66 | 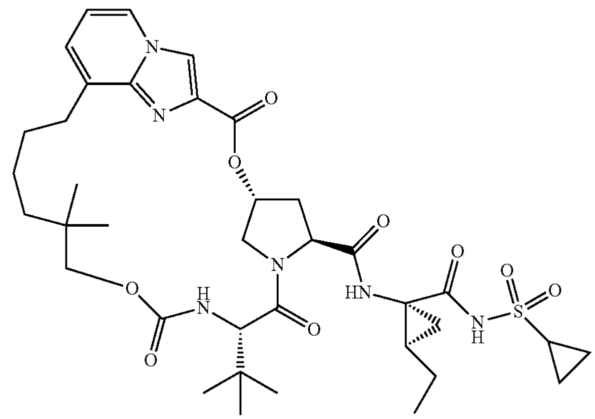 [SMILES: CC[C@@H]1C[C@]1(NC(=O)[C@@H]1C[C@@H]2CN1C(=O)[C@H](C(C)(C)C)NC(=O)OCC(C)(C)CCCCc1cccn3cc(nc13)C(=O)O2)C(=O)NS(=O)(=O)C1CC1] | (5R,7S,10S)-10-t-butyl-N-((1R,2R)-1-{[(cyclopropylsulfonyl)amino]carbonyl}-2-ethylcyclopropyl)-15,15-dimethyl-3,9,12-trioxo-6,7,9,10,11,12,14,15,16,17,18,19-dodecahydro-5H-5,8-methano-23,2-(metheno)pyrido[2,3-n][1,10,3,6,13]dioxatriaza cyclohenicosine-7-carboxamide | 757.5 | See Example 54 | A3, B13, C3 |
| 67 | Chiral | (5R,7S,10S,18E)-10-t-butyl-N-((1R,2S)-1-{[(cyclopropylsulfonyl)amino]carbonyl}-2-vinylcyclopropyl)-15,15-dimethyl-3,9,12-trioxo-24-phenyl-6,7,9,10,11,12,14,15,16,17-decahydro-3H,5H-2,23-epimino-5,8-methano-4,13,8,11-benzodioxa diazacyclohenicosine-7-carboxamide | 828.6 | See Example 52 | A1, B13, C6 |
| 68 | Chiral | (5R,7S,10S,18E)-10-t-butyl-N-((1R,2R)-1-{[(cyclopropylsulfonyl)amino]carbonyl}-2-ethylcyclopropyl)-15,15-dimethyl-3,9,12-trioxo-24-phenyl-6,7,9,10,11,12,14,15,16,17-decahydro-3H,5H-2,23-epimino-5,8-methano-4,13,8,11-benzodioxa diazacyclohenicosine-7-carboxamide | 830.6 | See Example 52 | A3, B13, C6 |

-continued

| Ex. | Structure | | Name | LRMS (M + H)+ | Procedure | Int. |
|---|---|---|---|---|---|---|
| 69 | 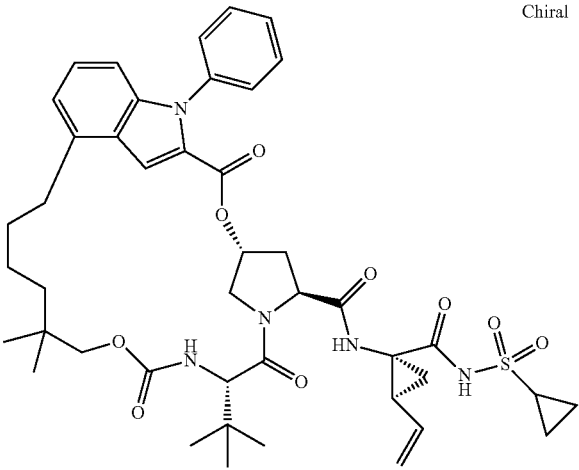 [SMILES: C=C[C@@H]1C[C@]1(NC(=O)[C@@H]1C[C@@H]2CN1C(=O)[C@H](C(C)(C)C)NC(=O)OCC(C)(C)CC/C=C/c1cccc3c1cc(n3-c1ccccc1)C(=O)O2)C(=O)NS(=O)(=O)C1CC1] | Chiral | (5R,7S,10S)-10-t-butyl-N-((1R,2S)-1-{[(cyclopropylsulfonyl)amino]carbonyl}-2-vinylcyclopropyl)-15,15-dimethyl-3,9,12-trioxo-24-phenyl-6,7,9,10,11,12,14,15,16,17,18,19-dodecahydro-3H,5H-2,23-epimino-5,8-methano-4,13,8,11-benzodioxa diazacyclohenicosine-7-carboxamide | 830.6 | See Example 53 | A1, B13, C6 |
| 70 | 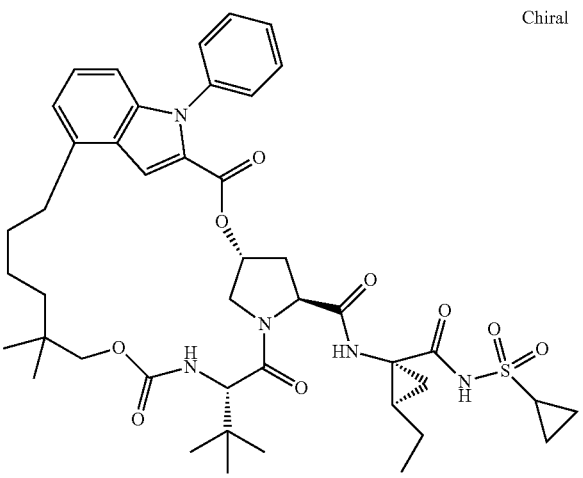 [SMILES: CC[C@@H]1C[C@]1(NC(=O)[C@@H]1C[C@@H]2CN1C(=O)[C@H](C(C)(C)C)NC(=O)OCC(C)(C)CCCCc1cccc3c1cc(n3-c1ccccc1)C(=O)O2)C(=O)NS(=O)(=O)C1CC1] | Chiral | (5R,7S,10S)-10-t-butyl-N-((1R,2R)-1-{[(cyclopropylsulfonyl)amino]carbonyl}-2-ethylcyclopropyl)-15,15-dimethyl-3,9,12-trioxo-24-phenyl-6,7,9,10,11,12,14,15,16,17,18,19-dodecahydro-3H,5H-2,23-epimino-5,8-methano-4,13,8,11-benzodioxa diazacyclohenicosine-7-carboxamide | 832.7 | See Example 54 | A3, B13, C6 |

Example 71

(10S,13S,15R)-10-Cyclohexyl-N-((1R,2S)-1-{[(cyclopropylsulfonyl)amino]carbonyl}-2-vinylcyclopropyl)-1-methylene-8,11-dioxo-1,2,3,4,5,6,8,9,10,11,14,15-dodecahydro-13H-12,15-methanonaphtho[2,1-k][1,10,3,6]dioxadiazacyclooctadecine-13-carboxamide

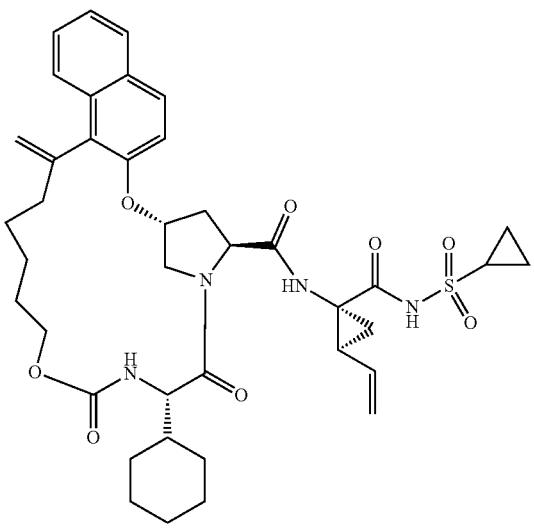 [SMILES: C=C[C@@H]1C[C@]1(NC(=O)[C@@H]1C[C@@H]2CN1C(=O)[C@H](C1CCCCC1)NC(=O)OCCCCCC(=C)c1c(ccc3ccccc13)O2)C(=O)NS(=O)(=O)C1CC1]

Step 1: 1-t-Butyl 2-methyl (2S,4R)-4-[(1-bromo-2-naphthyl)oxy]pyrrolidine-1,2-dicarboxylate

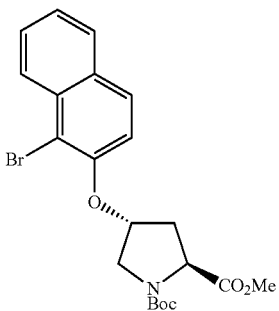 [SMILES: COC(=O)[C@@H]1C[C@@H](Oc2ccc3ccccc3c2Br)CN1C(=O)OC(C)(C)C]

To a solution of 1-t-butyl 2-methyl (2S,4S)-4-{[(4-bromophenyl)sulfonyl]oxy}pyrrolidine-1,2-dicarboxylate (0.5 g, 1.08 mmol) and 1-bromo-2-naphthol (0.29 g, 1.29 mmol) in NMP (5.5 ml) under $N_2$, $Cs_2CO_3$ (1.808 g, 5.55 mmol) was added. The mixture was then heated to 40° C. After 17 hours, the reaction was complete, and $H_2O$ and EtOAc were added. The organic layer was then extracted with $H_2O$ (3×), $NaHCO_3$ (2×) and brine (2×). The organic layer was dried over $MgSO_4$, and the solvent was removed in vacuo. The crude product was purified on $SiO_2$ (gradient elution, 10-60% EtOAc/hexanes) to yield 320 mg of the title compound. LRMS ESI$^+$ ((M-Boc)+H)$^+$ 350.1.

Step 2: Methyl (4R)-4-[(1-bromo-2-naphthyl)oxy]-L-prolinate hydrochloride

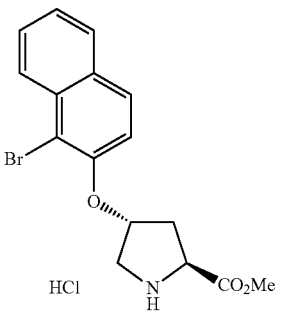 [SMILES: COC(=O)[C@@H]1C[C@@H](Oc2ccc3ccccc3c2Br)CN1 ; Cl]

A portion of the product from Step 1 (320 mg, 0.77 mmol) was dissolved in 4M HCl in dioxane (12.4 mL, 49.7 mmol). After 1 hour, the solvent was removed in vacuo, $Et_2O$ (50 mL) was added, and the solvent was removed in vacuo again to yield the title compound. LRMS ESI$^+$ (M+H)$^+$ 350.1.

Step 3: Methyl (4R)-4-[(1-bromo-2-naphthyl)oxy]-1-((2S)-2-cyclohexyl-2-{[(hept-6-en-1-yloxy)carbonyl]amino}acetyl)-L-prolinate

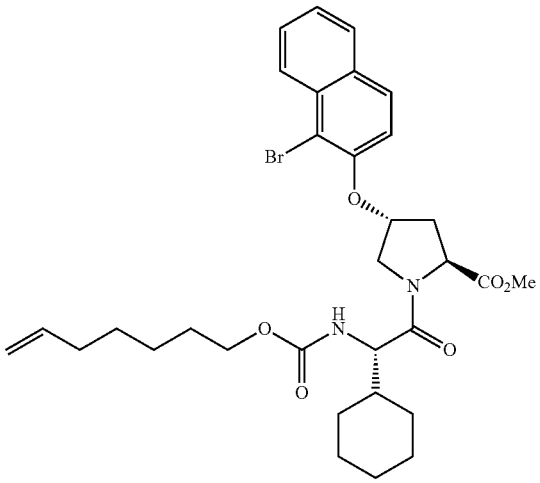 [SMILES: C=CCCCCCOC(=O)N[C@H](C(=O)N1C[C@H](Oc2ccc3ccccc3c2Br)C[C@H]1C(=O)OC)C1CCCCC1]

To a solution of the product from Step 2 (297 mg, 0.77 mmol) in DMF (7 mL), Intermediate B16 (254 mg, 0.85 mmol), DIEA (0.62 mL, 3.55 mmol), HOBT (131 mg, 0.85 mmol), and EDC (163 mg, 0.85 mmol) were added. After stirring overnight, the mixture was extracted with 1N HCl and EtOAc. The organic layer was washed with $H_2O$ and brine, and then dried over $MgSO_4$. The solvent was removed in vacuo, and the crude product was purified on $SiO_2$ (gradient elution, 0-40% EtOAc/hexanes) to yield 111 mg of the title compound. LRMS ESI$^+$ (M+H)$^+$ 631.3.

Step 4: Methyl (10S,13S,15R)-10-cyclohexyl-1-methylene-8,11-dioxo-1,2,3,4,5,6,8,9,10,11,14,15-dodecahydro-13H-12,15-methanonaphtho[2,1-k][1,10,3,6]dioxadiazacyclooctadecine-13-carboxylate

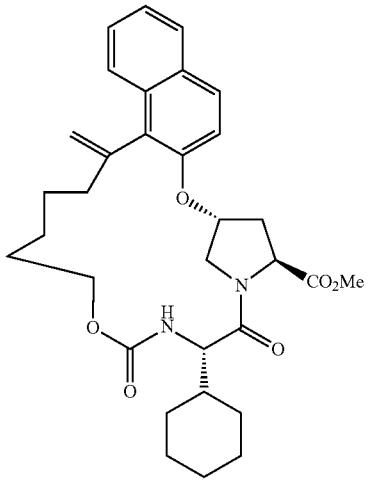 [SMILES: C=C1CCCCCOC(=O)N[C@@H](C2CCCCC2)C(=O)N2C[C@@H](C[C@H]2C(=O)OC)Oc2ccc3ccccc3c21]

To a solution of a portion of the product from Step 3 (111 mg, 0.176 mmol) in EtOH (3.5 mL) was added TEA (0.037 mL, 0.26 mmol), and PdCl$_2$(dppf)-DCM complex (7.2 mg, 0.008 mmol). The mixture was then heated to reflux for 48 hours. The EtOH was removed in vacuo, taken up in EtOAc, and washed with H$_2$O. The organic layer was then dried over MgSO$_4$, and the solvent was removed in vacuo. The crude product was purified on SiO$_2$ (gradient elution, 0-40% EtOAc/hexanes) to yield 51 mg of the title compound. LRMS ESI ((M-Boc)+H)$^+$ 549.3.

Step 5: (10S,13S,15R)-10-Cyclohexyl-1-methylene-8,11-dioxo-1,2,3,4,5,6,8,9,10,11,14,15-dodecahydro-13H-12,15-methanonaphtho[2,1-k][1,10,3,6]dioxadiazacyclooctadecine-13-carboxylic acid

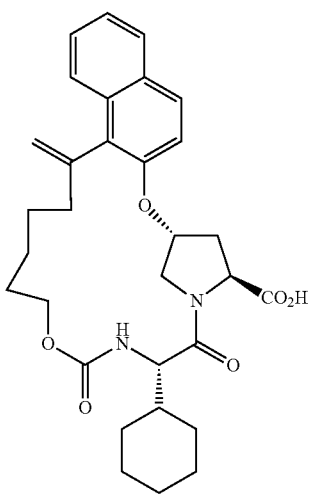 [SMILES: C=C1CCCCCOC(=O)N[C@@H](C2CCCCC2)C(=O)N2C[C@@H](C[C@H]2C(=O)O)Oc2ccc3ccccc3c21]

To a solution of a portion of the product from Step 4 (37 mg, 0.067 mmol) in THF (1.0 mL), EtOH (1.0 mL) and H$_2$O (1.0 mL), LiOH.H$_2$O (16 mg, 0.67 mmol) was added. After 1 hour, 1N HCl and Et$_2$O were added. The organic layer was separated, and the aqueous layer was washed with EtOAc. The combined organic layers were then dried over MgSO$_4$, and the solvent was removed in vacuo to yield 34 mg of the title compound. LRMS ESI$^+$ (M+H)$^+$ 535.3.

Step 6: (10S,13S,15R)-10-Cyclohexyl-N-((1R,2S)-1-{[(cyclopropylsulfonyl)amino]carbonyl}-2-vinylcyclopropyl)-1-methylene-8,11-dioxo-1,2,3,4,5,6,8,9,10,11,14,15-dodecahydro-13H-12,15-methanonaphtho[2,1-k][1,10,3,6]dioxadiazacyclooctadecine-13-carboxamide To a solution of a portion of the product from Step 5 (34 mg, 0.064 mmol) in DCM (6.4 mL), Intermediate A1 (19 mg, 0.070 mmol), DIEA (0.028 mL, 0.16 mmol), HATU (27 mg, 0.070 mmol), and DMAP (2.3 mg, 0.019 mmol) were added. After overnight stirring, the mixture was partitioned between EtOAc and 1N HCl. The organic layer was separated, dried over MgSO$_4$, and the solvent was removed in vacuo. The crude product was purified by reverse-phase chromatography to yield the title compound as a white powder. LRMS ESI$^+$ (M+H)$^+$ 747.3.

Example 72

(4R,6S,9S)-19-Bromo-9-butyl-N-((1R,2S)-1-{[(cyclopropylsulfonyl)amino]carbonyl}-2-vinylcyclopropyl)-16-methylene-8,11-dioxo-3,12-dioxa-7,10-diazatricyclo[15.3.1.1$^{4,7}$]docosa-1(21),17,19-triene-6-carboxamide

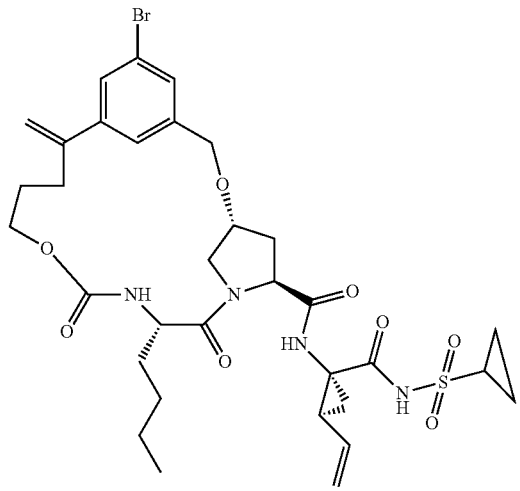 [SMILES: C=C[C@H](C)[C@@](C)(NC(=O)[C@@H]1C[C@@H]2CN1C(=O)[C@H](CCCC)NC(=O)OCCCC(=C)c1cc(Br)cc(c1)CO2)C(=O)NS(=O)(=O)C1CC1]

Step 1: Methyl N-[(pent-4-en-1-yloxy)carbonyl]-L-norleucyl-(4R)-4-[(3,5-dibromobenzyl)oxy]-L-prolinate

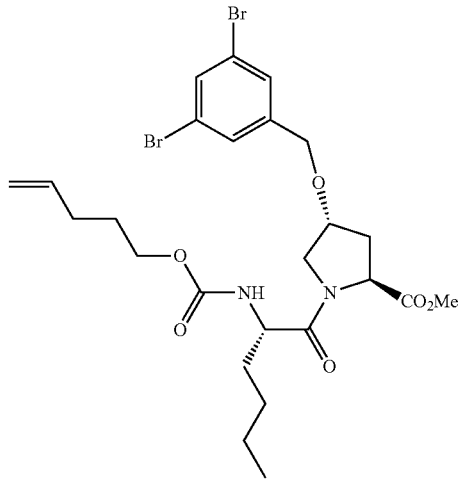 [SMILES: C=CCCCOC(=O)N[C@@H](CCCC)C(=O)N1C[C@H](OCc2cc(Br)cc(Br)c2)C[C@H]1C(=O)OC]

The title compound was prepared according to the procedure given in Example 24, Steps 1-3 using 1,3-dibromo-5-(bromomethyl)benzene in place of 1-bromo-3-(bromomethyl)benzene.

Step 2: Methyl (4R,6S,9S)-19-bromo-9-butyl-16-methylene-8,11-dioxo-3,12-dioxa-7,10-diazatricyclo[15.3.1.1$^{4,7}$]docosa-1(21),17,19-triene-6-carboxylate

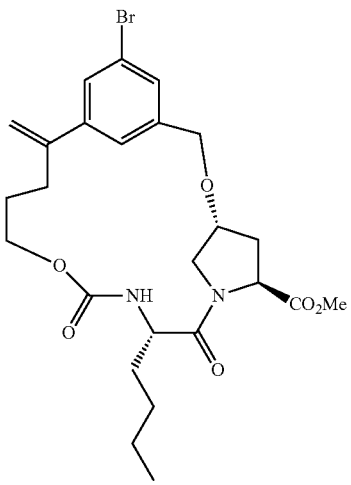 [SMILES: C=C1CCCOC(=O)N[C@@H](CCCC)C(=O)N2C[C@@H](C[C@H]2C(=O)OC)OCc2cc(Br)cc1c2]

To a solution of a portion of the product from Step 1 (250 mg, 0.404 mmol) in EtOH (81 mL), TEA (0.085 mL, 0.61 mmol), and PdCl$_2$(dppf)-DCM complex (16.5 mg, 0.02 mmol) were added. The mixture was then heated to reflux overnight. The EtOH was removed in vacuo, taken up in EtOAc, and washed with H$_2$O. The organic layer was then dried over MgSO$_4$, and the solvent was removed in vacuo. The crude product was purified on SiO$_2$ (gradient elution, 0-50% EtOAc/hexanes) to yield the title compound. LRMS ESI ((M-Boc)+H)$^+$ 549.3.

Step 3: (4R,6S,9S)-19-Bromo-9-butyl-N-((1R,2S)-1-{[(cyclopropylsulfonyl)amino]carbonyl}-2-vinylcyclopropyl)-16-methylene-8,11-dioxo-3,12-dioxa-7,10-diazatricyclo[15.3.1.1$^{4,7}$]docosa-1(21), 17,19-triene-6-carboxamide Using the product from Step 2, the title compound was prepared according to Example 1 using Intermediate A1. LRMS ESI$^+$ ((M-Boc)+H)$^+$ 737.4.

Example 73

((5R,7S,10S,19E)-10-t-Butyl-N-((1R,2S)-1-{[(cyclopropylsulfonyl)amino]carbonyl}-2-vinylcyclopropyl)-9,12-dioxo-1,2-didehydro-3,6,7,9,10,11,12,14,15,16,17,18-dodecahydro-5H-5,8-methano-4,13,8,11-benzodioxadiazacyclodocosine-7-carboxamide

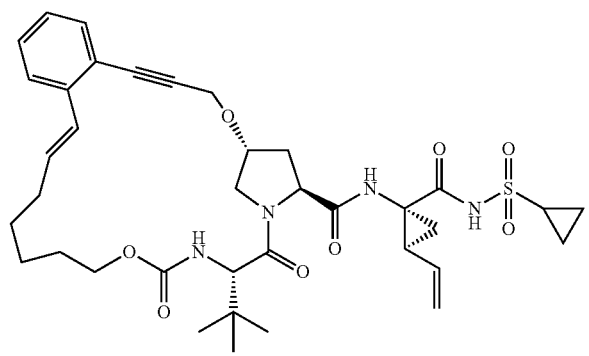 [SMILES: C=C[C@@H]1C[C@]1(NC(=O)[C@@H]1C[C@@H]2CN1C(=O)[C@H](C(C)(C)C)NC(=O)OCCCCC/C=C/c1ccccc1C#CCO2)C(=O)NS(=O)(=O)C1CC1]

Step 1: 1-t-Butyl 2-methyl (2S,4R)-4-(prop-2-yn-1-yloxy)pyrrolidine-1,2-dicarboxylate

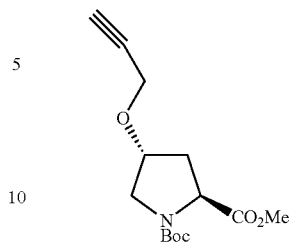

To a solution of 1-t-butyl 2-methyl (2S,4R)-4-hydroxypyrrolidine-1,2-dicarboxylate (1.0 g, 4.08 mmol) and propargyl bromide (2.262 ml, 20.39 mmol) in PhCH$_3$ (40.8 mL) cooled to 0° C., NaH (0.815 g, 20.39 mmol) was added. After 3.5 hours, the reaction was warmed to RT. After 3 days, the reaction was complete and was worked up with H$_2$O and EtOAc, and then brine. The organic layer was dried over MgSO$_4$, and the solvent was removed in vacuo to give 1.33 g of crude material. This was purified on SiO$_2$ (gradient elution, 0-40% EtOAc/hexanes) to yield 737 mg of the title compound. LRMS ESI$^+$ ((M-Boc)+H)$^+$ 184.2.

Step 2: 1-t-Butyl 2-methyl (2S,4R)-4-{[3-(2-bromophenyl)prop-2-yn-1-yl]oxy}pyrrolidine-1,2-dicarboxylate

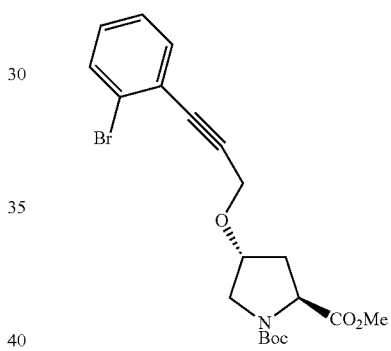

To a degassed solution of the product from Step 1 (735 mg, 2.59 mmol) and 1-bromo-2-iodobenzene (0.366 mL, 2.85 mmol) in TEA (8.647 mL), PdCl$_2$(PPh$_3$)$_2$ (18.21 mg, 0.026 mmol) and CuI (4.94 mg, 0.026 mmol) were added. The reaction was then heated to 50° C. After 2.5 hours, the reaction was worked up with H$_2$O and EtOAc. The organic layer was washed with H$_2$O and brine, dried over MgSO$_4$, and the solvent was removed in vacuo to yield 1.35 g of the title compound which was used directly in further reactions. LRMS ESI ((M-Boc)+H)$^+$ 340.2.

Step 3: Methyl (4R)-4-{[3-(2-bromophenyl)prop-2-yn-1-yl]oxy}-L-prolinate hydrochloride

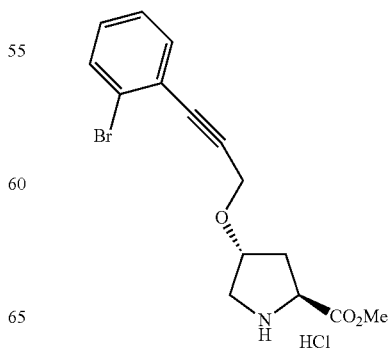

To the product from Step 2 (1.14 g, 2.60 mmol), HCl/dioxane (32.5 mL, 130 mmol) was added at RT. After 1 hour and 45 minutes, the dioxane was removed in vacuo to yield 1.0 g of the title compound as a dark oil. LRMS ESI$^+$ (M+H)$^+$ 340.2.

Step 4: Methyl N-[(hept-6-en-1-yloxy)carbonyl]-3-methyl-L-valyl-(4R)-4-{[3-(2-bromophenyl) prop-2-yn-1-yl]oxy}-L-prolinate

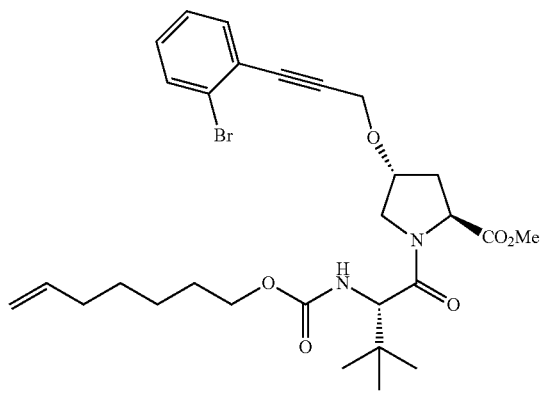 [SMILES: C=CCCCCCOC(=O)N[C@H](C(=O)N1C[C@H](OCC#Cc2ccccc2Br)C[C@H]1C(=O)OC)C(C)(C)C]

Using the procedure from Example 1 Step 4, the title compound was prepared starting with the product from Step 3 and Intermediate B7. LRMS ESI$^+$ (M+H)$^+$ 593.2.

Step 5: Methyl N-[(hept-6-en-1-yloxy)carbonyl]-3-methyl-L-valyl-(4R)-4-{[3-(2-vinylphenyl) prop-2-yn-1-yl]oxy}-L-prolinate

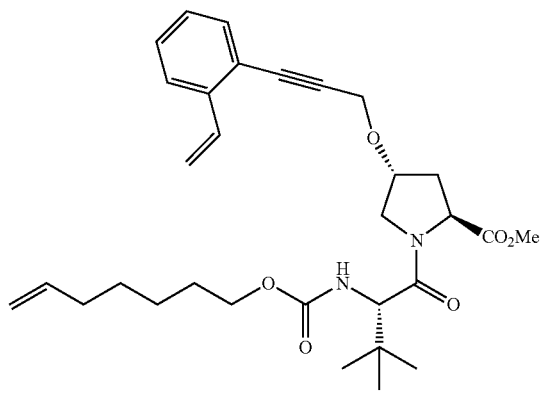 [SMILES: C=CCCCCCOC(=O)N[C@H](C(=O)N1C[C@H](OCC#Cc2ccccc2C=C)C[C@H]1C(=O)OC)C(C)(C)C]

To degassed solution of the product from Step 4 (715 mg, 1.209 mmol) in PhMe (12.100 mL), vinyltributyltin (0.500 mL, 1.450 mmol) and Pd(PPh$_3$)$_4$ (27.9 mg, 0.024 mmol) were added. The reaction was then heated to reflux. After 24 hours, the solvent was then removed in vacuo, and the crude material was purified on SiO$_2$ (gradient elution, 0-40% EtOAc/hexanes) to yield 292 mg of the title compound. LRMS ESI$^+$ (M+H)$^+$ 539.3.

Step 6: Methyl N-[(hept-6-en-1-yloxy)carbonyl]-3-methyl-L-valyl-(4R)-4-{[3-(2-vinylphenyl) prop-2-yn-1-yl]oxy}-L-prolinate-dicobalt hexacarbonyl complex

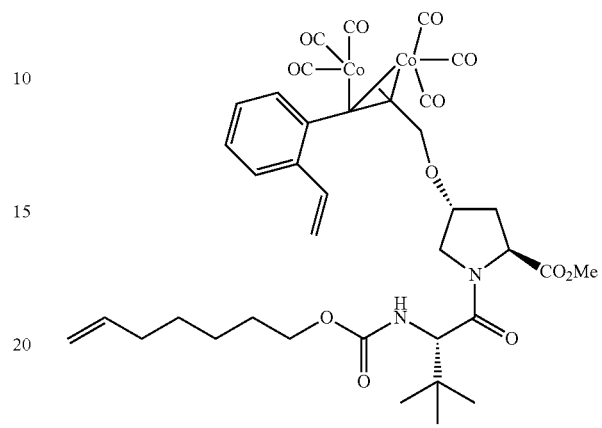

To a solution of the product from Step 5 (95 mg, 0.176 mmol) in DCM (8 mL), dicobaltoctacarbonyl (121 mg, 0.353 mmol) was added under N$_2$. This produces a dark red solution. After 30 minutes, the solvent was concentrated in vacuo to approximately 1 mL and the crude material was purified on SiO$_2$ (gradient elution, 0-35% EtOAc/hexanes) to yield 75 mg of the title compound as a red oil.

Step 7: Methyl (5R,7S,10S,19E)-10-t-butyl-9,12-dioxo-1,2-didehydro-3,6,7,9,10,11,12,14,15,16,17,18-dodecahydro-5H-5,8-methano-4,13,8,11-benzodioxadiazacyclodocosine-7-carboxylate-dicobalt hexacarbonyl complex

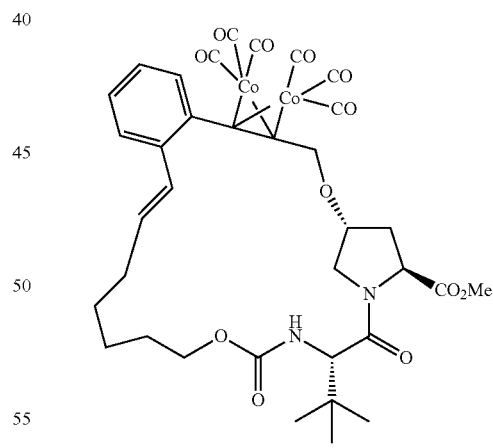

To a degassed solution of the product from Step 6 (75 mg, 0.090 mmol) in DCE (18.100 mL), the Zhan 1 b catalyst (6.63 mg, 9.03 µmol) was added. The mixture was then stirred at RT under N$_2$. After 19 hours, the mixture was then concentrated to approximately 1 mL and purified on SiO$_2$ (gradient elution, 0-30% EtOAc/hexanes) to yield 25 mg of the title compound as a red oil along with 43 mg of recovered methyl N-[(hept-6-en-1-yloxy)carbonyl]-3-methyl-L-valyl-(4R)-4-{[3-(2-vinylphenyl)prop-2-yn-1-yl]oxy}-L-prolinate-dicobalt hexacarbonyl complex.

Step 8: Methyl (5R,7S,10S,19E)-10-t-butyl-9,12-dioxo-1,2-didehydro-3,6,7,9,10,11,12,14,15,16,17,18-dodecahydro-5H-5,8-methano-4,13,8,11-benzodioxadiazacyclodocosine-7-carboxylate

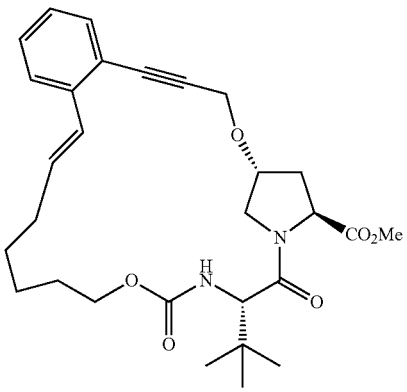 [SMILES: COC(=O)[C@@H]1C[C@@H]2CN1C(=O)[C@H](C(C)(C)C)NC(=O)OCCCCC/C=C/c1ccccc1C#CCO2]

To a solution of the product from Step 7 (25 mg, 0.031 mmol) in acetone (2 mL) cooled to −10° C., CAN (102 mg, 0.187 mmol) was added in portions. After completion, the reaction was quenched with DIEA (0.098 mL, 0.561 mmol), which caused a brown precipitate to form. The mixture was then filtered through neutral alumina with acetone as the eluent to yield 35 mg crude material. This was purified on $SiO_2$ (gradient elution, 0-35% EtOAc/hexanes) to yield 12 mg of the title compound. LRMS ESI$^+$ (M+H)$^+$ 511.5.

Step 9: ((5R,7S,10S,19E)-10-t-Butyl-N-((1R,2S)-1-{[(cyclopropylsulfonyl)amino]carbonyl}-2-vinylcyclopropyl)-9,12-dioxo-1,2-didehydro-3,6,7,9,10,11,12,14,15,16,17,18-dodecahydro-5H-5,8-methano-4,13,8,11-benzodioxadiazacyclodocosine-7-carboxamide Using the product from Step 8, the title compound was prepared according to the procedure in Example 1, Steps 6 and 7. LRMS ESI$^+$ (M+H)$^+$ 709.3

Example 74

(5R,7S,10S)-10-t-Butyl-N-((1R,2S)-1-{[(cyclopropylsulfonyl)amino]carbonyl}-2-vinylcyclopropyl)-9,12-dioxo-1,2,3,6,7,9,10,11,12,14,15,16,17,18,19,20-hexadecahydro-5H-5,8-methano-4,13,8,11-benzodioxadiazacyclodocosine-7-carboxamide

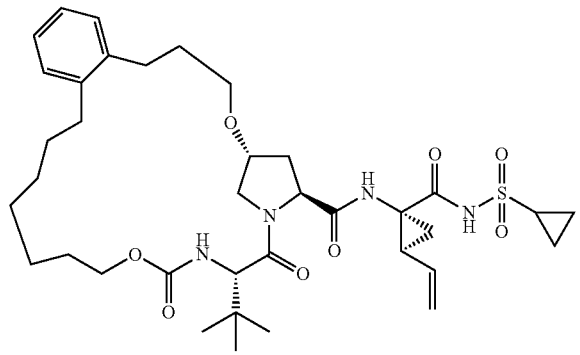 [SMILES: C=C[C@@H]1C[C@]1(NC(=O)[C@@H]1C[C@@H]2CN1C(=O)[C@H](C(C)(C)C)NC(=O)OCCCCCCCc1ccccc1CCCO2)C(=O)NS(=O)(=O)C1CC1]

Step 1: Methyl (5R,7S,10S)-10-t-butyl-9,12-dioxo-1,2,3,6,7,9,10,11,12,14,15,16,17,18,19,20-hexadecahydro-5H-5,8-methano-4,13,8,11-benzodioxadiazacyclodocosine-7-carboxylate

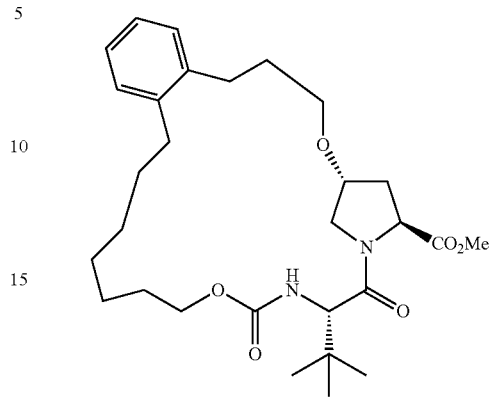

To a solution of the product from Example 73 Step 8 (24 mg, 0.047 mmol) in EtOAc (2 mL), 10% Pd/C (2.501 mg, 2.350 mol) was added under $H_2$. After 90 minutes, the mixture was then filtered through a glass wool pad with EtOAc as the eluent. The solvent was removed in vacuo to yield 22 mg of the title compound. LRMS ESI$^+$ (M+H)$^+$ 517.5.

Step 2: (5R,7S,10S)-10-t-Butyl-N-((1R,2S)-1-{[(cyclopropylsulfonyl)amino]carbonyl}-2-vinylcyclopropyl)-9,12-dioxo-1,2,3,6,7,9,10,11,12,14,15,16,17,18,19,20-hexadecahydro-5H-5,8-methano-4,13,8,11-benzodioxadiazacyclodocosine-7-carboxamide The title compound was prepared according to the procedure in Example 1 Steps 6 and 7, starting from the product from Step 1. LRMS ESI$^+$ (M+H)$^+$ 715.4.

Example 75

(9R,11S,14S)-14-t-Butyl-N-((1R,2S)-1-{[(cyclopropylsulfonyl)amino]carbonyl}-2-vinylcyclopropyl)-13,16-dioxo-6,7,10,11,13,14,15,16,18,19,20,21,22,23-tetradecahydro-5H,9H-9,12-methanopyrido[3,2-n][1,10,3,6]dioxadiazacyclohenicosine-11-carboxamide

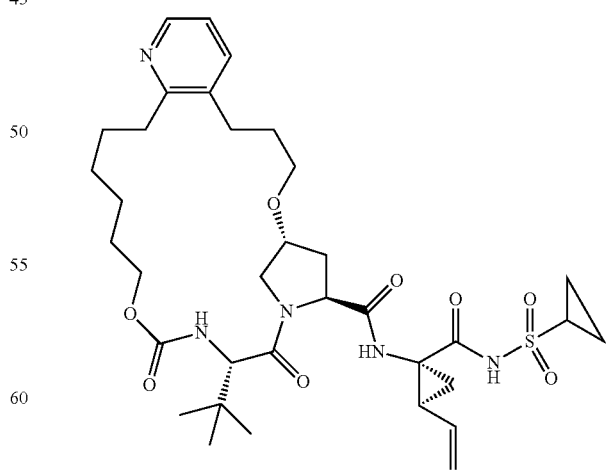

The title compound was prepared according to the Example 73 Steps 1-9, using 2-chloro-3-iodopyridine in place of 1-bromo-2-iodobenzene in Step 2. LRMS ESI$^+$ (M+H)$^+$702.6.

Example 76

(6R,8S,11S,20E)-11-t-Butyl-N-((1R,2S)-1-{[(cyclopropylsulfonyl)amino]carbonyl}-2-vinylcyclopropyl)-10,13-dioxo-5,14-dioxa-9,12-diazatricyclo[20.3.1.1^{6,9}]heptacosa-1(26),20,22,24-tetraen-2-yne-8-carboxamide

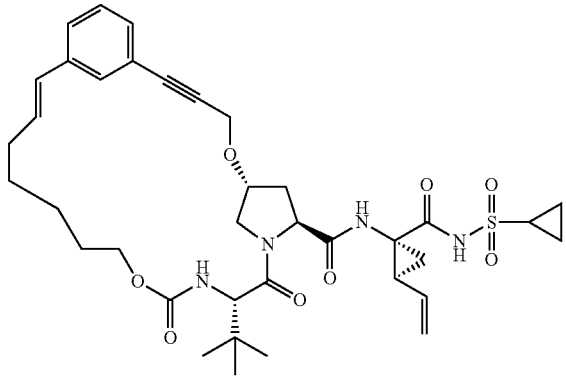 [SMILES: C=C[C@@H]1C[C@]1(NC(=O)[C@@H]1C[C@@H]2CN1C(=O)[C@H](C(C)(C)C)NC(=O)OCCCCC/C=C/c1cccc(c1)C#CCO2)C(=O)NS(=O)(=O)C1CC1]

The title compound was prepared according to the Example 73 Steps 1-9, using 1-bromo-3-iodobenzene in place of 1-bromo-2-iodobenzene in Step 2. LRMS ESI+ (M+H)+ 709.5.

Example 77

(6R,8S,11S)-11-t-Butyl-N-((1R,2S)-1-{[(cyclopropylsulfonyl)amino]carbonyl}-2-vinylcyclopropyl)-10,13-dioxo-5,14-dioxa-9,12-diazatricyclo[20.3.1.1^{6,9}]heptacosa-1(26),22,24-triene-8-carboxamide

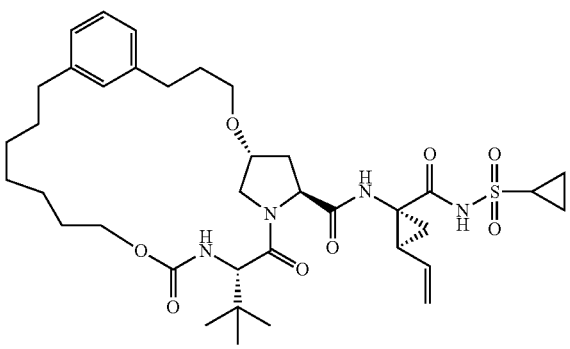 [SMILES: C=C[C@@H]1C[C@]1(NC(=O)[C@@H]1C[C@@H]2CN1C(=O)[C@H](C(C)(C)C)NC(=O)OCCCCCCCc1cccc(c1)CCCO2)C(=O)NS(=O)(=O)C1CC1]

The title compound was prepared according to the procedures in Examples 73 Steps 1-8 and Example 74 Steps, 1-2 using 1-bromo-3-iodobenzene in place of 1-bromo-2-iodobenzene in Example 73 Step 2. LRMS ESI+ (M+H)+ 715.5.

Example 78

(1R,2S)-1-({[(1R,16S,19S)-16-Isopropyl-14,17-dioxo-2,13-dioxa-5,6,7,15,18-pentaazatricyclo[16.2.1.1^{4,7}]docosa-4(22),5-dien-19-yl]carbonyl}amino)-2-vinylcyclopropanecarboxylic acid

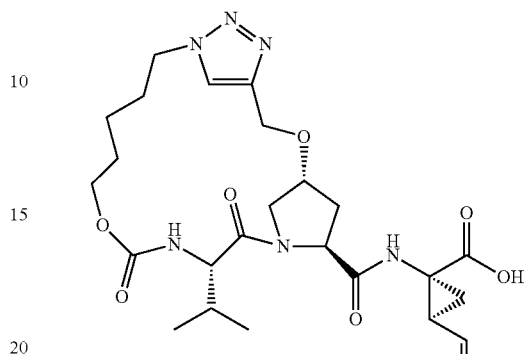

Step 1: 1-t-Butyl 2-methyl (2S,4R)-4-({1-[5-(acetyloxy)pentyl]-1H-1,2,3-triazol-4-yl}methoxy)pyrrolidine-1,2-dicarboxylate

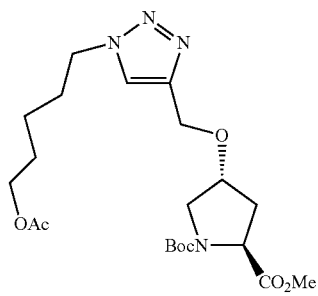

To a solution of the product from Example 77 Step 1 (803 mg, 2.834 mmol) and 5-azidopentyl acetate (509 mg, 2.97 mmol) in t-BuOH (6.67 mL) and H₂O (6.67 mL), ascorbic acid (112 mg, 0.567 mmol) and copper (II) sulfate (23 mg, 0.142 mmol) were added. After 24 hours, the mixture was extracted with H₂O and DCM. The organic layer was dried over MgSO₄, and the solvent was removed in vacuo. The crude product was purified on SiO₂ (gradient elution, 0-10% MeOH/DCM) to yield 1.2 g of the title compound. LRMS ESI+ (M+H)+ 455.5.

Step 2: 1-t-Butyl 2-methyl (2S,4R)-4-[(1-{5-[({[(1S)-1-(t-butoxycarbonyl)-2-methylpropyl]amino}carbonyl)oxy]pentyl}-1H-1,2,3-triazol-4-yl)methoxy]pyrrolidine-1,2-dicarboxylate

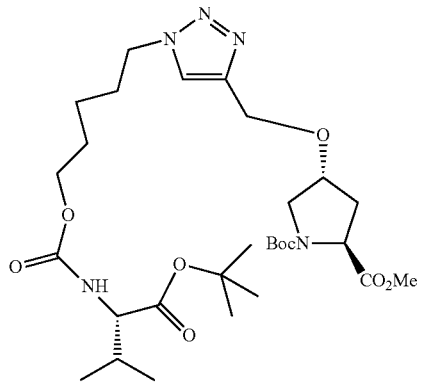 [SMILES: COC(=O)[C@@H]1C[C@@H](OCc2cn(CCCCCOC(=O)N[C@H](C(=O)OC(C)(C)C)C(C)C)nn2)CN1C(=O)OC(C)(C)C]

To a solution of the product from Step 1 (120 mg, 0.264 mmol) in MeOH (5 mL), K₂CO₃ (365 mg, 2.64 mmol) was added. After 30 minutes, the solids were filtered, and the mixture was extracted with EtOAc and 0.5N HCl. The organic layer was dried over K₂CO₃, and the solvent was removed in vacuo to yield 1-t-butyl 2-methyl (2S,4R)-4-{[1-(5-hydroxypentyl)-1H-1,2,3-triazol-4-yl]methoxy}pyrrolidine-1,2-dicarboxylate. To a solution of this material in PhMe (5 mL), t-butyl N-(oxomethylene)-L-valinate (46 mg, 230 mmol) was added, and the solution was heated to reflux for 3 days. The solvent was then removed in vacuo, and the crude product was purified on SiO₂ (gradient elution, 0-10% MeOH/DCM) to yield 130 mg of the title compound. LRMS ESI⁺ (M+H)⁺ 612.5.

Step 3: Methyl (1R,16S,19S)-16-isopropyl-14,17-dioxo-2,13-dioxa-5,6,7,15,18-pentaazatricyclo[16.2.1.1⁴,⁷]docosa-4(22),5-diene-19-carboxylate

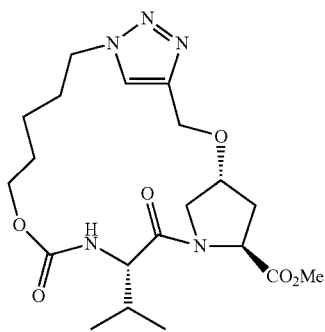

To the product from Step 2 (60 mg, 0.098 mmol), 4N HCl/dioxane (1.7 mL, 6.8 mmol) was added. After 12 hours, the solvent was removed in vacuo, and the residue was taken up in DCM (25 mL), and DIEA (0.088 mL, 0.49 mmol) and TBTU (47 mg, 0.147 mmol) were added. After 19 hours, the mixture was extracted with 1N HCl. The organic layer was dried over MgSO₄, and the solvent was removed in vacuo. The crude product was purified by reverse-phase chromatography to yield the title compound. LRMS ESI⁺ (M+H)⁺ 438.4.

Step 4: (1R,2S)-1-({[(1R,16S,19S)-16-Isopropyl-14,17-dioxo-2,13-dioxa-5,6,7,15,18-pentaazatricyclo[16.2.1.1⁴,⁷]docosa-4(22),5-dien-19-yl]carbonyl}amino)-2-vinylcyclopropanecarboxylic acid Starting from the product of Step 3, the title compound was prepared according to the procedures in Example 5 Step 7. LRMS ESI⁺ (M+H)⁺ 533.3.

Example 79

(1R,16S,19S)—N-((1R,2S)-1-{[(Cyclopropylsulfonyl)amino]carbonyl}-2-vinylcyclopropyl)-16-isopropyl-14,17-dioxo-2,13-dioxa-5,6,7,15,18-pentaazatricyclo[16.2.1.1⁴,⁷]docosa-4(22),5-diene-19-carboxamide

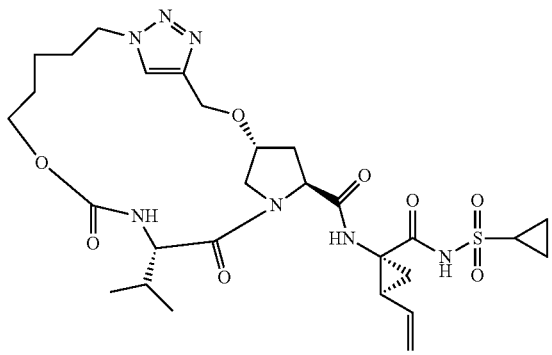 [SMILES: C=C[C@@H]1C[C@]1(NC(=O)[C@@H]1C[C@@H]2CN1C(=O)[C@H](C(C)C)NC(=O)OCCCCCn1cc(nn1)CO2)C(=O)NS(=O)(=O)C1CC1]

The title compound was prepared starting from the product of Example 78 Step 4 using the procedure outlined in Example 6. LRMS ESI⁺ (M+H)⁺ 636.4.

Example 80

(4R,6S,9S)-9-t-Butyl-6-{[((1R,2S)-1-{[(cyclopropylsulfonyl)amino]carbonyl}-2-vinylcyclopropyl)amino]carbonyl}-8,11-dioxo-3,12-dioxa-7,10-diaza-22-azoniatricyclo[16.3.1.1⁴,⁷]tricosane trifluoroacetate

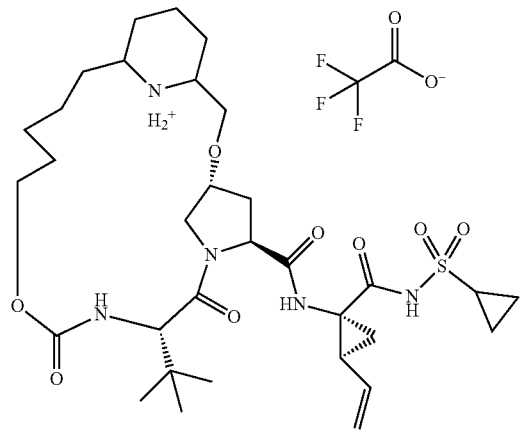

Step 1: Methyl (4R,6S,9S,16E)-9-t-butyl-8,11-dioxo-3.12-dioxa-7,10,22-triazatricyclo[16.3.1.1⁴,⁷]tricosa-1(22), 16,18,20-tetraene-6-carboxylate

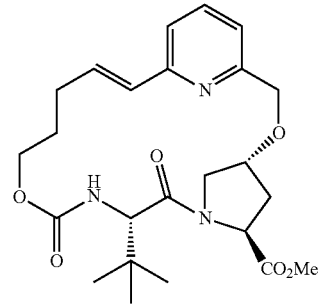 [SMILES: COC(=O)[C@@H]1C[C@@H]2CN1C(=O)[C@H](C(C)(C)C)NC(=O)OCCC/C=C/c1cccc(n1)CO2]

The title compound was prepared according to the procedure in Example 26, using (6-bromopyridin-2-yl)methyl methanesulfonate in place of 1-bromo-3-(bromomethyl) benzene in Step 1 and Intermediate B2 in place of B1. LRMS ESI+ (M+H)+ 460.4.

Step 2: Methyl (4R,6S,9S)-9-t-butyl-8,11-dioxo-3, 12-dioxa-7,10,22-triazatricyclo[16.3.1.1$^{4,7}$]tricosane-6-carboxylate

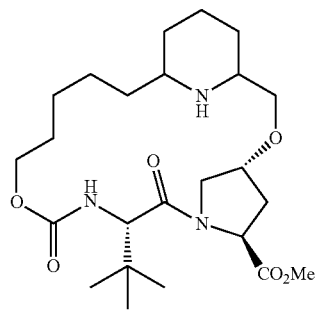 [SMILES: COC(=O)[C@@H]1C[C@@H]2CN1C(=O)[C@H](C(C)(C)C)NC(=O)OCCCCCC1CCCC(CO2)N1]

To a solution of the product from Step 1 (210 mg, 0.457 mmol) in EtOH (5 mL), 10% Pd/C (20 mg) was added. The mixture was then placed under H$_2$. After 18 hours, the starting material was consumed, and methyl (4R,6S,9S)-9-t-butyl-8,11-dioxo-3,12-dioxa-7,10,22-triazatricyclo [16.3.1.1$^{4,7}$]tricosa-1(22), 18,20-triene-6-carboxylate was formed along with the title compound in ~1.5:1 ratio. LRMS ESI+ (M+H)+ 468.4.

Step 3: (4R,6S,9S)-9-t-Butyl-6-{[((1R,2S)-1-{[(cyclopropylsulfonyl)amino]carbonyl}-2-vinylcyclopropyl)amino]carbonyl}-8,11-dioxo-3,12-dioxa-7,10-diaza-22-azoniatricyclo[16.3.1.1$^{4,7}$]tricosane trifluoroacetate Using the product from Step 2, the title compound was prepared using the procedures outlined in Example 1 Steps 6 and 7. LRMS ESI+ (M+H)+ 666.4.

Example 82

(4R,6S,9S,19aS,23aS)-9-t-Butyl-N-((1R,2S)-1-{[(cyclopropylsulfonyl)amino]carbonyl}-2-vinylcyclopropyl)-2,8,11-trioxoicosahydro-2H, 13H-4,7-methano-1,12,3,7,10-benzodioxatriazacyclohenicosine-6-carboxamide

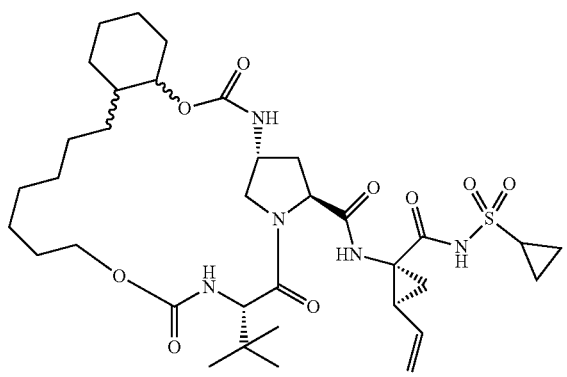 [SMILES: C=C[C@@H]1C[C@]1(NC(=O)[C@@H]1C[C@@H]2CN1C(=O)[C@H](C(C)(C)C)NC(=O)OCCCCCCCC1CCCCC1OC(=O)N2)C(=O)NS(=O)(=O)C1CC1]

Step 1: Methyl (4R)-4-[({[2-allylcyclohexyl] oxy}carbonyl)amino]-L-prolinate hydrochloride

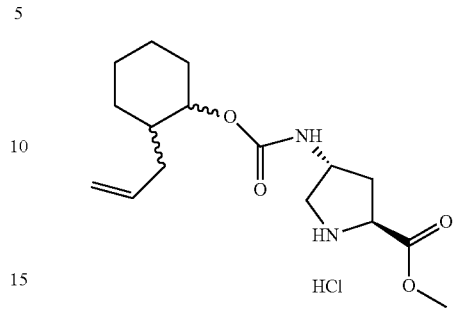

To a solution of racemic trans-2-allylcyclohexanol (200 mg, 1.42 mmol) in DMF (2 mL), CDI (0.23 g, 1.42 mmol) was added. After 1 hour, 1-t-butyl 2-methyl (2S,4R)-4-aminopyrrolidine-1,2-dicarboxylate (0.35 g, 1.42 mmol) was added, and the mixture was heated to 60° C. After complete conversion, the mixture was extracted with EtOAc and NH$_4$Cl$_{(aq.)}$. The organic layer was dried over Na$_2$SO$_4$, and the solvent was removed in vacuo. The crude material was purified on SiO$_2$ (gradient elution, 5-45% EtOAc/hexanes) to yield 170 mg of 1-t-butyl 2-methyl (2S,4R)-4-({[(2-allylcyclohexyl)oxy]carbonyl}amino)pyrrolidine-1,2-dicarboxylate. This material was dissolved in DCM/THF (5 mL), and HCl gas was bubbled through the mixture until complete removal of the Boc group. The solvent was then removed in vacuo to yield the title compound as a mixture of trans-diastereomers. LRMS ESI+ (M+H)+ 311.4.

Step 2: Methyl N-[(hex-5-en-1-yloxy)carbonyl]-3-methyl-L-valyl-(4R)-4-({[(2-allylcyclohexyl)oxy] carbonyl}amino)-L-prolinate

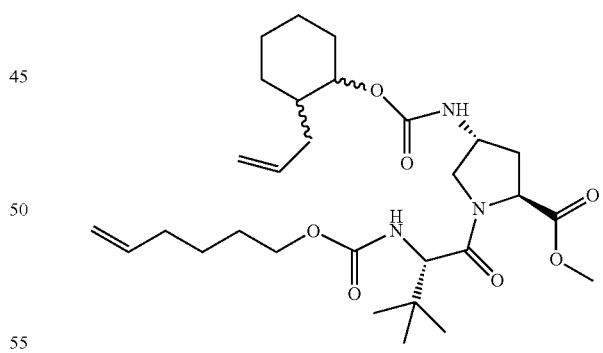

To a solution of the product of Step 1 (170 mg, 0.49 mmol) in DCM (10 mL), Intermediate B10 (132 mg, 0.515 mmol), Et$_3$N (0.27 mL, 1.96 mmol), EDC (113 mg, 0.588 mmol), and HOBT (90 mg, 0.588 mmol) were added. After 24 hours, the mixture was extracted with H$_2$O and then KHSO$_{4(aq.)}$. The organic layer was dried over MgSO$_4$, and the solvent was removed in vacuo. The crude material was purified on SiO$_2$ (50% EtOAc/hexanes) to yield 222 mg of the title compound as a mixture of trans-diastereomers. LRMS ESI+ (M+H)+ 550.5.

Step 3: Methyl (4R,6S,9S,17E/Z)-9-t-butyl-2,8,11-trioxo-3,4,5,6,8,9,10,11,14,15,16,19,19a,20,21,22,23,23a-octadecahydro-2H, 13H-4,7-methano-1,12,3,7,10-benzodioxatriazacyclohenicosine-6-carboxylate

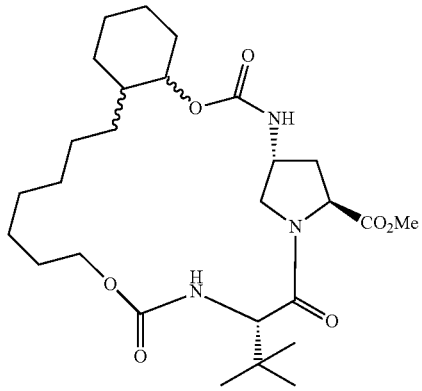 [SMILES: COC(=O)[C@@H]1C[C@@H]2CN1C(=O)[C@H](C(C)(C)C)NC(=O)OCCCCCCCC1CCCCC1OC(=O)N2]

To a solution of a portion of the product from Step 3 (222 mg, 0.40 mmol) in DCE (80 mL), the Zhan 1a catalyst (30 mg, 0.04 mmol) and the mixture was heated to reflux under $N_2$. After 90 minutes, the mixture was concentrated in vacuo, and the crude product was purified on $SiO_2$ (gradient elution, 10-50% EtOAc/hexanes) to yield 105 mg of the title compound as a mixture of olefin isomers and trans-diastereomers. LRMS ESI$^+$ (M+H)$^+$ 522.5.

Step 4: Methyl (4R,6S,9S)-9-t-butyl-2,8,11-trioxoicosahydro-2H, 13H-4,7-methano-1,12,3,7,10-benzodioxatriazacyclohenicosine-6-carboxylate

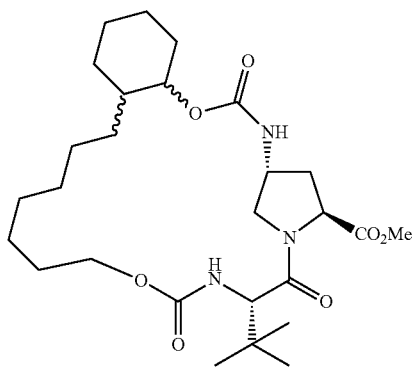 [SMILES: COC(=O)[C@@H]1C[C@@H]2CN1C(=O)[C@H](C(C)(C)C)NC(=O)OCCCCCCCC1CCCCC1OC(=O)N2]

To a solution of a portion of the product from Step 3 (105 mg, 0.20 mmol) in EtOAc (15 mL) was added 10% Pd/C (10 mg). The mixture was then place under $H_2$, stirred for 3 days, and filtered through a pad of glass wool. The solvent was then removed in vacuo to yield 105 mg of the title compound as a mixture of trans-diastereomers. LRMS ESI$^+$ (M+H)$^+$ 524.3.

Step 5: (4R,6S,9S,19aS,23aS)-9-t-Butyl-N-((1R,2S)-1-{[(cyclopropylsulfonyl)amino]carbonyl}-2-vinylcyclopropyl)-2,8,11-trioxoicosahydro-2H, 13H-4,7-methano-1,12,3,7,10-benzodioxatriazacyclohenicosine-6-carboxamide Using the product from Step 4, the title compound was prepared by the procedure outlined in Example 1, Steps 6 and 7. LRMS ESI$^+$ (M+H)$^+$ 722.4.

Example 83

(1R,2S)-1-({[(2R,4S,7S)-7-Isopropyl-6,9,15-trioxo-3,4,6,7,8,9,12,13,14,15-decahydro-2H,11H,17H-16,18-ethano-2,5-methano-1,10,5,8,16-benzodioxatriazacyclononadecin-4-yl]carbonyl}amino)-2-vinylcyclopropanecarboxylic acid

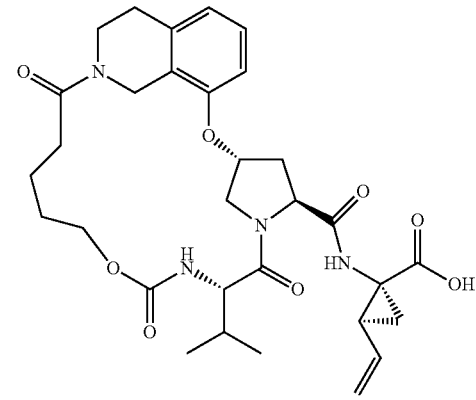 [SMILES: C=C[C@@H]1C[C@]1(NC(=O)[C@@H]1C[C@@H]2CN1C(=O)[C@H](C(C)C)NC(=O)OCCCCC(=O)N1CCc3cccc(c3C1)O2)C(=O)O]

Step 1: 8-[(Triisopropylsilyl)oxy]-1,2,3,4-tetrahydroisoquinoline

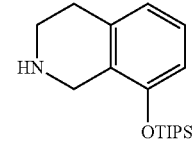

8-Methoxy-1,2,3,4-tetrahydroisoquinoline (3.5 g, 17.5 mmol) was dissolved in 48% HBr$_{(aq.)}$ (50 mL), and the mixture was stirred for 18 hours. The solids were then filtered, and the filtrate was concentrated to yield 3.43 g of 1,2,3,4-tetrahydroisoquinolin-8-ol hydrobromide. To a solution of 1,2,3,4-tetrahydroisoquinolin-8-ol hydrobromide (2.85 g, 12.4 mmol) in THF (75 mL), DIEA (7.57 mL, 43.3 mmol) and TIPSOTf (8.3 g, 27.2 mmol) were added. The mixture was then heated to reflux for 8 hours. The solvent was then removed in vacuo, and the residue partitioned between EtOAc and $H_2O$. The organic layer was washed with brine, dried, and the solvent was removed in vacuo. The crude product was purified on $SiO_2$ (gradient elution, 50/50 EtOAc/hexanes-90/10/1 EtOAc/MeOH/NH$_4$OH) to yield 4.2 g of the title compound. LRMS ESI$^+$ (M+H)$^+$ 306.4.

Step 2: 5-Oxo-5-[8-[(triisopropylsilyl)oxy]-3,4-di-hydroisoquinolin-2(1H)-yl]pentan-1-ol

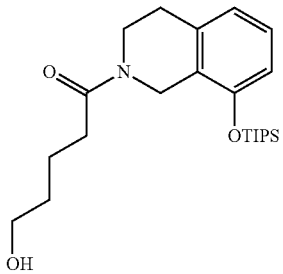

To a solution of a portion of the product from Step 1 (900 mg, 2.94 mmol) in DMF (9 mL) and H₂O (9 mL), TEA (0.74 mL, 5.3 mmol), sodium 5-hydroxypentanoate (1.24 g, 8.8 mol), EDC (621 mg, 3.24 mmol), and HOBT (495 mg, 3.24 mmol) were added. After 2 hours, the mixture was extracted with EtOAc and H₂O. The organic layer was washed with NaHCO₃(aq.) and brine, dried over Na₂SO₄, and the solvent was removed in vacuo. The crude product was purified on SiO₂ (gradient elution, 40-100% EtOAc/hexanes) to yield the title compound. LRMS ESI⁺ (M+H)⁺ 406.3.

Step 3: t-Butyl N-({[5-(8-hydroxy-3,4-dihydroiso-quinolin-2(1H)-yl)-5-oxopentyl]oxy}carbonyl)-L-valinate

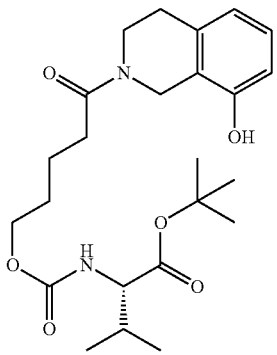 [SMILES: CC(C)[C@H](NC(=O)OCCCCC(=O)N1CCc2cccc(O)c2C1)C(=O)OC(C)(C)C]

To solution of a portion of the product from Step 2 (285 mg, 0.7 mmol) in toluene (1 mL), t-butyl N-(oxomethylene)-L-valinate (0.28 g, 1.4 mmol) was added. The mixture was then heated to reflux for 18 hours. The solvent was then removed in vacuo, and the crude product was taken up in THF (5 mL), and TBAF (1.05 mL, 1M solution in THF, 1.05 mmol) was added. After overnight, the solvent was removed in vacuo, and the residue was taken up in EtOAc, extracted with NaHCO₃(aq.), and dried over Na₂SO₄. The solvent was removed in vacuo. The crude material was purified on SiO₂ (gradient elution, 25-80% EtOAc/hexanes) to yield the title compound. LRMS ESI⁺ (M+H)⁺ 449.5.

Step 4: Methyl (4R)-4-[(2-{5-[({[(1S)-1-(t-butoxy-carbonyl)-2-methylpropyl]amino}carbonyl)oxy]pentanoyl}-1,2,3,4-tetrahydroisoquinolin-8-yl)oxy]-L-prolinate hydrochloride

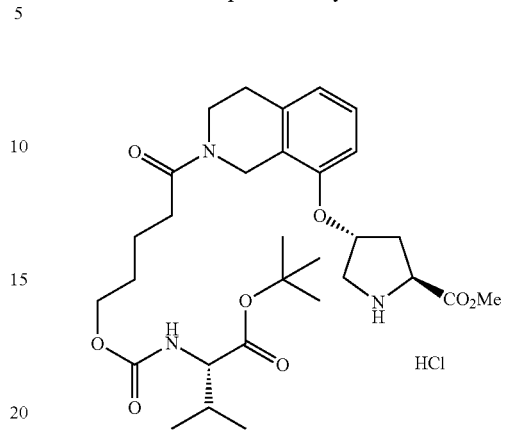

To a solution of a portion of the product from Step 3 (0.24 g, 0.53 mmol) and 1-t-butyl 2-methyl (2S,4S)-4-{[(4-bromophenyl)sulfonyl]oxy}pyrrolidine-1,2-dicarboxylate (0.25 g, 0.53 mmol) in NMP (5 ml) under N₂, Cs₂CO₃ (0.259 g, 0.796 mmol) was added. The mixture was then heated to 40° C. After 24 hours, the reaction was complete, and H₂O and EtOAc were added. The organic layer was then extracted with H₂O (3×), NaHCO₃ (2×) and brine (2×). The organic layer was dried over MgSO₄, and the solvent was removed in vacuo. The crude product was purified on SiO₂ (gradient elution, 30-100% EtOAc/hexanes) to yield 1-t-butyl 2-methyl (2S,4R)-4-[(2-{5-[({[(1S)-1-(t-butoxycarbonyl)-2-methylpropyl]amino}carbonyl)oxy]pentanoyl}-1,2,3,4-tetrahydroisoquinolin-8-yl)oxy]pyrrolidine-1,2-dicarboxylate. This material was then dissolved in 4N HCl/dioxane (5 mL) and stirred at RT for 3 hours. The solvent was then removed in vacuo to yield the title compound as a brown oil. LRMS ESI⁺ (M+H)⁺ 520.4.

Step 5: (2R,4S,7S)-7-Isopropyl-6,9,15-trioxo-3,4,6,7,8,9,12,13,14,15-decahydro-2H,11H,17H-16,18-ethano-2,5-methano-1,10,5,8,16-benzodioxatriazacy-clononadecine-4-carboxylic acid

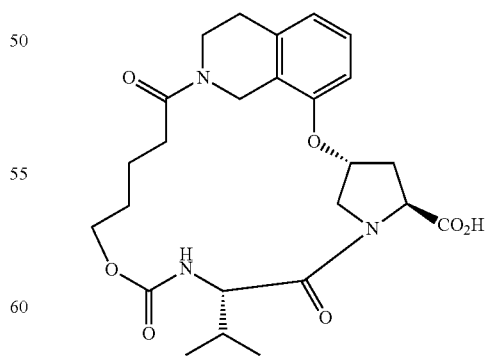

To a solution of the product from Step 4 (230 mg, 0.44 mmol) in DCM (40 mL), TEA (0.128 mL, 1.3 mmol), EDC (93 mg, 0.49 mmol), and HOBT (66 mg, 487 mmol) were added. After 18 hours, the mixture was extracted with NaHCO$_3$$_{(aq.)}$, dried over MgSO$_4$, and concentrated in vacuo. The crude product was purified on SiO$_2$ (gradient elution, 50% EtOAc/hexanes-90/10/1 EtOAc/MeOH/NH$_4$OH) to yield methyl (2R,4S,7S)-7-isopropyl-6,9,15-trioxo-3,4,6,7,8,9,12,13,14,15-decahydro-2H,11H, 17H-16,18-ethano-2,5-methano-1,10,5,8,16-benzodioxatriazacyclononadecine-4-carboxylate. This material was then dissolved in MeOH (0.5 mL), THF (5 mL) and 1N LiOH (5 mL, 5 mmol), and solid LiOH (100 mg, 2.3 mmol) was added. After 1 hour, 10% citric acid was added to adjust the pH to ~3. EtOAc was then added, and following extraction, the organic layer was dried over Na$_2$SO$_4$, and the solvent was removed in vacuo to yield 100 mg of the title compound. LRMS ESI$^+$ (M+H)$^+$ 488.3.

Step 6: (1R,2S)-1-({[(2R,4S,7S)-7-Isopropyl-6,9,15-trioxo-3,4,6,7,8,9,12,13,14,15-decahydro-2H, 11H, 17H-16,18-ethano-2,5-methano-1,10,5,8,16-benzodioxatriazacyclononadecin-4-yl]carbonyl}amino)-2-vinylcyclopropanecarboxylic acid The title compound was prepared according to the procedure outlined in Example 5, Step 7 using the product from Step 5. LRMS ESI$^+$ (M+H)$^+$ 597.3.

Example 84

(2R,4S,7S)-7-t-Butyl-N-((1R,2R)-1-{[(cyclopropylsulfonyl)amino]carbonyl}-2-ethylcyclopropyl)-6,9-dioxo-10-oxa-1,5,8,17,18-pentaazatricyclo[14.2.1.1$^{2,5}$]icosa-16(19), 17-diene-4-carboxamide

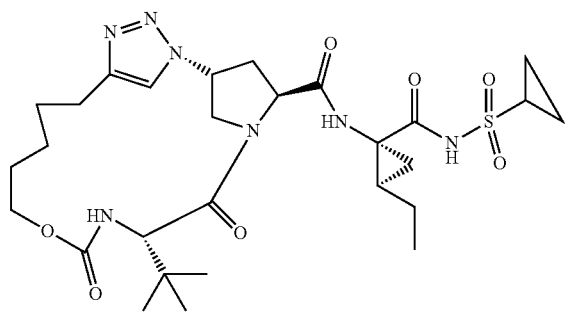

Step 1: N-{[(5-{1-[(3R,5S)-1-(t-Butoxycarbonyl)-5-(methoxycarbonyl)pyrrolidin-3-yl]-1H-1,2,3-triazol-4-yl}pentyl)oxy]carbonyl}-3-methyl-L-valine

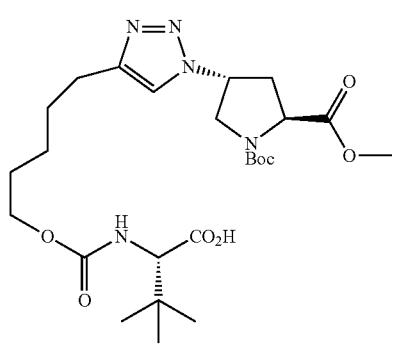 [SMILES: COC(=O)[C@@H]1C[C@@H](n2cc(CCCCCOC(=O)N[C@H](C(=O)O)C(C)(C)C)nn2)CN1C(=O)OC(C)(C)C]

To a solution of 1-t-butyl 2-methyl (2S,4R)-4-azidopyrrolidine-1,2-dicarboxylate (400 mg, 1.48 mmol) and Intermediate B18 (438 mg, 1.63 mmol) in t-BuOH (6 mL) and H$_2$O (6 mL), ascorbic acid (59 mg, 0.296 mmol) and copper(II) sulfate (16.5 mg, 0.074 mmol) were added. After overnight stirring, the mixture was extracted with H$_2$O and EtOAc. The organic layer was dried over MgSO$_4$, and the solvent was removed in vacuo to yield 799 mg of the title compound. LRMS ESI$^+$ (M+H)$^+$ 540.4.

Step 2: N-{[(5-{1-[(3R,5S)-5-(Methoxycarbonyl)pyrrolidin-3-yl]-1H-1,2,3-triazol-4-yl}pentyl)oxy]carbonyl}-3-methyl-L-valine hydrochloride

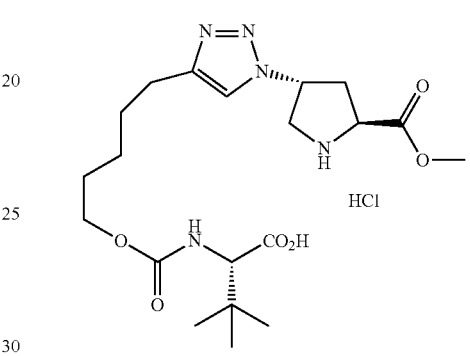

To the product from Step 1 (799 mg, 1.48 mmol), 4N HCl/dioxane (11.1 mL, 44.4 mmol) was added. After stirring overnight, the solvent was removed in vacuo to yield 705 mg of the title compound. LRMS ESI$^+$ ((M-Boc)+H)$^+$ 440.4.

Step 3: Methyl (2R,4S,7S)-7-t-butyl-6,9-dioxo-10-oxa-1,5,8,17,18-pentaazatricyclo[14.2.1.1$^{2,5}$]icosa-16(19), 17-diene-4-carboxylate

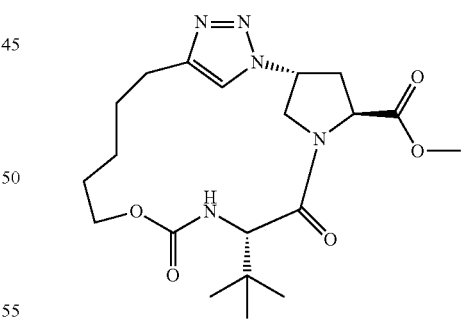

To a solution of the product from Step 2 (705 mg, 1.604 mmol) in DCM (200 mL), DIEA (0.84 mL, 4.8 mmol), and HATU (640 mg, 1.68 mmol) were added. After overnight stirring, the solvent was removed in vacuo, and the crude mixture was dissolved in EtOAc and 1.0N HCl. The EtOAc layer was washed with NaHCO$_3$, dried over MgSO$_4$, and the solvent was removed in vacuo. The crude material was purified on SiO$_2$ (gradient elution, 0-100% EtOAc/hexanes) to yield the title compound. LRMS ESI$^+$ (M+H)$^+$ 422.4.

Step 4: (2R,4S,7S)-7-t-Butyl-N-((1R,2R)-1-{[(cyclopropylsulfonyl)amino]carbonyl}-2-ethylcyclopropyl)-6,9-dioxo-10-oxa-1,5,8,17,18-pentaazatricyclo[14.2.1.1$^{2,5}$]icosa-16(19), 17-diene-4-carboxamide Using the product from Step 3, the title compound was prepared according to the procedure described in Example 1 Steps 6 and 7, using Intermediate A1. LRMS ESI$^+$ (M+H)$^+$ 622.4.

Example 85

(3R,5S,8S)—N-((1R,2S)-1-{[(Cyclopropylsulfonyl)amino]carbonyl}-2-vinylcyclopropyl)-8-isopropyl-1,7,10-trioxo-4,5,7,8,9,10,12,13,14,17-decahydro-1H,3H-3,6-methano[1,10,3,6,13]dioxatriazacyclononadecino[13,12-a]indole-5-carboxamide

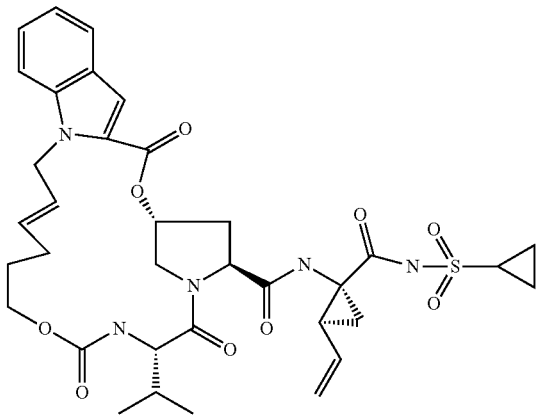 [SMILES: C=C[C@@H]1C[C@]1(NC(=O)[C@@H]1C[C@@H]2CN1C(=O)[C@H](C(C)C)NC(=O)OCCC/C=C/Cn1c(cc3ccccc31)C(=O)O2)C(=O)NS(=O)(=O)C1CC1]

Step 1: Ethyl 1-allyl-1H-indole-2-carboxylate

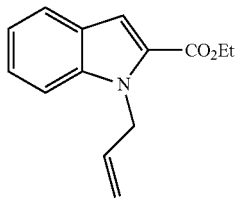 [SMILES: C=CCn1c(C(=O)OCC)cc2ccccc21]

To a suspension of NaH (254 mg, 60 wt %, 10.57 mmol) in THF (5 mL), a solution of ethyl 1H-indole-2-carboxylate (1 g, 5.29 mmol) in DMF (10 mL) was added. After 1 hour, the mixture was cooled to 0° C. and allyl bromide (0.55 mL, 6.34 mmol) was added. After stirring for 2 hours at 0° C., the mixture was slowly warmed to RT and stirred a further 15 hours. The reaction was quenched with H$_2$O and extracted with EtOAc. The organic layer was dried over MgSO$_4$, and the solvent was removed in vacuo. The crude product was purified on SiO$_2$ (gradient elution, 15-40% EtOAc/hexanes) to yield the title compound as a clear oil. LRMS ESI$^+$ (M+H)$^+$ 230.2.

Step 2: 1-Allyl-1H-indole-2-carboxylic acid

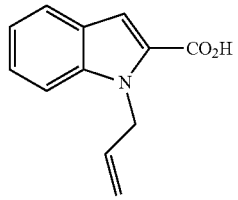

A solution of the product from Step 1 (560 mg, 2.44 mmol) in 1:1:1 2M KOH, dioxane, MeOH (10 mL) was refluxed for 2 hours and stirred at RT overnight. The solvent was then removed in vacuo and the residue was acidified with 1N HCl. The resulting solid was filtered to yield the title compound as a white solid. LRMS ESI$^+$ (M+H)$^+$ 202.2.

Step 3: 1-t-Butyl 2-[2-(trimethylsilyl)ethyl](2S,4R)-4-{[(1-allyl-1H-indol-2-yl)carbonyl]oxy}pyrrolidine-1,2-dicarboxylate

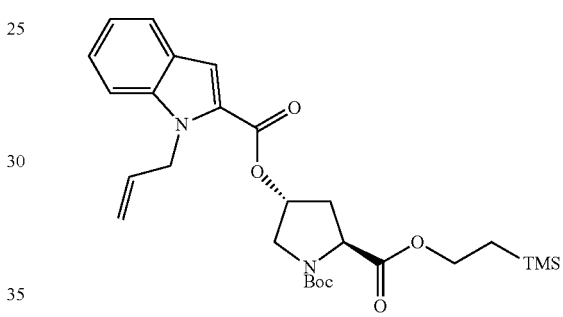

To a solution of the product from Step 2 (250 mg, 1.24 mmol) in DMF (5 mL), CDI (201 mg, 1.24 mmol) was added, and the resulting mixture was heated to 40° C. for 1 hour. At this time, 1-t-butyl 2-[2-(trimethylsilyl)ethyl](2S,4R)-4-hydroxypyrrolidine-1,2-dicarboxylate (494 mg, 1.49 mmol) and DBU (0.279 mL, 1.86 mmol) were added, and stirring was continued for 2 hours. The mixture was the diluted with Et$_2$O, washed with 1N HCl, brine, saturated NaHCO$_3$, brine, dried over Na$_2$SO$_4$, and the solvent was removed in vacuo. The crude product was purified on SiO$_2$ (gradient elution, 0-40% EtOAc/hexanes) to yield the title product as a clear oil. LRMS ESI$^+$ (M+H)$^+$ 515.4.

Step 4: 2-(Trimethylsilyl)ethyl N-[(pent-4-en-1-yloxy)carbonyl]-L-valyl-(4R)-4-{[(1-allyl-1H-indol-2-yl)carbonyl]oxy}-L-prolinate

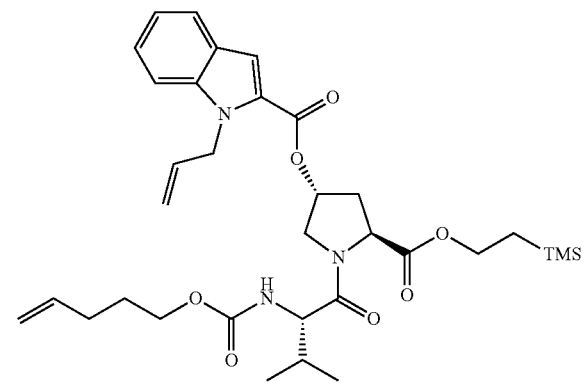 [SMILES: C=CCCCOC(=O)N[C@H](C(=O)N1C[C@H](OC(=O)c2cc3ccccc3n2CC=C)C[C@H]1C(=O)OCC[Si](C)(C)C)C(C)C]

To a solution of the product from Step 3 (550 mg, 1.07 mmol) in DCM (3 mL), TFA (1.5 mL) was added. After 30 minutes, the mixture was concentrated in vacuo, taken up in PhMe (2×) and concentrated, and finally taken up in Et₂O (2×) and concentrated. The residue was then partitioned between EtOAc and NaHCO₃ and extracted with EtOAc (2×). The combined organic layers were then washed with brine, dried over Na₂SO₄, and the solvent was removed in vacuo to yield (3R,5S)-5-{[2-(trimethylsilyl)ethoxy] carbonyl}pyrrolidin-3-yl 1-allyl-1H-indole-2-carboxylate. To this crude material (328 mg, 0.791 mmol) in DMF (5 mL), Intermediate B7 (200 mg, 0.870 mmol), TBTU (279 mg, 0.87 mmol), and DIEA (0.262 mL, 1.58 mmol) were added. After 4 hours, EtOAc was added, and the mixture was extracted with 1N HCl, NaHCO₃, and brine. The organic layer was then dried over Na₂SO₄, and the solvent was removed in vacuo. The crude material was purified on SiO₂ (gradient elution, 10-50% EtOAc/hexanes) to yield the title compound. LRMS ESI⁺ (M+H)⁺ 626.3.

Step 5: 2-(Trimethylsilyl)ethyl (3R,5S,8S,15E)-8-isopropyl-1,7,10-trioxo-4,5,7,8,9,10,12,13,14,17-decahydro-1H,3H-3,6-methano[1,10,3,6,13]dioxatriazacyclononadecino[13,12-a]indole-5-carboxylate

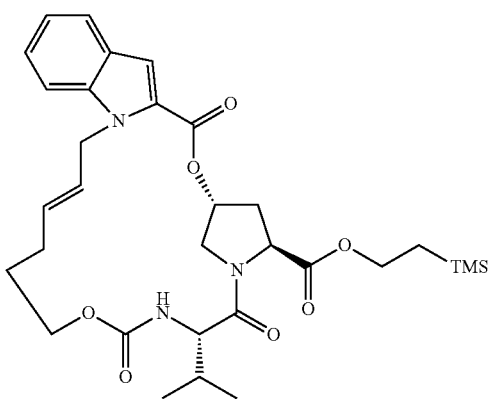 [SMILES: CC(C)[C@@H]1NC(=O)OCCC/C=C/Cn2c(cc3ccccc32)C(=O)O[C@@H]2C[C@@H](C(=O)OCC[Si](C)(C)C)N(C2)C1=O]

To a degassed solution of the product from Step 4 (480 mg, 0.767 mmol) in DCE (160 mL), the Zhan 1B catalyst (51 mg, 0.077 mmol) was added, and the mixture was heated to reflux for 2 hours. The solvent was then removed in vacuo, and the mixture was purified on SiO₂ (gradient elution, 10-50% EtOAc/hexanes) to yield the title compound as a tan foam. LRMS ESI⁺ (M+H)⁺ 598.4.

Step 6: (3R,5S,8S)—N-((1R,2S)-1-{[(Cyclopropylsulfonyl)amino]carbonyl}-2-vinylcyclopropyl-8-isopropyl-1,7,10-trioxo-4,5,7,8,9,10,12,13,14,17-decahydro-1H,3H-3,6-methano[1,10,3,6,13] dioxatriazacyclononadecino[13,12-a]indole-5-carboxamide To a solution of the product from Step 5 (50 mg, 0.084 mmol) in THF (2 mL), TBAF (0.42 mL, 1M solution in THF, 0.42 mmol) was added. After 30 minutes, the solvent was removed in vacuo, and the residue was dissolved in DMF (2 mL). Intermediate A1 (50 mg, 0.187 mmol), TBTU (60 mg, 0.187 mmol), and DIEA (0.086 mL, 0.52 mmol) were then added. After 15 hours, the reaction mixture was directly purified by reverse-phase chromatography (0-100% CH₃CN/H₂O (with 0.15% TFA) to yield the title compound as a white powder. LRMS ESI⁺ (M+H)⁺ 710.4.

Example 86

(3R,5S,8S)—N-((1R,2S)-1-{[(Cyclopropylsulfonyl)amino]carbonyl}-2-vinylcyclopropyl)-8-isopropyl-1,7,10-trioxo-4,5,7,8,9,10,12,13,14,15,16,17-dodecahydro-1H,3H-3,6-methano[1,10,3,6,13] dioxatriazacyclononadecino[13,12-a]indole-5-carboxamide

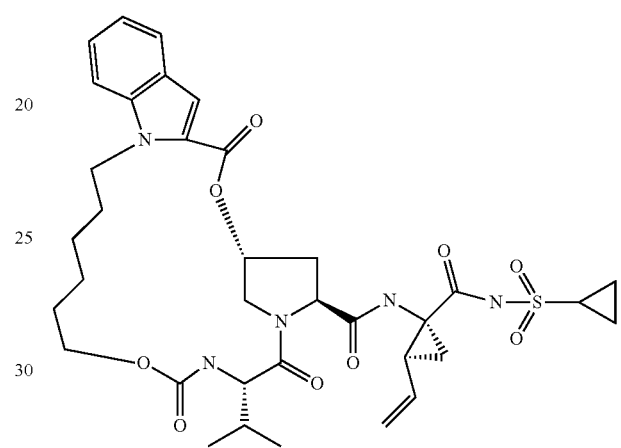

Step 1: 2-(Trimethylsilyl)ethyl (3R,5S,8S)-8-isopropyl-1,7,10-trioxo-4,5,7,8,9,10,12,13,14,15,16,17-dodecahydro-1H,3H-3,6-methano[1,10,3,6,13]dioxatriazacyclononadecino[13,12-a]indole-5-carboxylate

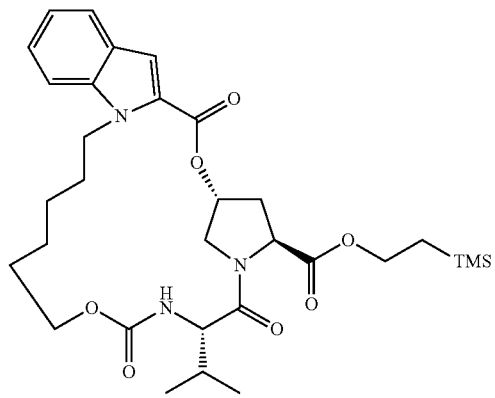 [SMILES: CC(C)[C@@H]1NC(=O)OCCCCCCn2c(cc3ccccc32)C(=O)O[C@@H]2C[C@@H](C(=O)OCC[Si](C)(C)C)N(C2)C1=O]

To a solution of the product from Example 85, Step 5 (141 mg, 0.236 mmol) in EtOAc (3 mL), 10% Pd/C (14 mg) was added. The mixture was then placed under H₂ for 1 hour and then filtered through CELITE. The solvent was removed in vacuo to yield the title compound as a tan foam. LRMS ESI⁺ (M+H)⁺ 600.4.

Step 2: (3R,5S,8S)—N-((1R,2S)-1-{[(Cyclopropyl-sulfonyl)amino]carbonyl}-2-vinylcyclopropyl)-8-isopropyl-1,7,10-trioxo-4,5,7,8,9,10,12,13,14,15,16,17-dodecahydro-1H,3H-3,6-methano[1,10,3,6,13]dioxatriazacyclononadecino[13,12-a]indole-5-carboxamide Using the product from Step 1, the title compound was prepared according to Example 85 Step 6. LRMS ESI⁺ (M+H)⁺ 712.4.

Example 87

(5R,7S,10S,19E)-10-t-Butyl-N-((1R,2S)-1-{[(cyclopropylsulfonyl)amino]carbonyl}-2-vinylcyclopropyl)-3,9,12-trioxo-1,2,3,4,5,6,7,9,10,11,12,14,15,16,17,18-hexadecahydro-5,8-methano-13,4,8,11-benzoxatriazacyclodocosine-7-carboxamide

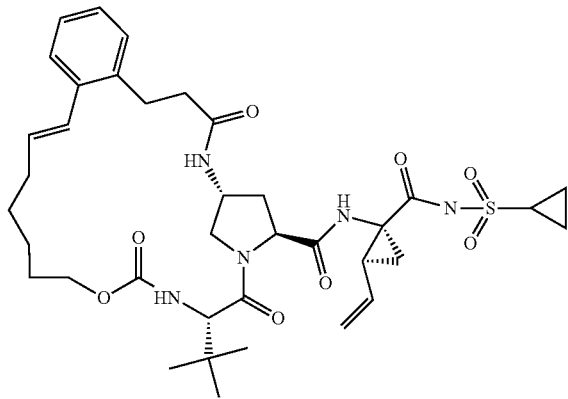 [SMILES: C=C[C@@H]1C[C@]1(NC(=O)[C@@H]1C[C@@H]2CN1C(=O)[C@H](C(C)(C)C)NC(=O)OCCCCC/C=C/c1ccccc1CCC(=O)N2)C(=O)NS(=O)(=O)C1CC1]

Step 1: 1-t-Butyl 2-methyl (2S,4R)-4-{[3-(2-bromophenyl)propanoyl]amino}pyrrolidine-1,2-dicarboxylate

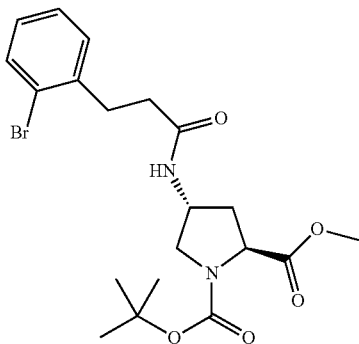 [SMILES: COC(=O)[C@@H]1C[C@@H](NC(=O)CCc2ccccc2Br)CN1C(=O)OC(C)(C)C]

To a solution of 1-t-butyl 2-methyl (2S,4R)-4-aminopyrrolidine-1,2-dicarboxylate hydrochloride (1 g, 3.56 mmol), 3-(2-bromophenyl)propanoic acid (0.898 g, 3.92 mmol) DMF (10 mL), EDC (0.751 g, 3.92 mmol), HOBT (0.600 g, 3.92 mmol), and DIEA (2.177 mL, 12.47 mmol) were added, and the mixture was left to stir for 2 days. The reaction was then diluted with EtOAc, washed with 1N HCl (2×) and brine (1×), and the organic layer was dried over Na₂SO₄, and the solvent was removed in vacuo. The resulting oil was purified by column chromatography on SiO₂ (gradient elu-tion, 20%-60% EtOAc/hexanes) to yield the title compound as a clear oil which slowly solidified. LRMS ESI⁺ (M+H)⁺ 455.2, 457.2.

Step 2: (5R,7S,10S,19E)-10-t-Butyl-N-((1R,2S)-1-{[(cyclopropylsulfonyl)amino]carbonyl}-2-vinylcyclopropyl)-3,9,12-trioxo-1,2,3,4,5,6,7,9,10,11,12,14,15,16,17,18-hexadecahydro-5,8-methano-13,4,8,11-benzoxatriazacyclodocosine-7-carboxamide Using the product from Step 1, the title compound was prepared according to the procedures in Example 1, Steps 2-7. LRMS ESI⁺ (M+H)⁺ 726.5.

Example 88

(5R,7S,10S,19E)-10-t-Butyl-N-((1R,2R)-1-{[(cyclopropylsulfonyl)amino]carbonyl}-2-ethylcyclopropyl)-3,9,12-trioxo-1,2,3,4,5,6,7,9,10,11,12,14,15,16,17,18-hexadecahydro-5,8-methano-13,4,8,11-benzoxatriazacyclodocosine-7-carboxamide

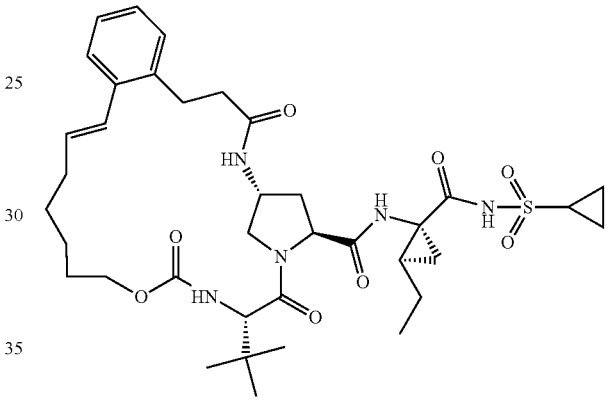

Using the product from Example 87, the title compound was prepared according to the procedures in Example 1 Steps 2-7, using Intermediate A3 in place of Intermediate A1 in Step 7. LRMS ESI⁺ (M+H)⁺ 728.5.

Example 89

(5R,7S,10S)-10-t-Butyl-N-((1R,2S)-1-{[(cyclopropylsulfonyl)amino]carbonyl}-2-vinylcyclopropyl)-3,9,12-trioxo-1,2,3,4,5,6,7,9,10,11,12,14,15,16,17,18,19,20-octadecahydro-5,8-methano-13,4,8,11-benzoxatriazacyclodocosine-7-carboxamide

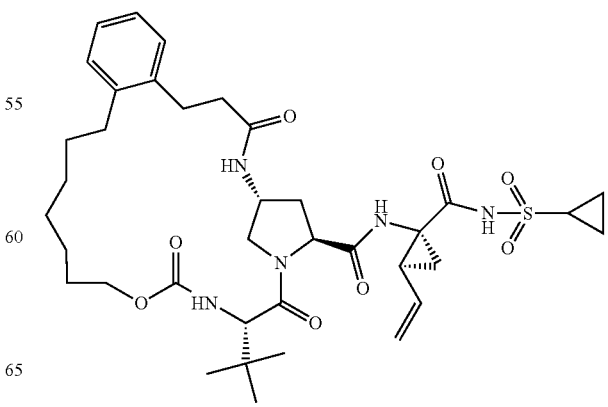

Using the product from Example 87, the title compound was prepared according to the procedures in Example 3. LRMS ESI+ (M+H)+ 728.6.

Example 90

(5R,7S,10S)-10-t-Butyl-N-((1R,2R)-1-{[(cyclopropylsulfonyl)amino]carbonyl}-2-ethylcyclopropyl)-3,9,12-trioxo-1,2,3,4,5,6,7,9,10,11,12,14,15,16,17,18,19,20-octadecahydro-5,8-methano-13,4,8,11-benzoxatriazacyclodocosine-7-carboxamide

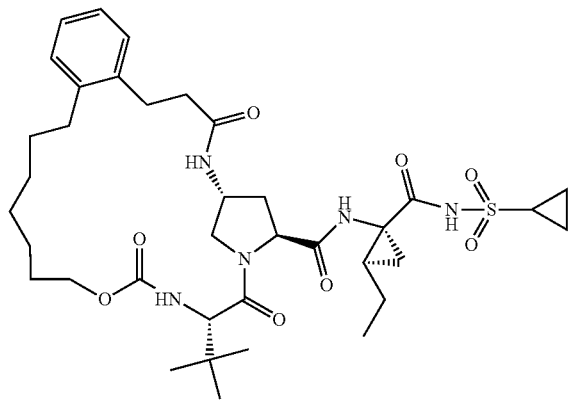 [SMILES: CC[C@@H]1C[C@]1(NC(=O)[C@@H]1C[C@@H]2CN1C(=O)[C@H](C(C)(C)C)NC(=O)OCCCCCCCc1ccccc1CCC(=O)N2)C(=O)NS(=O)(=O)C1CC1]

Using the product from Example 87, the title compound was prepared according to the procedures in Example 4. LRMS ESI+ (M+H)+ 730.6.

Example 91

(5R,7S,10S,18E)-10-t-Butyl-N-((1R,2R)-1-{[(cyclopropylsulfonyl)amino]carbonyl}-2-ethylcyclopropyl)-15,15,24-trimethyl-3,9,12-trioxo-4,5,6,7,9,10,11,12,14,15,16,17-dodecahydro-3H-2,23-epimino-5,8-methano-13,4,8,11-benzoxatriazacyclohenicosine-7-carboxamide

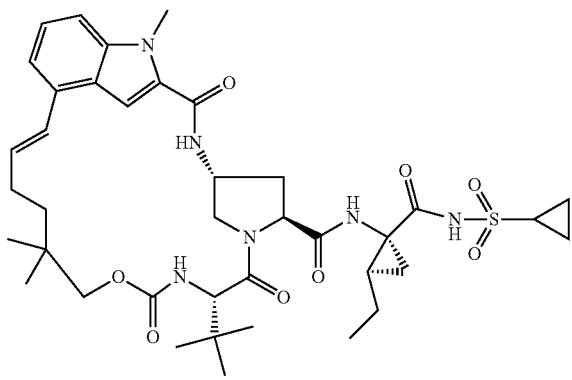 [SMILES: CC[C@@H]1C[C@]1(NC(=O)[C@@H]1C[C@@H]2CN1C(=O)[C@H](C(C)(C)C)NC(=O)OCC(C)(C)CC/C=C/c1cccc3c1cc(n3C)C(=O)N2)C(=O)NS(=O)(=O)C1CC1]

Step 1: 1-t-Butyl 2-methyl (2S,4R)-4-{[(4-bromo-1H-indol-2-yl)carbonyl]amino}pyrrolidine-1,2-dicarboxylate

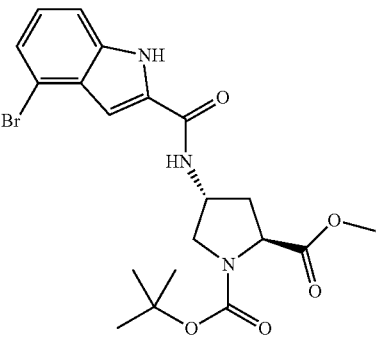 [SMILES: COC(=O)[C@@H]1C[C@@H](NC(=O)c2cc3c(Br)cccc3[nH]2)CN1C(=O)OC(C)(C)C]

To a solution of 1-t-butyl 2-methyl (2S,4R)-4-aminopyrrolidine-1,2-dicarboxylate hydrochloride (350 mg, 1.247 mmol), Intermediate C2 (299 mg, 1.247 mmol), and HATU (569 mg, 1.496 mmol) in DMF (8 mL), DIEA (0.871 mL, 4.99 mmol) was added, and left to stir overnight. The reaction mixture was then diluted with EtOAc, washed with HCl (1M), brine, saturated NaHCO$_3$ and brine, dried over Na$_2$SO$_4$ and filtered, and the solvent was evaporated. The residue was purified by column chromatography on SiO$_2$ (gradient elution, 20-60% EtOAc/hexanes) to give the title compound as a white foam. LRMS ESI+ (M+H)+ 468.1.

Step 2: 1-t-Butyl 2-methyl (2S,4R)-4-{[(4-bromo-1-methyl-1H-indol-2-yl)carbonyl]amino}pyrrolidine-1,2-dicarboxylate

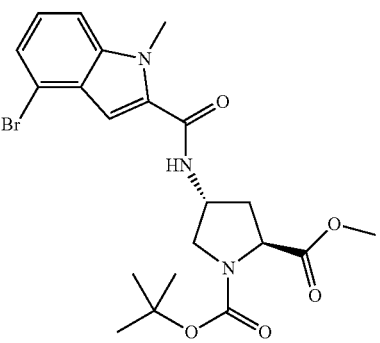 [SMILES: COC(=O)[C@@H]1C[C@@H](NC(=O)c2cc3c(Br)cccc3n2C)CN1C(=O)OC(C)(C)C]

To a mixture of the product from Step 1 (471 mg, 1.010 mmol) and K$_2$CO$_3$ (154 mg, 1.111 mmol) in DMF (8 ml), iodomethane (0.069 mL, 1.111 mmol) was added, and the mixture was left to stir overnight. The reaction mixture was then diluted with Et$_2$O and H$_2$O and the layers were separated the layers. The organics were then washed with saturated NaHCO$_3$ and brine. The organic layer was then dried over Na$_2$SO$_4$, filtered, concentrated, and re-concentrated from Et$_2$O to yield the title compound as a white foam. LRMS ESI$^+$ (M+H)$^+$ 480.1/482.1.

Step 3: Methyl (4R)-4-{[(4-bromo-1-methyl-1H-indol-2-yl)carbonyl]amino}-L-prolinate trifluoroacetate

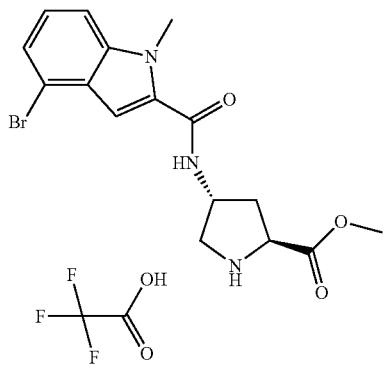 [SMILES: COC(=O)[C@@H]1C[C@@H](NC(=O)c2cc3c(Br)cccc3n2C)CN1 ; O=C(O)C(F)(F)F]

To a solution of the product from Step 2 (440 mg, 0.916 mmol) in DCM (4 ml), TFA (1 mL) was added, and left to stir for 1 hour. The reaction mixture was then concentrated, reconcentrated from PhMe (1×) and DCM (2×) to yield the title compound as a yellow oil. LRMS ESI$^+$ (M+H)$^+$ 380.0/382.0.

Step 4: Methyl N-{[(2,2-dimethylhex-5-en-1-yl)oxy]carbonyl}-3-methyl-L-valyl-(4R)-4-{[(4-bromo-1-methyl-1H-indol-2-yl)carbonyl]amino}-L-prolinate

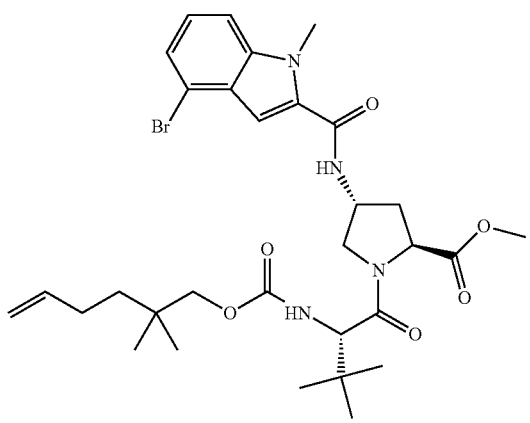 [SMILES: C=CCCC(C)(C)COC(=O)N[C@H](C(=O)N1C[C@H](NC(=O)c2cc3c(Br)cccc3n2C)C[C@H]1C(=O)OC)C(C)(C)C]

Using the product from Step 3, the title compound was prepared using the procedure from Example 1 Step 4, using Intermediate B13 in place of Intermediate B7. LRMS ESI$^+$ (M+H)$^+$ 647.3/649.3.

Step 5: Methyl N-{[(2,2-dimethylhex-5-en-1-yl)oxy]carbonyl-3-methyl-L-valyl-(4R)-4-{[(1-methyl-4-vinyl-1H-indol-2-yl)carbonyl]amino}-L-prolinate

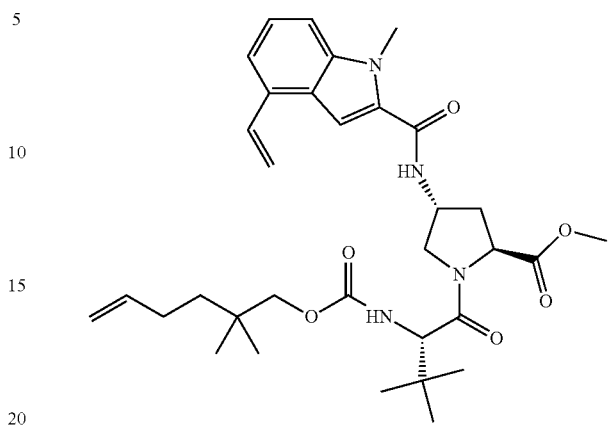

To a degassed (bubbled N$_2$ for 30 minutes) solution of the product from Step 4 (532 mg, 0.821 mmol) in PhMe (10 mL), tributylvinyltin (0.288 ml, 0.986 mmol) and Pd(PPh$_3$)$_4$ (95 mg, 0.082 mmol) were added, and the mixture was heated to reflux for 90 minutes. The reaction mixture was then concentrated, and the resulting residue was purified by column chromatography on SiO$_2$ (gradient elution, 20%-45% EtOAc/hexanes) to yield the title compound as a clear oil. LRMS ESI$^+$ (M+H)$^+$ 595.5.

Step 6: (5R,7S,10S,18E)-10-t-Butyl-N-((1R,2R)-1-{[(cyclopropylsulfonyl)amino]carbonyl}-2-ethylcyclopropyl)-15,15,24-trimethyl-3,9,12-trioxo-4,5,6,7,9,10,11,12,14,15,16,17-dodecahydro-3H-2,23-epimino-5,8-methano-13,4,8,11-benzoxatriazacyclohenicosine-7-carboxamide Using the product from Step 5, the title compound was prepared using the procedures in Example 1, Steps 5-7 with Intermediate A3 used in place of Intermediate A1 in Step 7. LRMS ESI$^+$ (M+H)$^+$ 767.6.

Example 92

(5R,7S,10S,18E)-10-t-Butyl-N-((1R,2S)-1-{[(cyclopropylsulfonyl)amino]carbonyl}-2-vinylcyclopropyl)-15,15,24-trimethyl-3,9,12-trioxo-4,5,6,7,9,10,11,12,14,15,16,17-dodecahydro-3H-2,23-epimino-5,8-methano-13,4,8,11-benzoxatriazacyclohenicosine-7-carboxamide

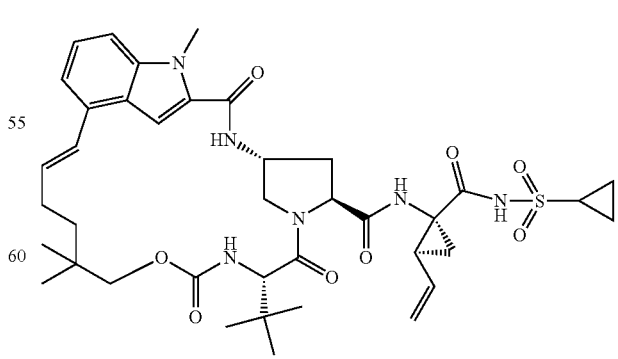

The title compound was prepared according to the procedures in Example 91, using Intermediate A1 in place of Intermediate A3. LRMS ESI$^+$ (M+H)$^+$ 765.6.

Example 93

(5R,7S,10S)-10-t-Butyl-N-((1R,2S)-1-{[(cyclopropylsulfonyl)amino]carbonyl}-2-vinylcyclopropyl)-15,15-dimethyl-9,12-dioxo-6,7,9,10,11,12,14,15,16,17,18,19-dodecahydro-5H-5,8-methano-23,2-(metheno)pyrido[2,3-n][1,10,3,6,13]dioxatriazacyclohenicosine-7-carboxamide

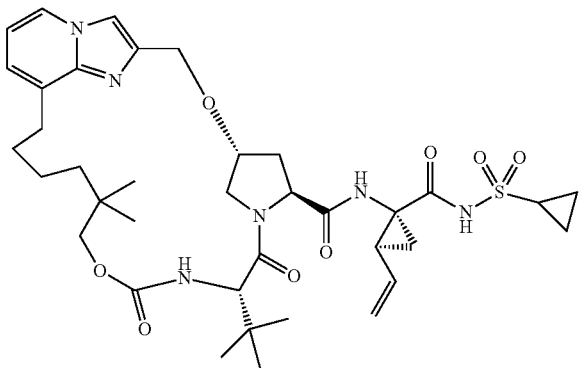 [SMILES: C=C[C@@H]1C[C@]1(NC(=O)[C@@H]1C[C@@H]2CN1C(=O)[C@H](C(C)(C)C)NC(=O)OCC(C)(C)CCCCc1cccn3cc(nc13)CO2)C(=O)NS(=O)(=O)C1CC1]

Step 1: 8-Bromo-2-(chloromethyl)imidazo[1,2-a]pyridine hydrochloride

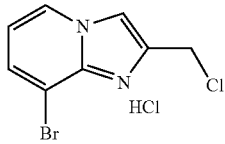

To a solution of 3-bromo-2-aminopyridine (10 g, 57.8 mmol) in EtOAc (200 mL), a solution of 1,3-dichloroacetone (7.34 g, 57.8 mmol) in EtOAc (50 mL) was added dropwise. The mixture was stirred at RT for 5 days. The solids were then filtered; the mother liquors separated; and the solids washed with Et₂O, dried in vacuo to give a white solid. The solids were then slurried in 15 mL HOAc and heated to 90° C. for 15 minutes to give a clear solution. The mixture was then cooled to RT and concentrated to remove most of the HOAc. The residue was treated with 30 mL Et₂O and let stir overnight to give the title compound as a white solid (3.0 g). LRMS ESI⁺ (M+H)⁺ 245.0/247.0.

Step 2: (4R)-4-[(8-Bromoimidazo[1,2-a]pyridin-2-yl)methoxy]-1-(t-butoxycarbonyl)-L-proline

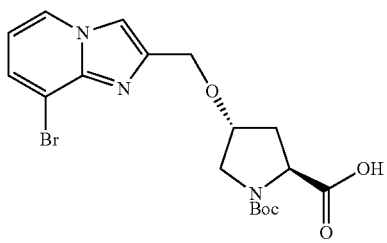 [SMILES: CC(C)(C)OC(=O)N1C[C@H](OCc2cn3cccc(Br)c3n2)C[C@H]1C(=O)O]

To a solution of (4R)-1-(t-butoxycarbonyl)-4-hydroxy-L-proline (1.0 g, 4.32 mmol) in DMF (20 mL), NaH (692 mg, 60%, 17.3 mmol) was added at RT. After 20 minutes, the product from the step 1 (1.22 g, 4.32 mmol) was added, and the mixture was stirred for 30 minutes at RT and at 45° C. for 1 hour. The reaction was then diluted with KHSO₄ and EtOAc. The pH was then adjusted to 5.5 with 2N NaOH. The organic layer was separated, and the aqueous layer was washed with additional EtOAc. The combined organic layers were dried over Na₂SO₄, and the solvent was removed in vacuo. The crude material was purified on SiO₂ (90/10/1 DCM/MeOH/HOAc) to give the title compound as a foam (1.7 g). LRMS ESI⁺ (M+H)⁺ 440.0/442.0.

Step 3: Ethyl (4R)-4-[(8-bromoimidazo[1,2-a]pyridin-2-yl)methoxy]-L-prolinate hydrochloride

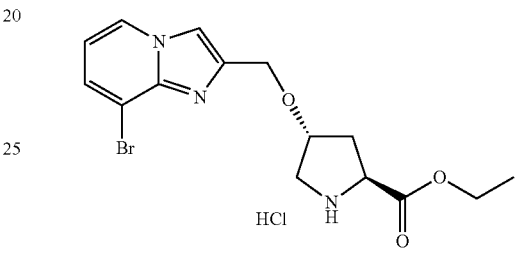

To a solution of the product from Step 2 (1.7 g, 3.86 mmol) in EtOH (200 mL) was bubbled HCl (g) for 30 minutes. The mixture was then stirred an additional 2 hours. The solvent was then removed in vacuo and the following tritration, the title compound was isolated as a solid (1.5 g). LRMS ESI⁺ (M+H)⁺ 340.0/342.0.

Step 4: Ethyl N-{[(2,2-dimethylhex-5-en-1-yl)oxy]carbonyl}-3-methyl-L-valyl-(4R)-4-[(8-bromoimidazo[1,2-a]pyridin-2-yl)methoxy]-L-prolinate

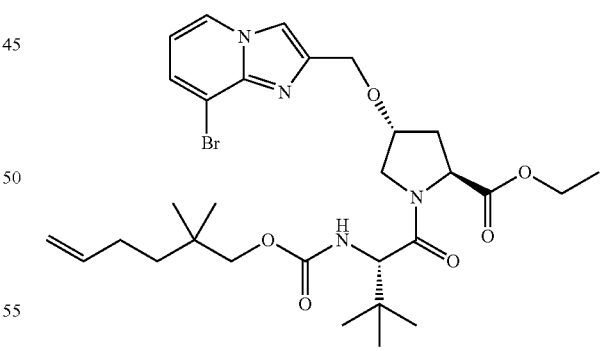

To a solution of the product from Step 3 (900 mg, 2.22 mmol) in DMF (12 mL), Intermediate B13 (698 mg, 2.45 mmol), DIEA (1.16 mL, 6.67 mmol), and HATU (1.26 g, 3.34 mmol) were added. After 1 hour, the mixture was extracted with KHSO₄ and EtOAc. The organic layer was washed with H₂O and brine, and then dried over Na₂SO₄. The solvent was removed in vacuo, and the crude product was purified on SiO₂ (20% EtOAc/hexanes) to yield 1.4 g of the title compound. LRMS ESI⁺ (M+H)⁺ 635.3/637.3.

Step 5: Ethyl N-{[(2,2-dimethylhex-5-en-1-yl)oxy]carbonyl}-3-methyl-L-valyl-(4R)-4-[(8-vinylimidazo[1,2-a]pyridin-2-yl)methoxy]-L-prolinate

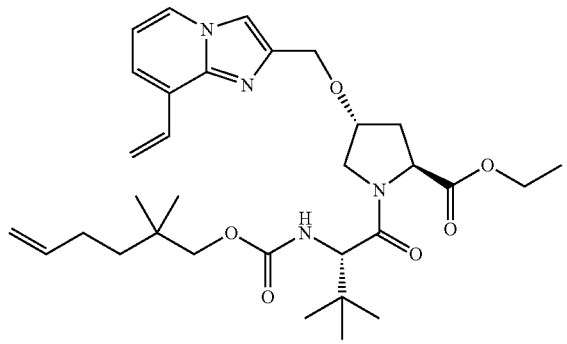 [SMILES: C=CCCC(C)(C)COC(=O)N[C@H](C(=O)N1C[C@H](OCc2cn3cccc(C=C)c3n2)C[C@H]1C(=O)OCC)C(C)(C)C]

Using the product from Step 4, the title compound was prepared according to the procedure in Example 1 Step 2. LRMS ESI+ (M+H)+ 583.5.

Step 6: 5R,7S,10S)-10-t-Butyl-N-((1R,2S)-1-{[(cyclopropylsulfonyl)amino]carbonyl}-2-vinylcyclopropyl)-15,15-dimethyl-9,12-dioxo-6,7,9,10,11,12,14,15,16,17,18,19-dodecahydro-5H-5,8-methano-23,2-(metheno)pyrido[2,3-n][1,10,3,6,13]dioxatriazacyclohenicosine-7-carboxamide Using the product from Step 5, the title compound was prepared according to the procedures in Example 2 Steps 1-3. LRMS ESI+ (M+H)+ 741.6.

Example 94

(1R,18R,22R,26S,29S)-26-cyclopentyl-N-((1R,2S)-1-{[(cyclopropylsulfonyl)amino]carbonyl}-2-vinyl-cyclopropyl)-24,27-dioxo-2,23-dioxa-11,25,28-tri-azapentacyclo[26.2.1.0$^{3,12}$.0$^{5,10}$.0$^{18,22}$]hentriaconta-3(12),4,5,7,9,10-hexaene-29-carboxamide

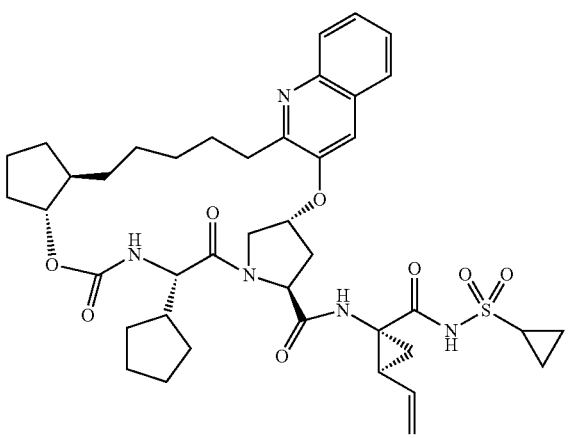 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCc1nc3ccccc3cc1O2)C(=O)NS(=O)(=O)C1CC1]

Step 1: Methyl (4R)-4-[(2-chloroquinolin-3-yl)oxy]-1-{(2S)-2-cyclopentyl-2-[({[(1R,2R)-2-pent-4-en-1-ylcyclopentyl]oxy}carbonyl)amino]acetyl}-L-prolinate

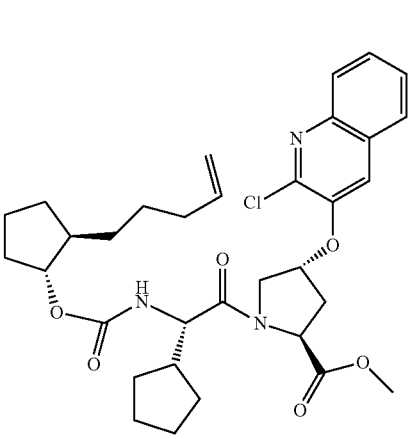 [SMILES: C=CCCC[C@@H]1CCC[C@H]1OC(=O)N[C@H](C(=O)N1C[C@H](Oc2cc3ccccc3nc2Cl)C[C@H]1C(=O)OC)C1CCCC1]

A solution of Intermediate C13 (0.50 g, 1.46 mmol) and Intermediate B23 in DMF (10 mL) was treated with DIPEA (1.53 mL, 8.74 mmol) and HATU (0.83 g, 2.19 mmol). The mixture was stirred for 1 hour, then partitioned between HCl$_{(aq.)}$ (1N) and EtOAc. The organic layer was separated, washed with saturated NaHCO$_{3(aq.)}$ and brine, and then dried over Na$_2$SO$_4$. Filtration and removal of the volatiles gave a residue that was purified by flash chromatography on SiO$_2$ (gradient elution, 1-100% EtOAc/petroleum ether) to afford the title compound (671 mg, 75%) as a solid. LCMS (ES+) m/z 612 (M+H)+.

Step 2: Methyl (4R)-1-{(2S)-2-cyclopentyl-2-[({[(trans)-2-pent-4-en-1-ylcyclopentyl]oxy}carbonyl)amino]acetyl}-4-[(2-vinylquinolin-3-yl)oxy]-L-prolinate

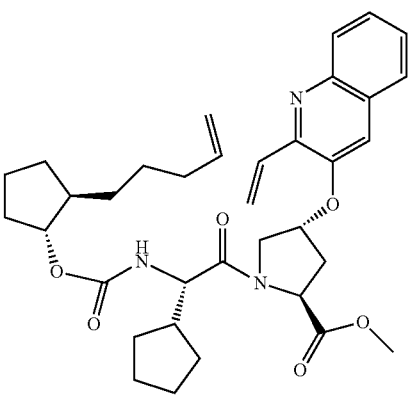 [SMILES: C=CCCC[C@@H]1CCC[C@H]1OC(=O)N[C@H](C(=O)N1C[C@H](Oc2cc3ccccc3nc2C=C)C[C@H]1C(=O)OC)C1CCCC1]

A solution of the product of Step 1 (669 mg, 1.09 mmol) in absolute EtOH (10.9 mL) was treated with potassium vinyltrifluoroborate (234 mg, 1.75 mmol) and TEA (244 µL, 1.75 mmol). Pd(dppf).DCM (178 mg, 0.22 mmol) was added, and the mixture was heated under reflux for 15 minutes. The mixture was cooled and diluted with H$_2$O and EtOAc. The organic layer was separated, washed with brine and dried over Na$_2$SO$_4$. The filtered solution was concentrated to afford a residue that was purified by column chromatography on SiO$_2$ (gradient elution, 1-100% EtOAc/petroleum ether) to give the title compound (485 mg, 74%) as a solid. LCMS (ES+) m/z 604 (M+H)$^+$.

Step 3: Methyl (3 aR,7S,10S,12R,20E,24aR)-7-cyclopentyl-5,8-dioxo-1,2,3,3a,5,6,7,8,11,12,22,23,24,24a-tetradecahydro-10H-9,12-methanocyclopenta[18,19][1,10,3,6]dioxadiazacyclo nonadecino[12,11-b]quinoline-10-carboxylate and methyl (3 aS,7S,10S,12R,20E,24aS)-7-cyclopentyl-5,8-dioxo-1,2,3,3a,5,6,7,8,11,12,22,23,24,24a-tetradecahydro-10H-9,12-methano cyclopenta[18,19][1,10,3,6]dioxadiazacyclononadecino[12,11-b]quinoline-10-carboxylate

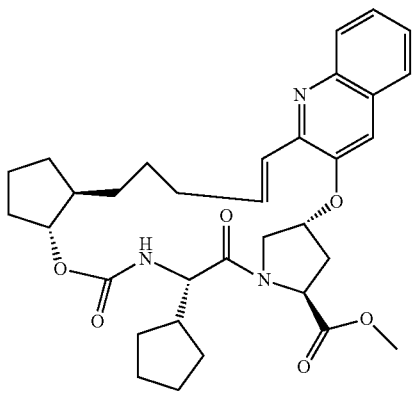 [SMILES: COC(=O)[C@@H]1C[C@@H]2CN1C(=O)[C@H](C1CCCC1)NC(=O)O[C@@H]1CCC[C@H]1CCC/C=C/c1nc3ccccc3cc1O2]

A solution of the product of Step 2 (483 mg, 0.800 mmol) in DCE (80 mL) was treated with Zhan catalyst (79 mg, 0.120 mmol), then heated at 90° C. for 90 minutes. The mixture was cooled and then concentrated in vacuo. The residue was purified by flash chromatography on SiO$_2$ (gradient elution, 15-65% EtOAc/petroleum ether) to give in the first fractions methyl (3 aR,7S,10S,12R,20E,24aR)-7-cyclopentyl-5,8-dioxo-1,2,3,3a,5,6,7,8,11,12,22,23,24,24a-tetradecahydro-10H-9,12-methanocyclopenta[18,19][1,10,3,6]dioxadiazacyclononadecino[12,11-b]quinoline-10-carboxylate (194 mg, 42%).

LCMS (ES+) m/z 576 (M+H)$^+$. The later fractions contained methyl (3aS,7S,10S,12R,20E,24aS)-7-cyclopentyl-5,8-dioxo-1,2,3,3a,5,6,7,8,11,12,22,23,24,24a-tetradecahydro-10H-9,12-methanocyclopenta[18,19][1,10,3,6]dioxadiazacyclononadecino[12,11-b]quinoline-10-carboxylate (148 mg, 32%). LCMS (ES+) m/z 576 (M+H)$^+$.

Step 4: Methyl(3aR,7S,10S,12R,24aR)-7-cyclopentyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclo nonadecino[12,11-b]quinoline-10-carboxylate

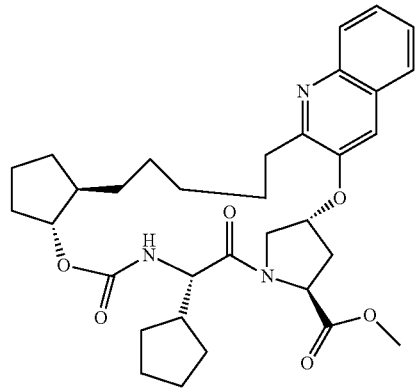 [SMILES: COC(=O)[C@@H]1C[C@@H]2CN1C(=O)[C@H](C1CCCC1)NC(=O)O[C@@H]1CCC[C@H]1CCCCCc1nc3ccccc3cc1O2]

Pd/C (10%, 29 mg) was added to a solution of (3aR,7S,10S,12R,20E,24aR)-7-cyclopentyl-5,8-dioxo-1,2,3,3a,5,6,7,8,11,12,22,23,24,24a-tetradecahydro-10H-9,12-methanocyclopenta[18,19][1,10,3,6]dioxadiazacyclononadecino[12,11-b]quinoline-10-carboxylate (115 mg, 0.20 mmol) in MeOH (20 mL), and the mixture was stirred under H$_2$ for 1 hour. The solution was filtered through CELITE, and the filtrate was concentrated to afford the title compound (95 mg, 83%) as a solid that was used directly in the next step. LCMS (ES+) m/z 578 (M+H)$^+$.

Step 5: (3aR,7S,10S,12R,24aR)-7-cyclopentyl-5,8-dioxo-1,2,3,3a,5,6,7,8,11,12,20,21,22,23,24,24a-hexadecahydro-10 OH-9,12-methanocyclopenta[18,19][1,10,3,6]dioxadiazacyclo nonadecino[12,11-b]quinoline-10-carboxylic acid

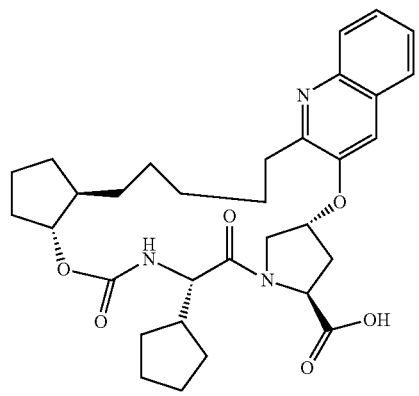 [SMILES: O=C1N[C@@H](C2CCCC2)C(=O)N2C[C@@H](C[C@H]2C(=O)O)Oc2cc3ccccc3nc2CCCCC[C@@H]2CCC[C@H]2O1]

LiOH.H$_2$O (34.6 mg, 0.825 mmol) was added to a stirred solution of the product of Step 4 (95.3 mg, 0.165 mmol) in a 1:1 mixture of H$_2$O:THF (5.4 mL). The solution was heated at 40° C. for 1 hour, then the THF was evaporated in vacuo, and the remaining aqueous solution was acidified to pH 4 by addition of HCl$_{(aq.)}$ (1N). EtOAc was added, and the organic layer was separated, washed with brine, then dried over Na₂SO₄. The mixture was filtered, and the volatiles were removed to afford the title compound (61.4 mg, 66%) as a solid that was used directly in the next step. LCMS (ES+) m/z 564 (M+H)⁺.

Step 6: (1R,18R,22R,26S,29S)-26-cyclopentyl-N-((1R,2S)-1-{[(cyclopropylsulfonyl)amino]carbonyl}-2-vinylcyclopropyl)-24,27-dioxo-2,23-dioxa-11,25,28-triazapentacyclo[26.2.1.0³,¹².0⁵,¹⁰.0¹⁸,²²]hentriaconta-3(12),4,5,7,9,10-hexaene-29-carboxamide

Example 95

(1R,13E,18R,22R,26S,29S)-26-cyclopentyl-N-((1R,2S)-1-{[(cyclopropylsulfonyl)amino]carbonyl}-2-vinylcyclopropyl)-24,27-dioxo-2,23-dioxa-11,25,28-triazapentacyclo[26.2.1.0³,¹².0⁵,¹⁰.0¹⁸,²²]hentriaconta-3(12),4,5,7,9,10,13-heptaene-29-carboxamide

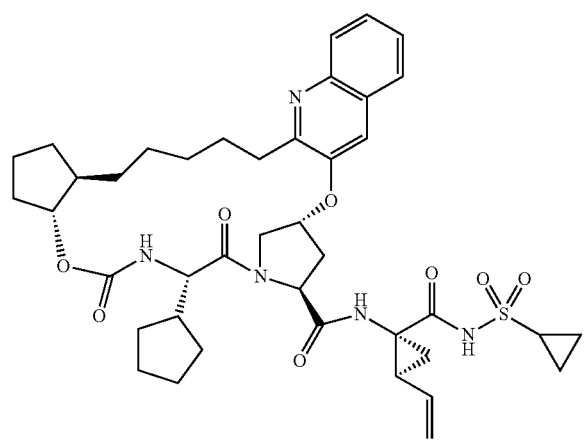 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCc1nc3ccccc3cc1O2)C(=O)NS(=O)(=O)C1CC1]

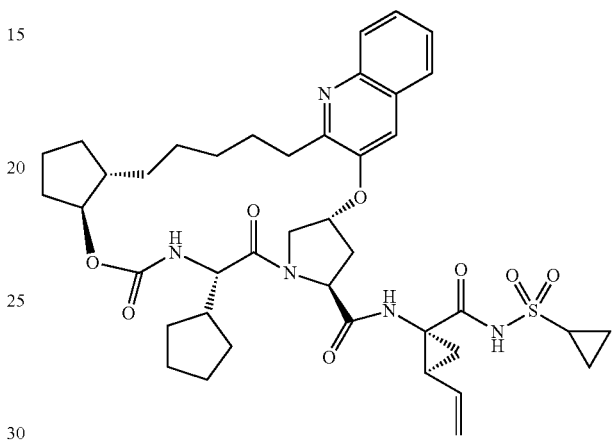

DIPEA (124 µl, 0.708 mmol), DMAP (6.65 mg, 0.054 mmol) and TBTU (45.5 mg, 0.142 mmol) were added to a stirred solution of the product of Step 5 (61.4 mg, 0.109 mmol) and Intermediate A1 (43.6 mg, 0.163 mmol) in DCM (5.7 mL). After 15 hours, the volatiles were evaporated, and the residue was purified by automated mass-triggered HPLC (FractionLynx) to afford after lyophilisation the title compound (51.9 mg, 61%) as a white powder. LCMS (ES+) m/z 776.3 (M+H)⁺.

Treatment of methyl (3aS,7S,10S,12R,20E,24aS)-7-cyclopentyl-5,8-dioxo-1,2,3,3a,5,6,7,8,11,12,22,23,24,24a-tetradecahydro-10H-9,12-methanocyclopenta[18,19][1,10,3,6]dioxadiazacyclononadecino[12,11-b]quinoline-10-carboxylate (87 mg, 0.151 mmol) as described in Example 94 Steps 4-6 afforded the title compound (72.8 mg, 62%) as a white powder. LCMS (ES+) m/z 776.3 (M+H)⁺.

By using the appropriate A, B, and C intermediates, the following compounds were prepared according to the procedures of Example 1.

| Ex. | Structure | Name | LRMS (M + H)⁺ | Intermediates according to Procedure | Int. |
|---|---|---|---|---|---|
| 96 | 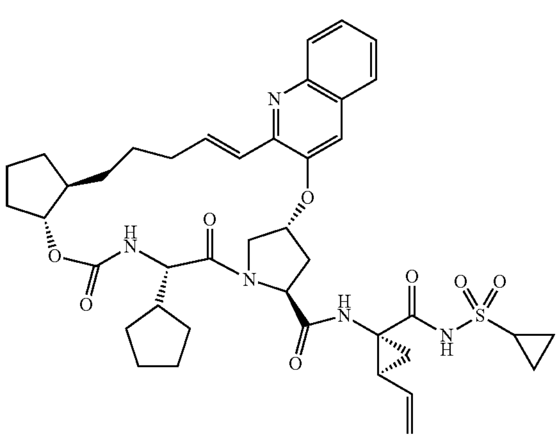 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCC/C=C/c1nc3ccccc3cc1O2)C(=O)NS(=O)(=O)C1CC1] | (1R,13E,18R,22R,26S,29S)-26-cyclopentyl-N-((1R,2S)-1-{[(cyclopropylsulfonyl)amino]carbonyl}-2-vinylcyclopropyl)-24,27-dioxo-2,23-dioxa-11,25,28-triazapentacyclo[26.2.1.0³,¹².0⁵,¹⁰.0¹⁸,²²]hentriaconta-3(12),4,5,7,9,10,13-heptaene-29-carboxamide | 774.3 | See Example 94, omit Step 4, separate isomers | A1, B23, C13 |

-continued

| Ex. | Structure | Name | LRMS (M + H)+ | Intermediates according to Procedure | Int. |
|---|---|---|---|---|---|
| 97 | 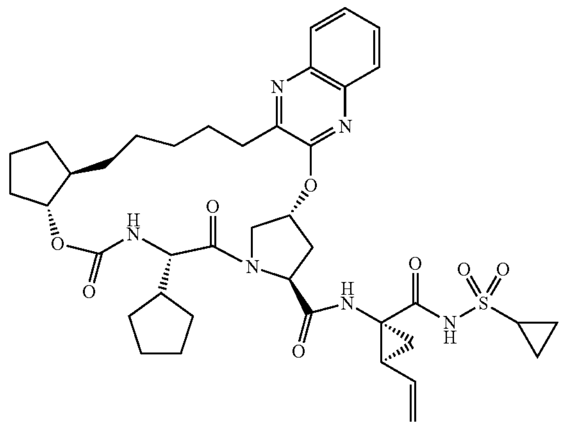 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCc1nc3ccccc3nc1O2)C(=O)NS(=O)(=O)C1CC1] | (1R,18R,22R,26S,29S)-26-cyclopentyl-N-((1R,2S)-1-{[(cyclopropylsulfonyl)amino]carbonyl}-2-vinylcyclopropyl)-24,27-dioxo-2,23-dioxa-4,11,25,28-tetraazapentacyclo[26.2.1.0$^{3,12}$.0$^{5,10}$.0$^{18,22}$]hentriaconta-3(12),4,5,7,9,10-hexaene-29-carboxamide | 777.2 | See Example 94, separate isomers | A1, B23, C15 |
| 98 | 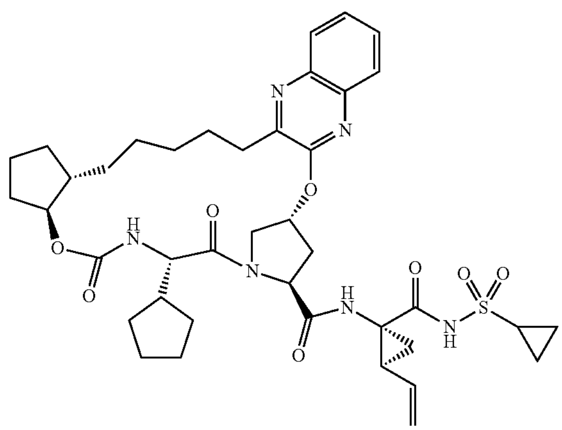 [SMILES: C=C[C@@H]1C[C@]1(NC(=O)[C@@H]1C[C@@H]2CN1C(=O)[C@H](C1CCCC1)NC(=O)O[C@H]1CCC[C@@H]1CCCCCc1nc3ccccc3nc1O2)C(=O)NS(=O)(=O)C1CC1] | (1R,18S,22S,26S,29S)-26-cyclopentyl-N-((1R,2S)-1-{[(cyclopropylsulfonyl)amino]carbonyl}-2-vinylcyclopropyl)-24,27-dioxo-2,23-dioxa-4,11,25,28-tetraazapentacyclo[26.2.1.0$^{3,12}$.0$^{5,10}$.0$^{18,22}$]hentriaconta-3(12),4,5,7,9,10-hexaene-29-carboxamide | 777.2 | See Example 94, separate isomers | A1, B23, C15 |
| 99 | 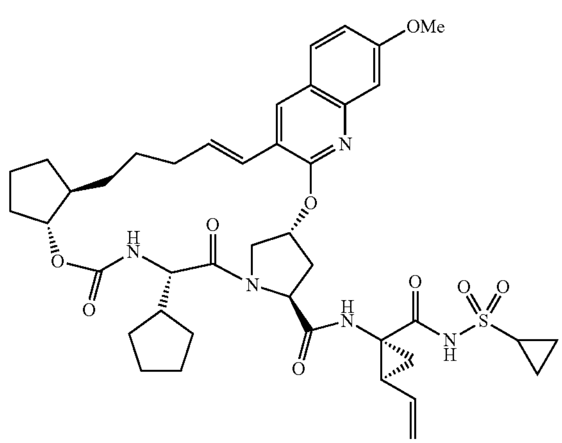 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCC/C=C/c1cc3ccc(OC)cc3nc1O2)C(=O)NS(=O)(=O)C1CC1] | (1R,13E,18R,22R,26S,29S)-26-cyclopentyl-N-((1R,2S)-1-{[(cyclopropylsulfonyl)amino]carbonyl}-2-vinylcyclopropyl)-7-methoxy-24,27-dioxo-2,23-dioxa-4,25,28-triazapentacyclo[26.2.1.0$^{3,12}$.0$^{5,10}$.0$^{18,22}$]hentriaconta-3(12),4,5,7,9,10,13-heptaene-29-carboxamide | 804.5 | See Example 1, Steps 4-7, separate isomers | A1, B23, C11 |

-continued

| Ex. | Structure | Name | LRMS (M + H)+ | Intermediates according to Procedure | Int. |
|---|---|---|---|---|---|
| 100 | 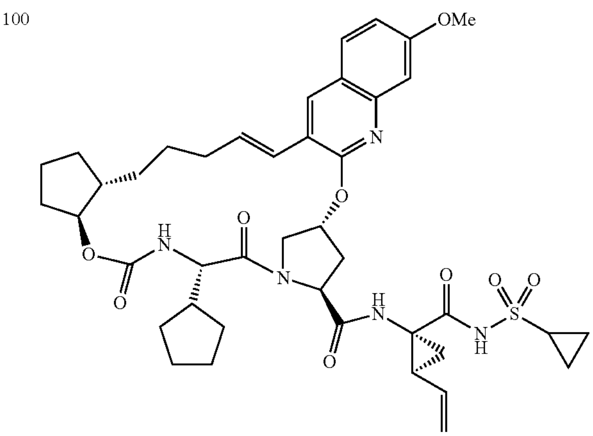 | (1R,13E,18S,22S,26S,29S)-26-cyclopentyl-N-((1R,2S)-1-{[(cyclopropylsulfonyl)amino]carbonyl}-2-vinylcyclopropyl)-7-methoxy-24,27-dioxo-2,23-dioxa-4,25,28-triazapentacyclo [26.2.1.0$^{3,12}$.0$^{5,10}$.0$^{18,22}$] hentriaconta-3(12),4,5,7,9,10,13-heptaene-29-carboxamide | 804.5 | See Example 1, Steps 4-7, separate isomers | A1, B23, C11 |
| 101 | 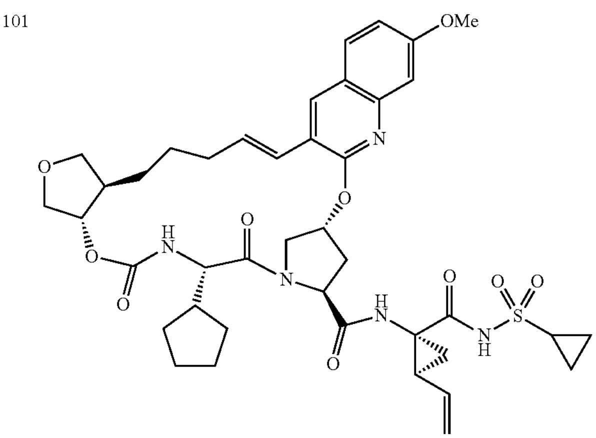 | (1R,13E,18R,22S,26S,29S)-26-cyclopentyl-N-((1R,2S)-1-{[(cyclopropylsulfonyl)amino]carbonyl}-2-vinylcyclopropyl)-7-methoxy-24,27-dioxo-2,20,23-trioxa-4,25,28-triazapentacyclo [26.2.1.0$^{3,12}$.0$^{5,10}$.0$^{18,22}$] hentriaconta-3(12),4,5,7,9,10,13-heptaene-29-carboxamide | 806.5 | See Example 1, steps 4-7, separate isomers | A1, B21a, C11 |
| 102 | 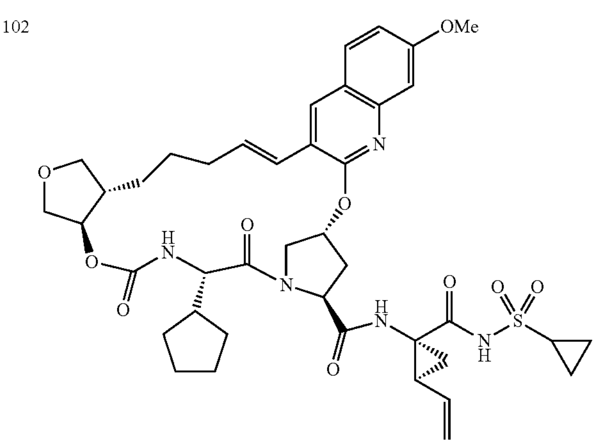 | (1R,13E,18S,22R,26S,29S)-26-cyclopentyl-N-((1R,2S)-1-{[(cyclopropylsulfonyl)amino]carbonyl}-2-vinylcyclopropyl)-7-methoxy-24,27-dioxo-2,20,23-trioxa-4,25,28-triazapentacyclo [26.2.1.0$^{3,12}$.0$^{5,10}$.0$^{18,22}$] hentriaconta-3(12),4,5,7,9,10,13-heptaene-29-carboxamide | 806.4 | See Example 1, Steps 4-7, separate isomers | A1, B21a, C11 |

| Ex. | Structure | Name | LRMS (M + H)+ | Intermediates according to Procedure | Int. |
|---|---|---|---|---|---|
| 103 | 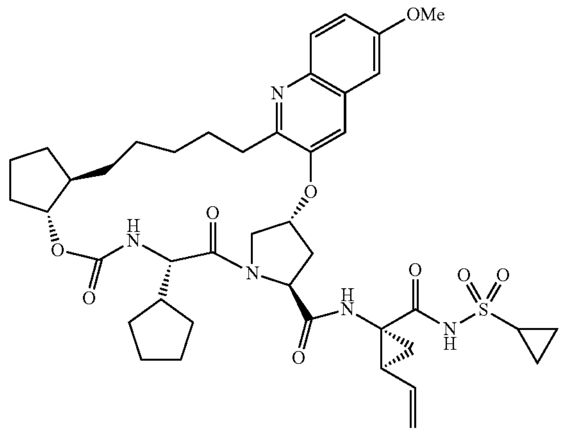 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCc1nc3ccc(OC)cc3cc1O2)C(=O)NS(=O)(=O)C1CC1] | (1R,18R,22R,26S,29S)-26-cyclopentyl-N-((1R,2S)-1-{[(cyclopropylsulfonyl)amino]carbonyl}-2-vinylcyclopropyl)-7-methoxy-24,27-dioxo-2,23-dioxa-11,25,28-triazapentacyclo[26.2.1.0$^{3,12}$.0$^{5,10}$.0$^{18,22}$]hentriaconta-3(12),4,5,7,9,10-hexaene-29-carboxamide | 806.3 | See Example 94 | A1, B23a, C14 |
| 104 | 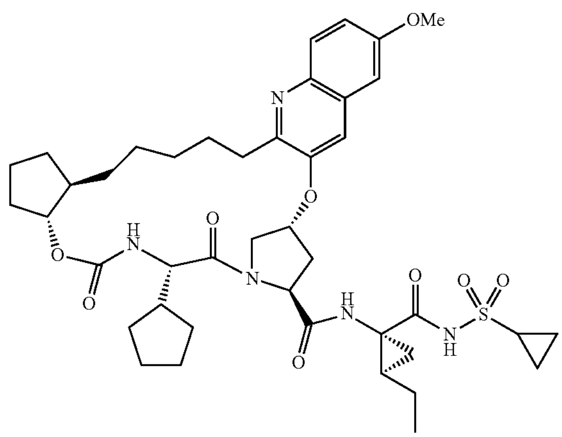 [SMILES: CC[C@@H]1C[C@]1(NC(=O)[C@@H]1C[C@@H]2CN1C(=O)[C@H](C1CCCC1)NC(=O)O[C@@H]1CCC[C@H]1CCCCCc1nc3ccc(OC)cc3cc1O2)C(=O)NS(=O)(=O)C1CC1] | (1R,18R,22R,26S,29S)-26-cyclopentyl-N-((1R,2R)-1-{[(cyclopropylsulfonyl)amino]carbonyl}-2-ethylcyclopropyl)-7-methoxy-24,27-dioxo-2,23-dioxa-11,25,28-triazapentacyclo[26.2.1.0$^{3,12}$.0$^{5,10}$.0$^{18,22}$]hentriaconta-3(12),4,5,7,9,10-hexaene-29-carboxamide | 808.3 | See Example 94 | A3, B23a, C14 |
| 105 | 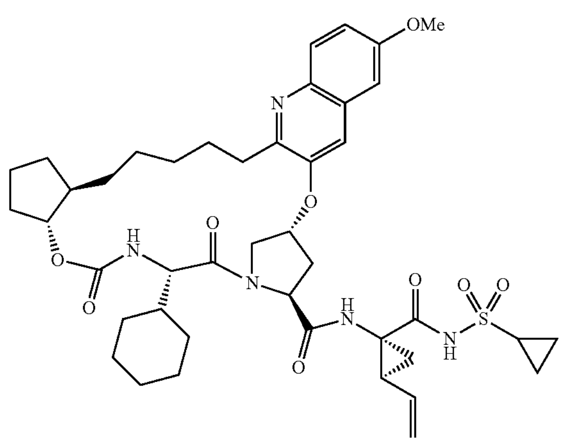 [SMILES: C=C[C@@H]1C[C@]1(NC(=O)[C@@H]1C[C@@H]2CN1C(=O)[C@H](C1CCCCC1)NC(=O)O[C@@H]1CCC[C@H]1CCCCCc1nc3ccc(OC)cc3cc1O2)C(=O)NS(=O)(=O)C1CC1] | (1R,18R,22R,26S,29S)-26-cyclohexyl-N-((1R,2S)-1-{[(cyclopropylsulfonyl)amino]carbonyl}-2-vinylcyclopropyl)-7-methoxy-24,27-dioxo-2,23-dioxa-11,25,28-triazapentacyclo[26.2.1.0$^{3,12}$.0$^{5,10}$.0$^{18,22}$]hentriaconta-3(12),4,5,7,9,10-hexaene-29-carboxamide | 820.3 | See Example 94 | A1, B24a, C14 |

| Ex. | Structure | Name | LRMS (M + H)+ | Intermediates according to Procedure | Int. |
|---|---|---|---|---|---|
| 106 | 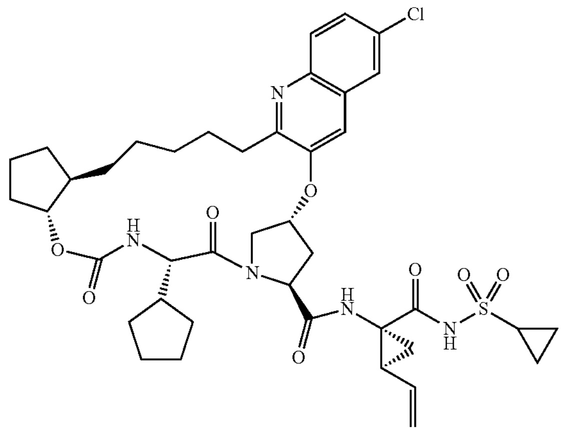 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCc1nc3ccc(Cl)cc3cc1O2)C(=O)NS(=O)(=O)C1CC1] | (1R,18R,22R,26S,29S)-7-chloro-26-cyclopentyl-N-((1R,2S)-1-{[(cyclopropylsulfonyl)amino]carbonyl}-2-vinylcyclopropyl)-24,27-dioxo-2,23-dioxa-11,25,28-triazapentacyclo[26.2.1.0$^{3,12}$.0$^{5,10}$.0$^{18,22}$]hentriaconta-3(12),4,5,7,9,10-hexaene-29-carboxamide | 810.6 | See Example 94, separate isomers | A1, B23, C16 |
| 107 | 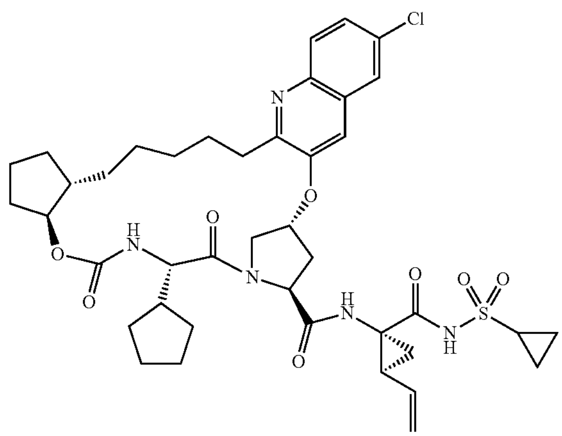 [SMILES: C=C[C@@H]1C[C@]1(NC(=O)[C@@H]1C[C@@H]2CN1C(=O)[C@H](C1CCCC1)NC(=O)O[C@H]1CCC[C@@H]1CCCCCc1nc3ccc(Cl)cc3cc1O2)C(=O)NS(=O)(=O)C1CC1] | (1R,18S,22S,26S,29S)-7-chloro-26-cyclopentyl-N-((1R,2S)-1-{[(cyclopropylsulfonyl)amino]carbonyl}-2-vinylcyclopropyl)-24,27-dioxo-2,23-dioxa-11,25,28-triazapentacyclo[26.2.1.0$^{3,12}$.0$^{5,10}$.0$^{18,22}$]hentriaconta-3(12),4,5,7,9,10-hexaene-29-carboxamide | 810.6 | See Example 94, separate isomers | A1, B23, C16 |
| 108 | 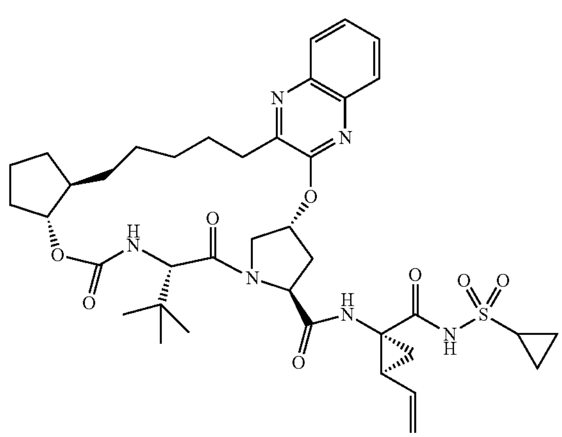 [SMILES: C=C[C@@H]1C[C@]1(NC(=O)[C@@H]1C[C@@H]2CN1C(=O)[C@H](C(C)(C)C)NC(=O)O[C@@H]1CCC[C@H]1CCCCCc1nc3ccccc3nc1O2)C(=O)NS(=O)(=O)C1CC1] | (1R,18R,22R,26S,29S)-26-t-butyl-N-((1R,2S)-1-{[(cyclopropylsulfonyl)amino]carbonyl}-2-vinylcyclopropyl)-24,27-dioxo-2,23-dioxa-4,11,25,28-tetraazapentacyclo[26.2.1.0$^{3,12}$.0$^{5,10}$.0$^{18,22}$]hentriaconta-3(12),4,5,7,9,10-hexaene-29-carboxamide | 765.2 | See Example 94 | A1, B22a, C15 |

Example 109

(1R,18R,22R,26S,29S)-26-t-butyl-N-((1R,2S)-1-{[(cyclopropylsulfonyl)amino]carbonyl}-2-vinylcyclopropyl)-7-methoxy-24,27-dioxo-2,23-dioxa-11,25,28-triazapentacyclo[26.2.1.0$^{3,12}$.0$^{5,10}$.0$^{18,22}$]hentriaconta-3(12),4,5,7,9,10-hexaene-29-carboxamide

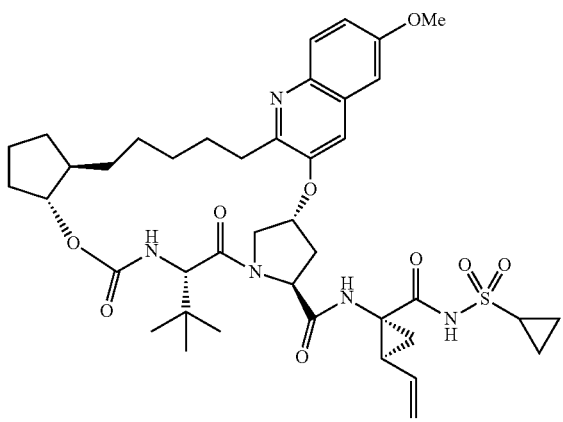 [SMILES: C=C[C@@H]1C[C@]1(NC(=O)[C@@H]1C[C@@H]2CN1C(=O)[C@H](C(C)(C)C)NC(=O)O[C@@H]1CCC[C@H]1CCCCCc1nc3ccc(OC)cc3cc1O2)C(=O)NS(=O)(=O)C1CC1]

Step 1: Methyl 3-methyl-N-({[(1R,2R)-2-pent-4-en-1-ylcyclopentyl]oxy}carbonyl)-L-valyl-(4R)-4-[(6-methoxy-2-vinylquinolin-3-yl)oxy]-L-prolinate

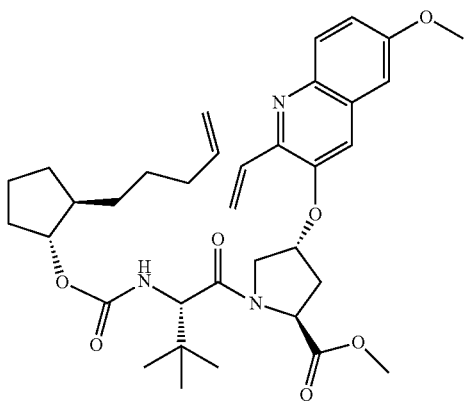 [SMILES: C=CCCC[C@@H]1CCC[C@H]1OC(=O)N[C@H](C(=O)N1C[C@H](Oc2cc3cc(OC)ccc3nc2C=C)C[C@H]1C(=O)OC)C(C)(C)C]

A solution of Intermediate C14 (0.50 g, 1.46 mmol) and Intermediate B23 was treated as described for Example 94 Step 1, to produce a residue that was then taken up in absolute EtOH. The resulting solution (0.2 M) was treated with potassium vinyltrifluoroborate (1.6 eq) and TEA (1.6 eq). Pd(dppf).CH$_2$Cl$_2$ (0.2 eq) was added, and the mixture was heated under reflux for 1 hour. The mixture was cooled and diluted with H$_2$O and EtOAc. The organic layer was separated, washed with brine and dried over Na$_2$SO$_4$. The filtered solution was concentrated to afford a residue that was purified by column chromatography on SiO$_2$ (gradient elution, 1-100% EtOAc/petroleum ether) to give the title compound (30%) as a solid. LCMS (ES+) m/z 622 (M+H)$^+$.

Step 2: Methyl (3 aR,7S,10S,12R,20E,24aR)-7-t-butyl-16-methoxy-5,8-dioxo-1,2,3,3a,5,6,7,8,11,12,22,23,24,24a-tetradecahydro-10H-9,12-methanocyclopenta[18,19][1,10,3,6]dioxadiazacyclononadecino[12,11-]quinoline-10-carboxylate

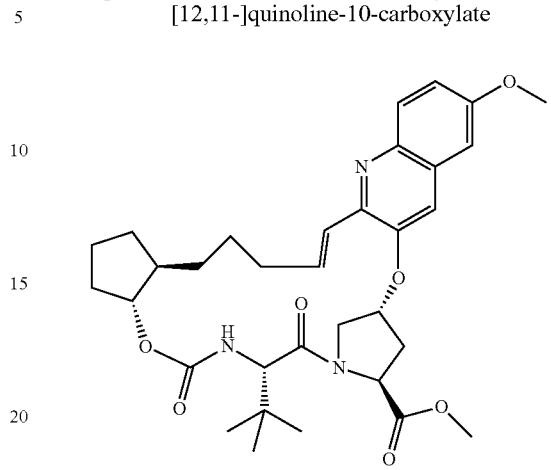

A solution of the product of Step 1 (300 mg, 0.48 mmol) in DCE (30 mL) was treated with Zhan catalyst (48 mg, 0.07 mmol), then heated at 90° C. for 2 hours. The mixture was cooled and concentrated in vacuo to furnish a residue that was purified by flash chromatography on SiO$_2$ (gradient elution, 10-80% EtOAc/petroleum ether) to give the title compound (228 mg, 84%). LCMS (ES+) m/z 594 (M+H)$^+$.

Step 3: (3 aR,7S,10S,12R,24aR)-7-t-Butyl-16-methoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[12,11-b]quinoline-10-carboxylic acid

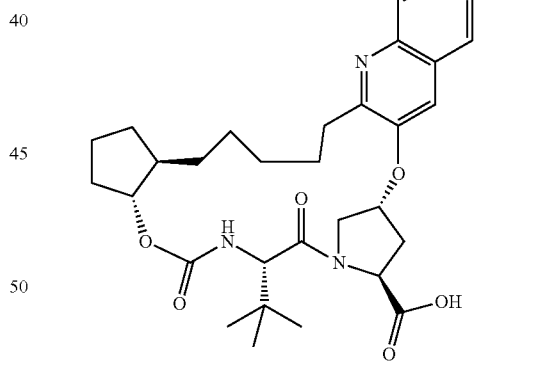

The product of Step 2 (125 mg, 0.21 mmol) was dissolved in a 1:2 mixture of H$_2$O:MeOH (30 mL) and treated with LiOH.H$_2$O (35 mg, 0.84 mmol). The solution was heated at 50° C. for 3 hours. The MeOH was evaporated in vacuo, and the aqueous solution was diluted with EtOAc and acidified to pH 4 with HCl$_{(aq.)}$ (1N). The organic layer was separated, then washed with brine and dried over Na$_2$SO$_4$. After filtration and removal of the volatiles, the residue was dissolved in MeOH (55 mL) and treated with Pd/C (10%, 10 mg). The solution was stirred under H$_2$ for 2 hours, then filtered through CELITE. The filtrate was concentrated to afford the title compound (120 mg, 98%) as a solid that was used directly in the next step. LCMS (ES+) m/z 582 (M+H)$^+$.

Step 4: (3 aR,7S,10S,12R,24aR)-7-t-Butyl-N-((1R,2S)-1-{[(cyclopropylsulfonyl)amino]carbonyl}-2-vinylcyclopropyl)-16-methoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[12,11-b]quinoline-10-carboxamide

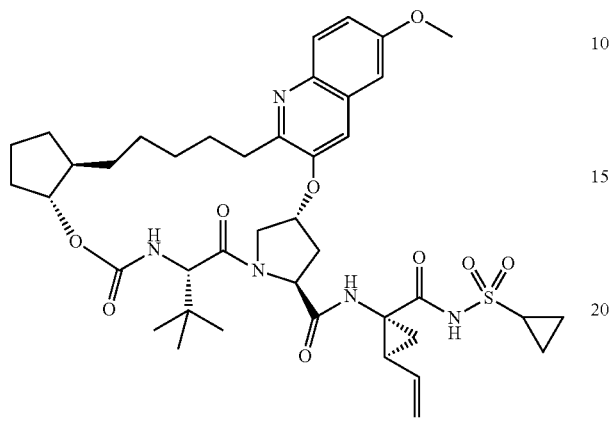

The product of Step 3 was treated as described in Example 94 Step 6 to afford a residue that was purified by automated mass-triggered HPLC (FractionLynx) to furnish, after freeze drying, the title compound (112 mg, 68%) as a white solid. LCMS (ES+) m/z 794 (M+H)+.

By using the appropriate A, B, and C intermediates, the following compounds were prepared according to the procedures of Example 94.

| Ex. | Structure | Name | LRMS (M + H)+ | Int. |
|---|---|---|---|---|
| 110 | 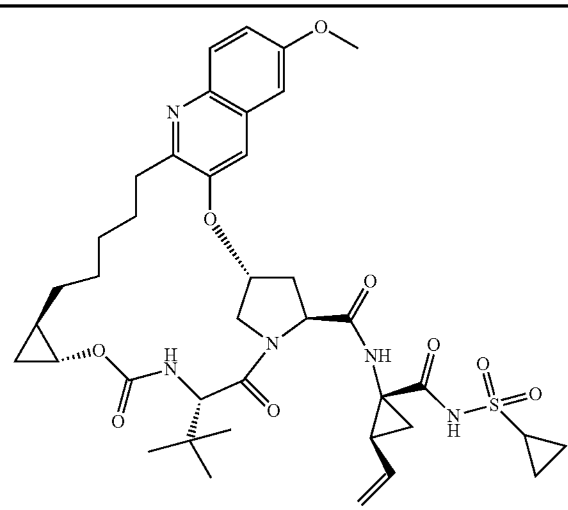 | (1aR,5S,8S,10R,22aR)-5-t-butyl-N-((1R,2S)-1-{[(cyclopropylsulfonyl)amino]carbonyl}-2-vinylcyclopropyl)-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[12,11-b]quinoline-8-carboxamide | 766.6 | A1, B25a, C14 |
| 111 | 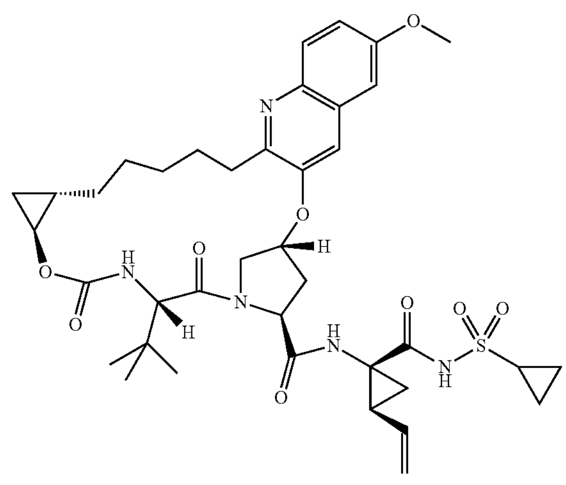 [SMILES: C=C[C@@H]1C[C@]1(NC(=O)[C@@H]1C[C@@H]2CN1C(=O)[C@H](C(C)(C)C)NC(=O)O[C@H]1C[C@@H]1CCCCCc1nc3ccc(OC)cc3cc1O2)C(=O)NS(=O)(=O)C1CC1] | (1aS,5S,8S,10R,22aS)-5-t-butyl-N-((1R,2S)-1-{[(cyclopropylsulfonyl)amino]carbonyl}-2-vinylcyclopropyl)-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[12,11-b]quinoline-8-carboxamide | 766.5 | A1, B25a, C14 |

| Ex. | Structure | Name | LRMS (M + H)+ | Int. |
|---|---|---|---|---|
| 112 | 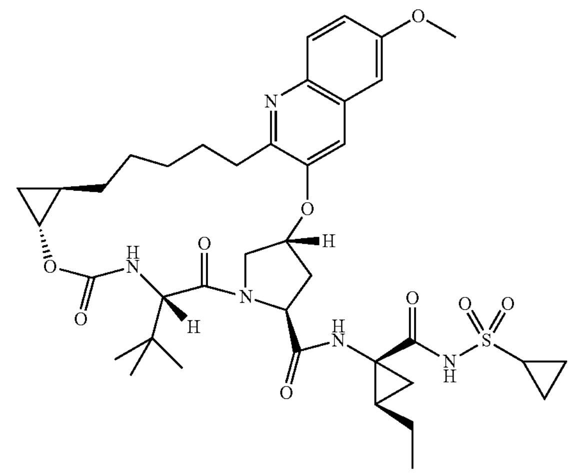 [SMILES: CC[C@@H]1C[C@]1(NC(=O)[C@@H]1C[C@@H]2CN1C(=O)[C@H](C(C)(C)C)NC(=O)O[C@@H]1C[C@H]1CCCCCc1nc3ccc(OC)cc3cc1O2)C(=O)NS(=O)(=O)C1CC1] | (1aR,5S,8S,10R,22aR)-5-t-butyl-N-((1R,2R)-1-{[(cyclopropylsulfonyl)amino]carbonyl}-2-ethylcyclopropyl)-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[12,11-b]quinoline-8-carboxamide | 768.5 | A3, B25a, C14 |
| 113 | 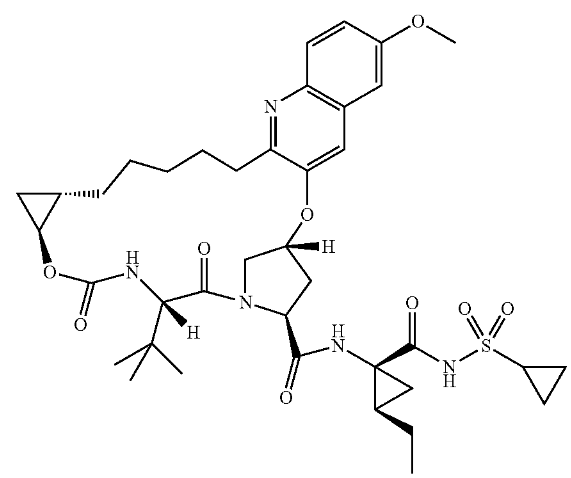 [SMILES: CC[C@@H]1C[C@]1(NC(=O)[C@@H]1C[C@@H]2CN1C(=O)[C@H](C(C)(C)C)NC(=O)O[C@H]1C[C@@H]1CCCCCc1nc3ccc(OC)cc3cc1O2)C(=O)NS(=O)(=O)C1CC1] | (1aS,5S,8S,10R,22aS)-5-t-butyl-N-((1R,2R)-1-{[(cyclopropylsulfonyl)amino]carbonyl}-2-ethylcyclopropyl)-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[12,11-b]quinoline-8-carboxamide | 768.5 | A3, B25a, C14 |
| 114 | 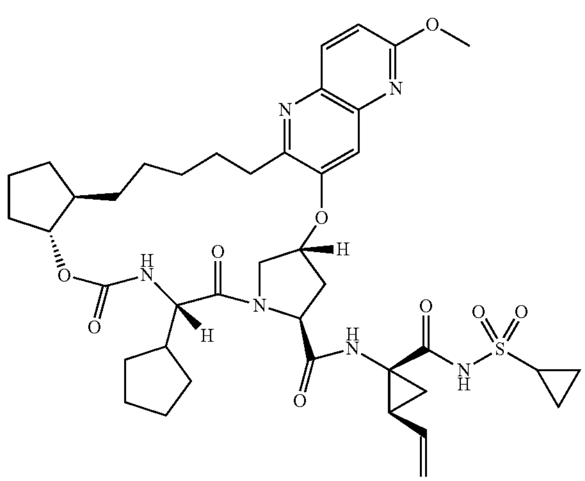 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCc1nc3ccc(OC)nc3cc1O2)C(=O)NS(=O)(=O)C1CC1] | (3aR,7S,10S,12R,24aR)-7-cyclopentyl-N-((1R,2S)-1-{[(cyclopropylsulfonyl)amino]carbonyl}-2-vinylcyclopropyl)-16-methoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[12,11-b]-1,5-naphthyridine-10-carboxamide | 807.9 | A1, B23a, C18 |

-continued

| Ex. | Structure | Name | LRMS (M + H)+ | Int. |
|---|---|---|---|---|
| 115 | 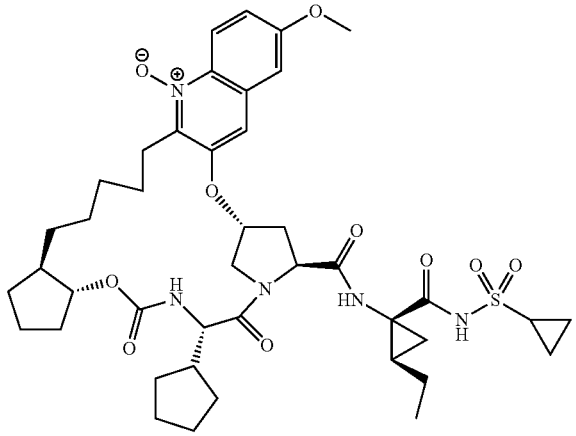 [SMILES: CC[C@@H]1C[C@]1(NC(=O)[C@@H]1C[C@@H]2CN1C(=O)[C@H](C1CCCC1)NC(=O)O[C@@H]1CCC[C@H]1CCCCCc1c(cc3cc(OC)ccc3[n+]1[O-])O2)C(=O)NS(=O)(=O)C1CC1] | (3aS,7S,10S,12R,24aS)-7-cyclopentyl-N-((1R,2R)-1-{[(cyclopropylsulfonyl)amino]carbonyl}-2-ethylcyclopropyl)-16-methoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[12,11-b]quinoline-10-carboxamide 19-oxide | 824.6 | A3, B23a, C14 |
| 116 | 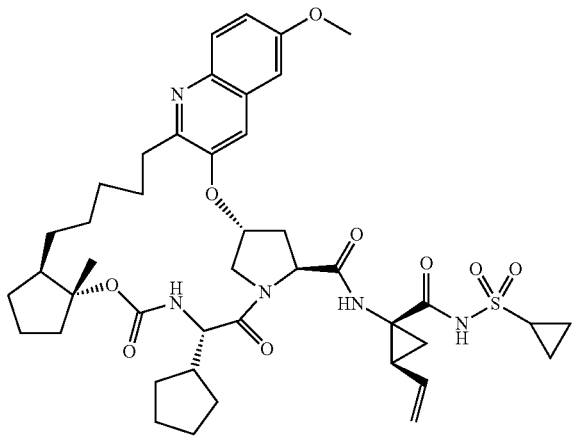 [SMILES: C=C[C@@H]1C[C@]1(NC(=O)[C@@H]1C[C@@H]2CN1C(=O)[C@H](C1CCCC1)NC(=O)O[C@]1(C)CCC[C@H]1CCCCCc1nc3ccc(OC)cc3cc1O2)C(=O)NS(=O)(=O)C1CC1] | (3aS,7S,10S,12R,24aS)-7-cyclopentyl-N-((1R,2R)-1-{[(cyclopropylsulfonyl)amino]carbonyl}-2-ethylcyclopropyl)-16-methoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[12,11-b]quinoline-10-carboxamide 19-oxide | 820.6 | A1, B26, C14 |

| Ex. | Structure | Name | LRMS (M + H)+ | Int. |
|---|---|---|---|---|
| 117 | 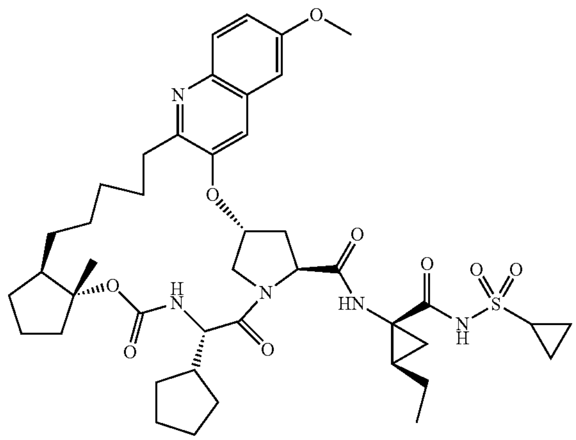 [SMILES: CC[C@@H]1C[C@]1(NC(=O)[C@@H]1C[C@@H]2CN1C(=O)[C@H](C1CCCC1)NC(=O)O[C@]1(C)CCC[C@H]1CCCCCc1nc3ccc(OC)cc3cc1O2)C(=O)NS(=O)(=O)C1CC1] | (3aR,7S,10S,12R,24aR)-7-cyclopentyl-N-((1R,2S)-1-{[(cyclopropylsulfonyl)amino]carbonyl}-2-vinylcyclopropyl)-16-methoxy-3a-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclo nonadecino[12,11-b]quinoline-10-carboxamide | 822.7 | A3, B26, C14 |
| 118 | 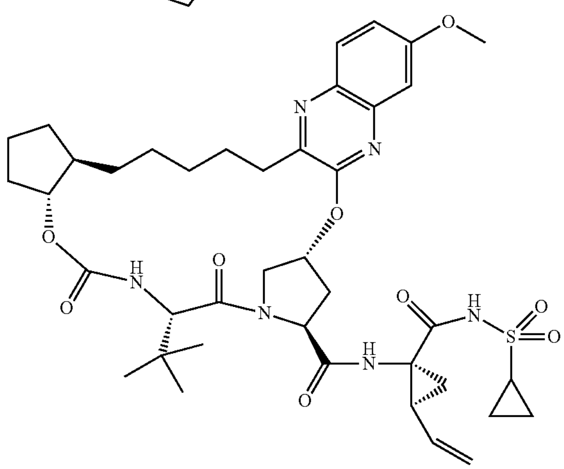 | (3aR,7S,10S,12R,24aR)-7-cyclopentyl-N-((1R,2R)-1-{[(cyclopropylsulfonyl)amino]carbonyl}-2-ethylcyclopropyl)-16-methoxy-3a-methyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclo nonadecino[12,11-b]quinoline-10-carboxamide | 795.8 | A1, B27, C17 |

Example 119

(3aR,7S,10S,12R,24aR)-7-t-butyl-N-((1R,2S)-1-{[(cyclopropylsulfonyl)amino]carbonyl}-2-vinylcyclopropyl)-16-methoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[11,12-b]quinoxaline-10-carboxamide Step 1: Methyl (3aS,7S,10S,12R,24aS)-7-cyclopentyl-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[12,11-b]quinoline-10-carboxylate

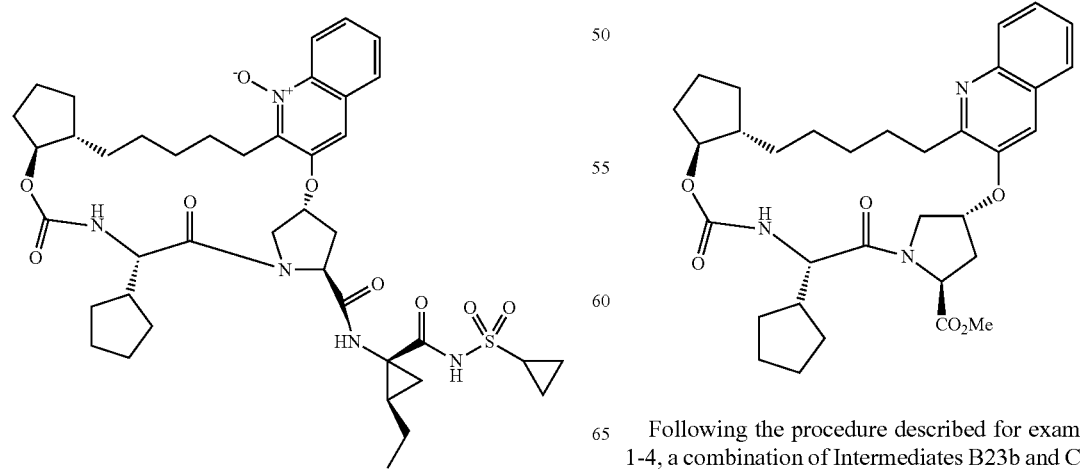

Following the procedure described for example 94 Steps 1-4, a combination of Intermediates B23b and C14 furnished the title compound as a solid.

Step 2: Methyl (3 aS,7S,10S,12R,24aS)-7-cyclopentyl-16-methoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[12,11-b]quinoline-10-carboxylate 19-oxide

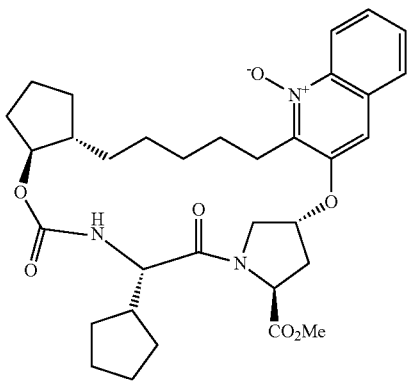

m-CPBA (46.6 mg, 0.27 mmol) was added to a stirred solution of the product of Step 1 (130 mg, 0.225 mmol) in DCM (1.13 ml) at 0° C. Additional mCPBA was added after 1 hour (66.0 mg, 0.383 mmol) and after 4 hours (38.8 mg, 0.225 mmol). The mixture was diluted with DCM (1 mL) and stirred for 1 hour. The reaction was diluted with DCM, and the organic layer was washed with 10% $Na_2S_2O_{3(aq.)}$ and 10% $NaHCO_{3(aq.)}$. The organics were washed with brine and dried over $Na_2SO_4$ and concentrated to give the title compound as a solid that was used directly in the subsequent step. LCMS (ES+) m/z 363.8 (M+H)+.

Step 3: (3aS,7S,10S,12R,24aS)-7-Cyclopentyl-N-((1R,2R)-1-{[(cyclopropylsulfonyl)amino]carbonyl}-2-ethylcyclopropyl)-16-methoxy-5,8-dioxo-1,2,3,3a,5,6,7,8,11,12,20,21,22,23,24,24a-hexadecahydro-10H-9,12-methanocyclopenta[18,19][1,10,3,6]dioxadiazacyclononadecino[12,11-b]quinoline-10-carboxamide 19-oxide Treatment of the product of Step 2, by the procedures described in Example 94 Steps 5-6, furnished the title compound (12% over 3 steps) as a solid. LCMS (ES+) m/z 824.6 (M+H)+.

By using the appropriate A, B, and C intermediates, the following compounds were prepared according to the procedures of Example 94.

| Ex. | Structure | Name | LRMS (M + H)+ | Example | Int. |
|---|---|---|---|---|---|
| 120 | 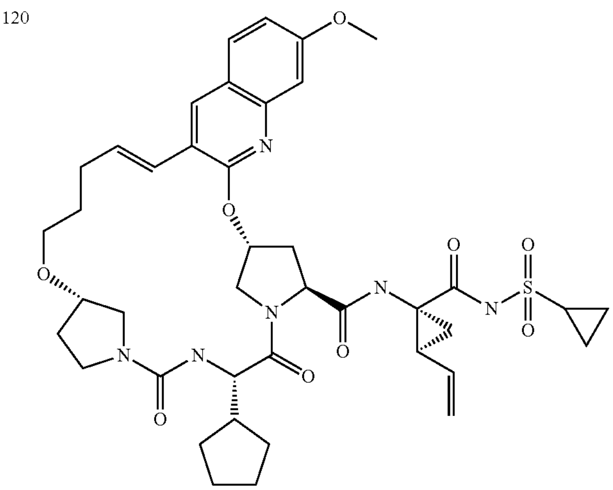 | ((1R,13E,19S,25S,28S)-25-cyclopentyl-N-((1R,2S)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10,13-heptaene-28-carboxamide | 805.5 | See Example 1, Steps 1-7 | A1, B30, C11 |
| 121 | 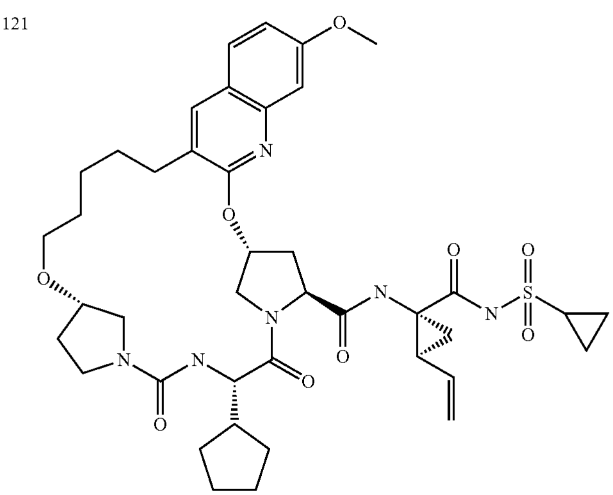 | (1R,19S,25S,28S)-25-cyclopentyl-N-((1R,2S)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10-hexaene-28-carboxamide | 807.4 | See Example 3, Steps 1 & 3, using product of Example 120, Step 6 | A1, B30, C11 |

| Ex. | Structure | Name | LRMS (M + H)+ | Example | Int. |
|---|---|---|---|---|---|
| 122 | 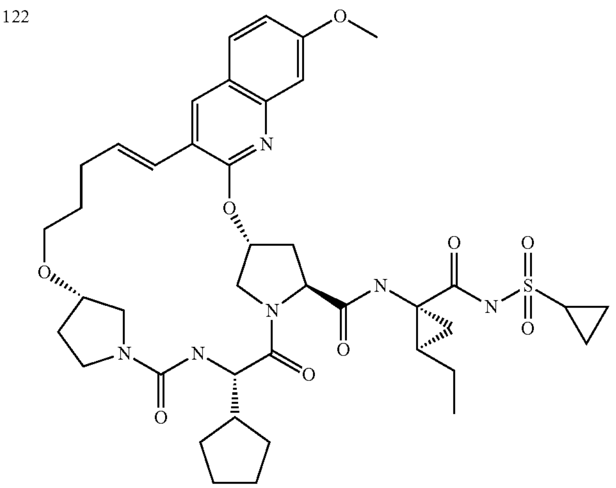 | (1R,13E,19S,25S,28S)-25-cyclopentyl-N-((1R,2R)-1-{[(cyclopropylsulfonyl)amino]carbonyl}-2-ethylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10,13-heptaene-28-carboxamide | 807.5 | See Example 2 | A3, B30, C11 |
| 123 | 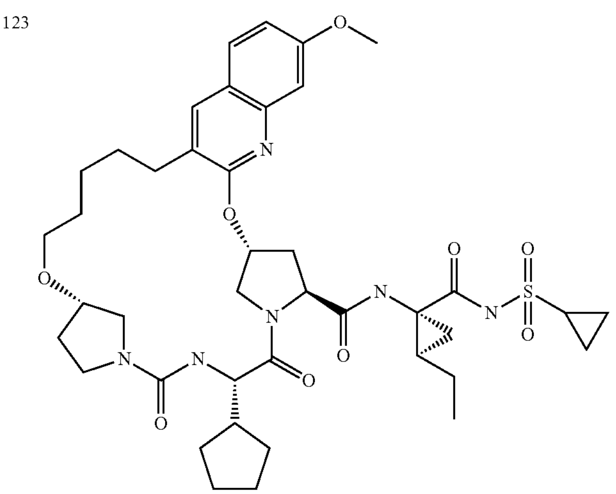 | (1R,19S,25S,28S)-25-cyclopentyl-N-((1R,2R)-1-{[(cyclopropylsulfonyl)amino]carbonyl}-2-ethylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10-hexaene-28-carboxamide | 809.4 | See Example 3, Steps 1 & 3, and Example 2, using product of Example 120, Step 6 | A3, B30, C11 |
| 124 | 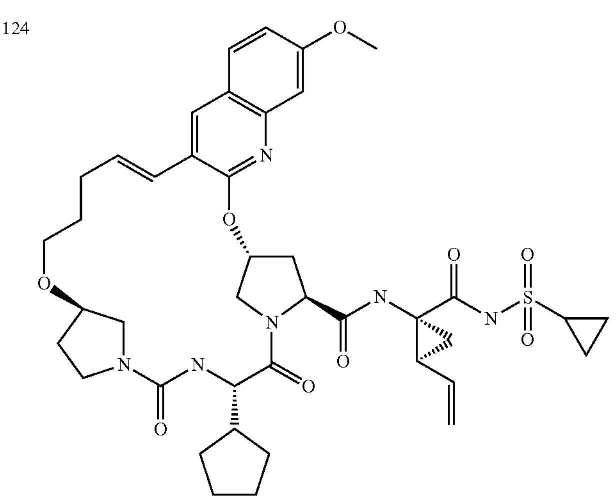 | (1R,13E,19R,25S,28S)-25-cyclopentyl-N-((1R,2S)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10,13-heptaene-28-carboxamide | 805.4 | See Example 1, Steps 1-7 | A1, B31, C11 |

| Ex. | Structure | Name | LRMS (M + H)+ | Example | Int. |
|---|---|---|---|---|---|
| 125 | 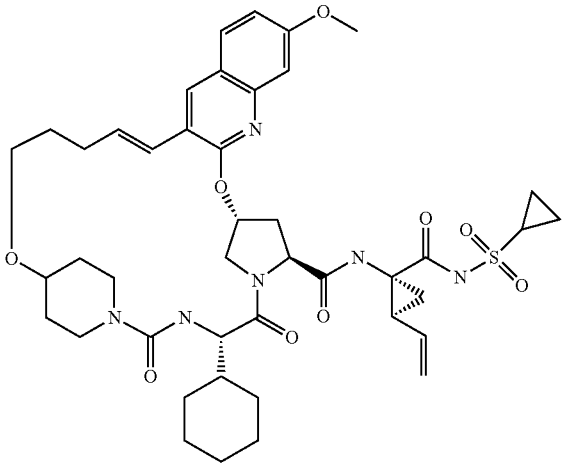 [SMILES: C=C[C@@H]1C[C@]1(NC(=O)[C@@H]1C[C@@H]2CN1C(=O)[C@H](C1CCCCC1)NC(=O)N1CCC(CC1)OCCC/C=C/c1cc3ccc(OC)cc3nc1O2)C(=O)NS(=O)(=O)C1CC1] | (4S,7S,9R,21E)-4-cyclohexyl-N-((1R,2S)-1-{[(cyclopropylsulfonyl)amino]carbonyl}-2-vinylcyclopropyl)-15-methoxy-2,5-dioxo-10,26-dioxa-1,3,6,12-tetraazapentacyclo[25.2.1.1$^{6,9}$.0$^{11,20}$.0$^{13,18}$]dotriaconta-11(20),12,13,15,17,18,21-heptaene-7-carboxamide | 834.1 | See Example 1, Steps 1-7 | A1, B32, C11 |
| 126 | 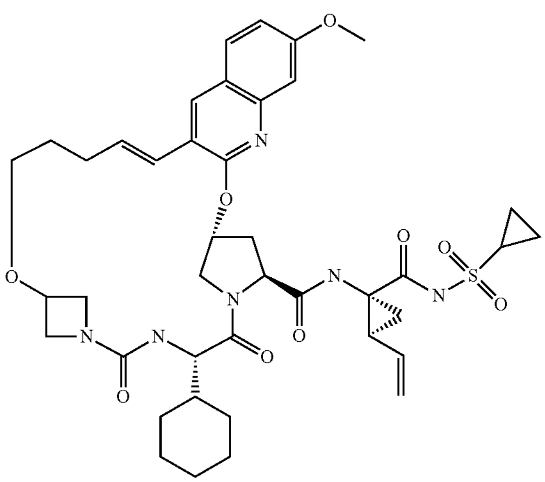 [SMILES: C=C[C@@H]1C[C@]1(NC(=O)[C@@H]1C[C@@H]2CN1C(=O)[C@H](C1CCCCC1)NC(=O)N1CC(C1)OCCC/C=C/c1cc3ccc(OC)cc3nc1O2)C(=O)NS(=O)(=O)C1CC1] | (1R,13E,24S,27S)-24-cyclohexyl-N-((1R,2S)-1-{[(cyclopropylsulfonyl)amino]carbonyl}-2-vinylcyclopropyl)-7-methoxy-22,25-dioxo-2,18-dioxa-4,21,23,26-tetraazapentacyclo[24.2.1.1$^{19,21}$.0$^{3,12}$.0$^{5,10}$]triaconta-3(12),4,5,7,9,10,13-heptaene-27-carboxamide | 805.2 | See Example 1, Steps 1-7 | A1, B33, C11 |
| 127 | 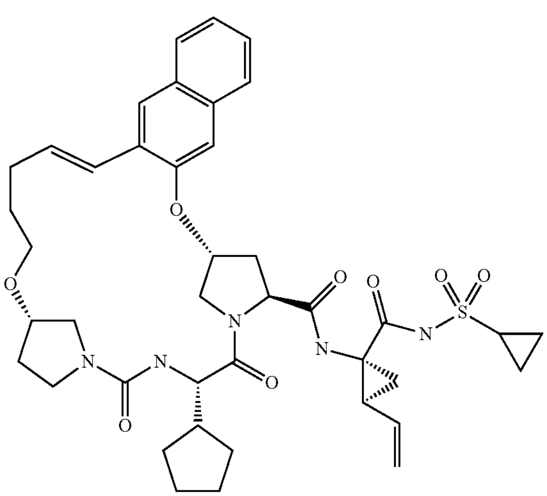 [SMILES: C=C[C@@H]1C[C@]1(NC(=O)[C@@H]1C[C@@H]2CN1C(=O)[C@H](C1CCCC1)NC(=O)N1CC[C@@H](C1)OCCC/C=C/c1cc3ccccc3cc1O2)C(=O)NS(=O)(=O)C1CC1] | (1R,13E,19S,25S,28S)-25-cyclopentyl-N-((1R,2S)-1-{[(cyclopropylsulfonyl)amino]carbonyl}-2-vinylcyclopropyl)-23,26-dioxo-2,18-dioxa-22,24,27-triazapentacyclo[25.2.1.1$^{19,22}$.0$^{3,12}$.0$^{5,10}$]hentriaconta-3(12),4,5,7,9,10,13-heptaene-28-carboxamide | 774.0 | See Example 1, Steps 4, 2 & 5-7 | A1, B30, C19 |

| Ex. | Structure | Name | LRMS (M + H)+ | Example | Int. |
|---|---|---|---|---|---|
| 128 | 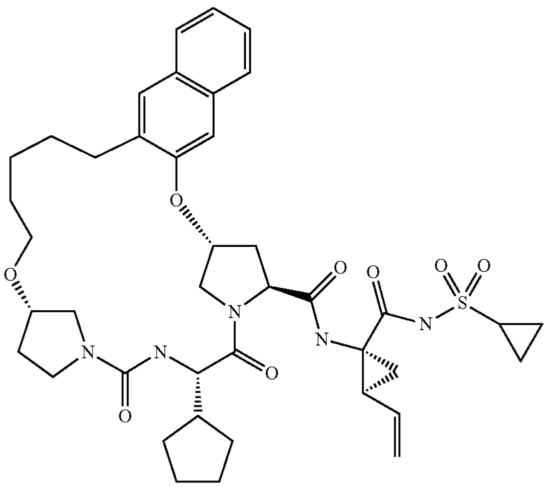 [SMILES: C=C[C@@H]1C[C@]1(NC(=O)[C@@H]1C[C@@H]2CN1C(=O)[C@H](C1CCCC1)NC(=O)N1CC[C@@H](C1)OCCCCCc1cc3ccccc3cc1O2)C(=O)NS(=O)(=O)C1CC1] | (1R,19S,25S,28S)-25-cyclopentyl-N-((1R,2S)-1-{[(cyclopropylsulfonyl)amino]carbonyl}-2-vinylcyclopropyl)-23,26-dioxo-2,18-dioxa-22,24,27-triazapentacyclo[25.2.1.1$^{19,22}$.0$^{3,12}$.0$^{5,10}$]hentriaconta-3(12),4,5,7,9,10-hexaene-28-carboxamide | 776.0 | See Example 3, Steps 1 & 3, using product of Example 127, Step 6 | A1, B30, C19 |
| 129 | 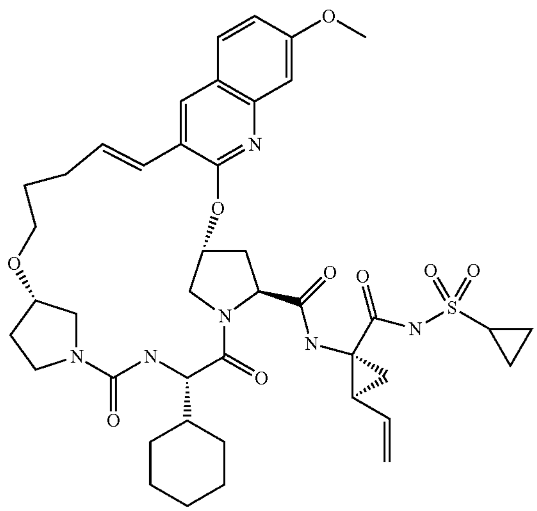 [SMILES: C=C[C@@H]1C[C@]1(NC(=O)[C@@H]1C[C@@H]2CN1C(=O)[C@H](C1CCCCC1)NC(=O)N1CC[C@@H](C1)OCCC/C=C/c1cc3ccc(OC)cc3nc1O2)C(=O)NS(=O)(=O)C1CC1] | (1R,13E,19S,25S,28S)-25-cyclohexyl-N-((1R,2S)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10,13-heptaene-28-carboxamide | 819.0 | See Example 1, Steps 1-7 | A1, B34, C11 |
| 130 | 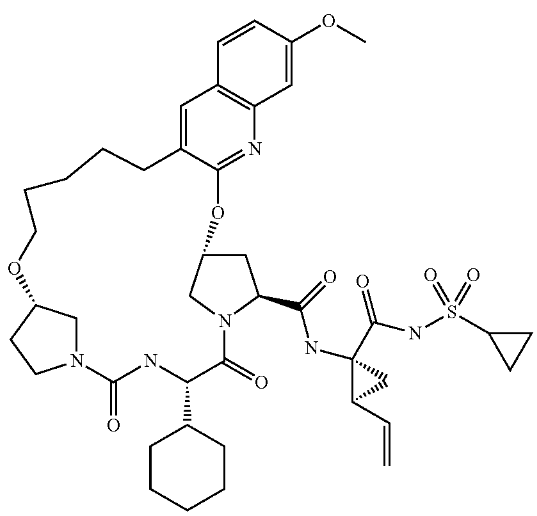 [SMILES: C=C[C@@H]1C[C@]1(NC(=O)[C@@H]1C[C@@H]2CN1C(=O)[C@H](C1CCCCC1)NC(=O)N1CC[C@@H](C1)OCCCCCc1cc3ccc(OC)cc3nc1O2)C(=O)NS(=O)(=O)C1CC1] | (1R,19S,25S,28S)-25-cyclohexyl-N-((1R,2S)-1-{[(cyclopropylsulfonyl)amino]carbonyl}-2-vinylcyclopropyl)-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10-hexaene-28-carboxamide | 821.0 | See Example 3, Steps 1 & 3 using product of Example 129, Step 6 | A1, B34, C11 |

-continued

| Ex. | Structure | Name | LRMS (M + H)+ | Example | Int. |
|---|---|---|---|---|---|
| 131 | 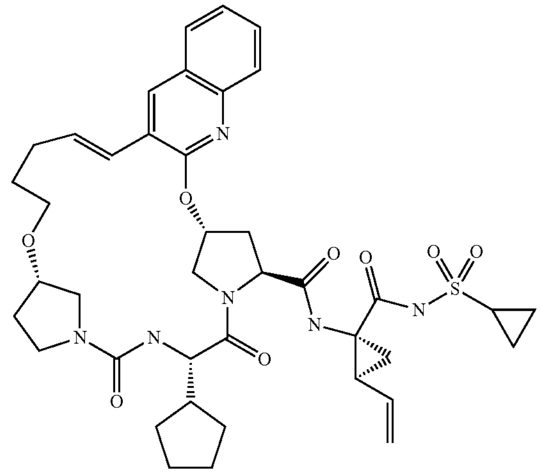 [SMILES: C=C[C@@H]1C[C@]1(NC(=O)[C@@H]1C[C@@H]2CN1C(=O)[C@H](C1CCCC1)NC(=O)N1CC[C@@H](C1)OCCC/C=C/c1cc3ccccc3nc1O2)C(=O)NS(=O)(=O)C1CC1] | (1R,13E,19S,25S,28S)-25-cyclopentyl-N-((1R,2S)-1-{[(cyclopropylsulfonyl)amino]carbonyl}-2-vinylcyclopropyl)-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10,13-heptaene-28-carboxamide | 775.2 | See Example 1, Steps 1-7 | A1, B30, C12 |
| 132 | 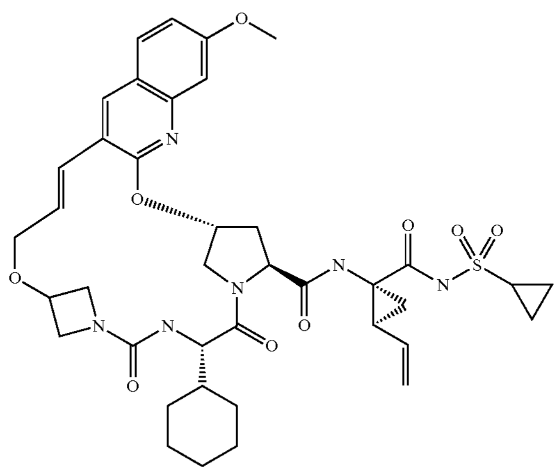 [SMILES: C=C[C@@H]1C[C@]1(NC(=O)[C@@H]1C[C@@H]2CN1C(=O)[C@H](C1CCCCC1)NC(=O)N1CC(C1)OC/C=C/c1cc3ccc(OC)cc3nc1O2)C(=O)NS(=O)(=O)C1CC1] | (1R,13E,22S,25S)-22-cyclohexyl-N-((1R,2S)-1-{[(cyclopropylsulfonyl)amino]carbonyl}-2-vinylcyclopropyl)-7-methoxy-20,23-dioxo-2,16-dioxa-4,19,21,24-tetraazapentacyclo[22.2.1.1$^{17,19}$.0$^{3,12}$.0$^{5,10}$]octacosa-3(12),4,5,7,9,10,13-heptaene-25-carboxamide | | See Example 1, Steps 1-7 | A1, B33, C11 |
| 133 | 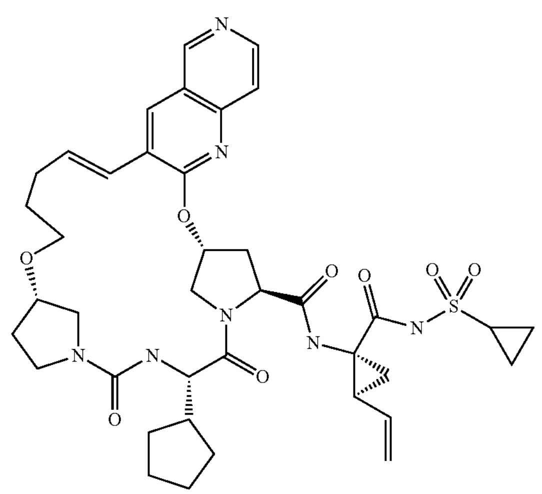 [SMILES: C=C[C@@H]1C[C@]1(NC(=O)[C@@H]1C[C@@H]2CN1C(=O)[C@H](C1CCCC1)NC(=O)N1CC[C@@H](C1)OCCC/C=C/c1cc3cnccc3nc1O2)C(=O)NS(=O)(=O)C1CC1] | (1R,13E,19S,25S,28S)-25-cyclopentyl-N-((1R,2S)-1-{[(cyclopropylsulfonyl)amino]carbonyl}-2-vinylcyclopropyl)-23,26-dioxo-2,18-dioxa-4,8,22,24,27-pentaazapentacyclo[25.2.1.1$^{19,22}$.0$^{3,12}$.0$^{5,10}$]hentriaconta-3(12),4,5,7,9,10,13-heptaene-28-carboxamide | 776.1 | See Example 1, Steps 4, 2 & 5-7 | A1, B30, C21 |

-continued

| Ex. | Structure | Name | LRMS (M + H)+ | Example | Int. |
|---|---|---|---|---|---|
| 134 | 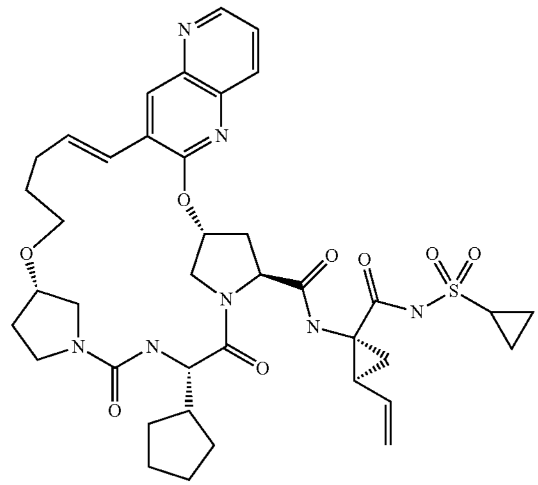 [SMILES: C=C[C@@H]1C[C@]1(NC(=O)[C@@H]1C[C@@H]2CN1C(=O)[C@H](C1CCCC1)NC(=O)N1CC[C@@H](C1)OCCC/C=C/c1cc3ncccc3nc1O2)C(=O)NS(=O)(=O)C1CC1] | (1R,13E,19S,25S,28S)-25-cyclopentyl-N-((1R,2S)-1-{[(cyclopropylsulfonyl)amino]carbonyl}-2-vinylcyclopropyl)-23,26-dioxo-2,18-dioxa-4,9,22,24,27-pentaazapentacyclo[25.2.1.1$^{19,22}$.0$^{3,12}$.0$^{5,10}$]hentriaconta-3(12),4,5,7,9,10,13-heptaene-28-carboxamide | 776.1 | See Example 1, Steps 4, 2 & 5-7 | A1, B30, C22 |
| 135 | 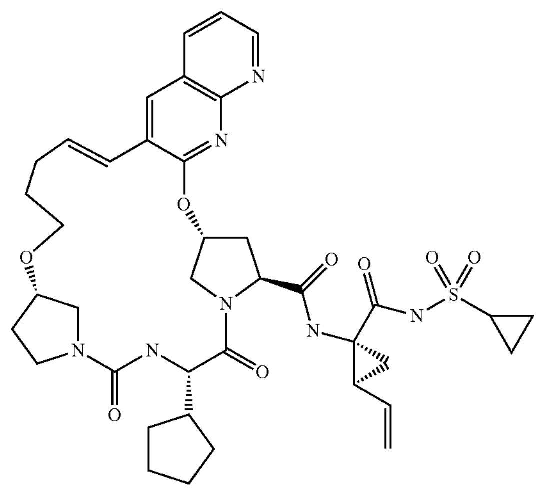 [SMILES: C=C[C@@H]1C[C@]1(NC(=O)[C@@H]1C[C@@H]2CN1C(=O)[C@H](C1CCCC1)NC(=O)N1CC[C@@H](C1)OCCC/C=C/c1cc3cccnc3nc1O2)C(=O)NS(=O)(=O)C1CC1] | (1R,13E,19S,25S,28S)-25-cyclopentyl-N-((1R,2S)-1-{[(cyclopropylsulfonyl)amino]carbonyl}-2-vinylcyclopropyl)-23,26-dioxo-2,18-dioxa-4,6,22,24,27-pentaazapentacyclo[25.2.1.1$^{19,22}$.0$^{3,12}$.0$^{5,10}$]hentriaconta-3(12),4,5,7,9,10,13-heptaene-28-carboxamide | 776.1 | See Example 1, Steps 4, 2 & 5-7 | A1, B30, C20 |
| 136 | 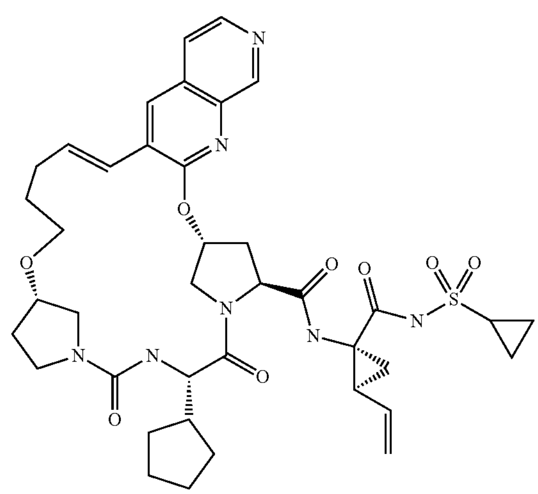 [SMILES: C=C[C@@H]1C[C@]1(NC(=O)[C@@H]1C[C@@H]2CN1C(=O)[C@H](C1CCCC1)NC(=O)N1CC[C@@H](C1)OCCC/C=C/c1cc3ccncc3nc1O2)C(=O)NS(=O)(=O)C1CC1] | (1R,13E,19S,25S,28S)-25-cyclopentyl-N-((1R,2S)-1-{[(cyclopropylsulfonyl)amino]carbonyl}-2-vinylcyclopropyl)-23,26-dioxo-2,18-dioxa-4,7,22,24,27-pentaazapentacyclo[25.2.1.1$^{19,22}$.0$^{3,12}$.0$^{5,10}$]hentriaconta-3(12),4,5,7,9,10,13-heptaene-28-carboxamide | 776.2 | See Example 1, Steps 4, 2 & 5-7 | A1, B30, C23 |

Example 137

(1R,20S,26S,29S)-26-cyclopentyl-N-((1R,2S)-1-{[(cyclopropylsulfonyl)amino]carbonyl}-2-vinylcyclopropyl)-7-methoxy-24,27-dioxo-2,19-dioxa-4,23,25,28-tetraazahexacyclo[26.2.1.1$^{20,23}$.0$^{3,12}$.0$^{5,10}$.0$^{13,15}$]dotriaconta-3(12),4,5,7,9,10-hexaene-29-carboxamide

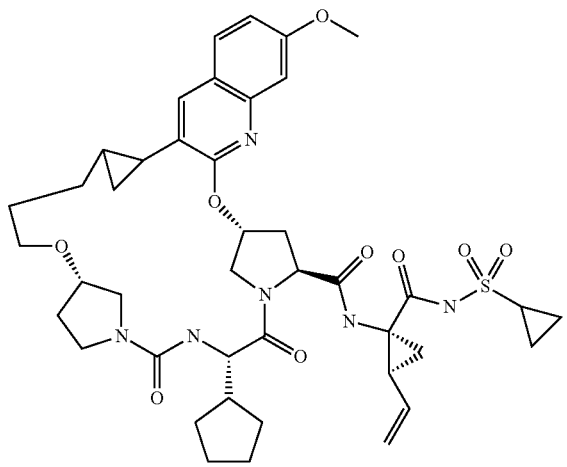 [SMILES: C=C[C@@H]1C[C@]1(NC(=O)[C@@H]1C[C@@H]2CN1C(=O)[C@H](C1CCCC1)NC(=O)N1CC[C@@H](C1)OCCCC1CC1c1cc3ccc(OC)cc3nc1O2)C(=O)NS(=O)(=O)C1CC1]

Step 1 Methyl (1R,13E,19S,25S,28S)-25-cyclopentyl-7-methoxy-23,26-dioxo-2,18-dioxa-4,22,24,27-tetraazapentacyclo[25.2.1.1$^{19,22}$.0$^{3,12}$.0$^{5,10}$]hentriaconta-3(12),4,5,7,9,10,13-heptaene-28-carboxylate

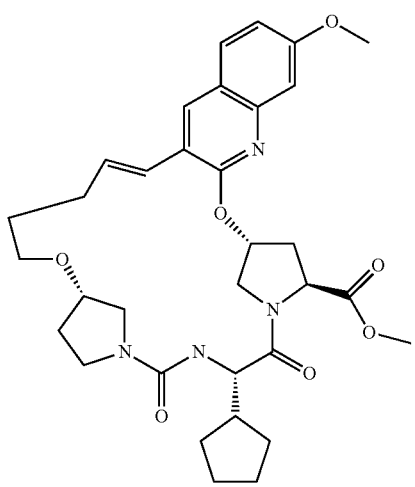 [SMILES: COC(=O)[C@@H]1C[C@@H]2CN1C(=O)[C@H](C1CCCC1)NC(=O)N1CC[C@@H](C1)OCCC/C=C/c1cc3ccc(OC)cc3nc1O2]

Methyl (1R,13E,19S,25S,28S)-25-cyclopentyl-7-methoxy-23,26-dioxo-2,18-dioxa-4,22,24,27-tetraazapentacyclo[25.2.1.1$^{19,22}$.0$^{3,12}$.0$^{5,10}$]hentriaconta-3 (12),4,5,7,9,10,13-heptaene-28-carboxylate was prepared using the procedures of Example 1 Steps 1-5, employing Intermediates B30 and C11. LCMS (ES) m/z 607.1 (M+H)$^+$.

Step 2: Methyl (1R,20S,26S,29S)-26-cyclopentyl-7-methoxy-24,27-dioxo-2,19-dioxa-4,23,25,28-tetraazahexacyclo[26.2.1.1$^{20,23}$.0$^{3,12}$.0$^{5,10}$.0$^{13,15}$]dotriaconta-3(12),4,5,7,9,10-hexaene-29-carboxylate

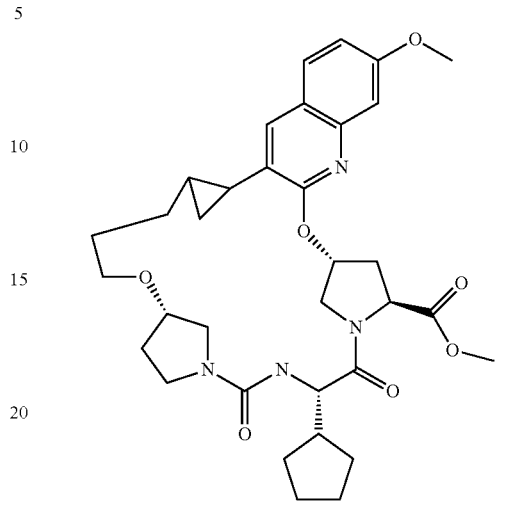

Pd(OAc)$_2$ (6.7 mg, 0.03 mmol) was added to a solution of the product of Step 1 (90 mg, 0.15 mmol) in Et$_2$O (6 mL). A freshly prepared solution of diazomethane in Et$_2$O was then added dropwise to this solution. Repeated additions of diazomethane solution gave ~60% conversion to product. N$_2$ was bubbled through the reaction mixture. The reaction mixture was concentrated and purified by reverse-phase HPLC to give the title product. LCMS (ES) m/z 621.1 (M+H)$^+$.

Step 3: (1R,20S,26S,29S)-26-cyclopentyl-N-((1R,2S)-1-{[(cyclopropylsulfonyl)amino]carbonyl}-2-vinylcyclopropyl)-7-methoxy-24,27-dioxo-2,19-dioxa-4,23,25,28-tetraazahexacyclo[26.2.1.1$^{20,23}$.0$^{3,12}$.0$^{5,10}$.0$^{13,15}$]dotriaconta-3(12),4,5,7,9,10-hexaene-29-carboxamide The title compound was prepared from the product of Step 2, using the procedures of Example 1 Steps 6 and 7. LCMS (ES) m/z 819.9 (M+H)$^+$.

Example 138

(1R,18R,22R,26S,29S)-26-Cyclopentyl-N-((1R,2S)-1-{[(cyclopropylsulfonyl)amino]carbonyl}-2-vinylcyclopropyl)-11,24,27-trioxo-2,23-dioxa-12,25,28-triazapentacyclo[26.2.1.0$^{3,12}$.0$^{5,10}$.0$^{18,22}$]hentriaconta-3,5,7,9-tetraene-29-carboxamide

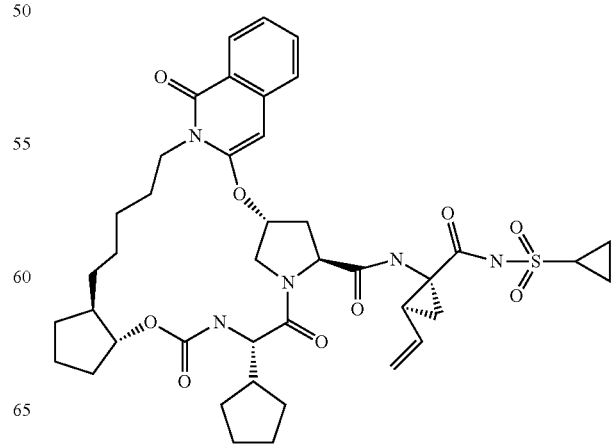

Step 1:
2-But-3-en-1-ylisoquinoline-1,3(2H,4H)-dione

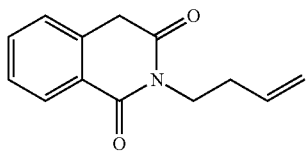 [SMILES: C=CCCN1C(=O)Cc2ccccc2C1=O]

A solution of homophthalic anhydride (250 mg, 1.54 mmol) and 3-buten-1-amine (132 mg, 1.85 mmol) in PhMe (5 mL) pound was heated to reflux and stirred for 18 hours. The reaction mixture was concentrated and purified by $SO_2$ chromatography (gradient elution, 10-40% EtOAc/hexanes) to give the title compound. LCMS (ES) m/z 353.5 (M+H)+ 216.0.

Step 2: (1R,18R,22R,26S,29S)-26-Cyclopentyl-N((1R,2S)-1-{[(cyclopropylsulfonyl)amino]carbonyl}-2-vinylcyclopropyl)-11,24,27-trioxo-2,23-dioxa-12,25,28-triazapentacyclo[26.2.1.0$^{3,12}$.0$^{5,10}$.0$^{18,22}$]hentriaconta-3,5,7,9-tetraene-29-carboxamide The title compound was prepared from the product of Step 1, using the following sequence of procedures: Example 1 Steps 1, 3, 4 (using Intermediate B24) and 5; and Example 3 Steps 1-3. LCMS (ES) m/z 792.2 (M+H)+.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound of formula (I):

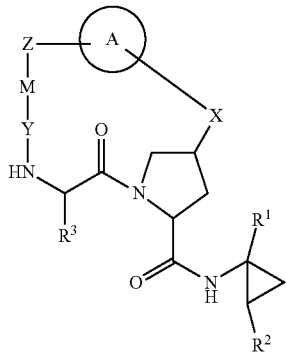

(I)

wherein:

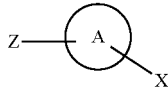

is one or more rings selected from the group consisting of:

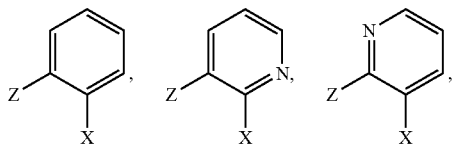

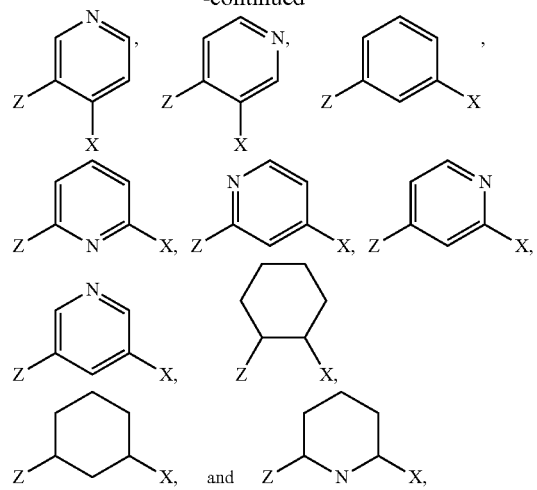

$R^1$ is selected from the group consisting of —$CO_2R^{10}$ and —$CONR^{10}SO_2R^6$;
$R^2$ is —CH=CH$_2$;
$R^3$ is $C_1$-$C_6$ alkyl;
$R^6$ is $C_3$ cycloalkyl;
Y is selected from the group consisting of —OC(O)—;
Z is a direct bond;
M is selected from the group consisting of $C_1$-$C_{12}$ alkylenes and $C_2$-$C_{12}$ alkenylenes, wherein said M is substituted with 1 to 2 substituents F independently selected from the group consisting of $C_1$-$C_8$ alkyl and =CH$_2$;
X is selected from the group consisting of —(CH$_2$)$_{0-3}$O—, wherein ⊙ is attached to —(CH$_2$)$_{0-3}$ if present; and
each $R^{10}$ is independently H.

2. The compound according to claim 1, wherein M is selected from the group consisting of —CH=CH(CH$_2$)$_5$—, —(CH$_2$)$_7$—, —CH$_2$CH=CH(CH$_2$)$_4$—, —(CH$_2$)$_6$—, —CH=CH(CH$_2$)$_4$—, —CH=CH(CH$_2$)$_3$C(CH$_3$)$_2$CH$_2$—, —CH=CH(CH$_2$)$_3$—, —(CH$_2$)$_5$—, —CH=CH(CH$_2$)$_3$—, —(CH$_2$)$_4$—, —(CH$_2$)$_3$—, —CH=CH(CH$_2$)$_2$C(CH$_3$)$_2$CH$_2$—, —(CH$_2$)$_4$C(CH$_3$)$_2$CH$_2$—, —C(=CH$_2$)(CH$_2$)$_5$—, —C(=CH$_2$)(CH$_2$)$_3$—, and —CH$_2$CH=CH(CH$_2$)$_3$—.

3. The compound according to claim 2, wherein M is selected from the group consisting of

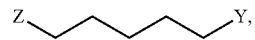

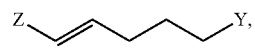

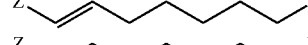

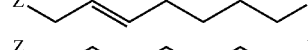

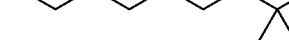

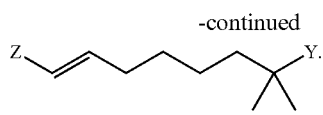
4. A compound selected from the group consisting of:
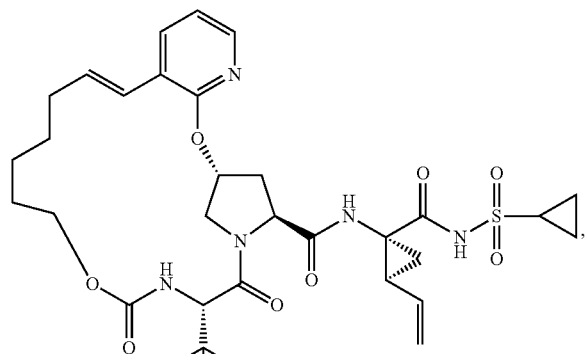
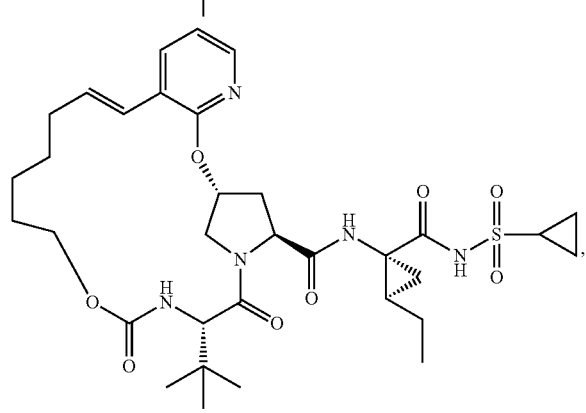
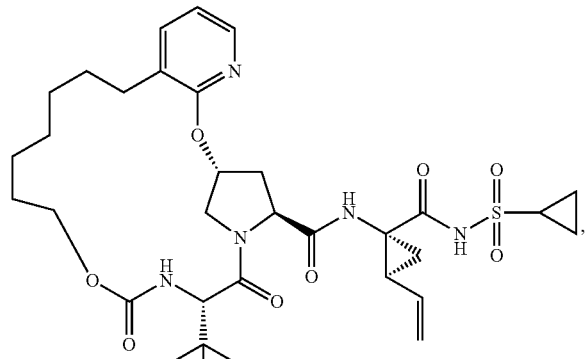
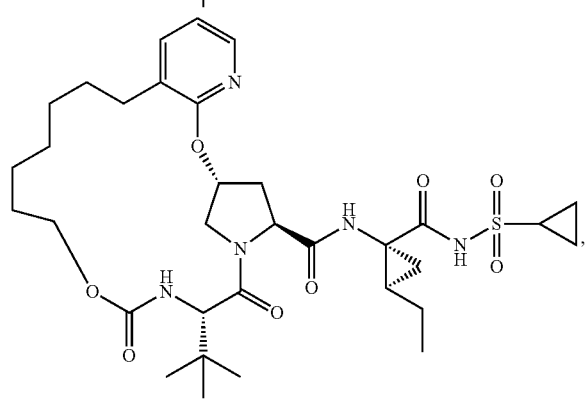
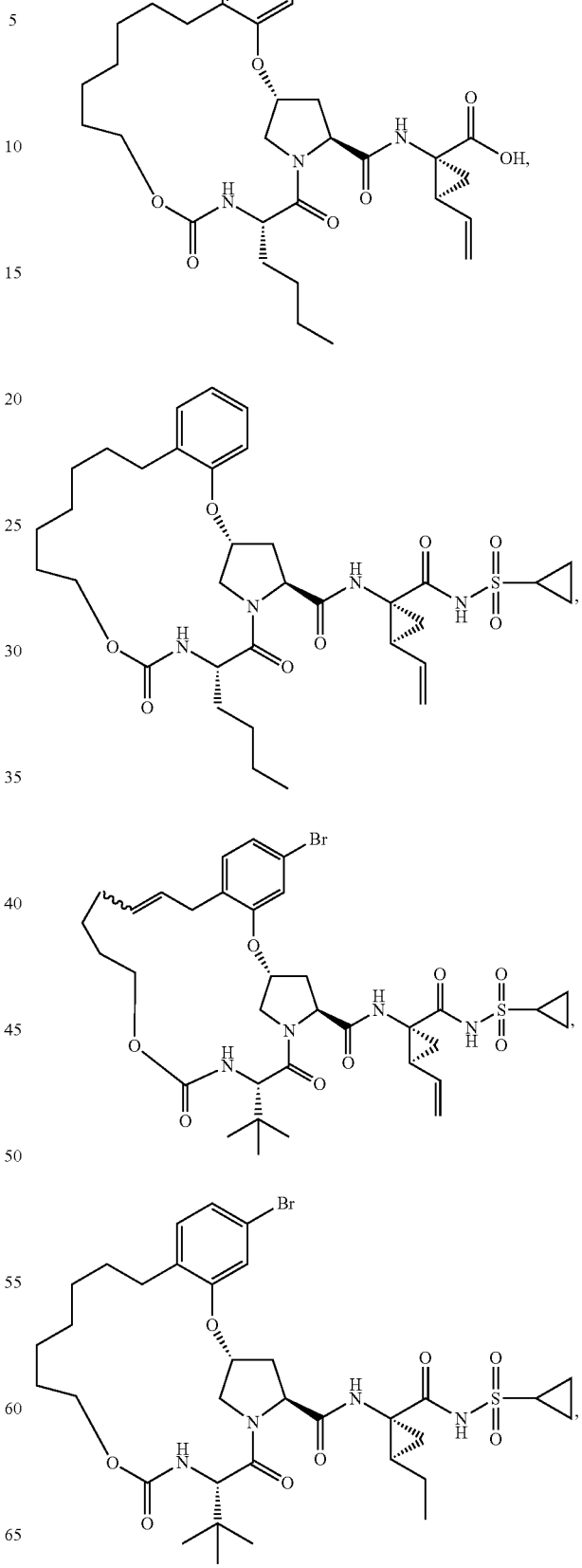

203
-continued
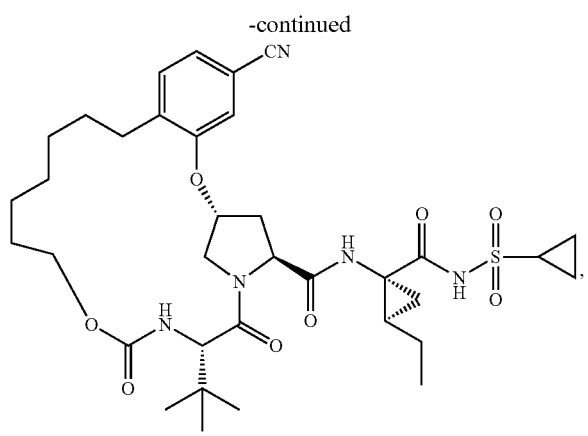
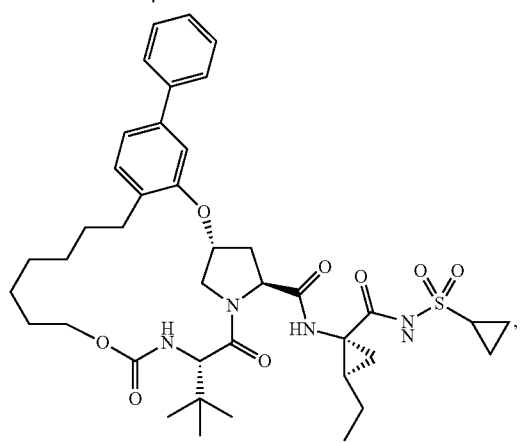
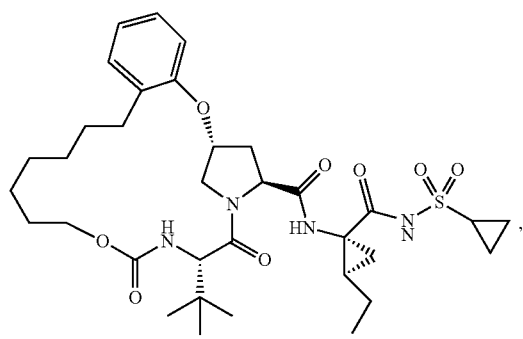
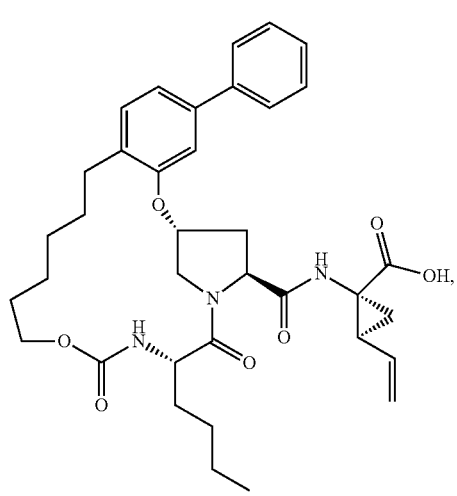
204
-continued
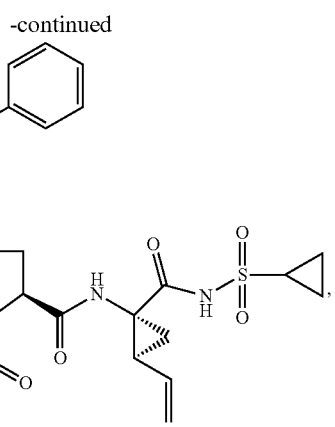
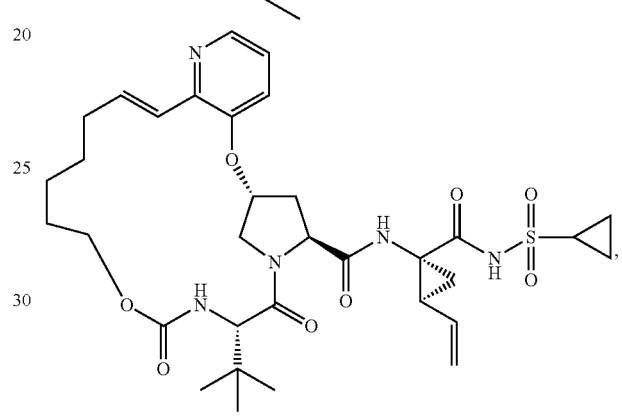
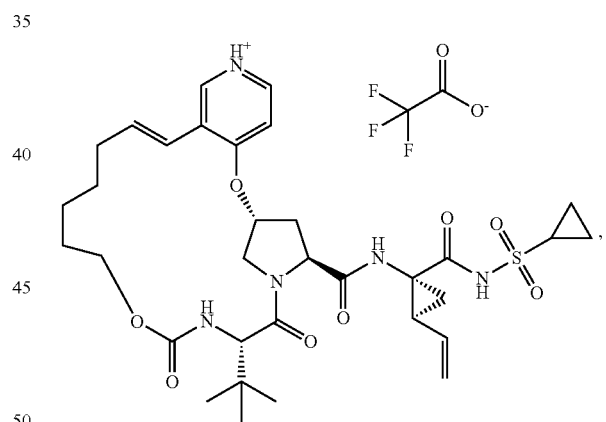
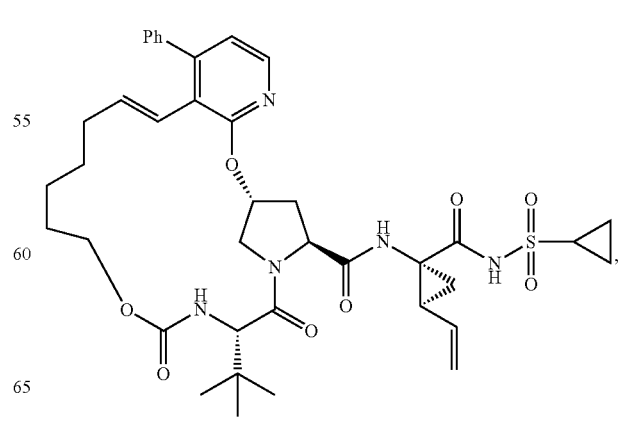

205
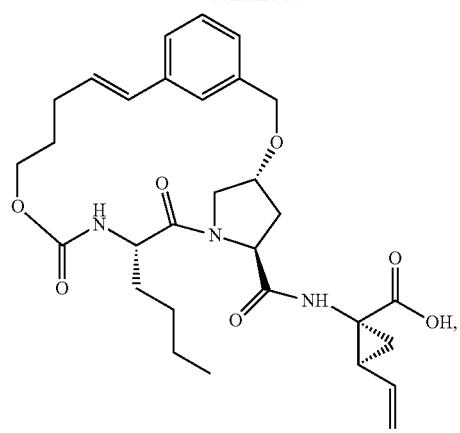
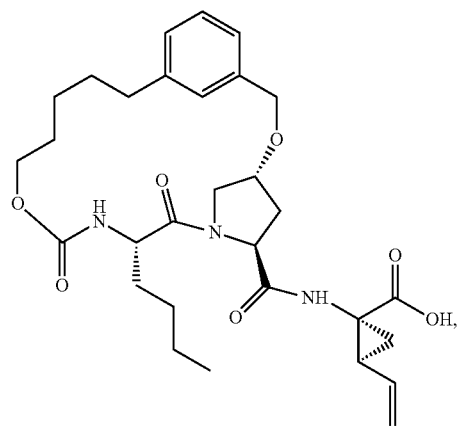
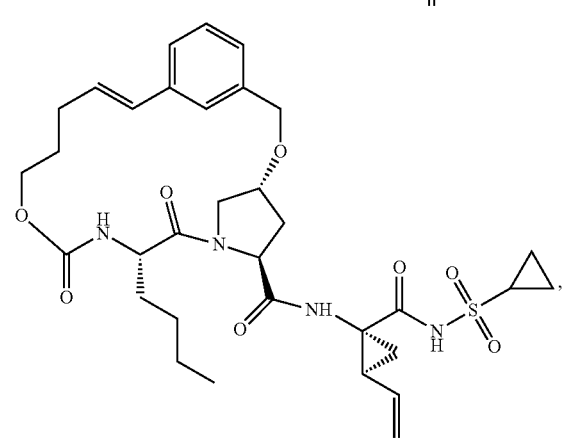
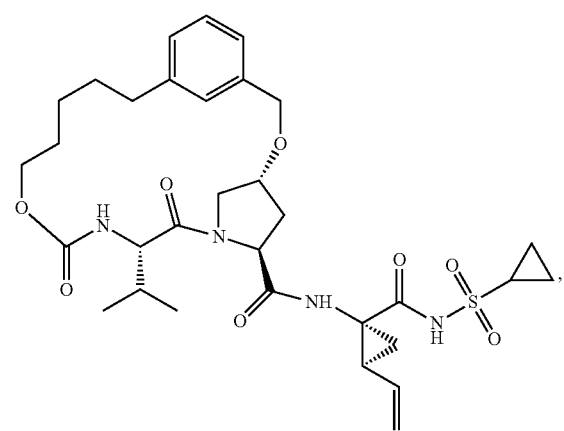
206
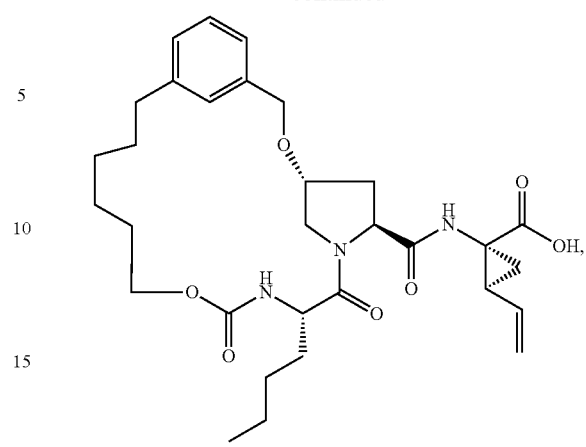
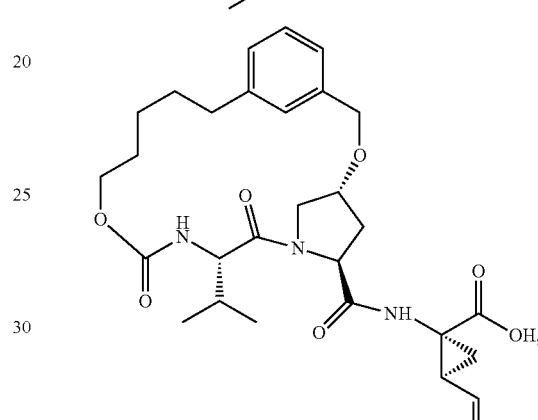
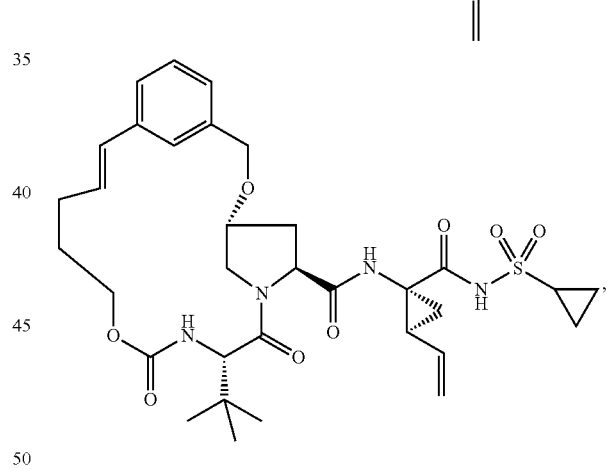
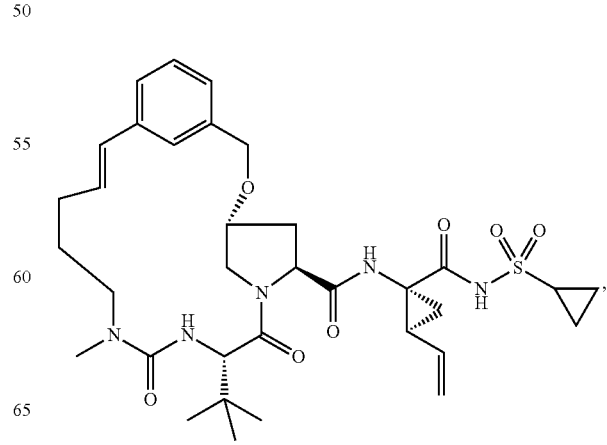

207
-continued
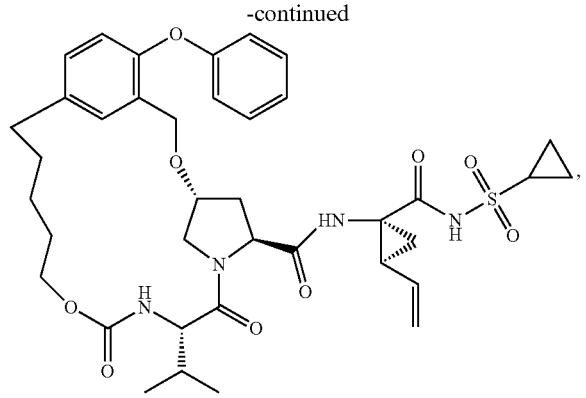
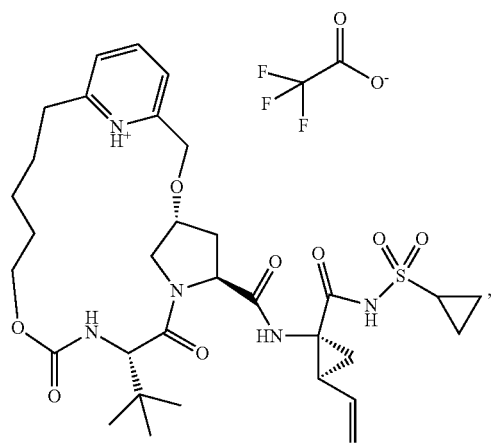
208
-continued
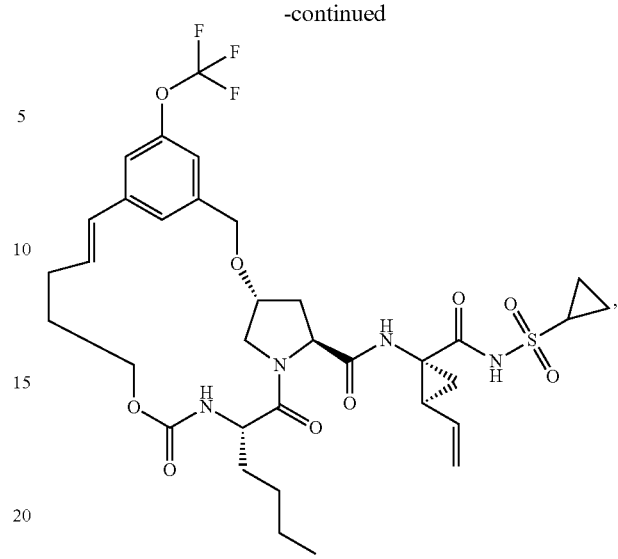
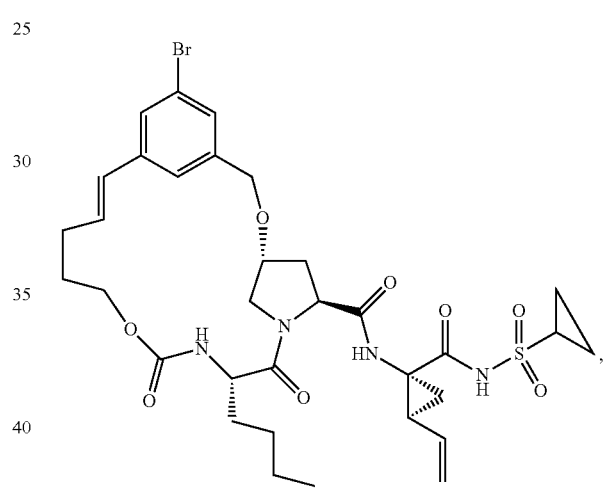
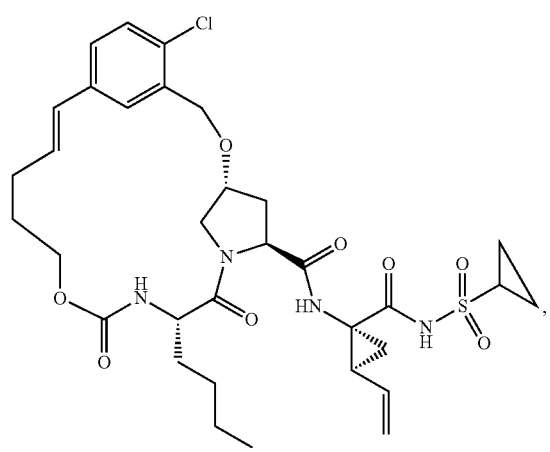
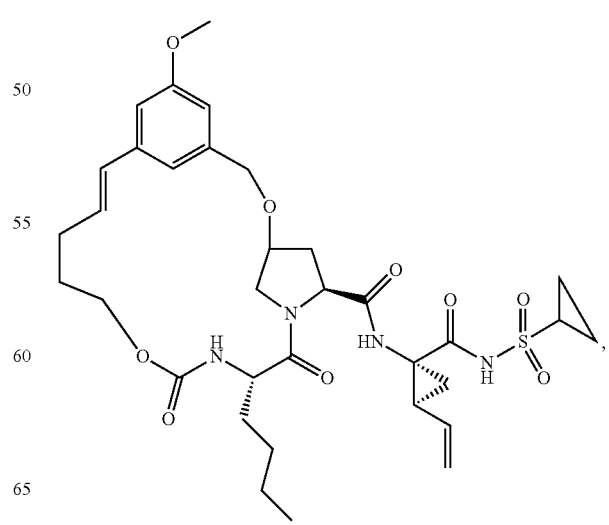

209
-continued
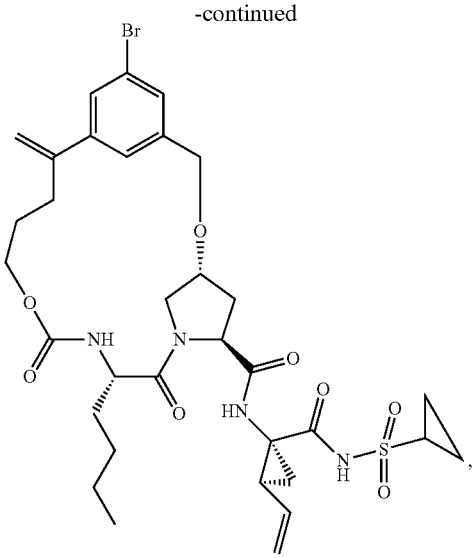
210
-continued
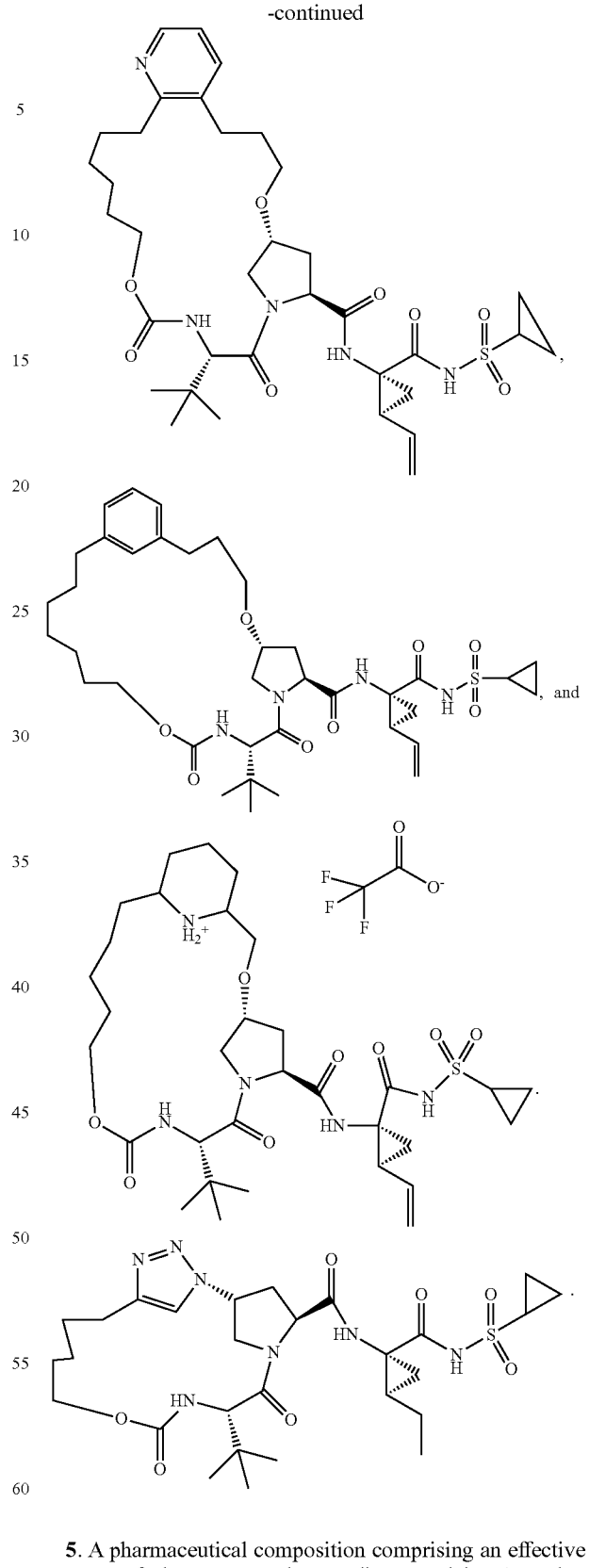
5. A pharmaceutical composition comprising an effective amount of the compound according to claim 1, and a pharmaceutically acceptable carrier.
6. The pharmaceutical composition according to claim 5, further comprising a second therapeutic agent selected from the group consisting of HCV antiviral agents, immuno-modulators, and anti-infective agents.

7. The pharmaceutical composition according to claim 5, further comprising a second therapeutic agent selected from the group consisting of HCV protease inhibitors and HCV NS5B polymerase inhibitors.

* * * * *